US012806223B2

(12) United States Patent
Packer et al.

(10) Patent No.: US 12,806,223 B2
(45) Date of Patent: Nov. 24, 2026

(54) LIPID NANOPARTICLE COMPOSITIONS AND METHODS OF FORMULATING THE SAME

(71) Applicant: MODERNATX, INC., Cambridge, MA (US)

(72) Inventors: Meredith Packer, Cambridge, MA (US); Dipendra Gyawali, Cambridge, MA (US); Serenus Hua, Cambridge, MA (US); Gabor Butora, Cambridge, MA (US); Gregory John Mercer, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 340 days.

(21) Appl. No.: 18/277,346

(22) PCT Filed: Feb. 18, 2022

(86) PCT No.: PCT/US2022/016902
§ 371 (c)(1),
(2) Date: Aug. 15, 2023

(87) PCT Pub. No.: WO2022/178199
PCT Pub. Date: Aug. 25, 2022

(65) Prior Publication Data

US 2024/0189242 A1 Jun. 13, 2024

Related U.S. Application Data

(60) Provisional application No. 63/151,523, filed on Feb. 19, 2021, provisional application No. 63/182,428, filed on Apr. 30, 2021, provisional application No. 63/191,655, filed on May 21, 2021.

(51) Int. Cl.

| | |
|---|---|
| ***A61K 31/7105*** | (2006.01) |
| ***A61K 9/16*** | (2006.01) |
| ***A61K 9/51*** | (2006.01) |
| ***A61K 47/18*** | (2017.01) |
| ***A61K 47/26*** | (2006.01) |

(52) U.S. Cl.
CPC ........ *A61K 31/7105* (2013.01); *A61K 9/1617* (2013.01); *A61K 9/1641* (2013.01); *A61K 9/5123* (2013.01); *A61K 47/18* (2013.01); *A61K 47/26* (2013.01)

(58) Field of Classification Search
CPC .... C12N 15/88; A61K 47/18; A61K 31/7105; A61K 9/5123
See application file for complete search history.

(56) References Cited

U.S. PATENT DOCUMENTS

| | | | |
|---|---|---|---|
| 6,652,886 | B2 | 11/2003 | Ahn et al. |
| 6,696,038 | B1 | 2/2004 | Mahato et al. |
| 7,268,120 | B1 | 9/2007 | Horton et al. |
| 7,371,404 | B2 | 5/2008 | Panzner et al. |
| 7,943,168 | B2 | 5/2011 | Schlesinger et al. |
| 8,058,069 | B2 | 11/2011 | Yaworski et al. |
| 8,158,601 | B2 | 4/2012 | Chen et al. |
| 8,420,123 | B2 | 4/2013 | Troiano et al. |
| 8,440,614 | B2 | 5/2013 | Castor |
| 8,450,298 | B2 | 5/2013 | Mahon et al. |
| 8,460,696 | B2 | 6/2013 | Slobodkin et al. |
| 8,460,709 | B2 | 6/2013 | Ausborn et al. |
| 8,568,784 | B2 | 10/2013 | Lillard et al. |
| 8,569,256 | B2 | 10/2013 | Heyes et al. |
| 8,580,297 | B2 | 11/2013 | Essler et al. |
| 8,642,076 | B2 | 2/2014 | Manoharan et al. |
| 8,652,487 | B2 | 2/2014 | Maldonado |
| 8,691,750 | B2 | 4/2014 | Constien et al. |
| 8,697,098 | B2 | 4/2014 | Perumal et al. |
| 8,709,483 | B2 | 4/2014 | Farokhzad et al. |
| 8,710,200 | B2 | 4/2014 | Schrum et al. |
| 8,715,736 | B2 | 5/2014 | Sachdeva et al. |
| 8,734,832 | B2 | 5/2014 | O'Hagan et al. |
| 8,734,846 | B2 | 5/2014 | Ali et al. |
| 8,754,062 | B2 | 6/2014 | De Fougerolles et al. |
| 8,822,663 | B2 | 9/2014 | Schrum et al. |
| 8,999,380 | B2 | 4/2015 | Bancel et al. |
| 9,221,891 | B2 | 12/2015 | Bancel et al. |
| 9,303,079 | B2 | 4/2016 | Chakraborty et al. |
| 9,464,124 | B2 | 10/2016 | Bancel et al. |
| 9,512,456 | B2 | 12/2016 | Wang et al. |
| 9,597,380 | B2 | 3/2017 | Chakraborty et al. |
| 9,868,691 | B2 | 1/2018 | Benenato |
| 9,872,900 | B2 | 1/2018 | Ciaramella et al. |

(Continued)

FOREIGN PATENT DOCUMENTS

| | | |
|---|---|---|
| CA | 3128215 | 8/2020 |
| CN | 102068701 A | 5/2011 |

(Continued)

OTHER PUBLICATIONS

Packer et al (Nature communications, Nov. 2021, https://doi.org/10.1038/s41467-021-26926-0) (Year: 2021).*

(Continued)

*Primary Examiner* — Mark V Stevens
(74) *Attorney, Agent, or Firm* — Foley & Lardner LLP

(57) ABSTRACT

Provided herein are methods of reducing adduct formation in lipid nanoparticle compositions comprising a polynucleotide, such as mRNA, and an ionizable lipid; also disclosed are lipid nanoparticle compositions having a reduced adduct content, and methods of detecting the adducts.

23 Claims, 32 Drawing Sheets

(56) References Cited

U.S. PATENT DOCUMENTS

| | | | |
|---|---|---|---|
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,646,549 | B2 | 5/2020 | Frederick et al. |
| 11,524,023 | B2 * | 12/2022 | Packer ............... A61K 31/7105 |
| 11,583,504 | B2 * | 2/2023 | Brader ................. A61K 9/0019 |
| 11,622,972 | B2 * | 4/2023 | Packer .................. A61K 47/18 514/44 R |
| 12,144,895 | B2 * | 11/2024 | Brader ................. A61K 9/0019 |
| 12,508,278 | B2 * | 12/2025 | Packer ............... A61K 31/7105 |
| 2003/0073619 | A1 | 4/2003 | Mahato et al. |
| 2003/0092653 | A1 | 5/2003 | Kisich et al. |
| 2004/0142474 | A1 | 7/2004 | Mahato et al. |
| 2005/0143336 | A1 | 6/2005 | Ramesh et al. |
| 2006/0008910 | A1 | 1/2006 | Maclachlan et al. |
| 2006/0083780 | A1 | 4/2006 | Heyes et al. |
| 2006/0172003 | A1 | 8/2006 | Meers et al. |
| 2006/0204566 | A1 | 9/2006 | Smyth-Templeton et al. |
| 2007/0252295 | A1 | 11/2007 | Panzner et al. |
| 2009/0042825 | A1 | 2/2009 | Matar et al. |
| 2009/0042829 | A1 | 2/2009 | Matar et al. |
| 2011/0200582 | A1 | 8/2011 | Baryza et al. |
| 2011/0244026 | A1 | 10/2011 | Guild et al. |
| 2011/0256175 | A1 | 10/2011 | Hope et al. |
| 2012/0021042 | A1 | 1/2012 | Panzner et al. |
| 2012/0065252 | A1 | 3/2012 | Schrum et al. |
| 2012/0157500 | A1 | 6/2012 | Tao |
| 2012/0172411 | A1 | 7/2012 | Heyes et al. |
| 2012/0177724 | A1 | 7/2012 | Irvine et al. |
| 2012/0178702 | A1 | 7/2012 | Huang et al. |
| 2012/0251618 | A1 | 10/2012 | Schrum et al. |
| 2012/0295832 | A1 | 11/2012 | Constien et al. |
| 2013/0017223 | A1 | 1/2013 | Hope et al. |
| 2013/0064894 | A1 | 3/2013 | Martin et al. |
| 2013/0065942 | A1 | 3/2013 | Matar et al. |
| 2013/0090372 | A1 | 4/2013 | Budzik et al. |
| 2013/0102034 | A1 | 4/2013 | Schrum |
| 2013/0115273 | A1 | 5/2013 | Yang et al. |
| 2013/0115274 | A1 | 5/2013 | Knopov et al. |
| 2013/0116307 | A1 | 5/2013 | Heyes et al. |
| 2013/0122104 | A1 | 5/2013 | Yaworski et al. |
| 2013/0123338 | A1 | 5/2013 | Heyes et al. |
| 2013/0129785 | A1 | 5/2013 | Manoharan et al. |
| 2013/0130348 | A1 | 5/2013 | Gu et al. |
| 2013/0142876 | A1 | 6/2013 | Howard et al. |
| 2013/0150625 | A1 | 6/2013 | Budzik et al. |
| 2013/0156845 | A1 | 6/2013 | Manoharan et al. |
| 2013/0164400 | A1 | 6/2013 | Knopov et al. |
| 2013/0171241 | A1 | 7/2013 | Geall |
| 2013/0178541 | A1 | 7/2013 | Stanton et al. |
| 2013/0183355 | A1 | 7/2013 | Jain et al. |
| 2013/0189351 | A1 | 7/2013 | Geall |
| 2013/0195765 | A1 | 8/2013 | Gho et al. |
| 2013/0195967 | A1 | 8/2013 | Guild et al. |
| 2013/0195968 | A1 | 8/2013 | Geall et al. |
| 2013/0195969 | A1 | 8/2013 | Geall et al. |
| 2013/0202684 | A1 | 8/2013 | Geall et al. |
| 2013/0236533 | A1 | 9/2013 | Von Andrian et al. |
| 2013/0236550 | A1 | 9/2013 | Ausborn et al. |
| 2013/0243848 | A1 | 9/2013 | Lobovkina et al. |
| 2013/0243867 | A1 | 9/2013 | Mohapatra et al. |
| 2013/0245104 | A1 | 9/2013 | De Fougerolles et al. |
| 2013/0245107 | A1 | 9/2013 | De Fougerolles et al. |
| 2013/0259923 | A1 | 10/2013 | Chakraborty et al. |
| 2013/0266640 | A1 | 10/2013 | De Fougerolles et al. |
| 2013/0274504 | A1 | 10/2013 | Colletti et al. |
| 2013/0274523 | A1 | 10/2013 | Bawiec et al. |
| 2013/0295043 | A1 | 11/2013 | Kallen et al. |
| 2013/0295183 | A1 | 11/2013 | Troiano et al. |
| 2013/0295191 | A1 | 11/2013 | Troiano et al. |
| 2013/0302432 | A1 | 11/2013 | Zale et al. |
| 2013/0302433 | A1 | 11/2013 | Troiano et al. |
| 2013/0315831 | A1 | 11/2013 | Shi et al. |
| 2013/0330401 | A1 | 12/2013 | Payne et al. |
| 2013/0336998 | A1 | 12/2013 | Kallen et al. |
| 2013/0338201 | A1 | 12/2013 | Song |
| 2013/0338210 | A1 | 12/2013 | Manoharan et al. |
| 2014/0037714 | A1 | 2/2014 | Quay et al. |
| 2014/0039032 | A1 | 2/2014 | Kuboyama et al. |
| 2014/0044772 | A1 | 2/2014 | Maclachlan et al. |
| 2014/0044791 | A1 | 2/2014 | Basilion et al. |
| 2014/0045913 | A1 | 2/2014 | Kuboyama et al. |
| 2014/0050775 | A1 | 2/2014 | Slobodkin et al. |
| 2014/0065172 | A1 | 3/2014 | Echeverri et al. |
| 2014/0065204 | A1 | 3/2014 | Hayes et al. |
| 2014/0065228 | A1 | 3/2014 | Yaworski et al. |
| 2014/0093579 | A1 | 4/2014 | Zale et al. |
| 2014/0113137 | A1 | 4/2014 | Podobinski et al. |
| 2014/0121263 | A1 | 5/2014 | Fitzgerald et al. |
| 2014/0121393 | A1 | 5/2014 | Manoharan et al. |
| 2014/0141070 | A1 | 5/2014 | Geall et al. |
| 2014/0141089 | A1 | 5/2014 | Liang |
| 2014/0141483 | A1 | 5/2014 | Bossard et al. |
| 2014/0142165 | A1 | 5/2014 | Grayson et al. |
| 2014/0142254 | A1 | 5/2014 | Fonnum et al. |
| 2014/0147432 | A1 | 5/2014 | Chakraborty et al. |
| 2014/0148502 | A1 | 5/2014 | Bancel et al. |
| 2014/0193482 | A1 | 7/2014 | Chakraborty et al. |
| 2014/0206752 | A1 | 7/2014 | Afeyan et al. |
| 2014/0206753 | A1 | 7/2014 | Guild et al. |
| 2014/0378538 | A1 | 12/2014 | Bancel |
| 2015/0141499 | A1 | 5/2015 | Bancel et al. |
| 2015/0166465 | A1 * | 6/2015 | Chen ...................... A61K 47/14 554/114 |
| 2015/0307542 | A1 | 10/2015 | Roy et al. |
| 2015/0315541 | A1 | 11/2015 | Bancel et al. |
| 2015/0376115 | A1 | 12/2015 | Ansell et al. |
| 2016/0024141 | A1 | 1/2016 | Issa et al. |
| 2016/0032273 | A1 | 2/2016 | Shahrokh et al. |
| 2016/0038612 | A1 | 2/2016 | Hoge et al. |
| 2016/0271272 | A1 | 9/2016 | Bancel et al. |
| 2016/0317647 | A1 | 11/2016 | Ciaramella et al. |
| 2016/0331828 | A1 | 11/2016 | Ciaramella et al. |
| 2017/0065675 | A1 | 3/2017 | Bancel et al. |
| 2017/0130255 | A1 | 5/2017 | Wang et al. |
| 2017/0202979 | A1 | 7/2017 | Chakraborty et al. |
| 2017/0340724 | A1 | 11/2017 | Ciaramella et al. |
| 2018/0000953 | A1 | 1/2018 | Almarsson et al. |
| 2018/0002393 | A1 | 1/2018 | De Fougerolles et al. |
| 2018/0021258 | A1 | 1/2018 | Graham et al. |
| 2018/0028664 | A1 | 2/2018 | Besin et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0280496 | A1 | 10/2018 | Ciaramella et al. |
| 2018/0289792 | A1 | 10/2018 | Ciaramella et al. |
| 2018/0303929 | A1 | 10/2018 | Ciaramella et al. |
| 2018/0311336 | A1 | 11/2018 | Ciaramella et al. |
| 2018/0312549 | A1 | 11/2018 | Ciaramella |
| 2018/0318409 | A1 | 11/2018 | Valiante et al. |
| 2018/0363019 | A1 | 12/2018 | Hoge et al. |
| 2019/0008938 | A1 | 1/2019 | Ciaramella et al. |
| 2019/0336452 | A1 * | 11/2019 | Brader ..................... A61K 9/19 |
| 2021/0361761 | A1 | 11/2021 | Lutz et al. |
| 2021/0378980 | A1 | 12/2021 | Horhota et al. |
| 2022/0002716 | A1 | 1/2022 | Kore et al. |

FOREIGN PATENT DOCUMENTS

| | | | |
|---|---|---|---|
| CN | 102204920 | A | 10/2011 |
| CN | 102813929 | A | 12/2012 |
| CN | 104644555 | | 5/2015 |
| EP | 1 404 860 | | 4/2004 |
| EP | 2 073 848 | | 7/2009 |
| WO | WO-99/14346 | A2 | 3/1999 |
| WO | WO-99/52503 | A2 | 10/1999 |
| WO | WO-2005/034979 | A2 | 4/2005 |
| WO | WO-2008/042973 | A2 | 4/2008 |
| WO | WO-2009/024599 | A1 | 2/2009 |
| WO | WO-2009/127060 | | 10/2009 |

(56) References Cited

FOREIGN PATENT DOCUMENTS

| | | | |
|---|---|---|---|
| WO | WO-2010/042877 | A1 | 4/2010 |
| WO | WO-2010/054406 | A1 | 5/2010 |
| WO | WO-2010/088537 | A2 | 8/2010 |
| WO | WO-2010/129709 | A1 | 11/2010 |
| WO | WO-2010/144710 | A1 | 12/2010 |
| WO | WO-2010/144740 | A1 | 12/2010 |
| WO | WO-2011/017108 | A2 | 2/2011 |
| WO | WO-2011/068810 | A1 | 6/2011 |
| WO | WO-2012/006376 | A2 | 1/2012 |
| WO | WO-2012/006378 | A1 | 1/2012 |
| WO | WO-2012/030901 | A1 | 3/2012 |
| WO | WO-2012/031043 | A1 | 3/2012 |
| WO | WO-2012/129483 | A1 | 9/2012 |
| WO | WO-2012/149252 | A2 | 11/2012 |
| WO | WO-2012/149393 | A2 | 11/2012 |
| WO | WO-2012/153338 | A2 | 11/2012 |
| WO | WO-2013/006825 | A1 | 1/2013 |
| WO | WO-2013/006834 | A1 | 1/2013 |
| WO | WO-2013/006837 | A1 | 1/2013 |
| WO | WO-2013/006838 | A1 | 1/2013 |
| WO | WO-2013/006842 | A2 | 1/2013 |
| WO | WO-2013/033563 | A1 | 3/2013 |
| WO | WO-2013/049328 | A1 | 4/2013 |
| WO | WO-2013/052167 | A2 | 4/2013 |
| WO | WO-2013/056132 | A2 | 4/2013 |
| WO | WO-2013/057715 | A1 | 4/2013 |
| WO | WO-2013/059496 | A1 | 4/2013 |
| WO | WO-2013/059922 | A1 | 5/2013 |
| WO | WO-2013/064911 | A2 | 5/2013 |
| WO | WO-2013/066903 | A1 | 5/2013 |
| WO | WO-2013/067537 | A1 | 5/2013 |
| WO | WO-2013/086322 | A1 | 6/2013 |
| WO | WO-2013/086373 | A1 | 6/2013 |
| WO | WO-2013/086526 | A1 | 6/2013 |
| WO | WO-2013/087083 | A1 | 6/2013 |
| WO | WO-2013/090186 | A1 | 6/2013 |
| WO | WO-2013/093648 | A2 | 6/2013 |
| WO | WO-2013/135359 | A1 | 9/2013 |
| WO | WO-2013/143555 | A1 | 10/2013 |
| WO | WO-2013/143683 | A1 | 10/2013 |
| WO | WO-2013/148186 | A1 | 10/2013 |
| WO | WO-2013/148541 | A1 | 10/2013 |
| WO | WO-2013/149141 | A1 | 10/2013 |
| WO | WO-2013/158127 | A1 | 10/2013 |
| WO | WO-2013/158579 | A1 | 10/2013 |
| WO | WO-2013/166498 | A1 | 11/2013 |
| WO | WO-2013/173693 | | 11/2013 |
| WO | WO-2013/185069 | A1 | 12/2013 |
| WO | WO-2014/008334 | A1 | 1/2014 |
| WO | WO-2014/026284 | A1 | 2/2014 |
| WO | WO-2014/028487 | A1 | 2/2014 |
| WO | WO-2014/054026 | A1 | 4/2014 |
| WO | WO-2014/071072 | A2 | 5/2014 |
| WO | WO-2014/072997 | A1 | 5/2014 |
| WO | WO-2014/081507 | A1 | 5/2014 |
| WO | WO-2014/144196 | A1 | 9/2014 |
| WO | WO-2014/152774 | A1 | 9/2014 |
| WO | WO-2014/160243 | A1 | 10/2014 |
| WO | WO-2014/172045 | A1 | 10/2014 |
| WO | WO-2014/182661 | A2 | 11/2014 |
| WO | WO-2014/210356 | A1 | 12/2014 |
| WO | WO-2015/095340 | A1 | 6/2015 |
| WO | WO-2015/130584 | A2 | 9/2015 |
| WO | WO-2015/148247 | A1 | 10/2015 |
| WO | WO-2015/164674 | A1 | 10/2015 |
| WO | WO-2015/164786 | A1 | 10/2015 |
| WO | WO-2016/037053 | A1 | 3/2016 |
| WO | WO-2016/118724 | A1 | 7/2016 |
| WO | WO-2016/118725 | A1 | 7/2016 |
| WO | WO-2016/164762 | A1 | 10/2016 |
| WO | WO-2016/201377 | A1 | 12/2016 |
| WO | WO-2017/015457 | A1 | 1/2017 |
| WO | WO-2017/015463 | A2 | 1/2017 |
| WO | WO-2017/019935 | A1 | 2/2017 |
| WO | WO-2017/020026 | A1 | 2/2017 |
| WO | WO-2017/031232 | A1 | 2/2017 |
| WO | WO-2017/031241 | A1 | 2/2017 |
| WO | WO-2017/049245 | A2 | 3/2017 |
| WO | WO-2017/062513 | A1 | 4/2017 |
| WO | WO-2017/066789 | A1 | 4/2017 |
| WO | WO-2017/070601 | A1 | 4/2017 |
| WO | WO-2017/070613 | A1 | 4/2017 |
| WO | WO-2017/070616 | A2 | 4/2017 |
| WO | WO-2017/070618 | A1 | 4/2017 |
| WO | WO-2017/070620 | A2 | 4/2017 |
| WO | WO-2017/070622 | A1 | 4/2017 |
| WO | WO-2017/070623 | A1 | 4/2017 |
| WO | WO-2017/070624 | A1 | 4/2017 |
| WO | WO-2017/070626 | A2 | 4/2017 |
| WO | WO-2017/099823 | A1 | 6/2017 |
| WO | WO-2017/201333 | A1 | 11/2017 |
| WO | WO-2017/201340 | A2 | 11/2017 |
| WO | WO-2017/201342 | A1 | 11/2017 |
| WO | WO-2017/201347 | A1 | 11/2017 |
| WO | WO-2018/053209 | A1 | 3/2018 |
| WO | WO-2018/075980 | A1 | 4/2018 |
| WO | WO-2018/081459 | A1 | 5/2018 |
| WO | WO-2018/081462 | A1 | 5/2018 |
| WO | WO-2018/089540 | | 5/2018 |
| WO | WO-2018/089851 | A2 | 5/2018 |
| WO | WO-2018/107088 | A2 | 6/2018 |
| WO | WO-2018/111967 | A1 | 6/2018 |
| WO | WO-2018/144082 | A1 | 8/2018 |
| WO | WO-2018/144778 | A1 | 8/2018 |
| WO | WO-2018/151816 | A1 | 8/2018 |
| WO | WO-2018/170245 | A1 | 9/2018 |
| WO | WO-2018/170256 | A1 | 9/2018 |
| WO | WO-2018/170260 | A1 | 9/2018 |
| WO | WO-2018/170270 | A1 | 9/2018 |
| WO | WO-2018/170347 | A1 | 9/2018 |
| WO | WO-2018/175783 | A1 | 9/2018 |
| WO | WO-2018/187590 | A1 | 10/2018 |
| WO | WO-2018/200737 | A1 | 11/2018 |
| WO | WO-2018/232355 | A1 | 12/2018 |
| WO | WO-2019/036670 | A2 | 2/2019 |
| WO | WO-2019/036682 | A1 | 2/2019 |
| WO | WO-2019/036683 | A1 | 2/2019 |
| WO | WO-2019/036685 | A1 | 2/2019 |
| WO | WO-2019/226650 | | 11/2019 |
| WO | WO-2021/159040 | | 8/2021 |
| WO | WO-2021/159130 | A2 | 8/2021 |
| WO | WO-2021/211343 | A1 | 10/2021 |
| WO | WO-2022/101486 | A1 | 5/2022 |

OTHER PUBLICATIONS

Abu Lila et al., Application of polyglycerol coating to plasmid DNA lipoplex for the evasion of the accelerated blood clearance phenomenon in nucleic acid delivery. J Pharm Sci. Feb. 2014; 103(2):557-66. doi: 10.1002/ips.23823. Epub Dec. 17, 2013.

Abu Lila et al., Use of polyglycerol (PG), instead of polyethylene glycol (PEG), prevents induction of the accelerated blood clearance phenomenon against long-circulating liposomes upon repeated administration. Int J Pharm. Nov. I, 2013;456(1):235-42. doi: 10.1016/j.ijpharm.2013.07..059..Epub Aug. 5, 2013.

Akinc etal., Targeted Delivery of RNAi Therapeutics With Endogenous and Exogenous Ligand-Based Mechanisms, Mol Ther. 2009 17:872-879.

Anderson, D.M et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.

Andreakos et al., Amphoteric liposomes enable systemic antigen-presenting cell-directed delivery of CD40 antisense and are therapeutically effective in experimental arthritis. Arthritis Rheum. Apr. 2009; 60(4): 994-1005. doi: 10.1002/art.24434.

Andries, O., et al, Comparison of the gene transfer efficiency of mRNA/GL67 and pDNA/GL67 complexes in respiratory cells. Mal Pharmaceutics. 2012; 9: 2136-2145.

Bag, J., Recovery of normal protein synthesis iu heat-shocked chicken myon1bes by liposome-mediated transfer of mRNAs. Can J. Biochem. Cell Biol. 1985; 63(3): 231-235.

(56) References Cited

OTHER PUBLICATIONS

Belliveau, N.M., et al., Microfluidic synthesis of highly potent limit-size lipid nanoparticles for in vivo delivery of siRNA. Mol Ther Nucleic Acids. Aug. 2012; I(8): e37.
Bettinger, T. et al., Peptide-mediated RNA delivery: a novel approach for enhanced transfection of primary and past-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion. J Infect Dis. Mar. 15. 2015:211(6):947-55. doi: 1O I093/infdis/iiu522, Epub Sep. 18. 2014.
Bolhassani et al, Improvement of Different Vaccine Delivery Systems for Cancer Therapy, Molecular Cancer, Biomed Central, London, GB, 2011 vol. 10, No. 3, pp. 1-20.
Chamberlain et al, Recurrent lymphomatous meningitis treated with intra-CSP rituximab and liposomal ara-C. J Neurooncol. Feb. 2009 91(3):271-7. doi: 10.1007/sl 1060-008-9707-1. Epub Sep. 27, 2008.
Chen, D., et al., Rapid discovery of potent siRNA-contai.ni11g lipid nanoparticles enabled by co11trolled microfluidic formulation. J Am Chem Soc. 2012; 134: 6948-6951.
Corazzelli et al., Biweekly rin1ximab, cyclophosphamide, vincristine, non-pegylated liposome-encapsulated dox:ombicin and prednisone (R-COMP-14) in elderly patients with poor-risk diffuse large B-cell lymphoma and moderate to high 'life threat' impact cardiopathy. Br J Haematol. Sep. 2011;154(5):579-89. doi: 10.IIII/i.1 365-2141. 2011.08786.x. Epub Jun. 28, 2011.
Cun et al., Preparation and characterization of poly(DL-lactide-co-glycolide) nanoparticles for siRNA delivery. International Journal of Pharmaceutics 390 (2010) 70-75.
Dahlman et al., In vivo endothelial siRNA delivery using polymeric nanoparticles with low molecular weight, Nature Nanotechnology, 2014, No. vol.#, pp. 1-8.
Delehanty Peptides for Specific Intracellular Delivery and Targeti11g of Nanoparticles: Implications for Developing Nanoparticle-Mediated Drug Delivery, Future Science, Therapeutic Delivery, 2010 vol. 1, No. 3 pp. 411-433.
Delmas et al., Encapsulation and Release Behavior from Lipid Nanopa1ticles: Model Study with Nile RedFluorophore. J. Colloid Sci. Biotechnol. 2012; 1:16-25.
Felgner, Cationic lipid/polynucleotide condensates for in vitro and in vivo polynucleotide delivery—the cytofectins. J. of Liposome Research. 1993; 3(1): 3-16.
Felgner, et al., Lipofection: a highly efficient, lipid-mediated DNA-transfection procedure. Proc Natl Acad Sci USA. Nov. 1987;84(21):7413-7.
Felgner, Particulate systems and polymers for in vitro and in vivo delivery of polynucleotides. Adv, Drug Delivery Rev. 1990; 5(3): 163-187.
Fleeton et al., Self-replicative RNA vaccines elicit protection against influenza a virus, respiratory syncytial virus, and a tickborne encephalitis vims. J Infect Dis. May 1, 2001;183(9):1395-8. Epub. Mar. 30, 2001.
Geall et al., Nonviral delivery of self-amplifying RNA vaccines Proc Natl Acad Sci US A. Sep. 4, 2012;09(36): 14604-9. doi: 10. 1073/ona.s.1209367109 Epub Aug. 20, 2012.
Hashimoto et al., Relationship between the concentration of anti-polyethylene glycol (PEG) immunoglobulin M (IgM) and the intensity of the accelerated blood clearance (ABC) phenomenon against PEGylated liposomes in mice. Biol Pharm Bull2015;38(3): 417-24. doi: 101248/bpb.bl4-00653.
He el al., Synthesis and Separation of Diastereomers of Ribonucleoside 5'-(alpha-P-Borano) triphosphates. J Org Chem. Aug. 21, 1998; 63( 17):5769-5773.
Hecker et al., Non-Viral DNA and mRNA Gene Delivery to the CNS Pre-Operatively for Neuroprotection and Following Neurotrauma. Molecular Therapy. 2004;9. S258-S258.
Juliano et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kallen et al. A development that may evolve into a revolution in medicine: mRNA as the basis for novel, nucleotide-based vaccines and drugs. Ther Adv Vaccines. Jan. 2014;2(1): 10-31. doi 10.1177/2051013613508729.
Kallen et al., A novel, disruptive vaccination technology: self-adjuvanted RNActive(RTM) vaccines. Hum Vaccin Immunother. Oct. 2013;9(10):2263-76. doi: 10.4161/hv.25181. Epub Jun. 4, 2013. Review.
Kanapathipillai et al., Nanoparticle targeting of anti-cancer drugs that alter intracellular signaling or influence the tumor microenvironment, Adv. Drug Deliv. Rev. (2014), DD. 1-12.
Kariko et al., Generating the optimal mRNA for therapy: HPLC purification eliminates immune activation and improves translation of nucleoside-modified, protein-encoding mRNA. Nucleic Acids Res. vol. 39, No. 21, Nov. 1, 2011, PD. el42-el4 I, XP002696 I90.
Kariko et al., In vivo protein expression from mRNA delivered into adult rat brain. J_of Neuroscience Methods. Jan. 2001; 105(1): 77-86.
Kariko et al., Incorporation of pseudouridine into mRNA yields superior nonimmunogenic vector with increased trru1slational capacity and biological stability, Molecular Therapy, Nature Publishing Group GB vol. 16 No. 11 Nov. 1, 2008 (Nov. I. 2008). pp. 1833-1840.
Kariko et al., Phosphate-enhanced transfection of cationic lipid-complexed mRNA and plasmid DNA. Biochim Biophys Acta. Mar. 2, 1998; 1369(2):320-34.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Keown et al., Methods for Introducing DNA into Mammalian Cells. Methods in Enzymology, 1990, 185:527-37.
Kirpotin et al., Antibody targeting of long-circulating lipidic nanoparticles does not increase tumor localization but does increase internalization in animal models. Cancer Res. 2006; 66: 6732-67 40.
Kozielski et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8, 'No. 4', pp. 3232-3241.
Krause et al., Prevention of the hemodynamic effects of iopromide-carrying liposomes in rats and pigs. Invest Radio!. Aug. 2000; 35(8):493-503.
Lai et al., Mucus-penetrating nanoparticles for drug and gene delivery to mucosal tissues. Adv Dmg DelivRev. Feb. 27, 2009; 61(2): 158-171.
Lai et al., Rapid transport of large polymeric nanoparticles in fresh undiluted human mucus. PNAS. Jan. 30, 2007; 104(5): 1482-1487.
Lee et al., Lipid Nanoparticle siRNA Systems for Silencing the Androgen Receptor in Human Prostate Cancer in Vivo, International Journal of Cancer, 2012, vol. 131, pp. 781-790.
Lehto el al., Cell-penetrating peptides for the delivery of nucleic acids. Expert Opin. Drug Deliv. Jul. 2012; 9(7): 823-836.
Lewis, Dynamic Polyconjugates (DPC) Technology: An elegant solution to the siRNA delively problem. Arrowhead Research Corp (Nasdaq: ARWR). Nov. 2011.
Li et al., Overcoming obstacles to develop effective and safe siRNA therapeutics. Expert Opin Biol Ther. Mav 2009; 9(5): 609-19.
Li et al., Preparation and gene delivery of alkaline amino acids-based cationic liposomes. Arch Pharm Res. Jul. 2008;31(7):924-31. Epub Aug. 14, 2008.
Lopez-Berestein et al., Treatment of systemic fungal infections with liposomal amphotericin B. Arch Intern Med. Nov. 1989;149(11):2533-6.
Maclachlan, Lipid Nanoparticle-mediated delivery of messenger RNA Presentation. 1st International mRNA Health Conference. Tubingen, Germa1ly. Oct. 24, 2013. http://files.shareholder.com/downloads/ ABEA-50QJTB/262824 I 206x0x699789/47-543dl2-db34- 4e6e-88a9-f3ae5d97bld2/MacLachlan mRNA Conf 2013 .pdf. Last accessed Dec. 22, 2016.

(56) References Cited

OTHER PUBLICATIONS

Madden et al., Systemic delivery of mRNA therapeutics using lipid nanoparticles (LNP): improved potency for novel LNP and influence of route of administration on protein expression. 2nd International mRNA Health Conference. Nov. 12, 2014.https://acuitastx.com/wpcontent/uploads/2015/0l/Poster-Second-International- mRNA-Health-Conference.pdf. 1 page.
Magee et al, Marked stimulation of lymphocyte-mediated attack on tumor cells by target-directed liposomes containing immune RNA, Cancer Res., 1978, 38(4):1173-6.
Malone et al. Cationic liposome-mediated RNA transfection Proc Natl Acad Sci USA. Aug. 1989;86 (16):6077-81.
Marina et al., Dose escalation and pharmacokinetics of pegylated liposomal doxombicin (Doxil) in children with solid tumors: a pediatric oncology group study. Clin Cancer Res. Feb. 2002;8(2):413-8.
Martinon et al., Induction of virus-specific cytotoxic T lymphocytes in vivo by liposome-entrapped mRNA. EurJ ImmunoL Jul. 1993;23(7): 1719-22.
Maurer et al., Spontaneous entrapment of poly nucleotides upon electrostatic interaction with ethanol-destabilized cationic liposomes. Biophys J. May 2001; 80(5): 2310-2326.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mishra et al., Improved leishmanicidal effect of phosphorothioate antisense oligonucleotides by LDL-mediated delivery Biochim Biophys Acta. Nov. 7, 1995; 1264(2):229-37.
Mockey et al, mRNA-based cancer vaccine: prevention ofBI6 melanoma progression and metastasis by systemic injection of MARTI mRNA histidylated lipopolyplexes, Cancer Gene Therapy, 2007, 14, OD. 802-814.
Nair et al., Soluble proteins delivered to dendritic cells via pH-sensitive liposomes induce primary cytotoxic T lymohocyte responses in vitro. J Exp Med. Feb. 1, 1992;175(2):609-12.
Oja et al., Doxorubicin entrapped within liposome-associated antigens results in a selective inhibition of the antibody response to the linked antigen. Biochim Biophys Acta. Sep. 29, 2000;1468(1-2):31-40.
Oster et al., Comparative study of DNA encapsulation into PLGA microparticles using modified double emulsion methods and spray drying techniques. Journal of Microencapsulation, May 2005; 22(3): 235-244.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.
PCT/US2016/000129, dated Dec. 11, 2017, International Search Report and Written Opinion.
Pollard et al., Type I IFN counteracts the induction of antigen-specific immune responses by lipid-based delivery of mRNA vaccines. Mol Ther. Jan. 2013; 21 (1): 251-259.
Popov et al., Multivalent rituximab lipid nanoparticles as improved lymphoma therapies: indirect mechanisms of action and in vivo activity nNanomedicine (Land). Nov. 2011;6(9): 1575-91. doi: 10.2217/ nnm.11.50 Epub Oct. 20, 2011.
Pulford et al., Liposome-siRNA-peptide complexes cross the blood-brain barrier and significantly decrease PrP on neuronal cells and PrP in infected cell cultures. PLoS One. 2010; 5(6): e 11085.
Saito et al., Distribution of liposomes into brain and rat brain tumor models by convection-enhanced delivery monitored with magnetic resonance imaging Cancer Res. Apr. 2004; 64: 2572-2579.
Sakuma et al., Mucoadhesion of polystyrene nanoparticles having surface hydrophilic polymeric chains in the gastrointestinal tract. Int J Pharm. Jan. 25, 1999) 77(2):161-72.
Schott et al., Viral and non-viral approaches for transient delivery of mRNA and proteins. Current Gene Ther. 2011; 11 (5): 382-398.
Shea et al., Synthesis, hybridization properties and antiviral activity of lipid-oligodeoxynucleotide conjugates. Nucleic Acids ResJul. 11, 1990;18 (13):3777-83.
Shimizu et al., Transport of PEGylated liposomes from the splenic marginal zone to the follicle in the induction phase of the accelerated blood clearance phenomenon. Immunobiology. May 2013;218(5):725-32. doi: 10.1016/iimbio.2012.08.274. Epub Aug. 23, 2-012.
Strobel et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Taguchi et al., Effect of Repeated Injections of Adenosine Diphosphate-Encapsulated Liposomes Coated with a Fibrinogenganuna-Chain Dodecapeptide Developed as a Synthetic Platelet Substitute on Accelerated Blood Clearance in a Healthy and an Anticancer Dmg-Induced Thrombocytopenia Rat Model. J Pharm Sci. Sep. 2015;104(9):3084-91. doi: 10.1002/jps.24418. Epub Mar. 9, 2015.
Taguchi et al., Hemoglobin vesicles, polyethylene glycol (PEG)ylated liposomes developed as a red blood cell substin1te, do not induce the accelerated blood clearance phenomenon in mice. Drug Metab DiSDOs. Nov. 2009;37(11):2197-203. doi:101124/dmd 109 028852. Epub Aug. 13, 2009.
Tavernier et al., mRNA as gene therapeutic: How to control protein expression. I of Controlled Release. Mar. 2011; 150(3): 238-247.
Thess et al., Sequence-engineered mRNA Without Chemical Nucleoside Modifications Enables an Effective Protein Therapy in Large Animals. Mol Ther. Sep. 2015:23(9):1456-64. doi: 10.1038/mt.2015.103. Epub Jun. 8, 2015.
Torchilin el al., Multifunctional and Stimuli-Sensitive Pharmaceutical Nanocarriers, Eur J. Pharm Biopharm, 2009, vol. 71, No. 3, pp. 431-444.
Tracy, "Progress in the Development of LNP Delivery for siRNA Advancing LNPs to the Clinic" International Liposome Research Days Meeting, Vancouver, Canada. Aug. 2010, pp. 1-52.
Treat et al., Liposomes in the Therapy of Infectious Disease and Cancer, Lopez-Berestein and Fidler (eds.), Liss, New York. 1989. 353-65.
Uzgun et al, PEGylation improves nanoparticle formation and transfection efficiency of messenger RNA. Pharm Res. Sep. 2011; 28(9); 2223-2232.
Wan et al., Lipid nanoparticle delivery systems for siRNA-based therapeutics. Drug Deliv Transl Res. Feb. 2014; 4(1):74-83. doi: 10.1007/s13346-013-0161-z.
Wang et al., Systemic delivery of modified mRNA encoding herpes simplex virus 1 thymidine kinase for targeted cancer gene therapy. Mol Ther Feb. 2013;21(2); 358-67. doi: 10.1038/mt.2012 250. Epub Dec. 11, 2012.
Weilhammer et al., The use of nanolipoprotein particles to enhance the immunostimulatory properties of innate immune agonists against lethal influenza challenge. Biomaterials. Dec. 2013; 34(38):10305-18. doi: 10.1016/j_biomaterials. 2013.09 038. Epub Sep. 27, 2013.
Yamamoto et al., Current prospects for mRNA gene delivery, European Journal of Pharmaceutics and Biopharmaceutics 7 I (2009) 484-489.
Zhigaltsev et al., Bottom-Up design and synthesis of limit size lipid nanoparticle systems with aqueous and triglyceride cores using millisecond microfluidic mixing. Langmuir. Feb. 21, 2012; 28(7):3633-3640.
Zimmermann et al., Electrolyte- and pH-stabilities of aqueous solid lipid nanoparticle (SLN.TM.). Dispersions in artificial gastrointestinal media. Eur J Pharm Biopharm. Sep. 2001; 52(2):203-10.
Zohra et al., Drastic effect of nanoapatite particles Oil liposome-media led mRNA delivery to mammalian cells. Analytical Biochem. Oct. 2005; 345(1):164-166.
Zohra et al., Effective delivery with enhanced translational activity synergistically accelerates mRNA-based transfection. Biochem Biophys Res Comm. Jun. 2007; 358(1): 373-378.
U.S. Appl. No. 18/205,229, filed Jun. 2, 2023.
Azarani, A. et al., "RNA analysis by ion-pair reversed-phase high performance liquid chromatography," Nucleic Acids Res 29, E7 (2001).
Baden et al., "Efficacy and safety of the mRNA-1273 SARS-CoV-2 vaccine," N. Engl. J. Med 384, 403-416 (2021).

(56) References Cited

OTHER PUBLICATIONS

Baumeister et al., "Continuous flow synthesis of amine oxides by oxidation of tertiary amines," React. Chem. Eng. 4, 1270-1276 (2019).
Crommelin et al., "Addressing the cold reality of mRNA vaccine stability," J. Pharm. Sci. 110, 997-1001 (2021).
Cullis et al., "Lipid nanoparticle systems for enabling gene therapies," Mol. Ther. 25, 1467-1475 (2017).
Fenton et al., "Bioinspired alkenyl amino alcohol ionizable lipid materials for highly potent in vivo mRNA delivery," Adv. Mater. 28, 2939-2943 (2016).
Garaycoechea et al., "Alcohol and endogenous aldehydes damage chromosomes and mutate stem cells," Nature 553, 171-177 (2018).
Gilleron et al., "Image-based analysis of lipid nanoparticle-mediated siRNA delivery, intracellular trafficking and endosomal escape," Nat. Biotechnol. 31, 638-646 (2013).
Gomez-Aguado et al., "Nanomedicines to deliver mRNA: state of the art and future perspectives," Nanomaterials 10, 364 (2020).
Guevara et al., "Advances in lipid nanoparticles for mRNA-based cancer immunotherapy," Front Chem. 8, 589959 (2020).
Heyes et al., "Cationic lipid saturation influences intracellular delivery of encapsulated nucleic acids," J. Control Release 107, 276-287 (2005).
Houseley et al., "The many pathways of RNA degradation," Cell 136, 763-776 (2009).
Huang et al., "Enhanced delivery of siRNA to retinal ganglion cells by intravitreal lipid nanoparticles of positive charge," Mol. Pharm. 18, 377-385 (2021).
International Search Report and Written Opinion for PCT/US2022/016902 mailed Jul. 25, 2022. (12 pages).
Kanavarioti, A. "HPLC methods for purity evaluation of man-made singlestranded RNAs," Sci. Rep. 9, 1019 (2019).
Khurana et al., "Role of nanotechnology behind the success of mRNA vaccines for COVID-19," Nano Today 38, 101142 (2021).
Kim et al., "Engineered ionizable lipid nanoparticles for targeted delivery of RNA therapeutics into different types of cells in the liver," Sci. Adv. 7, eabf4398 (2021).
Kok et al., "N-demethylation of N-methyl alkaloids with ferrocene," Bioorg. Med Chem. Lett. 20, 4499-4502 (2010).
Kowalski et al., "Delivering the messenger: advances in technologies for therapeutic mRNA delivery," Mol. Ther. 27, 710-728 (2019).
Levin et al., "Combining ion pairing agents for enhanced analysis of oligonucleotide therapeutics by reversed phase-ion pairing ultra performance liquid chromatography (UPLC)," J. Chromatogr. B Anal. Technol. Biomed. Life Sci. 879, 1587-1595 (2011).
Liu, S et al., "Membrane-destabilizing ionizable phospholipids for organselective mRNA delivery and CRISPR-Cas gene editing," Nat. Mater. 20, 701-710 (2021).
Nelson et al. "Impact of mRNA chemistry and manufacturing process on innate immune activation," Sci. Adv. 6, eaaz6893 (2020).
Packer et al., "A novel mechanism for the loss of mRNA activity in lipid nanoparticle delivery systems," Nature Comm. 12:6777 (Nov. 2021).
Pogocki et al. "Chemical stability of nucleic acid-derived drugs," J. Pharm. Sci. 89, 443-456 (2000).
Polack et al., "Safety and efficacy of the BNT162b2 mRNA Covid-19 vaccine," N. Engl. J. Med 383, 2603-2615 (2020).
Prieve et al., "Targeted mRNA therapy for ornithine transcarbamylase deficiency," Mol. Ther. 26, 801-813 (2018).
Reichmuth et al., "mRNA vaccine delivery using lipid nanoparticles," Ther. Deliv. 7, 319-334 (2016).
Sabnis et al., "A novel amino lipid series for mRNA delivery: improved endosomal escape and sustained pharmacology and safety in non-human primates," Mol. Ther. 26, 1509-1519 (2018).
Takeshita et al., "In vitro DNA/RNA adductomics to confirm DNA damage caused by benzo[a]pyrene in the Hep G2 cell line," Front Chem. 7, 491 (2019).
Wang et al., "AN1616: SEC-MALS Method for Characterizing mRNA Biophysical Attributes," WYATT Technology, https://wyattfiles.s3-US-west-2.amazonaws.com/literature/app-notes/sec-malsbiopolymers/AN1616-SEC-MALS-method-for-characterizing-mRNA.pdf (Date accessed: May 28, 2021).
Wu et al., "Nanoparticle-mediated cytoplasmic delivery of messenger RNA vaccines: challenges and future perspectives," Pharm. Res. 38, 473-478 (2021).
Yang et al., "Factors affecting DNA damage caused by lipid hydroperoxides and aldehydes," Free Radic. Biol. Med 20, 225-236 (1996).
Zhang al., "Helper lipid structure influences protein adsorption and delivery of lipid nanoparticles to spleen and liver," Biomater. Sci. 9, 1449-1463 (2021).
Rutkowski, Krzysztof et al.; "Adverse reactions to COVID-19 vaccines: A practical approach"; Clin. Exp. Allergy, vol. 51; May 2021; pp. 770-777.
Lian, et al., Trends and developments in liposome drug delivery systems. J Pharm Sci. Jun. 2001;90(6):667-80.

* cited by examiner

Cytidine
$C_9H_{13}N_3O_5$
MW: 243.0855
Straight chain aldehyde
R = $C_9H_{20}$
$C_{17}H_{32}O_3$
MW: 284.2351
$C_{26}H_{43}N_3O_8$
MW: 525.3050 a b

LIPID NANOPARTICLE COMPOSITIONS AND METHODS OF FORMULATING THE SAME

CROSS-REFERENCE TO RELATED APPLICATIONS

This application is the U.S. national stage of International Application PCT/US2022/016902, filed Feb. 18, 2022, and claims priority under 35 U.S.C. § 119 (e) to U.S. Provisional Applications 63/151,523, filed Feb. 19, 2021; 63/182,428, filed Apr. 30, 2021, and 63/191,655, filed May 21, 2021.

TECHNICAL FIELD

Provided are compositions and methods of formulating lipid nanoparticles encapsulating polynucleotides. More specifically, provided herein are methods of reducing adduct formation in lipid compositions comprising a polynucleotide, such as mRNA, and an ionizable lipid; also disclosed are lipid-polynucleotide compositions having a reduced adduct content; isolated adducts, and methods of detecting the adducts disclosed herein.

BACKGROUND

The degradability of mRNA makes it an appealing target from a safety and pharmacokinetic perspective; however, this same instability is a significant hurdle both in preserving potency in storage and effective delivery through various in vivo routes of administration. mRNA reactivity can lead to loss in potency through the formation of lipid-mRNA adducts. There is a need to control the unwanted reactions, e.g., on the level of the raw material, formulation process, and final drug product, to control such adduct formation.

SUMMARY

In some aspects, the disclosure provides a lipid nanoparticle (LNP) composition comprising a polynucleotide, such as mRNA, and an ionizable lipid, such as an ionizable lipid comprising a tertiary amine group that can decompose into a secondary amine and/or a reactive aldehyde species capable of interacting with the polynucleotide to form an ionizable lipid-polynucleotide adduct impurity, wherein the composition comprises less than about 10% of an ionizable lipid-polynucleotide adduct impurity relative to the amount of the polynucleotide as measured by HPLC. Thus, a composition provided herein may comprise a lipid nanoparticle comprising a polynucleotide and an ionizable lipid comprising an amine group, wherein less than about 10%, less than about 5%, or less than about 1% of the polynucleotide is in the form of an ionizable lipid-polynucleotide adduct impurity. In some embodiments, the ionizable lipid of the composition forms a secondary amine and/or a reactive aldehyde species when decomposed. In some embodiments, the ionizable lipid-polynucleotide adduct impurity comprises an aldehyde-polynucleotide adduct impurity. In some embodiments, an amount of lipid aldehydes in the composition is less than about 50 ppm.

In some embodiments, the ionizable lipid is selected from:

(Compound II)

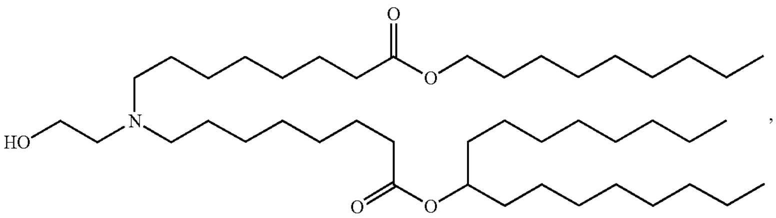

, (Compound III)

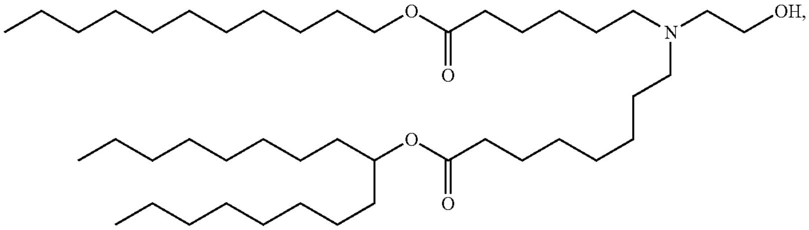

(Compound VI)

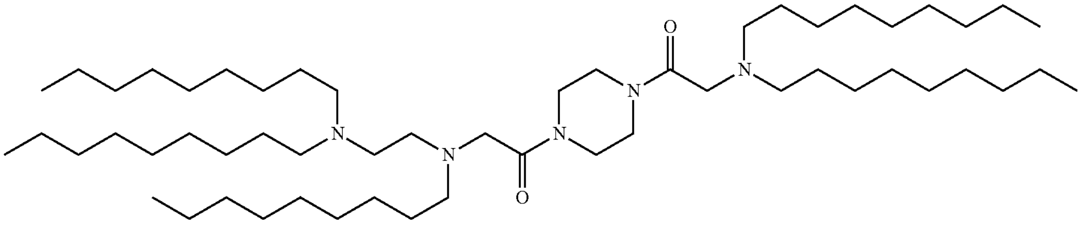

,

-continued (Compound A1)

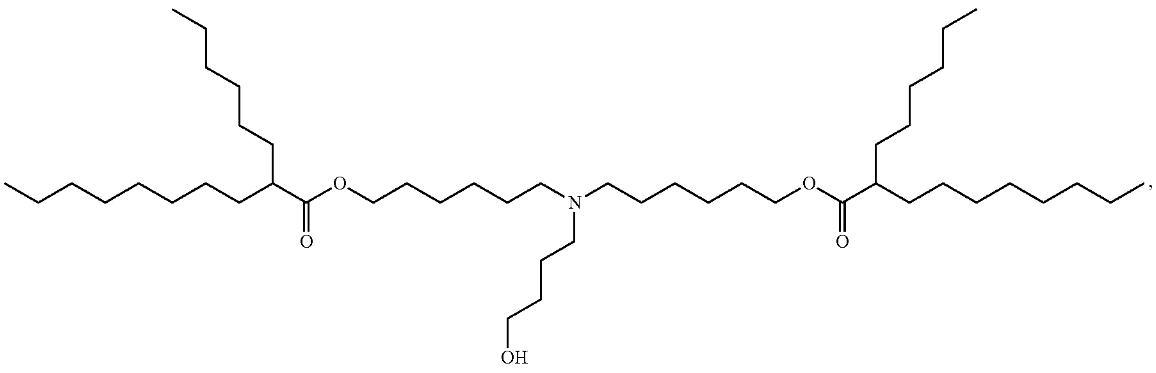

, and (Compound A2)

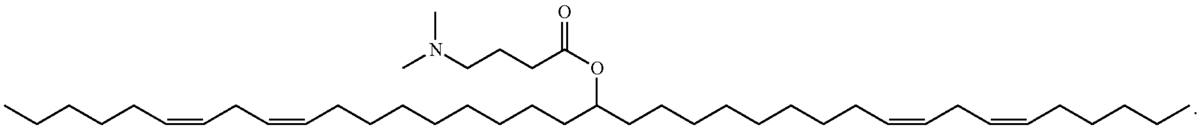

.

In some embodiments, an amount of the ionizable lipid-polynucleotide adduct impurity in the composition increases at an average rate of less than about 2% per day when stored at a temperature at about 25° C. or below, or increases at an average rate of less than about 0.5% per day when stored at a temperature at about 5° C. or below, or increases at an average rate of less than about 0.5% per day when stored at a refrigerated temperature, optionally wherein the refrigerated temperature is about 5° C.

In accordance with any of the foregoing embodiments, the lipid nanoparticle may further comprise a phospholipid, a cholesterol, and a PEG-lipid.

In accordance with any of the foregoing embodiments, the composition may further comprise a buffer, such as sodium phosphate, sodium citrate, sodium succinate, histidine, histidine-HCl, sodium malate, sodium carbonate, or TRIS (tris(hydroxymethyl)aminomethane).

In accordance with any of the foregoing embodiments, the composition may further comprise a cryoprotectant, such as mannitol, sucrose, trehalose, lactose, glycerol, dextrose, and combinations thereof.

In accordance with any of the foregoing embodiments, the composition may further comprise a free reducing agent, such as may be selected from potassium metabisulfite, sodium thioglycolate, TCEP, sodium thiosulfate, N-acetyl cysteine, glutathione, DTT, cystamine, DTE, DDT, homocysteine, and lipoic acid.

In accordance with any of the foregoing embodiments, the amount of transition metals, such as Fe, in the composition is less than about 50 ppm. In accordance with any of the foregoing embodiments, the amount of N-oxide compounds in the composition is less than about 50 ppm. In accordance with any of the foregoing embodiments, the amount of lipid aldehydes in the composition is less than about 50 ppm.

In some aspects, the disclosure provides a method for preparing a composition comprising an ionizable lipid and a polynucleotide, including a lipid nanoparticle composition, comprising: combining the ionizable lipid and the polynucleotide to provide the composition, and then treating the composition to reduce adduct formation.

In some aspects, the disclosure provides a method for inhibiting formation of one or both of N-oxides and aldehydes in a composition comprising an ionizable lipid and a polynucleotide, including a lipid nanoparticle composition, wherein the ionizable lipid comprises a tertiary amine group and can decompose into a secondary amine and/or a reactive aldehyde species capable of interacting with the polynucleotide to form an ionizable lipid-polynucleotide adduct impurity, wherein the method comprises treating the composition to reduce formation of ionizable lipid-polynucleotide adduct, wherein less than about 10% of the polynucleotide is in the form of ionizable lipid-polynucleotide adduct impurity.

In accordance with any of the foregoing embodiments, the treating may comprise one or more of treating the composition with a reducing agent; treating the composition with a chelating agent; adjusting the pH of the composition; adjusting the temperature of the composition; and adjusting the buffer in the composition.

In some aspects, the disclosure provides a method for preparing a composition comprising an ionizable lipid and a polynucleotide, including a lipid nanoparticle composition, the method comprising one or more of:

(a) treating the ionizable lipid with a reductive treatment agent;
(b) treating the ionizable lipid with a reducing agent;
(c) treating the ionizable lipid with a chelating agent;
(d) treating the polynucleotide with a reducing agent; and
(e) treating the polynucleotide with a chelating agent;

and then combining the ionizable lipid with the polynucleotide.

Additionally or alternatively, the method may comprise performing one or more of the following steps before combining the ionizable lipid and the polynucleotide:

(a) treating the ionizable lipid with a scavenging agent;
(b) treating the ionizable lipid with a reductive treatment agent;
(c) treating the ionizable lipid with a reducing agent;
(d) treating the ionizable lipid with a chelating agent;
(e) treating the polynucleotide with a reducing agent; and
(f) treating the polynucleotide with a chelating agent.

Such methods may further comprise combining the ionizable lipid and the polynucleotide.

In some embodiments, a method for preparing a lipid nanoparticle composition comprising an ionizable lipid and a polynucleotide, comprises one or more, or any combination, of:

(a) treating the ionizable lipid with a scavenging agent;
(b) treating the ionizable lipid with a reductive treatment agent;
(c) treating the ionizable lipid with a reducing agent;
(d) treating the ionizable lipid with a chelating agent;
(e) treating the polynucleotide with a reducing agent; and
(f) treating the polynucleotide with a chelating agent;

and then combining the ionizable lipid with the polynucleotide.

In some aspects, the disclosure provides a method for preparing a lipid nanoparticle composition comprising a polynucleotide and an ionizable lipid, wherein the composition comprises a reduced amount of an ionizable lipid-polynucleotide adduct impurity as compared to a control composition, the method comprising combining a first preparation comprising the ionizable lipid and a second preparation comprising the polynucleotide, wherein one or both of the preparations has been treated with a reducing agent, a chelating agent, or a combination thereof, wherein in the control composition neither the first nor second preparation has been treated with a reducing agent or a chelating agent.

In accordance with any of the foregoing embodiments, the scavenging agent, reductive treatment agent, and/or reducing agent may be an agent that reacts with aldehyde, ketone, anhydride and/or diene compounds. In accordance with any of the foregoing embodiments, the scavenging agent may comprise one or more selected from (O-(2,3,4,5,6-Pentafluorobenzyl)hydroxylamine hydrochloride) (PFBHA), methoxy amine (e.g., methoxyamine hydrochloride), benzyloxyamine (e.g., benzyloxyamine hydrochloride), ethoxyamine (e.g., ethoxyamine hydrochloride), 4-[2-(aminooxy)ethyl]morpholine dihydrochloride, butoxyamine (e.g., tert-butoxyamine hydrochloride), 4-Dimethylaminopyridine (DMAP), 1,4-diazabicyclo[2.2.2]octane (DABCO), Triethylamine (TEA), Piperidine 4-carboxylate (BPPC), and combinations thereof. In accordance with any of the foregoing embodiments, the reductive treatment agent may comprise a boron compound (e.g., sodium borohydride and/or bis(pinacolato)diboron). In accordance with any of the foregoing embodiments, the chelating agent may comprise immobilized iminodiacetic acid. In accordance with any of the foregoing embodiments, the reducing agent may comprise an immobilized reducing agent, such as immobilized diphenylphosphine on silica (Si-DPP), immobilized thiol on agarose (Ag-Thiol), immobilized cysteine on silica (Si-Cysteine), immobilized thiol on silica (Si-Thiol), or a combination thereof. In accordance with any of the foregoing embodiments, the reducing agent may comprise a free reducing agent, such as potassium metabisulfite, sodium thioglycolate, tris(2-carboxyethyl)phosphine (TCEP), sodium thiosulfate, N-acetyl cysteine, glutathione, dithiothreitol (DTT), cystamine, dithioerythritol (DTE), dichlorodiphenyltrichloroethane (DDT), homocysteine, lipoic acid, or a combination thereof.

In accordance with any of the foregoing embodiments of compositions and methods, the pH may be, or adjusted to be, a pH of from about 7 to about 9.

In accordance with any of the foregoing embodiments of compositions and methods, a buffer may be, or adjusted to be, from about 20 mM to about 150 mM TRIS.

In accordance with any of the foregoing embodiments of compositions and methods, the temperature of the composition may be, or adjusted to be, 25° C. or less.

In accordance with any of the foregoing embodiments of methods, the method may inhibit the formation of adduct impurity or reduce the amount of adduct impurity as compared to a control composition. In accordance with any of the foregoing embodiments of methods, the method inhibit the formation of one or both of N-oxides and aldehydes in the composition.

In some aspects, provided herein is a lipid nanoparticle composition prepared by a method as described herein.

Also provided is an isolated ionizable lipid-polynucleotide adduct formed from a polynucleotide and an ionizable lipid comprising a tertiary amine group by a process comprising decomposition of the tertiary amine group of the ionizable lipid into a secondary amine or reactive aldehyde species, and interaction of the secondary amine or reactive aldehyde species with the polynucleotide.

Also provided is an isolated ionizable lipid-polynucleotide adduct formed from a polynucleotide and an ionizable lipid comprising a tertiary amine group, wherein the adduct is an adduct of an aldehyde of the ionizable lipid and the polynucleotide, an adduct of an alkyl halide of the ionizable lipid and the polynucleotide, an adduct of an anhydride of the ionizable lipid and the polynucleotide, or an adduct of an alkyl conjugated diene of the ionizable lipid and the polynucleotide.

Also provided is a method for detecting ionizable lipid-polynucleotide adduct in a composition comprising a polynucleotide and an ionizable lipid, wherein the ionizable lipid comprises a tertiary amine group that can decompose into a secondary amine or reactive aldehyde species capable of interacting with the polynucleotide to form ionizable lipid-polynucleotide adduct, the method comprising subjecting a sample of the composition to reverse-phase ion pair HPLC (RP IP HPLC), and, optionally, detecting a main peak characteristic of the polynucleotide and a late-eluting peak characteristic of the adduct.

BRIEF DESCRIPTION OF THE DRAWINGS

(FIG. 10A: percent positive; FIG. 10B: mean fluorescence intensity).

FIG. 12B is an expanded portion of the chromatogram in FIG. 12A.

FIG. 24A shows that RP-IP HPLC provides high resolution mRNA length-based separations to assess content and quality of mRNA products, as shown by the separation of 6 mRNAs of different lengths (659, 785, 914, 1106, 2498, and 2993 nucleotides) across retention times of 9.5-15 minutes. FIG. 24B shows the RP-IP analysis of pure mRNA (blue) yields a single main peak (retention time 15 min), with shorter degradation products and impurities eluting prior (retention time 10-14.5 min), while mRNA extracted from an mRNA-LNP formulation (black) yields an additional late-eluting peak (retention time 19-21 min); the UV spectrum at each peak apex obtained from an on-line 3D UV detector shows an identical profile with maximum absorbance of 260 nm (inset). FIG. 24C shows that CE analysis of the same extract mRNA as FIG. 24B shows a single peak, with no additional late-eluting species. FIG. 24D shows LP species in mRNA extracted from an mRNA-LNP formulation can be further resolved with adjusted gradient conditions and show a polydisperse fingerprint of species. FIG. 24E provides a graphical representation of data from experiments in which an mRNA-LNP formulation was held for three months at four different storage temperatures, and sampled at 1, 2, and 3 months for analysis by RP-IP; each data point is a single incubation condition run in a single RP-IP assay (40° C.: (▼); 25° C.: (♦); 5° C.: (■); –20° C.: (●)).

FIG. 25A shows a RP-IP chromatogram of mRNA extracted from the mRNA-LNP (black) (middle curve) overlaid with RP-IP re-analysis of isolated MP (blue) (top curve of first peak, bottom curve of second peak) and LP (red) (bottom curve of first peak; top curve of second peak), showing preserved retention time of each isolated region. FIG. 25B shows the CE electropherogram of mRNA extracted from the mRNA-LNP (black) (top curve) overlaid with electropherograms of the isolate MP (blue) (middle curve) and LP (red) (bottom curve), showing no different in migration time. FIG. 25C shows the SEC chromatograms of mRNA extracted from the mRNA-LNP (black) (bottom curve) overlaid with the SEC chromatograms of isolated MP (blue) (middle curve) and LP (red) (top curve), showing no presence of aggregation in either fraction.

FIG. 26A shows that isolated MP and LP were subjected to enzymatic degradation to single nucleosides and analyzed by LC/MS/MS; extracted ion chromatograms (EIC) of selected m/z corresponding to various unmodified nucleosides, lipid-modified nucleosides, and carry-over lipid in LP (red) and MP mRNA (blue) fractions are overlaid. The selected m/z for EICs include unmodified nucleosides (cytidine [C; 2.3 min], N1-methylpseudouridine (N1-MeΨ; 3 mini, adenosine [A; 5 min], guanosine [G; 6 min], lipid (11.9 min), and several lipid-modified nucleosides (9.5 and 11 min) observed in LP mRNA fractions. FIG. 26B shows the precursor ion at m/z 526.30 is isolated and subjected to collision-induced dissociation. Based on fragmentation pattern, the original nucleoside was determined to be cytidine. The fragment ion of in/z 112.05 corresponds to the exact mass of protonated cytosine (nucleobase). The characteristic neutral mass loss of 132 Da corresponds to the monoisotopic residue mass of ribose. MS/MS fragmentation pattern of lipid modified cytidine is provided as an example, but similar characteristic neutral mass losses (132.05 Da) and their corresponding base fragments were observed for other lipid-modified nucleosides as well.

FIG. 27A provides a lipid component deconvolution that shows that combinations including ionizable lipid resulted in significant adduct formation with mRNA by RP-IP. FIG. 27B shows that RP-IP adduct profiles of mRNA extracted from a binary system (black) (bottom curve) and mRNA-LNP (blue) (top curve) with the corresponding ionizable lipid show the same qualitative peak profile. FIG. 27C shows that seven different ionizable lipids were prepared in binaries with mRNA, yielding a variety of peak profiles and abundances of adduct species in the overlaid RP-IP chromatograms. FIG. 27D shows that adduct formation in a binary reaction with a highly reactive lipid was evaluated by RP-IP at 1 day (black) (top curve in first peak of inset), 2 days (blue) (middle curve in first peak of inset), and 7 days (red) (bottom curve in first peak of inset). The discrete peak at 1 day likely corresponds to a single modification, and the broad peak at 7 days likely corresponds to the accumulation of multiple modifications per mRNA molecule. FIG. 27E shows that adduct formation in binary reactions was evaluated with mRNA molecules of different lengths by RP-IP at equivalent mRNA masses. An increase in LP with length is consistent with a constant rate of modification on the single nucleotide level. FIG. 27F shows that RP-IP chromatographs of 659 (red) (first peak; bottom curve of first peak of inset), 1106 (black) (second peak; middle curve of first peak of inset), and 2498-nucleotide (blue) (third peak; top curve of first peak of inset) mRNAs show an increase and left shift of each adduct peak with increasing mRNA length. FIG. 27G shows adduct formation as a function of mRNA length was assessed by RP-IP for mRNA-LNP and corresponding binaries. A positive correlation was observed, with more adduct at longer mRNA lengths.

FIG. 28A shows tertiary-amine containing ionizable lipids currently used in RNA LNP products. FIG. 28B shows how N-oxide can form through oxidation of the tertiary amine and can further undergo acid/base-catalyzed hydrolysis at the amine to generate aldehydes and secondary amines. FIG. 28C shows that N-oxide acid hydrolysis products were detected by RP-UPLC-CAD MS/MS. A CAD chromatogram shows the N-oxide standard (brown) (top curve), acid-precipitated N-oxide standard with (pink) (second curve) and without (blue) (third curve) aminooxy-PEG label, and a buffer baseline (black) (bottom curve). Secondary amines from the hydrolysis of N-oxide eluted at 8.7, 10.3, and 25 minutes. Corresponding aminooxy-PEG-derivatized aldehydes eluted at 9.5 and 16 minutes, with the third likely in the column void. FIG. 28D shows that binary reactions of mRNA with pure N-oxide result in high LP. RP-IP analysis of mRNA extracted from the binary is shown at 3 hours (black) (bottom curve), 1 day (blue) (middle curve), and 3 days (red) (top curve). FIGS. 28E and 28F show that binary reactions spiked with pure 17-carbon aldehyde (28E) and pure 25-carbon aldehyde (28F) result in high levels of mRNA modification. RP-IP chromatograms of the extracted mRNA are shown with no spike (black) (bottom curve of inset), 0.5% (red) (middle curve of inset in FIG. 28E; initially top curve of inset in FIG. 28F), and 2% (green) (top curve of inset in FIG. 28E; initially middle curve of inset in FIG. 28F). FIGS. 28G and 28H show that binary reactions with the pure 17-carbon aldehyde were analyzed for single nucleoside modifications. Binaries were prepared with no spike (black) (bottom curve), 0.5% (red) (second-from-bottom curve), 1% (blue) (third-from-bottom curve), and 2% (green) (top curve) spike. mRNA was enzyme-digested following extraction and analyzed by LC-MS/MS. The m/z corresponding to aldehyde-cytidine adducts (m/z 526.3 and 540.3) increased with aldehyde spike level. N-Oxide degradation pathway and Lipid-mRNA adduct work demonstrated here is based on heptadecan-9-yl 8-((2-hydroxyethyl)(6-oxo-6-(undecyloxy)hexyl)amino)octanoate as a representative ionizable lipid system.

FIG. 29A shows that isolated MP and LP alongside control mRNA-LNP and an assay positive control were tested for in vitro protein expression in BJ fibroblasts after 48 hours. RNA was extracted from two hEPO-LNP formulations by isopropanol precipitation and purified by RP-IP to generate MP and LP prior to transfection. The assay control was a pure hEPO mRNA standard, the control sample was mRNA extracted from each formulation prior to RP-IP separation, and the MP and LP were isolated fractions. FIG. 29B shows that five different mRNA-LNP samples were incubated under stress conditions to generate varying levels of adduct and degradation. RNA was extracted from the mRNA-LNP by isopropanol precipitation and evaluated by RP-IP, CE, and in vitro protein expression as measured by mean fluorescence intensity. Relative expression as a percentage of the neat mRNA expression was plotted versus relative integrity as a percentage of the neat mRNA integrity by CE and RP-IP HPLC.

DETAILED DESCRIPTION

Figure 1A:
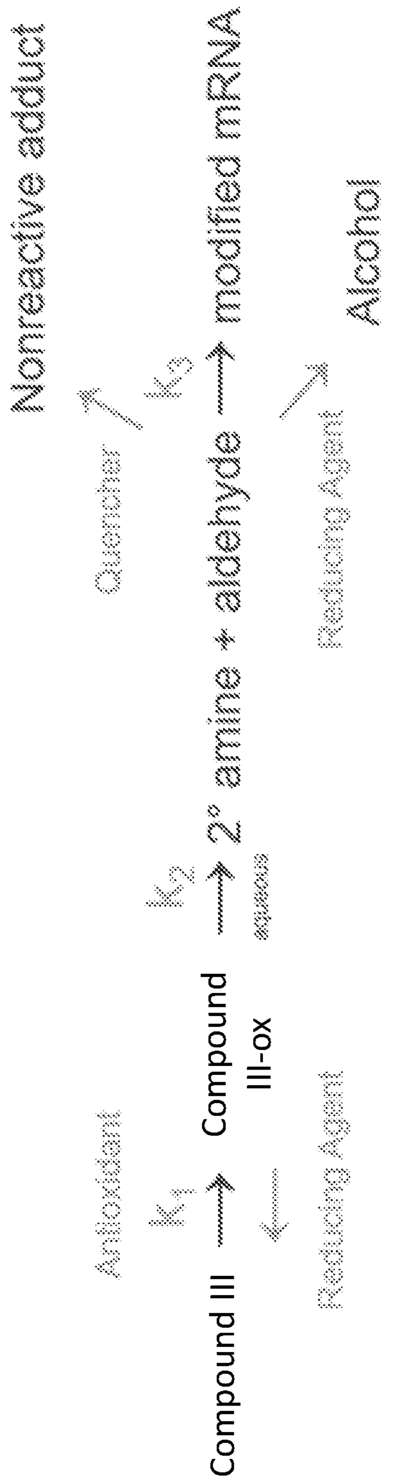
FIG. 1A is a schematic diagram of an exemplary oxidation and degradation pathway that leads to formation of the mRNA-aldehyde (branched or unbranched) adduct species.
Figure 1B:
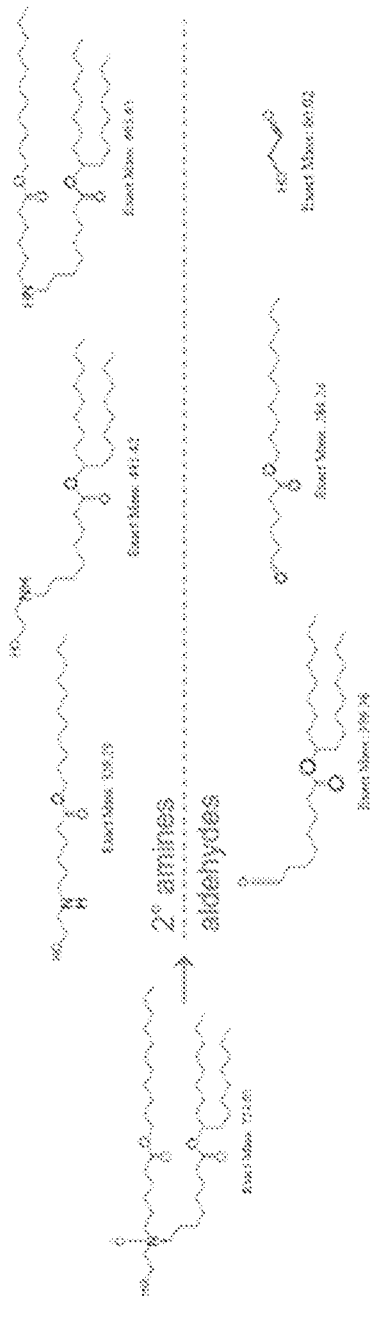
FIG. 1B depicts chemical structures of oxidized Compound III (herein referred to as "Compound III-N-oxide"), secondary amines, and aldehydes.

Provided are novel lipid nanoparticle (LNP) compositions encapsulating polynucleotides (e.g., mRNA) that have enhanced stability over time, and methods of preparing these compositions. Specifically, in the context of LNP compositions encapsulating mRNA, the compositions have higher amounts of translation competent mRNA per LNP. Additionally provided are methods of formulating the aforementioned compositions. Overall, the provided LNPs encapsulating polynucleotides (e.g., mRNAs) can have higher therapeutic potential as these formulations can deliver higher amounts of stable and biologically active (e.g. translation competency for mRNA) to target cells per LNP administered. Some embodiments relate to the identification of a heterogeneous impurity group (IG) species present in LNP formulations, also referred to herein as ionizable lipid-polynucleotide adduct. Analytical chemistry techniques such as high performance liquid chromatography (HPLC) and mass spectrometry (MS) identified the IG as a complex mixture of mRNA-aldehyde (unbranched and branched) adduct species. Biochemical characterization with cell-free translation systems, fluorescently activated cell sorting (FACs) assays, and ribosomal-profiling of reporter mRNAs revealed that the IG species have low translation competency. Such reduced translation competency, without being bound by theory, is likely due to the chemical modifications, mRNA-aldehyde (unbranched and branched) adduct species, formed across the length of the mRNA. Chemical characterization of the lipid molecules utilized as components of the LNP revealed that the lipids can decompose into secondary amine and reactive aldehyde species. The decomposition can be accelerated by low pH conditions and presence of trace metals, and can be inhibited by antioxidant agents, or by reducing agents, or removal of trace metals. The aforementioned reactive aldehyde species are believed to react with polynucleotides (e.g., mRNA) to generate the IGs. An exemplary IG formation pathway is shown in FIGS. 1A and 1B. Herein, process steps are disclosed that minimize IG formation, including one or more of pre-treatment of polynucleotide (e.g., mRNA) and/or lipids with reducing or anti-oxidant agents, pre-treatment of polynucleotide (e.g., mRNA) and/or lipids with immobilized resins that remove trace metals or contain reducing agents, addition of excipients or buffering components, and LNP storage conditions (e.g. temperature, pressure, lyophilization). Also provided are isolated ionizable lipid-polynucleotide adduct species as described herein, and methods of detecting ionizable lipid-polynucleotide adducts.

1. Lipid Nanoparticle Compositions

Some embodiments relate to a lipid nanoparticle composition comprising a polynucleotide and an ionizable lipid, wherein the composition comprises less than about 10% of an ionizable lipid-polynucleotide adduct impurity relative to a total amount of the polynucleotide as measured by HPLC. Some embodiments relate to a lipid nanoparticle composition comprising polynucleotides and ionizable lipids, wherein the composition comprises less than about 10% of an ionizable lipid-polynucleotide adduct impurity relative to a total amount of polynucleotides as measured by HPLC, wherein the adduct impurity comprises one or more of the polynucleotides which is/are modified to include one or more covalently-appended lipid groups derived from the ionizable lipids. In some embodiments, the composition comprises less than about 5%, less than about 3%, less than about 2%, or less than about 1% of ionizable lipid-polynucleotide adduct impurity relative to the total amount of polynucleotides. In some embodiments, the composition is substantially free of ionizable lipid-polynucleotide adduct impurity.

The term "adduct" or "adduct impurity" refers to the covalent addition of a lipid or other entity (e.g., hydrophobic entity) or polymer chain to a polynucleotide, such as mRNA. An "ionizable lipid-polynucleotide adduct impurity" (also referred to as "impurity group" or "IG") is a type of adduct that comprises the covalent modification of a polynucleotide (e.g., in a LNP) with an ionizable lipid or a derivative thereof (such as a secondary amine or reactive aldehyde produced from decomposed ionizable lipids).

The presence of adduct impurities can lead to low translation competency of the polynucleotide of the adduct impurity. For instance, in the context of mRNA, an adduct includes covalent modification of the mRNA in such a way as to prevent translation of the mRNA. Without being bound by any particular theory, the low translation competency of adduct impurity polynucleotides may be due to chemical modifications across the length of the polynucleotide in the form of the polynucleotide-aldehyde (unbranched and/or branched) adduct species. Translation competency may be determined by assays known in the art and described herein (see, e.g., the working examples below). For example, translation competency may be determined by biochemical characterization with cell-free translation systems, fluorescently activated cell sorting (FACs) assays, and/or ribosomal-profiling of reporter mRNAs comprising adduct impurities.

In some embodiments, adduct impurities are formed as a result of the reaction between (i) polynucleotides and (ii) secondary amine and/or reactive aldehyde species produced from decomposed ionizable lipids. See FIGS. 1A and 1B for an exemplary adduct impurity formation pathway.

The amount of ionizable lipid-polynucleotide adduct impurity in a composition may be measured by assays known in the art, such as high performance liquid chromatography (HPLC), mass spectrometry (including MS/MS), reverse phase ion pair chromatography (RP-IP), capillary electrophoresis, size exclusion chromatography, positive mode LC-MS/MS, ultra-high-performance liquid chromatography (e.g., RP-UPLC-CAD), or any combination thereof.

Figure 2:
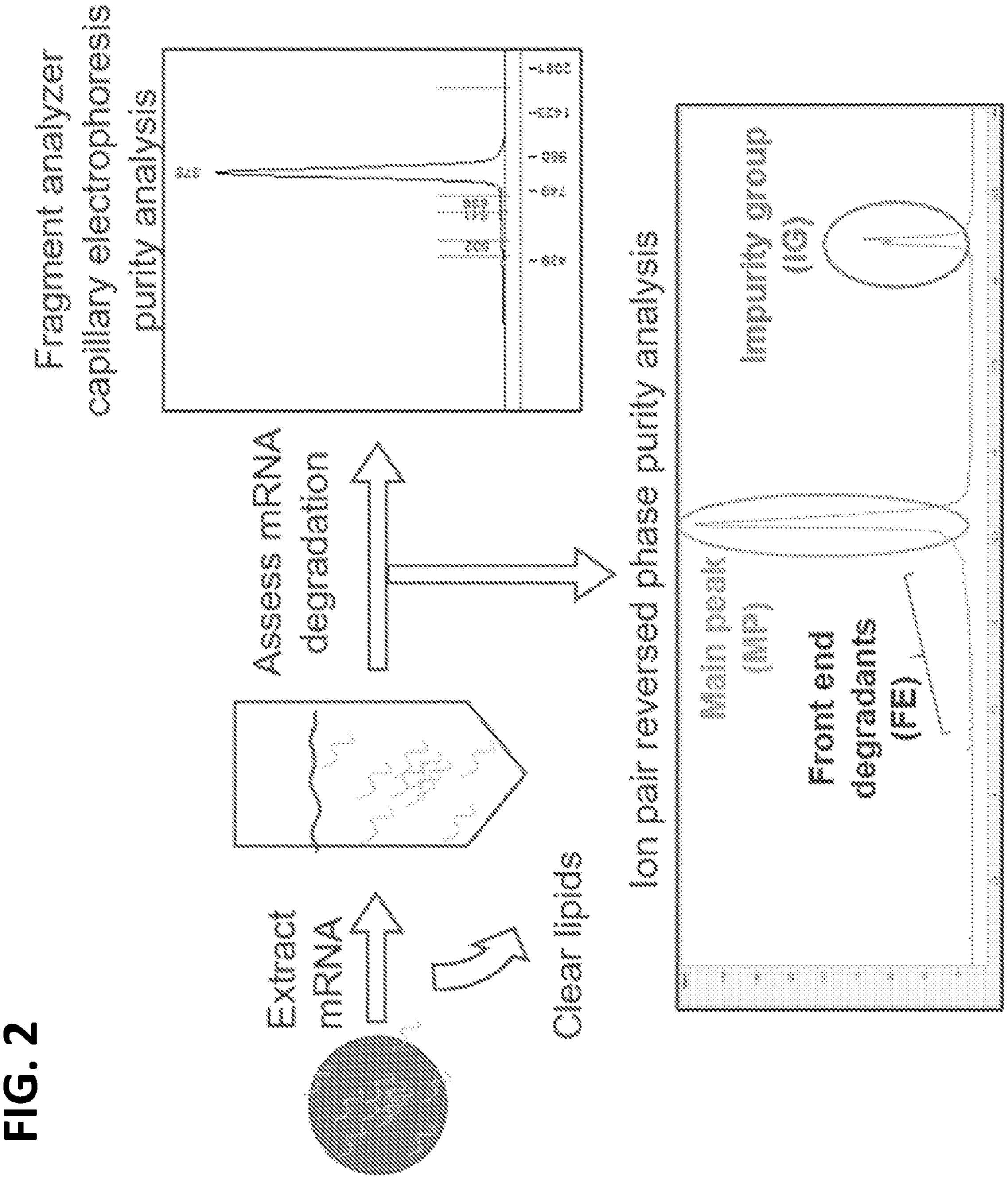
FIG. 2 is a schematic diagram of how a heterogeneous impurity group (IG) as described herein can be isolated and detected from compositions comprising mRNA.

For instance, the presence and amount of ionizable lipid-polynucleotide adduct impurity in an LNP composition comprising polynucleotides may be detected and/or quantified by: (i) extracting the polynucleotides from the LNP composition; (ii) assessing the integrity of the extracted polynucleotides; and (iii) analyzing the extracted polynucleotides by HPLC. Extraction of the polynucleotide molecules from the LNP compositions may be performed by methods known in the art, such as precipitation and liquid:liquid extraction (see Example 1 below). The purity and/or length of the extracted polynucleotides may be used to characterize the integrity of the extracted polynucleotides. Assays such as fragment analyzer capillary electrophoresis and gel electrophoresis (see Example 1 below) may be used to assess the integrity of the extracted polynucleotides. Finally, HPLC analysis may be performed. For the HPLC analysis, an ion pair reversed phase purity HPLC method may be performed on an appropriate column (e.g., on a Thermo DNApac RP 100×2.1 mm column) at an appropriate temperature (e.g., at 65° C.), with mobile phases (e.g. containing dibutylammonium acetate (e.g., 50 mM) and triethylammonium acetate (e.g., 100 mM) in water and acetonitrile). Elution with the acetonitrile gradient provides an RNA separation primarily driven by mRNA length and sensitive to any added hydrophobic elements. The appearance of two prominent peaks on the HPLC chromatogram can be indicative of the presence of an IG (see, e.g., Example 1, FIG. 2, below): a "main peak" and an "impurity group (IG)" peak. Without being bound by any particular theory, the main peak is believed to comprise non-adduct mRNA from the LNP composition, and the IG peak comprises mRNA from the LNP composition having one or more covalent modifications. The percentage of IG in the composition can be calculated as the mass fraction of RNA containing at least one lipid adduct, and it can determined by integrating the area under the curve (AUC) of all RNA peaks (including products shorter than the full-length product, the full-length product, and the adduct RNA) and taking the late-eluting region as an area percent of the total peak.

The adduct impurity may comprise carbon chains covalently appended to the polynucleotides. The carbon chains, which are believed to be derived from the ionizable lipids, may be saturated or unsaturated and of various lengths. In some embodiments, the carbon chain is a $C_{6-30}$ carbon chain. In some embodiments, one or more covalently-appended lipids or derivatives thereof in the adduct impurity comprises a $C_{6-30}$ saturated carbon chain. In some embodiments, one or more covalently-appended lipids or derivatives thereof in the adduct impurity comprises a $C_{6-30}$ unsaturated carbon chain.

In some embodiments, one or more covalently-appended lipids or derivatives thereof in the adduct impurity comprises a carbon chain interrupted by a non-carbon group. In some embodiments, the carbon chain of an adduct impurity is interrupted by a —C(O)O— ester group. In some embodiments, one or more covalently-appended lipids or derivatives thereof in the adduct impurity comprises a $C_{6-30}$ saturated carbon chain interrupted by a —C(O)O— ester group. In some embodiments, one or more covalently-appended lipids or derivatives thereof in the adduct impurity comprises a $C_{6-30}$ unsaturated carbon chain interrupted by a —C(O)O— ester group.

In some embodiments, one or more covalently-appended lipids or derivatives thereof in the adduct impurity is attached to a nucleobase. Exemplary nucleobases include, but are not limited to, guanosine, cytidine, and methyl pseudouridine.

In some embodiments, a lipid nanoparticle composition comprises less than about 10%, less than about 5%, less than about 3%, less than about 2%, or less than about 1% of ionizable lipid-polynucleotide adduct impurity relative to the total amount of polynucleotides. In some embodiments, the composition comprises less than 10%, less than 5%, less than 3%, less than 2%, or less than 1% of ionizable lipid-polynucleotide adduct impurity relative to the total amount of polynucleotides. In some embodiments, the composition comprises less than about 10% of ionizable lipid-polynucleotide adduct impurity relative to the amount of polynucleotides. In some embodiments, the composition comprises less than about 5% of ionizable lipid-polynucleotide adduct impurity relative to the total amount of polynucleotides. In some embodiments, the composition comprises less than about 3% of ionizable lipid-polynucleotide adduct impurity relative to the total amount of polynucleotides. In some embodiments, the composition comprises less than about 2% of ionizable lipid-polynucleotide adduct impurity relative to the total amount of polynucleotides. In some embodiments, the composition comprises less than about 1% of ionizable lipid-polynucleotide adduct impurity relative to the total amount of polynucleotides. In some embodiments, the composition is substantially free of ionizable lipid-polynucleotide adduct impurity. In some embodiments, a composition is "substantially free" of ionizable lipid-polynucleotide adduct impurity when the percent of adduct impurity in the composition relative to the total amount of polynucleotides is less than 0.5%, including less than 0.4%, less than 0.3%, less than 0.2%, less than 0.1%, less than 0.05%, less than 0.01%, or less than 0.001%. In some embodiments, the composition is free of ionizable lipid-polynucleotide adduct impurity.

In some embodiments, the composition comprises between 0% and 10%, between 1% and 9%, between 2% and 8%, between 3% and 7%, or between 4% and 6% of ionizable lipid-polynucleotide adduct impurity relative to the total amount of polynucleotides. In some embodiments, the composition comprises between 1% and 10%, between 1% and 7%, between 1% and 5%, or between 1% and 3% or between 4% and 6% of ionizable lipid-polynucleotide adduct impurity relative to the total amount of polynucleotides.

The LNP compositions described herein can also be advantageous in that the amount of adduct impurity in the composition does not increase substantially over time or under different storage conditions. For example, in some embodiments, the amount of adduct impurity in an LNP composition increases at an average rate of less than about 2%, less than about 1%, less than about 0.5%, or less than about 0.2% per day when stored at a temperature at about 40° C. or below (such as when stored at a temperature of about 25° C., about 20° C., about 15° C., about 10° C., about 8° C., about 5° C., about 2° C., about 0° C., about −10° C., or about −20° C.).

In some embodiments, the amount of adduct impurity in an LNP composition increases at an average rate of less than 2%, less than 1%, less than 0.5%, or less than 0.2% per day when stored at a temperature at about 25° C. or below. In some embodiments, the amount of adduct does not substantially increase when stored at a temperature at about 25° C. or below (e.g., does not increase by more than 0.05%, more than 0.01%, more than 0.005%, or more than 0.001%).

The average rate of increase of adduct impurity group at various temperatures can be measured over a period of time, e.g., 2-10 consecutive dates, 2-5 consecutive days, 5-7 consecutive days, or 7-10 consecutive days, starting on the day (t=0), or one day after (t=1), the lipid nanoparticle composition was formed. In some embodiments, the average rate of increase of adduct impurity is measured over 2-5 consecutive days starting on the day the lipid nanoparticle composition was formed. In some embodiments, the average rate of increase of adduct impurity is measured over 2-5 consecutive days starting on one day after the lipid nanoparticle composition was formed. In some embodiments, the average rate of increase of adduct impurity is measured over 7-10 consecutive days starting on the day the lipid nanoparticle composition was formed. In some embodiments, the average rate of increase of adduct impurity is measured over 7-10 consecutive days starting on one day after the lipid nanoparticle composition was formed.

Some embodiments comprise adjusting the buffer or pH of the composition to reduce the amount of adduct impurity formed in the LNP composition (e.g., to inhibit ionizable lipid decomposition). For example, some embodiments comprise a composition with a TRIS (tris(hydroxymethyl) aminomethane) buffer at a concentration of about 10 mM or more, such as a concentration of about 20 mM, about 30 mM, about 50 mM, about 60 mM, about 75 mM, about 100 mM, about 120 mM, or about 150 mM TRIS buffer. In some embodiments, the composition comprises from about 10 mM to about 150 mM TRIS, such as from about 15 mM to about 120 mM TRIS or about 20 mM to about 100 mM TRIS. In some embodiments, the composition does not contain a PBS buffer.

In some embodiments, the composition is at a pH of from about 6.5 to about 9.0, such as about 7-8, about 7-7.5, about 7.4, or about 7.5.

The composition may also comprise a free reducing agent or antioxidant. Exemplary free reducing agents or antioxidants include, but are not limited to, potassium metabisulfite, sodium thioglycolate, tris(2-carboxyethyl)phosphine (TCEP), sodium thiosulfate, N-acetyl cysteine, glutathione, dithiothreitol (DTT), cystamine, dithioerythritol (DTE), dichlorodiphenyltrichloroethane (DDT), homocysteine, and lipoic acid.

Some embodiments comprise reducing the presence of trace metals in the composition (e.g., to inhibit ionizable lipid decomposition). Thus, the amount of transition metals in the LNP composition may be modified to reduce the amount of adduct impurity formed in the LNP composition. In some embodiments, the LNP composition comprises an amount of transition metals that is less than about 500 ppm, less than about 250 ppm, less than about 100 ppm, or less than about 50 ppm. In some embodiments, the LNP composition comprises an amount of transition metals that is less than 500 ppm, less than 250 ppm, less than 100 ppm, or less than 50 ppm. In some embodiments, the LNP composition comprises an amount of transition metals that is between 5 ppm and 500 ppm, between 25 ppm and 250 ppm, or between 50 and 100 ppm. In some embodiments, the LNP composition comprises an amount of transition metals that is between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, the composition is substantially free of transition metals (e.g., the amount of transition metals is less than 5 ppm, less than 4 ppm, less than 3 ppm less than 2 ppm, less than 1 ppm, less than 0.1 ppm, less than 0.05 ppm, or less than 0.01 ppm). Exemplary transition metals include, but are not limited to, Pd, Cu, Fe, Ni, Pb, and Mn. In some embodiments, the composition comprises Fe. In some embodiments, the Fe has an oxidation state of 2+.

Some embodiments comprise reducing the presence of N-oxide compounds in the composition. In some embodiments, the N-oxide compound is an ionizable lipid in the LNP which has been oxidized to form an N-oxide group. Thus, the amount of N-oxide compound in the LNP composition may be modified to reduce the amount of adduct impurity formed in the LNP composition. In some embodiments, the LNP composition comprises an amount of N-oxide compound that is less than about 500 ppm, less than about 250 ppm, less than about 100 ppm, or less than about 50 ppm. In some embodiments, the LNP composition comprises an amount of N-oxide compound that is less than 500 ppm, less than 250 ppm, less than 100 ppm, or less than 50 ppm. In some embodiments, the LNP composition comprises an amount of N-oxide compound that is between 5 ppm and 500 ppm, between 25 ppm and 250 ppm, or between 50 and 100 ppm. In some embodiments, the LNP composition comprises an amount of N-oxide compound that is between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, the composition is substantially free of N-oxide compounds (e.g., the amount of N-oxide compound is less than 5 ppm, less than 4 ppm, less than 3 ppm less than 2 ppm, less than 1 ppm, less than 0.1 ppm, less than 0.05 ppm, or less than 0.01 ppm).

In some embodiments, the LNP composition comprises an amount of lipid aldehyde that is less than about 500 ppm, less than about 250 ppm, less than about 100 ppm, or less than about 50 ppm. In some embodiments, the LNP composition comprises an amount of lipid aldehyde that is less than 500 ppm, less than 250 ppm, less than 100 ppm, or less than 50 ppm. In some embodiments, the LNP composition comprises an amount of lipid aldehyde that is between 5 ppm and 500 ppm, between 25 ppm and 250 ppm, or between 50 and 100 ppm. In some embodiments, the LNP composition comprises an amount of lipid aldehyde that is between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, the composition is substantially free of lipid aldehyde (e.g., the amount of lipid aldehyde is less than 5 ppm, less than 4 ppm, less than 3 ppm less than 2 ppm, less than 1 ppm, less than 0.1 ppm, less than 0.05 ppm, or less than 0.01 ppm).

In some embodiments, the LNP composition comprises an amount of alkyl halide compounds that is less than about 500 ppm, less than about 250 ppm, less than about 100 ppm, or less than about 50 ppm. In some embodiments, the LNP composition comprises an amount of alkyl halide compounds that is less than 500 ppm, less than 250 ppm, less than 100 ppm, or less than 50 ppm. In some embodiments, the LNP composition comprises an amount of alkyl halide compounds that is between 5 ppm and 500 ppm, between 25 ppm and 250 ppm, or between 50 and 100 ppm. In some embodiments, the LNP composition comprises an amount of alkyl halide compounds that is between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, the composition is substantially free of alkyl halide compounds (e.g., the amount of alkyl halide compound is less than 5 ppm, less than 4 ppm, less than 3 ppm less than 2 ppm, less than 1 ppm, less than 0.1 ppm, less than 0.05 ppm, or less than 0.01 ppm). In some embodiments, the alkyl halide compound comprises one or more selected from alkyl iodide compounds and alkyl bromide compounds.

In some embodiments, the LNP composition comprises an amount of anhydride compounds that is less than about 500 ppm, less than about 250 ppm, less than about 100 ppm, or less than about 50 ppm. In some embodiments, the LNP composition comprises an amount of anhydride compounds that is less than 500 ppm, less than 250 ppm, less than 100 ppm, or less than 50 ppm. In some embodiments, the LNP composition comprises an amount of anhydride compounds that is between 5 ppm and 500 ppm, between 25 ppm and 250 ppm, or between 50 and 100 ppm. In some embodiments, the LNP composition comprises an amount of anhydride compounds that is between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, the composition is substantially free of anhydride compounds (e.g., the amount of anhydride compounds is less than 5 ppm, less than 4 ppm, less than 3 ppm less than 2 ppm, less than 1 ppm, less than 0.1 ppm, less than 0.05 ppm, or less than 0.01 ppm).

In some embodiments, the LNP composition comprises an amount of ketone compounds that is less than about 500 ppm, less than about 250 ppm, less than about 100 ppm, or less than about 50 ppm. In some embodiments, the LNP composition comprises an amount of ketone compounds that is less than 500 ppm, less than 250 ppm, less than 100 ppm, or less than 50 ppm. In some embodiments, the LNP composition comprises an amount of ketone compounds that is between 5 ppm and 500 ppm, between 25 ppm and 250 ppm, or between 50 and 100 ppm. In some embodiments, the LNP composition comprises an amount of ketone compounds that is between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, the composition is substantially free of ketone compounds (e.g., the amount of alkyl ketone compounds is less than 5 ppm, less than 4 ppm, less than 3 ppm less than 2 ppm, less than 1 ppm, less than 0.1 ppm, less than 0.05 ppm, or less than 0.01 ppm).

In some embodiments, the LNP composition comprises an amount of conjugated diene compounds that is less than about 500 ppm, less than about 250 ppm, less than about 100 ppm, or less than about 50 ppm. In some embodiments, the LNP composition comprises an amount of conjugated diene compounds that is less than 500 ppm, less than 250 ppm, less than 100 ppm, or less than 50 ppm. In some embodiments, the LNP composition comprises an amount of conjugated diene compounds that is between 5 ppm and 500 ppm, between 25 ppm and 250 ppm, or between 50 and 100 ppm. In some embodiments, the LNP composition comprises an amount of conjugated diene compounds that is between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, the composition is substantially free of conjugated diene compounds (e.g., the amount of conjugated diene compounds is less than 5 ppm, less than 4 ppm, less than 3 ppm less than 2 ppm, less than 1 ppm, less than 0.1 ppm, less than 0.05 ppm, or less than 0.01 ppm).

In some embodiments, the LNP composition is in liquid form.

a. Lipid Nanoparticles

Lipid nanoparticles (LNPs) typically comprise one or more lipids and a nucleic acid cargo (i.e., polynucleotide) of interest. In some embodiments, the lipid is an ionizable lipid (e.g., an ionizable amino lipid), sometimes referred to in the art as an "ionizable cationic lipid". In some embodiments, lipid nanoparticles further comprise other components, including one or more of a phospholipid, a structural lipid, and a molecule capable of reducing particle aggregation, for example a PEG or PEG-modified lipid. In some embodiments, the lipid nanoparticle comprises at least one ionizable cationic lipid, at least one non-cationic lipid, at least one sterol, and/or at least one polyethylene glycol (PEG)-modified lipid. The lipid nanoparticles can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entireties.

In some embodiments, the lipid nanoparticle is a lipid nanoparticle described in Intl. Pub. Nos. WO2013123523, WO2012170930, WO2011127255, WO2008103276; or U.S. Pub. No. US20130171646, each of which is herein incorporated by reference in its entirety.

In some embodiments, the lipid nanoparticle comprises a molar ratio of 20-60% ionizable cationic lipid, based on the lipid components, e.g., not including the nucleotide cargo. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid, based on the lipid components, e.g., not including the nucleotide cargo. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol, based on the lipid components, e.g., not including the nucleotide cargo. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid, based on the lipid components, e.g., not including the nucleotide cargo. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid, based on the lipid components, e.g., not including the nucleotide cargo.

In some embodiments, the lipid nanoparticles described herein have a diameter from about 1 nm to about 100 nm such as, but not limited to, from about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles described herein have a diameter from about 10 to 500 nm. In some embodiments, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

The ratio between the lipid components of the LNP composition and the polynucleotide cargo can be from about 10:1 to about 60:1 (wt/wt). In some embodiments, the ratio between the lipid components and the polynucleotide (e.g., mRNA) can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid components of the LNP composition to the polynucleotide (such as a polynucleotide encoding a therapeutic agent) is about 20:1 or about 15:1.

In some embodiments, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In some embodiments, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

In some embodiments, the composition or pharmaceutical composition disclosed herein can contain more than one polynucleotide. For example, a composition or pharmaceutical composition disclosed herein can contain two or more polynucleotides (e.g., RNA, e.g., mRNA) formulated in the same lipid nanoparticle. A single LNP can contain two or more polynucleotides. Additionally or alternatively, a composition or pharmaceutical composition disclosed herein can comprise a mixture of LNPs, each containing one or more polynucleotides, which may be the same or different. For example LNP1 can contain polynucleotide A; LNP2 can contain polynucleotides B and C; LNP3 can contain polynucleotides D, E, and F; LNP4 can contain polynucleotides E, F, and G, etc.

The lipid nanoparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO 2013/082111, herein incorporated by reference in its entirety). Other physical features the geometrically engineering particles can include are, but are not limited to, fenestrations, angled arms, asymmetry and surface roughness, and charge that can alter the interactions with cells and tissues.

In some embodiments, the lipid nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM) from the Institut fur Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

i. Ionizable Lipids

The lipid nanoparticles described herein comprise ionizable lipids. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In some embodiments, the charged moieties comprise amine groups. Examples of negatively charged groups or precursors thereof include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In some embodiments, the ionizable amino lipid may have a positively charged hydrophilic head and a hydrophobic tail that are connected via a linker structure.

In addition to these, an ionizable lipid may also be a lipid including a cyclic amine group.

In some embodiments, the ionizable lipid may be selected from, but not limited to, a ionizable lipid described in International Publication Nos. WO2013086354 and WO2013116126; each of which is herein incorporated by reference in its entirety.

In some embodiments, the ionizable lipid may be selected from, but not limited to, formula CLI-CLXXXXII of U.S. Pat. No. 7,404,969; which is herein incorporated by reference in its entirety.

In some embodiments, the lipid may be a cleavable lipid such as those described in International Publication No. WO2012170889, herein incorporated by reference in its entirety. In some embodiments, the lipid may be synthesized by methods known in the art and/or as described in International Publication No. WO2013086354; each of which is herein incorporated by reference in its entirety.

In some aspects, the lipid comprises at least one tertiary amino group, wherein at least one of the three groups of the tertiary amino group comprises a $C_{6-30}$ saturated or unsaturated carbon chain optionally interrupted by an —C(O)O— ester group.

In some aspects, the disclosure relates to a compound of Formula (I):

(I)

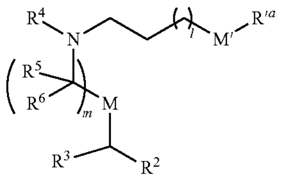

or its N-oxide, or a salt or isomer thereof, wherein $R'^{a}$ is $R'^{branched}$; wherein $R'^{branched}$ is:

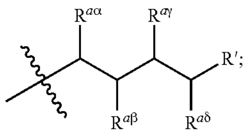

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$, wherein n is selected from the group consisting of 1, 2, 3, 4, and 5, and

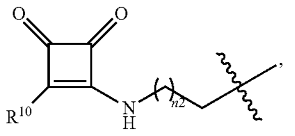

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and

—OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments of the compounds of Formula (I), $R'^{a}$ is $R'^{branched}$; $R'^{branched}$ is

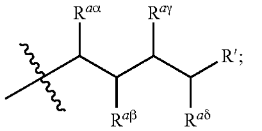

denotes a point of attachment; $R^{a\alpha}$, $R^{a\beta}$, $R^{a\gamma}$, and $R^{a\delta}$ are each H; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; 1 is 5; and m is 7.

In some embodiments of the compounds of Formula (I), $R'^{a}$ is $R'^{branched}$; $R'^{branched}$ is

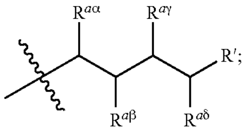

denotes a point of attachment; $R^{a\alpha}$, $R^{a\beta}$, $R^{a\gamma}$, and $R^{a\delta}$ are each H; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; 1 is 3; and m is 7.

In some embodiments of the compounds of Formula (I), $R'^{a}$ is $R'^{branched}$; $R'^{branched}$ is

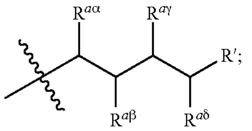

denotes a point of attachment; $R^{a\alpha}$ is $C_{2-12}$ alkyl; $R^{a\beta}$, $R^{a\gamma}$, and $R^{a\delta}$ are each H; $R^2$ and $R^3$ are each $C_{1-14}$ alkyl; $R^4$ is

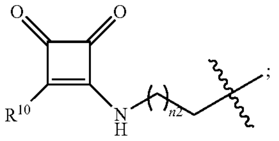

$R^{10}$ NH($C_{1-6}$ alkyl); n2 is 2; $R^5$ is H; each $R^6$ is H; M and M' are each —C(O)O—; R' is a $C_{1-12}$ alkyl; is nd m is 7.

In some embodiments of the compounds of Formula (I), $R'^{a}$ is $R'^{branched}$; $R'^{branched}$ is

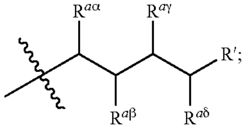

denotes a point of attachment; $R^{a\alpha}$, $R^{a\beta}$, and $R^{a\delta}$ are each H; $R^{a\gamma}$ is $C_{2-12}$ alkyl; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; 1 is 5; and m is 7.

In some embodiments, the compound of Formula (I) is selected from:

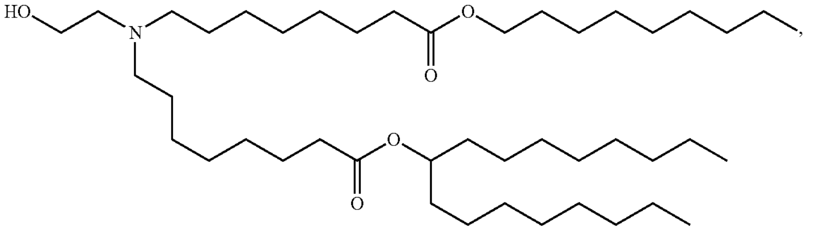

-continued
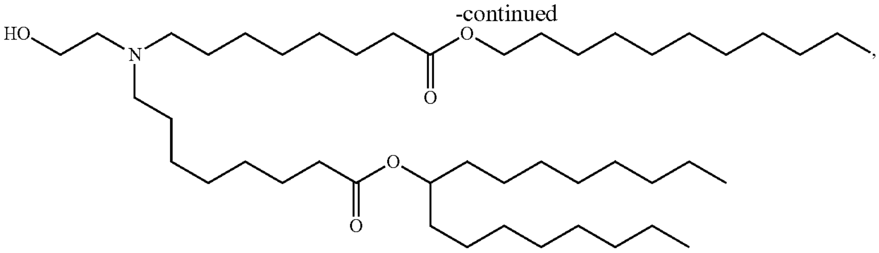
,
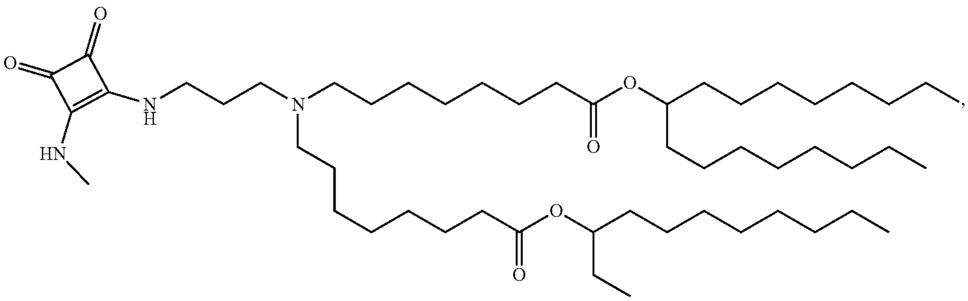
, and
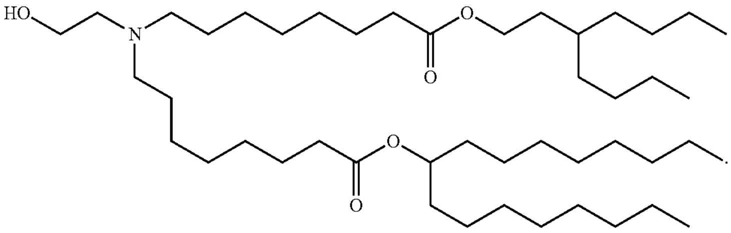
.
In some embodiments, the compound of Formula (I) is:
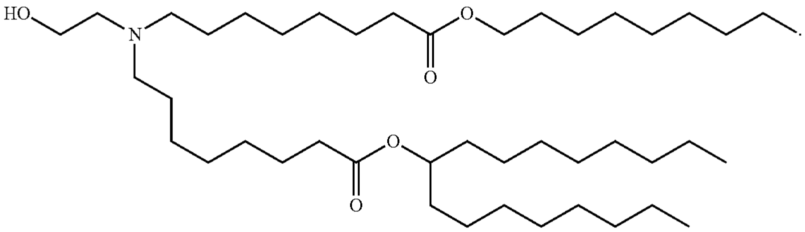
.
In some embodiments, the compound of Formula (I) is:
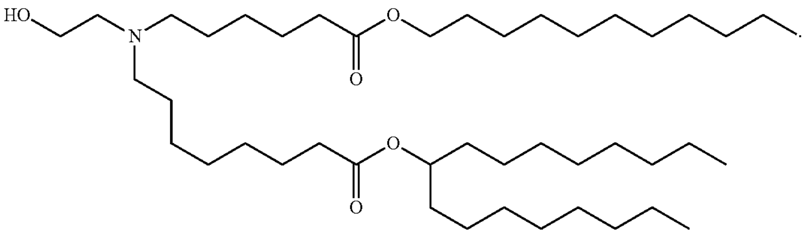
.

In some embodiments, the compound of Formula (I) is:

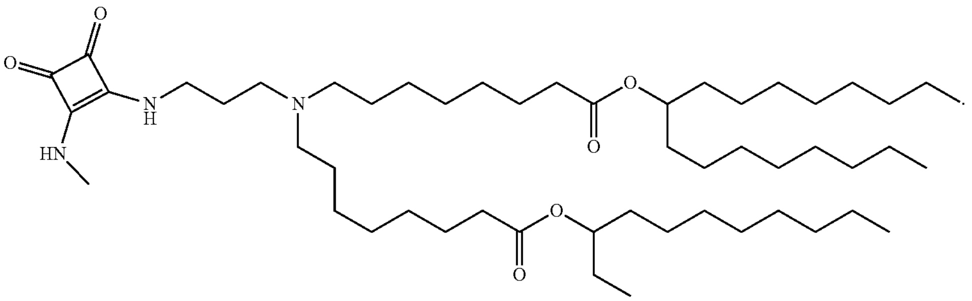

In some embodiments, the compound of Formula (I) is:

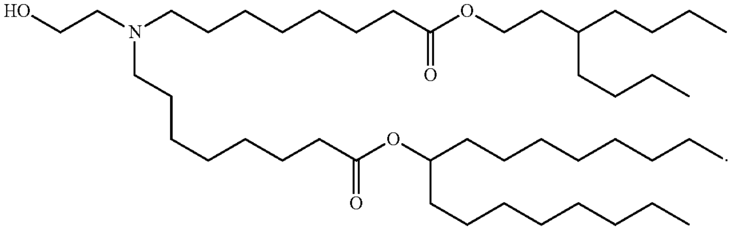

In some aspects, the disclosure relates to a compound of Formula (Ia):

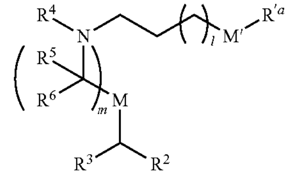

(Ia)

or its N-oxide, or a salt or isomer thereof, wherein $R'^{a}$ is $R'^{branched}$; wherein $R'^{branched}$ is:

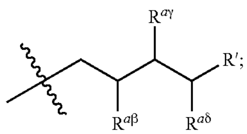

wherein

denotes a point of attachment;

wherein $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$ wherein n is selected from the group consisting of 1, 2, 3, 4, and 5, and

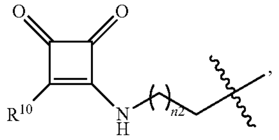

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some aspects, the disclosure relates to a compound of Formula (Ib):

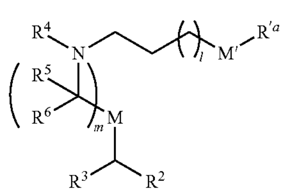

(Ib)

or its N-oxide, or a salt or isomer thereof, wherein $R'^{a}$ is $R'^{branched}$; wherein $R'^{branched}$ is:

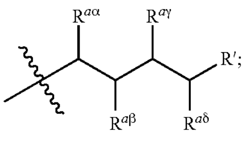

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is $—(CH_2)_nOH$, wherein n is selected from the group consisting of 1, 2, 3, 4, and 5;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and

—OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments of Formula (I) or (Ib), $R'^{a}$ is $R'^{branched}$; $R'^{branched}$ is

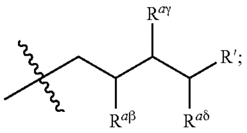 

denotes a point of attachment; $R^{a\beta}$, $R^{a\gamma}$, and $R^{a\delta}$ are each H; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; 1

In some embodiments of Formula (I) or (Ib), $R'^{a}$ is $R'^{branched}$; $R'^{branched}$ is

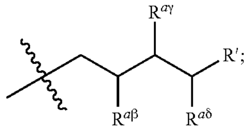 

denotes a point of attachment; $R^{a\beta}$, $R^{a\gamma}$, and $R^{a\delta}$ are each H; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; 1 is 3; and m is 7.

In some embodiments of Formula (I) or (Ib), $R'^{a}$ is $R'^{branched}$; $R'^{branched}$ is

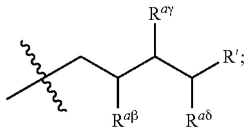 

denotes a point of attachment; $R^{a\beta}$ and $R^{a\delta}$ are each H; $R^{a\gamma}$ is $C_{2-12}$ alkyl; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; 1 is 5; and m is 7.

In some aspects, the disclosure relates to a compound of Formula (Ic):

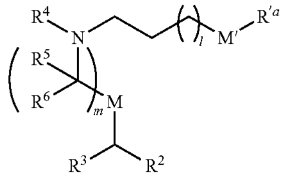

(Ic)

or its N-oxide, or a salt or isomer thereof, wherein $R'^{a}$ is $R'^{branched}$; wherein $R'^{branched}$ is:

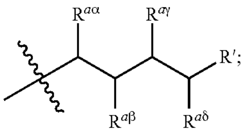

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is

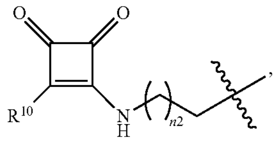

wherein

denotes a point of attachment; wherein $R^{10}$ is $N(R)_2$; each R is independently selected from the group consisting of $C_{1-6}$ alkyl, $C_{2-3}$ alkenyl, and H; n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments, $R'^{a}$ is $R'^{branched}$; $R'^{branched}$ is

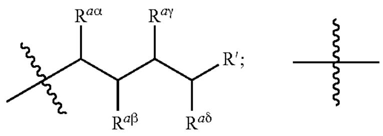

denotes a point of attachment; $R^{a\beta}$, $R^{a\gamma}$, and $R^{a\delta}$ are each H; $R^{a\alpha}$ is $C_{2-12}$ alkyl; $R^2$ and $R^3$ are each $C_{1-14}$ alkyl; $R^4$ is

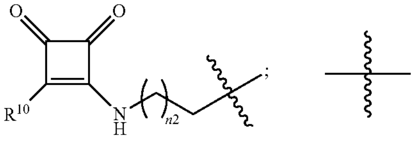

denotes a point of attachment; $R^{10}$ is NH($C_{1-6}$ alkyl); n2 is 2; each $R^5$ is H; each $R^6$ is H; M and M' are each —C(O)O—; R' is a $C_{1-12}$ alkyl; 1 is 5; and m is 7.

In some embodiments, the compound of Formula (Ic) is:

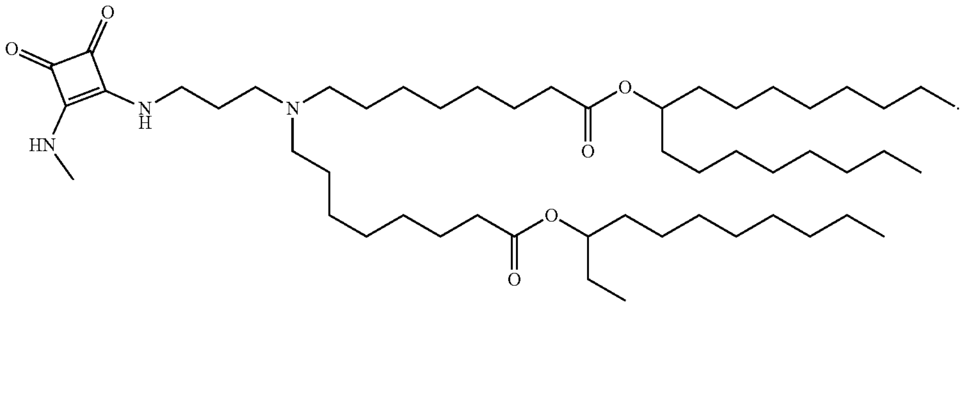

In some aspects, the disclosure relates to a compound of Formula (II):

(II)

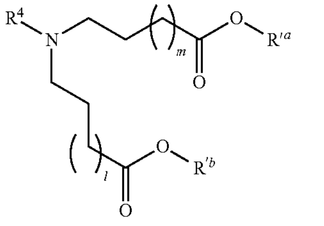

or its N-oxide, or a salt or isomer thereof, wherein $R'^{a}$ is $R'^{branched}$ or $R'^{cyclic}$; wherein $R'^{branched}$ is

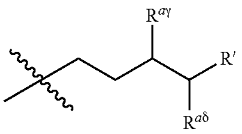

and $R'^{cyclic}$ is:

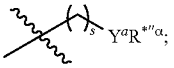

and $R'^{b}$ is:

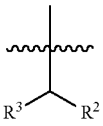

or

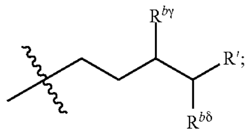

wherein

denotes a point of attachment;

$R^{a\gamma}$ and $R^{a\delta}$ are each independently selected from the group consisting of H, $C_{1-12}$ alkyl, and $C_{2-12}$ alkenyl, wherein at least one of $R^{a\gamma}$ and $R^{a\delta}$ is selected from the group consisting of $C_{1-12}$ alkyl and $C_{2-12}$ alkenyl;

$R^{b\gamma}$ and $R^{b\delta}$ are each independently selected from the group consisting of H, $C_{1-12}$ alkyl, and $C_{2-12}$ alkenyl, wherein at least one of $R^{b\gamma}$ and $R^{b\delta}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$ wherein n is selected from the group consisting of 1, 2, 3, 4 and 5 and

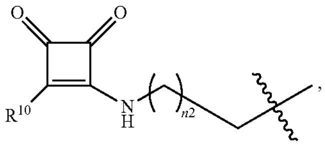

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10; each R' independently is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl; and s is 2 or 3;

m is selected from 1, 2, 3, 4, 5, 6, 7, 8, and 9;

l is selected from 1, 2, 3, 4, 5, 6, 7, 8, and 9.

In some aspects, the disclosure relates to a compound of Formula (II-a):

(II-a)

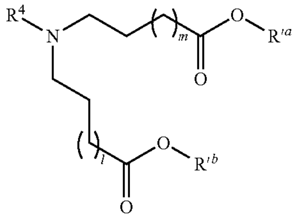

or its N-oxide, or a salt or isomer thereof, wherein $R'^{a}$ is $R'^{branched}$ or $R'^{cyclic}$; wherein $R'^{branched}$ is:

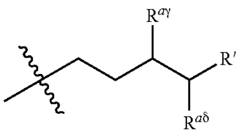

and $R'^{b}$ is:

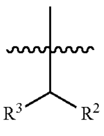

or

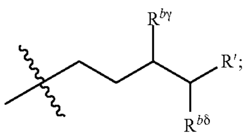

wherein

denotes a point of attachment;

$R^{a\gamma}$ and $R^{a\delta}$ are each independently selected from the group consisting of H, $C_{1-12}$ alkyl, and $C_{2-12}$ alkenyl, wherein at least one of $R^{a\gamma}$ and $R^{a\delta}$ is selected from the group consisting of $C_{1-12}$ alkyl and $C_{2-12}$ alkenyl; $R^{b\gamma}$ and $R^{b\delta}$ are each independently selected from the group consisting of H, $C_{1-12}$ alkyl, and $C_{2-12}$ alkenyl, wherein at least one of $R^{b\gamma}$ and $R^{b\delta}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

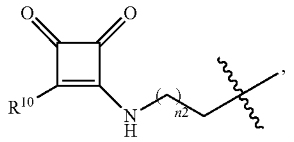

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some aspects, the disclosure relates to a compound of Formula (II-b):

(II-b)

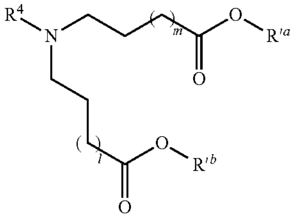

or its N-oxide, or a salt or isomer thereof, wherein $R'^{a}$ is $R'^{branched}$ or $R'^{cyclic}$; wherein $R'^{branched}$ is:

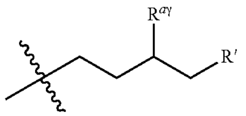

and $R'^{b}$ is:

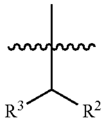

or

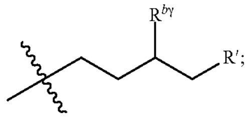

wherein

denotes a point of attachment;

$R^{a\gamma}$ and $R^{b\gamma}$ are each independently selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

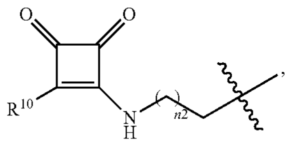

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some aspects, the disclosure relates to a compound of Formula (II-c):

(II-c)

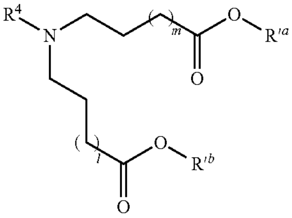

or its N-oxide, or a salt or isomer thereof, wherein $R'^a$ is $R'^{branched}$ or $R'^{cyclic}$; wherein $R'^{branched}$ is:

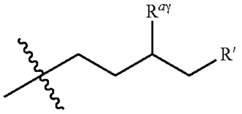

and $R'^b$ is:

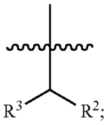

wherein

denotes a point of attachment;

wherein $R^{a\gamma}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$ wherein n is selected from the group consisting of 1, 2, 3, 4, and 5, and

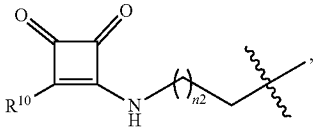

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

R' is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some aspects, the disclosure relates to a compound of Formula (II-d):

(II-d)

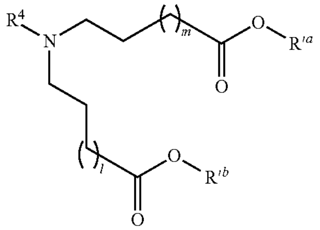

or its N-oxide, or a salt or isomer thereof, wherein $R'^a$ is $R'^{branched}$ or $R'^{cyclic}$; wherein $R'^{branched}$ is:

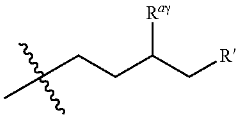

and $R'^b$ is:

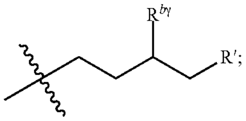

wherein

denotes a point of attachment;

wherein $R^{a\gamma}$ and $R^{b\gamma}$ are each independently selected from the group consisting of $C_{1-12}$ alkyl and $C_{2-12}$ alkenyl;

$R^4$ is selected from the group consisting of $-(CH_2)_nOH$ wherein n is selected from the group consisting of 1, 2, 3, 4, and 5, and

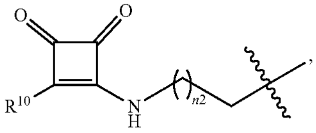

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some aspects, the disclosure relates to a compound of Formula (II-e):

(II-e)

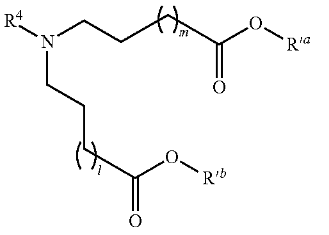

or a salt or isomer thereof, wherein $R'^{a}$ is $R'^{branched}$ or $R'^{cyclic}$; wherein $R'^{branched}$ is:

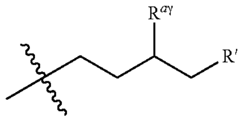

and $R'^{b}$ is:

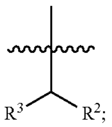

wherein

denotes a point of attachment;

wherein $R^{a\gamma}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is —$(CH_2)_n$OH wherein n is selected from the group consisting of 1, 2, 3, 4, and 5;

R' is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments of the compound of Formula (II), (II-a), (II-b), (II-c), (II-d), or (II-e), m and l are each independently selected from 4, 5, and 6.

In some embodiments of the compound of Formula (II), (II-a), (II-b), (II-c), (II-d), or (II-e), m and l are each 5.

In some embodiments of the compound of Formula (II), (II-a), (II-b), (II-c), (II-d), or (II-e), each R' independently is a $C_{1-12}$ alkyl. In some embodiments of the compound of Formula (II), (II-a), (II-b), (II-c), (II-d), or (II-e), each R' independently is a $C_{2-5}$ alkyl.

In some embodiments of the compound of Formula (II), (II-a), (II-b), (II-c), (II-d), or (II-e), $R'^{b}$ is:

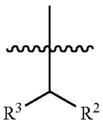

and $R^2$ and $R^3$ are each independently a $C_{1-14}$ alkyl.

In some embodiments of the compound of Formula (II), (II-a), (II-b), (II-c), (II-d), or (II-e), $R'^{b}$ is:

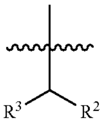

and $R^2$ and $R^3$ are each independently a $C_{6-10}$ alkyl.

In some embodiments of the compound of Formula (II), (II-a), (II-b), (II-c), (II-d), or (II-e), $R'^{b}$ is:

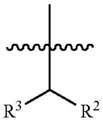

and $R^2$ and $R^3$ are each a $C_8$ alkyl.

In some embodiments of the compound of Formula (II), (II-a), (II-b), (II-c), (II-d), or (II-e), $R'^{branched}$ is:

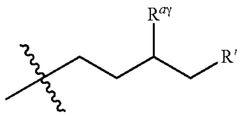

and $R'^{b}$ is:

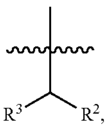

$R^{a\gamma}$ is a $C_{1-12}$ alkyl and $R^2$ and $R^3$ are each independently a $C_{6-10}$ alkyl.

In some embodiments of the compound of Formula (II), (II-a), (II-b), (II-c), (II-d), or (II-e), $R'^{branched}$ is:

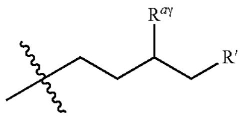

and $R'^{b}$ is:

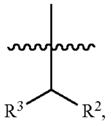

$R^{a\gamma}$ is a $C_{2-6}$ alkyl and $R^2$ and $R^3$ are each independently a $C_{6-10}$ alkyl.

In some embodiments of the compound of Formula (II), (II-a), (II-b), (II-c), (II-d), or (II-e), $R'^{branched}$ is:

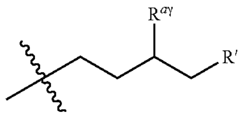

and $R'^{b}$ is:

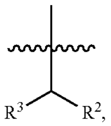

$R^{a\gamma}$ is a $C_{2-6}$ alkyl, and $R^2$ and $R^3$ are each a $C_8$ alkyl.

In some embodiments of the compound of Formula (II), (II-a), (II-b), (II-c), (II-d), or (II-e), $R'^{branched}$ is:

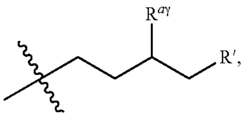

$R'^{b}$ is:

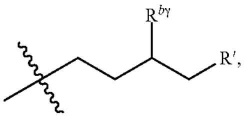

and $R^{a\gamma}$ and $R^{b\gamma}$ are each a $C_{1-12}$ alkyl.

In some embodiments of the compound of Formula (II), (II-a), (II-b), (II-c), (II-d), or (II-e), $R'^{branched}$ is:

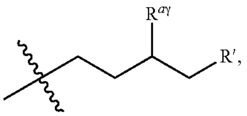

$R'^{b}$ is:

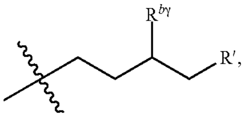

and $R^{a\gamma}$ and $R^{b\gamma}$ are each a $C_{2-6}$ alkyl.

In some embodiments of the compound of Formula (II), (II-b), (II-c), (II-d), or (II-e), m and l are each independently selected from 4, 5, and 6 and each R' independently is a $C_{1-12}$ alkyl.

In some embodiments of the compound of Formula (II), (II-a), (II-b), (II-c), (II-d), or (II-e), m and l are each 5 and each R' independently is a $C_{2-5}$ alkyl.

In some embodiments of the compound of Formula (II), (II-a), (II-b), (II-c), (II-d), or (II-e), $R'^{branched}$ is:

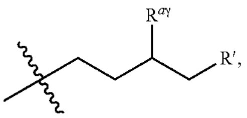

$R^{b}$ is:

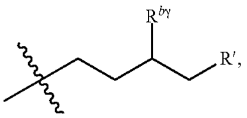

m and l are each independently selected from 4, 5, and 6, each R' independently is a $C_{1-12}$ alkyl, and $R^{a\gamma}$ and $R^{b\gamma}$ are each a $C_{1-12}$ alkyl.

In some embodiments of the compound of Formula (II), (II-a), (II-b), (II-c), (II-d), or (II-e), $R'^{branched}$ is:

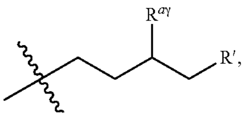

$R'^{b}$ is:

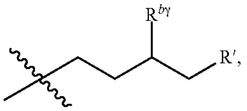

m and l are each 5, each R' independently is a $C_{2-5}$ alkyl, and $R^{a\gamma}$ and $R^{b\gamma}$ are each a $C_{2-6}$ alkyl.

In some embodiments of the compound of Formula (II), (II-a), (II-b), (II-c), (II-d), or (II-e), $R'^{branched}$ is:

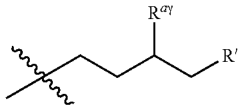

and $R'^{b}$ is:

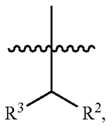

m and l are each independently selected from 4, 5, and 6, R' is a $C_{1-12}$ alkyl, $R^{a\gamma}$ is a $C_{1-12}$ alkyl and $R^2$ and $R^3$ are each independently a $C_{6-10}$ alkyl.

In some embodiments of the compound of Formula (II), (II-a), (II-b), (II-c), (II-d), or (II-e), $R'^{branched}$ is:

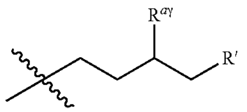

$R'^{b}$ is:

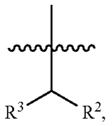

m and l are each 5, R' is a $C_{2-5}$ alkyl, $R^{a\gamma}$ is a $C_{2-6}$ alkyl, and $R^2$ and $R^3$ are each a $C_8$ alkyl.

In some embodiments of the compound of Formula (II), (II-a), (II-b), (II-c), (II-d), or (II-e), $R^4$ is

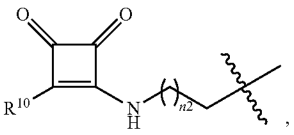

wherein $R^{10}$ is $NH(C_{1-6}$ alkyl) and n2 is 2.

In some embodiments of the compound of Formula (II), (II-a), (II-b), (II-c), (II-d), or (II-e), $R^4$ is

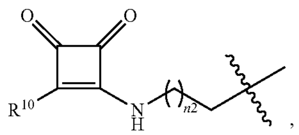

wherein $R^{10}$ is $NH(CH_3)$ and n2 is 2.

In some embodiments of the compound of Formula (II), (II-a), (II-b), (II-c), (II-d), or (II-e), $R'^{branched}$ is:

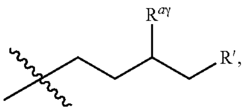

$R'^{b}$ is:

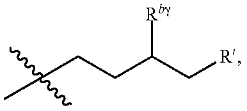

m and l are each independently selected from 4, 5, and 6, each R' independently is a $C_{1-12}$ alkyl, $R^{a\gamma}$ and $R^{b\gamma}$ are each a $C_{1-12}$ alkyl, and $R^4$ is

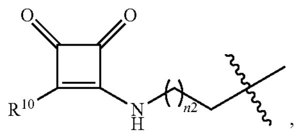

wherein $R^{10}$ is $NH(C_{1-6}$ alkyl), and n2 is 2.

In some embodiments of the compound of Formula (II), (II-a), (II-b), (II-c), (II-d), or (II-e), $R'^{branched}$ is:

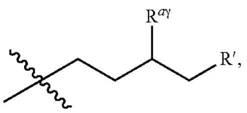

$R'^{b}$ is:

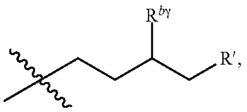

m and l are each 5, each R' independently is a $C_{2-5}$ alkyl, $R^{a\gamma}$ and $R^{b\gamma}$ are each a $C_{2-6}$ alkyl, and $R^4$ is

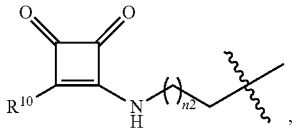

wherein $R^{10}$ is $NH(CH_3)$ and n2 is 2.

In some embodiments of the compound of Formula (II), (II-a), (II-b), (II-c), (II-d), or (II-e), $R'^{branched}$ is:

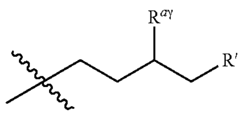

and $R'^{b}$ is:

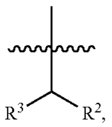

m and l are each independently selected from 4, 5, and 6, R' is a $C_{1-12}$ alkyl, $R^2$ and $R^3$ are each independently a $C_{6-10}$ alkyl, $R^{a\gamma}$ is a $C_{1-12}$ alkyl, and $R^4$ is

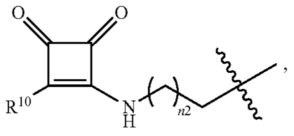

wherein $R^{10}$ is $NH(C_{1-6}$ alkyl) and n2 is 2.

In some embodiments of the compound of Formula (II), (II-a), (II-b), (II-c), (II-d), or (II-e), $R'^{branched}$ is:

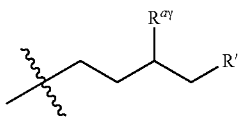

and $R'^{b}$ is:

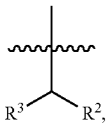

m and l are each 5, R' is a $C_{2-5}$ alkyl, $R^{a\gamma}$ is a $C_{2-6}$ alkyl, $R^2$ and $R^3$ are each a $C_8$ alkyl, and $R^4$ is

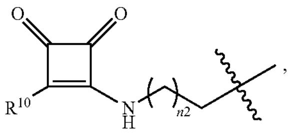

wherein $R^{10}$ is $NH(CH_3)$ and n2 is 2.

In some embodiments of the compound of Formula (II), (II-a), (II-b), (II-c), (II-d), or (II-e), $R^4$ is —$(CH_2)_n$OH and n is 2, 3, or 4. In some embodiments of the compound of Formula (II), (II-a), (II-b), (II-c), (II-d), or (II-e), $R^4$ is —$(CH_2)_n$OH and n is 2.

In some embodiments of the compound of Formula (II), (II-a), (II-b), (II-c), (II-d), or (II-e), $R'^{branched}$ is:

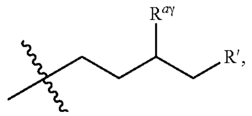

$R'^{b}$ is:

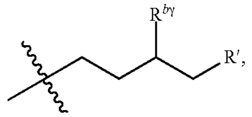

m and l are each independently selected from 4, 5, and 6, each R' independently is a $C_{1-12}$ alkyl, $R^{a\gamma}$ and $R^{b\gamma}$ are each a $C_{1-12}$ alkyl, $R^4$ is —$(CH_2)_n$OH, and n is 2, 3, or 4.

In some embodiments of the compound of Formula (II), (II-a), (II-b), (II-c), (II-d), or (II-e), $R'^{branched}$ is:

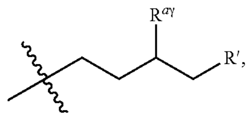

$R'^{b}$ is:

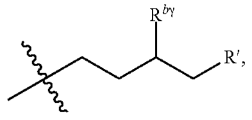

m and l are each 5, each R' independently is a $C_{2-5}$ alkyl, $R^{a\gamma}$ and $R^{b\gamma}$ are each a $C_{2-6}$ alkyl, $R^4$ is —$(CH_2)_n$OH, and n is 2.

In some aspects, the disclosure relates to a compound of Formula (II-f):

(II-f)

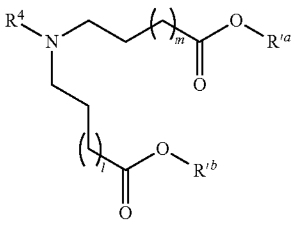

or its N-oxide, or a salt or isomer thereof, wherein $R'^{a}$ is $R'^{branched}$ or $R'^{cyclic}$; wherein $R'^{branched}$ is:

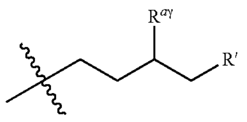

and $R'^{b}$ is:

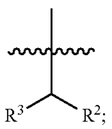

wherein

denotes a point of attachment;

$R^{a\gamma}$ is a $C_{1-12}$ alkyl;

$R^2$ and $R^3$ are each independently a $C_{1-14}$ alkyl;

$R^4$ is —$(CH_2)_nOH$ wherein n is selected from the group consisting of 1, 2, 3, 4, and 5;

R' is a $C_{1-12}$ alkyl;

m is selected from 4, 5, and 6; and l is selected from 4, 5, and 6.

In some embodiments of the compound of Formula (II-f), m and l are each 5, and n is 2, 3, or 4.

In some embodiments of the compound of Formula (II-f) R' is a $C_{2-5}$ alkyl, $R^{a\gamma}$ is a $C_{2-6}$ alkyl, and $R^2$ and $R^3$ are each a $C_{6-10}$ alkyl.

In some embodiments of the compound of Formula (II-f), m and l are each 5, n is 2, 3, or 4, R' is a $C_{2-5}$ alkyl, $R^{a\gamma}$ is a $C_{2-6}$ alkyl, and $R^2$ and $R^3$ are each a $C_{6-10}$ alkyl.

In some aspects, the disclosure relates to a compound of Formula (II-g):

(II-g)

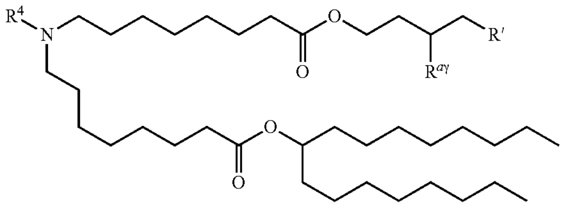

, wherein $R^{a\gamma}$ is a $C_{2-6}$ alkyl;

R' is a $C_{2-5}$ alkyl; and $R^4$ is selected from the group consisting of —$(CH_2)_nOH$ wherein n is selected from the group consisting of 3, 4, and 5, and

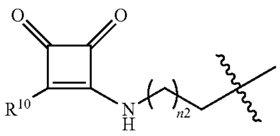

, wherein

denotes a point of attachment, $R^{10}$ is $NH(C_{1-6}$ alkyl), and n2 is selected from the group consisting of 1, 2, and 3.

In some aspects, the disclosure relates to a compound of Formula (II-h):

(II-h)

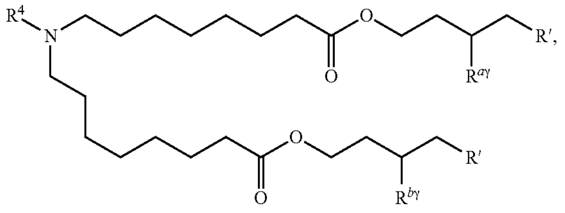

wherein $R^{a\gamma}$ and $R^{b\gamma}$ are each independently a $C_{2-6}$ alkyl;

each R' independently is a $C_{2-5}$ alkyl; and $R^4$ is selected from the group consisting of —$(CH_2)_nOH$ wherein n is selected from the group consisting of 3, 4, and 5, and

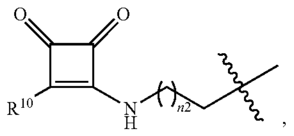

wherein

denotes a point of attachment, $R^{10}$ is $NH(C_{1-6}$ alkyl), and n2 is selected from the group consisting of 1, 2, and 3.

In some embodiments of the compound of Formula (II-g) or (II-h), $R^4$ is

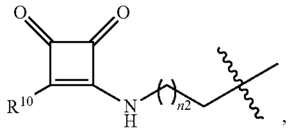

wherein $R^{10}$ is $NH(CH_3)$ and n2 is 2.

In some embodiments of the compound of Formula (II-g) or (II-h), $R^4$ is $-(CH_2)_2OH$.

In some aspects, the disclosure relates to a compound having the Formula (III):

(III)

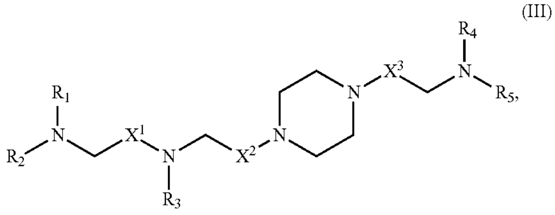

or a salt or isomer thereof, wherein $R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, $-S(O)_2-$, an aryl group, and a heteroaryl group;

$X^1$, $X^2$, and $X^3$ are independently selected from the group consisting of a bond, $-CH_2-$, $-(CH_2)_2-$, —CHR—, —CHY—, —C(O)—, —C(O)O—, —OC(O)—, $-C(O)-CH_2-$, $-CH_2-C(O)-$, $-C(O)O-CH_2-$, $-OC(O)-CH_2-$, $-CH_2-C(O)O-$, $-CH_2-OC(O)-$, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, and wherein:

i) at least one of $X^1$, $X^2$, and $X^3$ is not $-CH_2-$; and/or ii) at least one of $R_1$, $R_2$, $R_3$, $R_4$, and $R_5$ is —R"MR'.

In some embodiments, $R_1$, $R_2$, $R_3$, $R_4$, and $R_5$ are each $C_{5-20}$ alkyl; $X^1$ is $-CH_2-$; and $X^2$ and $X^3$ are each —C(O)—.

In some embodiments, the compound of Formula (III) is:

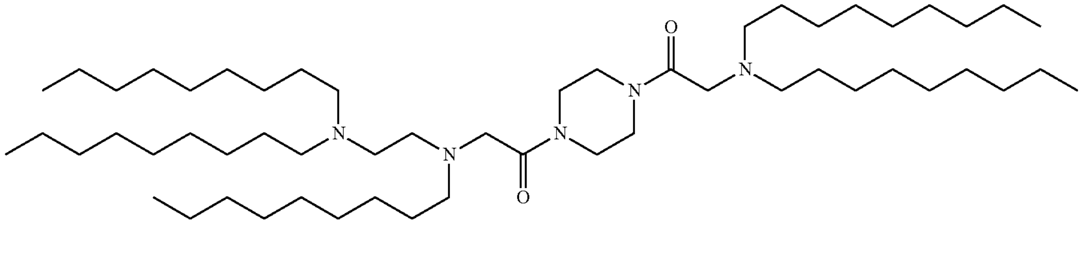 [SMILES: CCCCCCCCCN(CCCCCCCCC)CCN(CCCCCCCCC)CC(=O)N1CCN(C(=O)CN(CCCCCCCCC)CCCCCCCCC)CC1]

.

In some embodiments, the ionizable lipids are one or more of the compounds described in WO/2020/146805; WO/2020/081938; WO/2020/214946; WO/2019/036030; WO/2019/036000; WO/2019/036028; WO/2019/036008; WO/2018/200943; WO/2018/191657; WO/2017/117528; WO/2017/075531; WO/2017/004143; WO/2015/199952; and WO/2015/074085; each of which is incorporated herein in its entirety.

In some embodiments, the ionizable lipids are one or more of the compounds described in WO/2020/146805 having structure:

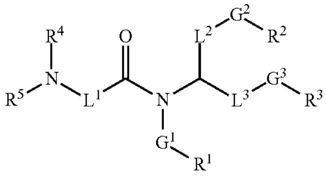

or a pharmaceutically acceptable salt, tautomer, or stereoisomer thereof, wherein:

$R^1$ is optionally substituted $C_{1-24}$ alkyl or optionally substituted $C_2$-$C_{24}$ alkenyl;

$R^2$ and $R^3$ are each independently optionally substituted $C_1$-$C_{36}$ alkyl;

$R^4$ and $R^5$ are each independently optionally substituted $C_1$-$C_6$ alkyl, or $R^4$ and $R^5$ join, along with the N to which they are attached, to form a heterocyclyl or heteroaryl;

$L^1$, $L^2$, and $L^3$ are each independently optionally substituted $C_1$-$C_{18}$ alkylene;

$G^1$ is a direct bond, $-(CH_2)_nO(C{=}O)-$, $-(CH_2)_n(C{=}O)O-$ or $-(C{=})-$;

$G^2$ and $G^3$ are each independently $-(C{=}O)O-$ or $-O(C{=}O)-$; and n is an integer greater than 0.

In some embodiments, the ionizable lipids are one or more of the compounds described in WO/2020/081938 having structure:

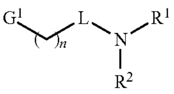

or a pharmaceutically acceptable salt, tautomer or stereoisomer thereof, wherein:

$G^1$ is $-N(R^3)R^4$ or $-OR^5$;

$R^1$ is optionally substituted branched, saturated or unsaturated $C_{12}$-$C_{36}$ alkyl;

$R^2$ is optionally substituted branched or unbranched, saturated or unsaturated $C_{12}$-$C_{36}$ alkyl when L is $-C({=}O)-$; or $R^2$ is optionally substituted branched or unbranched, saturated or unsaturated $C_4$-$C_{36}$ alkyl when L is $C_6$-$C_{12}$ alkylene, $C_6$-$C_{12}$ alkenylene, or $C_2$-$C_6$ alkynylene;

$R^3$ and $R^4$ are each independently H, optionally substituted branched or unbranched, saturated or unsaturated $C_1$-$C_6$ alkyl; or $R^3$ and $R^4$ are each independently optionally substituted branched or unbranched, saturated or unsaturated $C_1$-$C_6$ alkyl when L is $C_6$-$C_{12}$ alkylene, $C_6$-$C_{12}$ alkenylene, or $C_2$-$C_6$ alkynylene; or $R^3$ and $R^4$, together with the nitrogen to which they are attached, join to form a heterocyclyl;

$R^5$ is H or optionally substituted $C_1$-$C_6$ alkyl;

L is $-C({=}O)-$, $C_6$-$C_{12}$ alkylene, $C_6$-$C_{12}$ alkenylene, or $C_2$-$C_{12}$alkynylene (e.g., $C_2$-$C_6$ alkynylene); and n is an integer from 1 to 12.

In some embodiments, the ionizable lipids are one or more of the compounds described in WO/2020/214946 having structure:

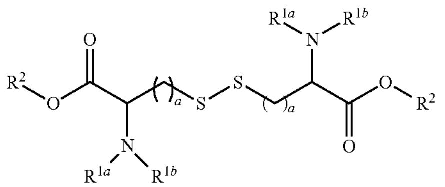

or a pharmaceutically acceptable salt thereof, wherein each $R^{1a}$ is independently hydrogen, $R^{1c}$, or $R^{3d}$;

each $R^{1b}$ is independently $R^{1c}$ or $R^{1d}$;

each $R^{1c}$ is Independently $-(CH)_2C(O)X^1R^3$;

each $R^{1d}$ is independently $-C(O)R^4$;

each $R^2$ is independently $-[C(R^{2a})_2]_c$; $R^{2b}$;

each $R^{2a}$ is independently hydrogen or lower alkyl (e.g., $C_1$-$C_6$alkyl);

$R^{2b}$ is $-N(L_1\text{-}B)_2$, $-(OCH_2CH_2)_6OH$; or $-(OCH_2CH_2)_6OCH_3$;

each $R^3$ and $R^4$ is independently aliphatic (e.g., $C_6$-$C_{30}$ aliphatic);

each $L_1$ is independently alkylene (e.g., $C_1$-$C_{10}$ alkylene);

each B is independently hydrogen or an ionizable nitrogen-containing group;

each $X^1$ is independently a covalent bond or O;

each a is independently an integer (e.g., 1-10);

each b is independently an integer (e.g., 1-10); and each c is independently an integer (e.g., 1-10).

In some embodiments, the ionizable lipids are one or more of the compounds described in WO/2019/036030 having the structure:

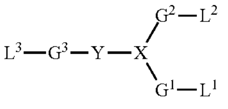

or a pharmaceutically acceptable salt, prodrug or stereoisomer thereof, wherein:

X is N, and Y is absent; or X is CR, and Y is NR;

$L^1$ is $-O(C{=}O)R^1$, $-(C{=}O)OR^1$, $-C({=}O)R^1$, $-OR^1$, $S(O)_xR^1$, $-S-SR^1$, $-C({=}O)SR^1$, $-SC({=}O)R^1$, $-NR^aC({=}O)R^1$, $-C({=}O)NR^bR^c$, $-NR^aC({=}O)NR^bR^c$, $-OC({=}O)NR^bR^c$ or $-NR^aC({=}O)OR^1$;

$L^2$ is $-O(C{=}O)R^2$, $-(C{=}O)OR^2$, $-C({=}O)R^2$, $-OR^2$, $-S(O)_xR^2$, $-S-SR^2$, $-C({=}O)SR^2$, $-SC({=}O)R^2$, $-NR^dC(({=}O)R^2$, $-C({=}O)NR^eR^f$, $-NR^dC({=}O)NR^eR^f$, $-OC({=}O)NR^eR^f$; $-NR^dC({=}O)OR^2$ or a direct bond to $R^2$;

$L^3$ is $-O(C{=}O)R^3$ or $-(C{=}O)OR^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene when X is CR, and Y is NR; and $G^3$ is $C_1$-$C_{24}$ heteroalkylene or $C_2$-$C_{24}$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In some embodiments, the ionizable lipids are one or more of the compounds described in WO/2019/036000 having the structure:

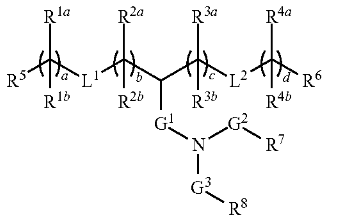

or a pharmaceutically acceptable salt, tautomer, prodrug or stereoisomer thereof, wherein:

$L^1$ and $L^2$ are each independently —O(C═O)—, —(C═O)O—, —C(═O)—, —O—, —S(O)$_x$—, —S—S—, —C(═O)S—, —SC(═O)—, —NR$^a$C(O)—, —C(═O)NR$^a$—, —NR$^a$C(═O)NR$^a$—, —OC(═O)NR$^a$—, —NR$^a$C(═O)O— or a direct bond;

$G^1$ is $C_1$-$C_2$ alkylene, —(C═O)—, —O(C═O)—, —SC(═O)—, —NR$^a$C(═O)— or a direct bond;

$G^2$ is —C(═O)—, —(C═O)O—, —C(═O)S—, —C(═O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is H or $C_1$-$C_{20}$ alkyl;

$R^8$ is OH, —N($R^9$)(C═O)$R^{10}$, —(C═O)N$R^9R^{10}$, —N$R^9R^{10}$, —(C═O)O$R^{11}$ or —O(C═O)$R^{11}$, provided that $G^3$ is $C_4$-$C_6$ alkylene when $R^8$ is —N$R^9R^{10}$, $R^9$ and $R^{10}$ are each independently H or $C_1$-$C_{12}$ alkyl;

$R^{11}$ is aralkyl;

a, b, c and d are each independently an integer from 1 to 24; and x is 0, 1 or 2, wherein each alkyl, alkylene and aralkyl is optionally substituted.

In some embodiments, the ionizable lipids are one or more of the compounds described in WO/2019/036028 having the structure:

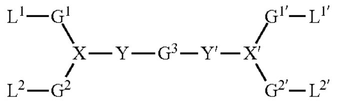

or a pharmaceutically acceptable salt, prodrug or stereoisomer thereof, wherein:

X and X' are each independently N or CR;

Y and Y' are each independently absent, —O(C═O)—, —(C═O)O— or NR, provided that:

a) Y is absent when X is N;

b) Y' is absent when X' is N;

c) Y is —O(C═O)—, —(C═O)O— or NR when X is CR; and d) Y' is —O(C═O)—, —(C═O)O— or NR when X' is CR, $L^1$ and $L^{1'}$ are each independently —O(C═O)$R^1$, —(C═O)O$R^2$, —C(═O)$R^2$, —O$R^2$, —S(O)$_z R^1$, —S—S$R^2$, —C(═O)S$R^2$, —SC(═O)R', —NR$^d$C(═O)$R^2$, —C(═O)NR$^b$R$^c$, —NR$^a$C(═O)NR$^b$R$^c$, —OC(═O)NR$^b$R$^c$ or —NR$^d$C(═O)O$R^1$;

$L^2$ and $L^{2'}$ are each independently —O(C═O)$R^2$, —(C═O)O$R^2$, —C(═O)$R^2$, —O$R^2$, —S(O)$_z R^2$, —S—S$R^2$, —C(═O)S$R^2$, —SC(═O)$R^2$, —NR$^d$C(═O)$R^2$, —C(═O))NR$^e$R$^f$, —NR$^d$C(═O)NR$^e$R$^f$, —OC(═O)NR$^e$R$^f$; —NR$^d$C(═O)O$R^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

$G^3$ is $C_2$-$C_{24}$ heteroalkylene or $C_2$-$C_{24}$ heteroalkenylene;

$R^a$, $R^b$, $R^d$ and $R^e$ are, at each occurrence, independently H, $C_1$-$C_{12}$ alkyl or $C_2$-$C_{12}$ alkenyl;

$R^e$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, heteroalkylene and heteroalkenylene is independently substituted or unsubstituted unless otherwise specified.

In some embodiments, the ionizable lipids are one or more of the compounds described in WO/2019/036008 have the structure:

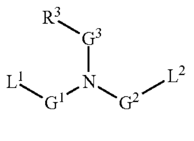

or a pharmaceutically acceptable salt, prodrug or stereoisomer thereof, wherein:

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)(I)$R^1$;

$L^2$ is —O(C═O)$R^2$, —(C═O)O$R^2$, —C(═O)R', —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$(═O)N$R^e$$R^f$, —OC(═O)N$R^e$$R^f$ or —N$R^d$C(═O)O$R^2$ or a direct bond to $R^2$;

$G^1$ and $G^2$ are each independently $C_2$-$C_{12}$ alkylene or $C_2$-$C_{12}$ alkenylene;

$G^3$ is $C_1$-$C_4$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^3$ is —N($R^4$)$R^5$;

$R^4$ is $C_1$-$C_{12}$ alkyl;

$R^5$ is substituted $C_1$-$C_{12}$ alkyl;

and x is 0, 1 or 2, and wherein each alkyl, alkenyl, alkylene, alkenylene, cycloalkylene, cycloalkenylene, aryl and aralkyl is independently substituted or unsubstituted unless otherwise specified.

In some embodiments, the ionizable lipids are one or more of the compounds described in WO 2018/200943 having the structure:

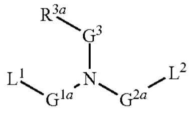

or

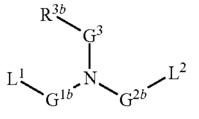

or a pharmaceutically acceptable salt, prodrug or stereoisomer thereof, wherein:

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(O)N$R^b$$R^c$, —OC(═O)N$R^b$$R^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$(═O)N$R^e$$R^f$, —OC(═O)N$R^e$$R^f$; —N$R^d$C(═O)O$R^2$ or a direct bond to $R^2$;

$G^{1a}$ and $G^{2a}$ are each independently $C_2$-$C_{12}$ alkylene or $C_2$-$C_2$ alkenylene;

$G^{1b}$ and $G^{2a}$ are each independently $C_1$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^{3a}$ is —C(═O)N($R^{4a}$)$R^{5a}$ or —C(═O)O$R^6$;

$R^{3b}$ is —N$R^{4b}$ C(═O)$R^{5b}$;

$R^{4a}$ is $C_1$-$C_{12}$ alkyl;

$R^{4b}$ is H, $C_1$-$C_{12}$ alkyl or $C_2$-$C_{12}$ alkenyl;

$R^{5a}$ is H, $C_1$-$C_8$ alkyl or $C_2$-$C_8$ alkenyl;

$R^{5b}$ is $C_2$-$C_{12}$ alkyl or $C_2$-$C_2$ alkenyl when $R^{4b}$ is H; or $R^{5b}$ is $C_1$-$C_{12}$ alkyl or $C_2$-$C_{12}$ alkenyl when $R^{4b}$ is $C_1$-$C_{12}$ alkyl or $C_2$-$C_{12}$ alkenyl;

$R^6$ is H, aryl or aralkyl; and x is 0, 1 or 2, and wherein each alkyl, alkenyl, alkylene, alkenylene, cycloalkylene, cycloalkenylene, aryl, and aralkyl is independently substituted or unsubstituted.

In some embodiments, the ionizable lipids are one or more of the compounds described in WO/2018/191657 having the structure

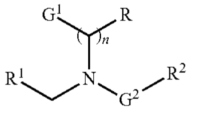

or a pharmaceutically acceptable salt, prodrug or stereoisomer thereof, wherein:

$G^1$ is —OH, —N$R^3$$R^4$, —(C═O)N$R^5$ or —N$R^3$(C═O)$R^5$;

$G^2$ is —$CH_2$— or —(C═O)—;

R is, at each occurrence, independently H or OH;

$R^1$ and $R^2$ are each independently optionally substituted branched, saturated or unsaturated $C_{12}$-$C_{36}$ alkyl;

$R^3$ and $R^4$ are each independently 1 or optionally substituted straight or branched, saturated or unsaturated $C_1$-$C_6$ alkyl;

$R^5$ is optionally substituted straight or branched, saturated or unsaturated $C_1$-$C_6$ alkyl; and n is an integer from 2 to 6.

In some embodiments, the ionizable lipids are one or more of the compounds described in WO/2017/117528 having the structure:

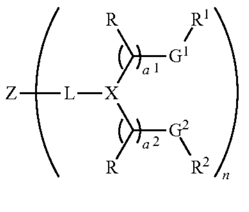

or a pharmaceutically acceptable salt, prodrug or stereoisomer thereof, wherein:

one of $G^1$ or $G^2$ is, at each occurrence, —O(C═O)—, —(C═O)O—, —C(═O)—, —O—, —S(O)—$_y$, —S—S—, —C(═O)S—, SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O—, and the other of $G^1$ or $G^2$ is, at each occurrence, —O(C═O)—, —(C═O)O—, —C(═O)—, —O—, —S(O)$_y$, —S—S—, —C(═O)S—, —SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O— or a direct bond;

L is, at each occurrence, ~O(C═O)—, wherein ~ represents a covalent bond to X;

X is C$R^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

$R^1$

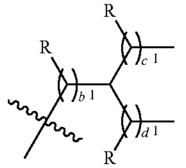

and $R^2$

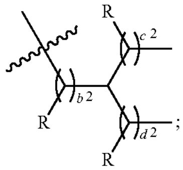

;

$a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 5 to 10;

$d^1$ and $d^2$ are, at each occurrence, independently an integer from 5 to 10;

y is, at each occurrence, independently an integer from 0 to 2; and n is an integer from 1 to 6, wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In some embodiments, the ionizable lipids are one or more of the compounds described in WO 2017/075531 having the structure:

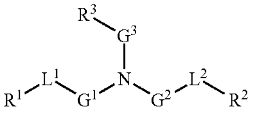

or a pharmaceutically acceptable salt, prodrug or stereoisomer thereof, wherein:

one of $L^1$ or $L^2$ is —O(C═O)—, —(C═O)O—, —C(═O)—, —O—, —S(O)$_x$—, —S—S—, —C(═O)S—, —SC(═O)—, —NR$^a$C(═O)—, —C(═O)N$^a$—, NR$^a$C(O)NR$^a$—, —OC(═O)NR$^a$— or —NR$^a$C(═O)O—, and the other of $L^1$ or $L^2$ is —O(C═O)—, —(C═O)O—, —C(═O)—, —O—, —S(O)$_x$—, —S—S—, —C(═O)S—, SC(═O), —NR$^a$C(═O)—, —C(═O)NR$^a$—, NR$^a$C(═O)NR$^a$—, —OC(═O)NR$^a$— or —NR$^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)OR$^4$, —OC(═O)R$^4$ or —NR$^5$C(═O)R$^4$;

$R^4$ is $C_1$-$C_{12}$ alkyl;

$R^5$ is H or $C_1$-$C_6$ alkyl; and x is 0, 1 or 2.

In some embodiments, the ionizable lipids are one or more of the compounds described in WO 2017/004143 having the structure:

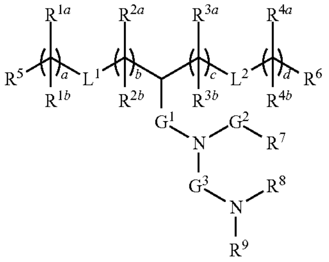

or a pharmaceutically acceptable salt, tautomer, prodrug or stereoisomer thereof, wherein:

$L^1$ and $L^2$ are each independently —O(C═O)—, —(C═O)O—, —C(═O)—, —O—, —S(O)$_x$—, —S—S—, —C(═O)S—, —SC(═O)—, —NR$^a$C(═O)—, —C(═O)NR$^a$—, —NR$^a$C(═O)NR$^a$—, —OC(═O)NR$^a$—, —NR$^a$C(═O)O— or a direct bond;

$G^1$ is $C_1$-$C_{22}$ alkylene, —(C═O)—, —O(C═O)—, —SC(═O)—, —NR$^a$C(═O)— or a direct bond;

$G^2$ is —C(═O)—, —(C═O)O—, —C(═O)S—, —C(═O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments, the ionizable lipids are one or more of the compounds described in WO 2015/199952 having the structure:

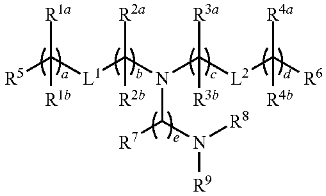

or a pharmaceutically acceptable salt, tautomer, prodrug or stereoisomer thereof, wherein:

$L^1$ and $L^2$ are each independently —O(C═O)—, —(C═O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2, provided that:

at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—; and $R^{1a}$ and $R^{1b}$ are not isopropyl when a is 6 or n-butyl when a is 8.

In some embodiments, the ionizable lipids are one or more of the compounds described in WO/2015/074085 having the structure:

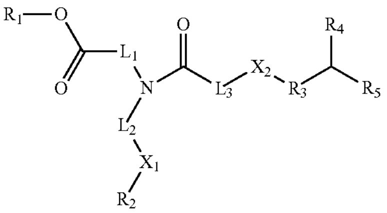

wherein $R_1$ and $R_2$ are the same or different, each a linear or branched alkyl with 1-9 carbons, or an alkenyl or alkynyl with 2 to 11 carbon atoms, $L_1$ and $L_2$ are the same or different, each a linear alkyl having 5 to 18 carbon atoms, or form a heterocycle with N, $X_1$ is a bond, or is —CO—O— whereby $L_2$-CO—O—$R_2$ is formed $X_2$ is S or O, $L_3$ is a bond or a lower alkyl, or form a heterocycle with N, $R_3$ is a lower alkyl, and $R_4$ and $R_5$ are the same or different, each a lower alkyl;

or a pharmaceutically acceptable salt thereof.

In some embodiments, the ionizable lipids are one or more of the compounds described in Buschmann, M. D. et al., Vaccines, 2021, 9, 65, which incorporated herein in its entirety (the structures provided below include their theoretical pKas):

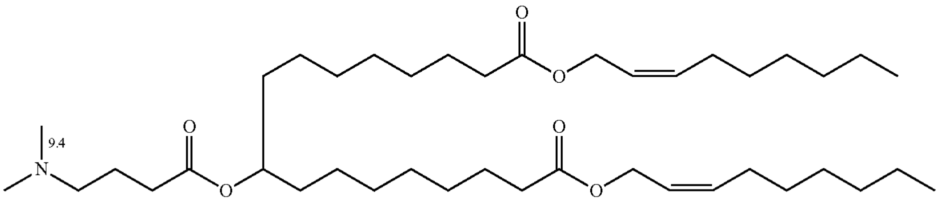

-continued
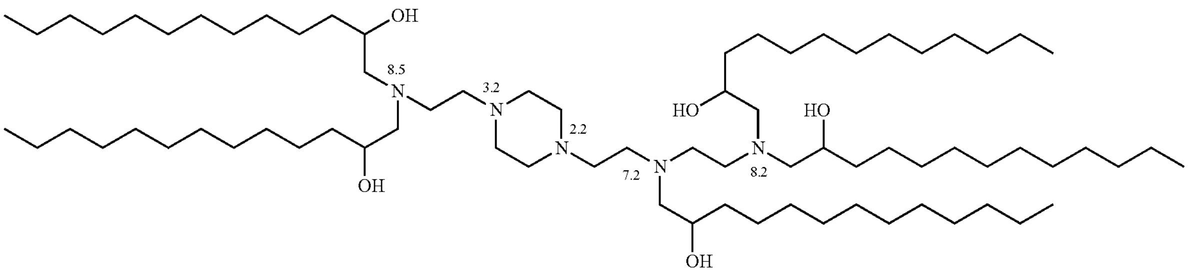
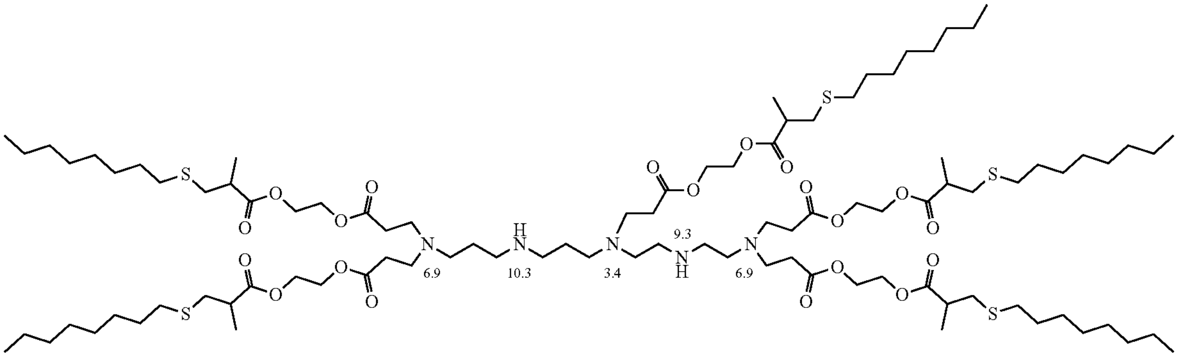
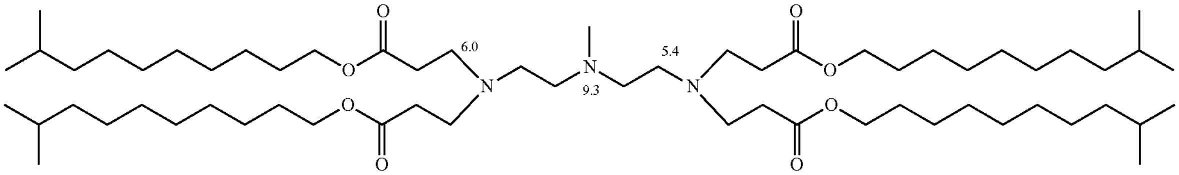
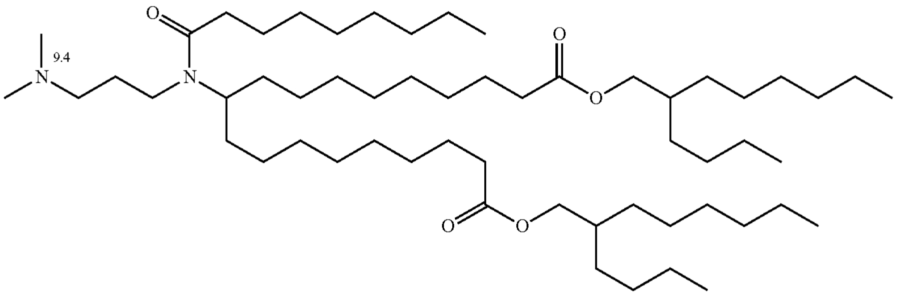
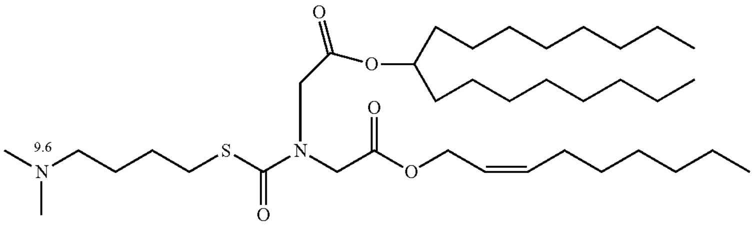
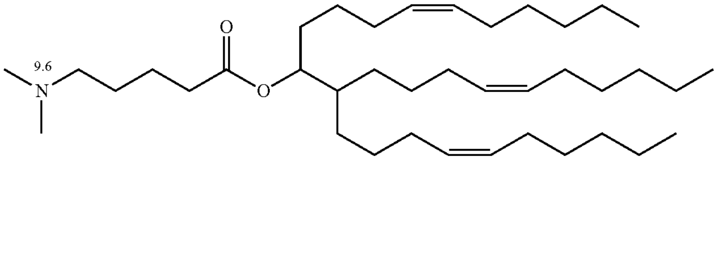

In some embodiments, the ionizable lipid is selected from Compound II, Compound III, Compound VI, Compound A1, and Compound A2:

Compound II

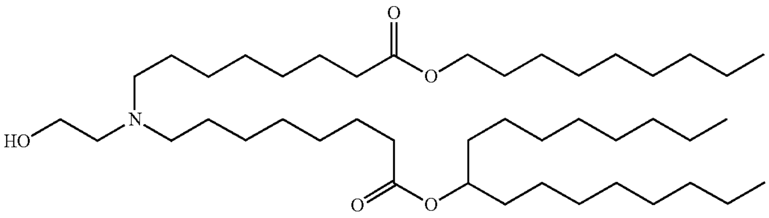

Compound III

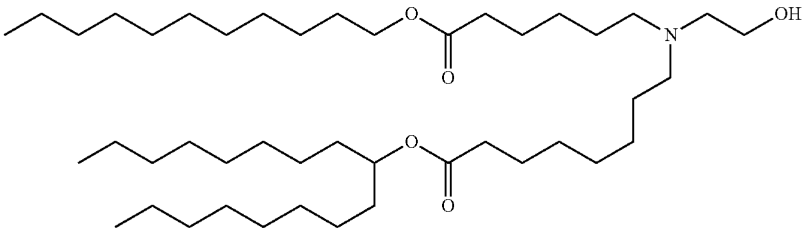

Compound VI

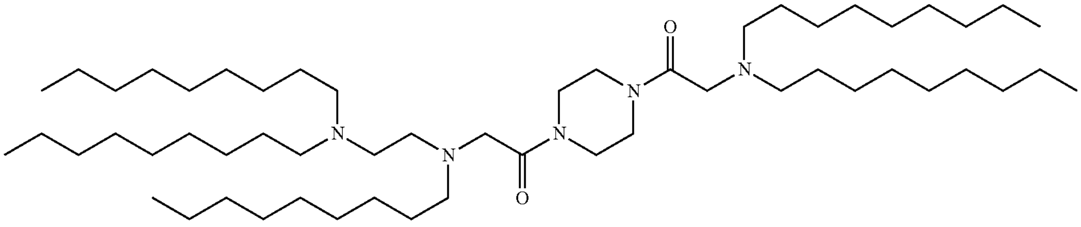

Compound A1

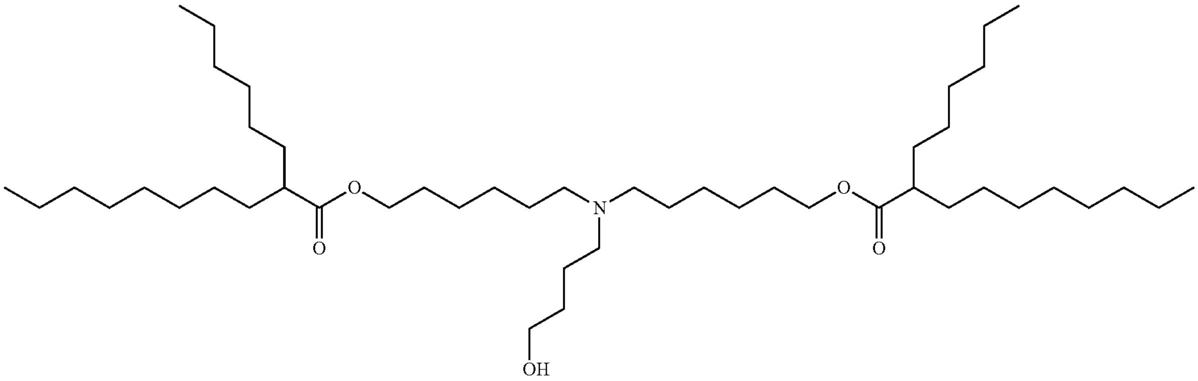

Compound A2

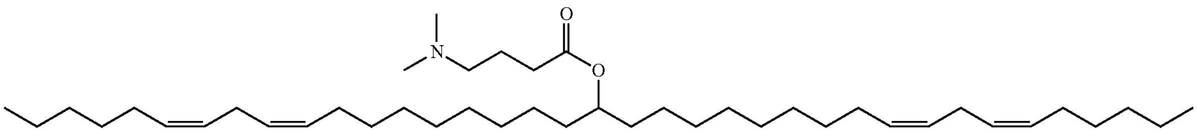

ii. Polynucleotides Polynucleotides for use in accordance with the present disclosure include, but are not limited to, one or more of DNA, RNA including messenger RNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

In some embodiments, the polynucleotide is RNA. In some embodiments, the polynucleotide is mRNA.

In some embodiments, the polynucleotide (e.g., a RNA, e.g., an mRNA) of the lipid nanoparticle comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,187 to 1,200, from 1,187 to 1,400, from 1,187 to 1,600, from 1,187 to 1,800, from 1,187 to 2,000, from 1,187 to 3,000, from 1,187 to 5,000, from 1,187 to 7,000, from 1,187 to 10,000, from 1,187 to 25,000, from 1,187 to 50,000, from 1,187 to 70,000, or from 1,187 to 100,000 nucleotides).

In some embodiments, the polynucleotide (e.g., a RNA, e.g., an mRNA) of the lipid nanoparticle comprises a nucleotide sequence (e.g., an open reading frame (ORF)) encoding a polypeptide, wherein the length of the nucleotide sequence (e.g., an ORF) is at least 500 nucleotides in length, e.g., at least about 500, 600, 700, 80, 900, 1,000, 1,050, 1,100, 1,187, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, or 90,000 nucleotides. In some embodiments, the length is up to and including 100,000 nucleotides.

In some embodiments, the polynucleotide of the composition that comprises a nucleotide sequence (e.g., an ORF) encoding a polypeptide is DNA.

In some embodiments, the polynucleotide of the composition is RNA. In some embodiments, the polynucleotide is, or functions as, an mRNA. In some embodiments, the mRNA comprises a nucleotide sequence (e.g., an ORF) that encodes at least one polypeptide, and is capable of being translated to produce the encoded polypeptide in vitro, in vivo, in situ or ex vivo.

In some embodiments, the polynucleotide (e.g., a RNA, e.g., an mRNA) of the lipid nanoparticle comprises a nucleotide sequence (e.g., an ORF) encoding a polypeptide and further comprises at least one nucleic acid sequence that is noncoding, e.g., a microRNA binding site, e.g., a miRNA binding site that binds to miR-142 and/or a miRNA binding site that binds to miR-126.

In some embodiments, the polynucleotide (e.g., a RNA, e.g., an mRNA) of the lipid nanoparticle comprises a 5'-UTR and a 3'UTR.

In some embodiments, the polynucleotide (e.g., a RNA, e.g., an mRNA) of the lipid nanoparticle comprises a 5' terminal cap. Nonlimiting examples of 5' terminal caps include Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the polynucleotide (e.g., a RNA, e.g., an mRNA) of the lipid nanoparticle comprises a poly-A-tail. In some embodiments, the polyA tail is about 100 nucleotides in length. In some instances, the poly A tail is 100 nucleotides in length. In some instances, the poly A tail is 50-150, 75-150, 85-150, 90-150, 90-120, 90-130, or 90-150 nucleotides in length.

The polynucleotides (e.g., a RNA, e.g., an mRNA) can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes a polypeptide of interest, such as a therapeutic polypeptide.

In some embodiments, the "signal sequence" or "signal peptide" is a polynucleotide or polypeptide, respectively, which is from about 30-210, e.g., about 45-80 or 15-60 nucleotides (e.g., about 20, 30, 40, 50, 60, or 70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide (e.g., a RNA, e.g., an mRNA) is sequence optimized. In some embodiments, the polynucleotide (e.g., a RNA, e.g., an mRNA) comprises a 5' cap, a 5'-UTR, a nucleotide sequence (e.g., an ORF, e.g., a sequence optimized ORF) encoding a polypeptide, a 3'-UTR, and a polyA tail, or any combination thereof, the 5' UTR or 3' UTR optionally comprising at least one microRNA binding site.

A sequence-optimized nucleotide sequence, e.g., a codon-optimized mRNA sequence encoding a polypeptide, is a sequence comprising at least one synonymous nucleobase substitution with respect to a reference sequence (e.g., a wild type nucleotide sequence encoding the polypeptide).

A sequence-optimized nucleotide sequence can be partially or completely different in sequence from the reference sequence. For example, a reference sequence encoding polyserine uniformly encoded by UCU codons can be sequence-optimized by having 100% of its nucleobases substituted (for each codon, U in position 1 replaced by A, C in position 2 replaced by G, and U in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or are proprietary methods.

In some embodiments, the sequence optimization method is multiparametric and comprises one, two, three, four, or more methods disclosed herein and/or other optimization methods known in the art.

In some embodiments, a polynucleotide (e.g., a RNA, e.g., an mRNA) of the composition comprises a sequence-optimized nucleotide sequence (e.g., an ORF) encoding a polypeptide, wherein the polypeptide encoded by the sequence-optimized nucleotide sequence has improved properties (e.g., compared to the polypeptide as encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or preventing misfolding of the expressed proteins, reducing toxicity of the expressed products, reducing cell death caused by the expressed products, increasing and/or decreasing protein aggregation.

In some embodiments, the sequence-optimized nucleotide sequence (e.g., an ORF) is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

Methods for optimizing codon usage are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or are proprietary methods. In some embodiments, the open reading frame (ORF) sequence is optimized using optimization algorithms.

Features, which can be considered beneficial in some embodiments, can be encoded by or within regions of the polynucleotide and such regions can be upstream (5') to, downstream (3') to, or within the region that encodes the polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide comprises a 5' UTR, a 3' UTR and/or a microRNA binding site. In some embodiments, the polynucleotide comprises two or more 5' UTRs and/or 3' UTRs, which can be the same or different sequences. In some embodiments, the polynucleotide comprises two or more microRNA binding sites, which can be the same or different sequences. Any portion of the 5' UTR, 3' UTR, and/or microRNA binding site, including none, can be sequence-optimized and can independently contain one or more different structural or chemical modifications, before and/or after sequence optimization.

In some embodiments, the polynucleotides of the compositions are modified. The modified polynucleotides can be chemically modified and/or structurally modified. When the polynucleotides of the compositions are chemically and/or structurally modified the polynucleotides can be referred to as "modified polynucleotides."

The present disclosure provides for modified nucleosides and modified nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell, can exhibit one or more desirable properties, e.g., improved protein expression, reduced immunogenicity, or reduced degradation in the cell, as compared to an unmodified polynucleotide.

In some embodiments, a polynucleotide of the lipid nanoparticles are structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

Therapeutic lipid nanoparticles comprise, in some embodiments, at least one nucleic acid (e.g., RNA), wherein the nucleic acid comprises nucleotides and/or nucleosides that can be standard (unmodified) or modified as is known in the art. In some embodiments, nucleotides and nucleosides comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleoside is one as is generally known or recognized in the art. Non-limiting examples of such naturally occurring modified nucleotides and nucleosides can be found, inter alia, in the MODOMICS database.

In some embodiments, a non-naturally occurring modified nucleotide or nucleoside is one as is generally known or recognized in the art. Non-limiting examples of such non-naturally occurring modified nucleotides and nucleosides can be found, inter alia, in published International Patent Application Nos. PCT/US2012/058519; PCT/US2013/075177; PCT/US2014/058897; PCT/US2014/058891; PCT/

US2014/070413; PCT/US2015/36773; PCT/US2015/36759; PCT/US2015/36771; or PCT/IB2017/051367, each of which is incorporated by reference herein in its entirety.

In some embodiments, at least one RNA (e.g., mRNA) is not chemically modified and comprises the standard ribonucleotides consisting of adenosine, guanosine, cytosine and uridine. In some embodiments, nucleotides and nucleosides comprise standard nucleoside residues such as those present in transcribed RNA (e.g. A, G, C, or U). In some embodiments, nucleotides and nucleosides comprise standard deoxyribonucleosides such as those present in DNA (e.g. dA, dG, dC, or dT).

Hence, nucleic acids (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminus of a chain or anywhere else in the chain. Any of the regions of a nucleic acid may be chemically modified.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as in those nucleic acids having at least one chemical modification. One example of such non-standard base pairing is the base pairing between the modified nucleotide inosine and adenine, cytosine or uracil. Any combination of base/sugar or linker may be incorporated into nucleic acids.

In some embodiments, modified nucleobases in nucleic acids (e.g., RNA nucleic acids, such as mRNA nucleic acids) comprise N1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with N1-methyl-pseudouridine, meaning that all uridine residues in the mRNA sequence are replaced with N1-methyl-pseudouridine. Similarly, a nucleic acid can be uniformly modified for any type of nucleoside residue present in the sequence by replacement with a modified residue such as those set forth above.

The nucleic acids may be partially or fully modified along the entire length of the molecule. For example, one or more or all or a given type of nucleotide (e.g., purine or pyrimidine, or any one or more or all of A, G, U, C) may be uniformly modified in a nucleic acid, or in a predetermined sequence region thereof (e.g., in the mRNA including or excluding the polyA tail). In some embodiments, all nucleotides X in a nucleic acid (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

The polynucleotides of the lipid nanoparticles can be generated using components, compositions, and methods as are generally known in the art, see, e.g., International Patent Application Publication Nos. WO 2015/051173, WO 2017/049286, WO 2016/100812, WO 2016/014846, WO 2016/011226, WO 2016/011222, WO 2016/011306, WO 2015/196128, WO 2013/151736, WO 2013/151672, WO 2013/151671, WO 2013/151670, WO 2013/151669, WO 2013/151668, WO 2013/151666, WO 2013/151667, WO 2013/151665, WO 2013/151664, WO 2013/151663, WO 2013/151736, WO 2013/151668, WO 2013/151666, WO 2013/151665, WO 2013/151670, WO 2013/151672, WO 2015/089511, WO 2015/051173, WO 2015/051169, each of which is incorporated by reference herein in its entirety.

In some aspects, a polynucleotide (e.g., a RNA, e.g., an mRNA) disclosed herein can be constructed using in vitro transcription (IVT). In other aspects, a polynucleotide (e.g., a RNA, e.g., an mRNA) disclosed herein can be constructed by chemical synthesis using an oligonucleotide synthesizer.

In other aspects, a polynucleotide (e.g., a RNA, e.g., an mRNA) disclosed herein is made by using a host cell. In certain aspects, a polynucleotide (e.g., a RNA, e.g., an mRNA) disclosed herein is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA). The resultant polynucleotides, e.g., mRNAs, can then be examined for their ability to produce protein and/or produce a therapeutic outcome.

1) Purification of Polynucleotides

The polynucleotides can be purified prior to their inclusion in the lipid nanoparticles. Purification of the polynucleotides described herein can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNATM oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

In some embodiments, purification of a polynucleotide removes impurities that can reduce or remove an unwanted immune response, e.g., reducing cytokine activity.

In some embodiments, the polynucleotide is purified prior to inclusion in a lipid nanoparticle using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure prior to inclusion in a lipid nanoparticle.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

2) Quantification of Polynucleotides

In some embodiments, the polynucleotides, their expression products, as well as degradation products and metabolites can be quantified according to methods known in the art.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, or to check that no degradation of the polynucleotide has occurred. Degradation of the polynucleotide can be checked by methods (such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE), capillary gel electrophoresis (CGE)); and UPLC (e.g., RP-UPLC).

ii. Other Lipid Nanoparticle Components

The lipid composition of a lipid nanoparticle disclosed herein can include one or more components in addition to the lipid components described above (e.g., in addition to the ionizable cationic lipid, non-cationic lipid, sterol, and PEG-modified lipid). For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof). A polymer can be included in and/or used to encapsulate or partially encapsulate a composition disclosed herein (e.g., an LNP composition). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The LNP can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNPs can comprise a conjugate to enhance the delivery of nanoparticles in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNPs can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNPs can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNPs can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNPs engineered to penetrate mucus can comprise a polymeric material (e.g., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyleneimines, polyisocyanates, polyacrylates, polymethacrylates, polyacrylonitriles, and polyarylates.

LNPs engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

1) Other Lipids a) Phospholipids

The lipid composition of a lipid nanoparticle disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidyl glycerols, and phosphatidic acids. Phospholipids also include phosphosphingolipid, such as sphingomyelin.

In some embodiments, a phospholipid comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or mixtures thereof.

In certain embodiments, a phospholipid useful or potentially useful in the present disclosure is an analog or variant of DSPC. In certain embodiments, a phospholipid useful or potentially useful in the present disclosure is a compound of Formula (IV):

(IV)

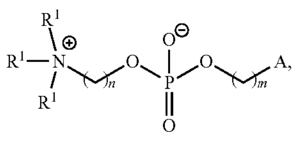

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

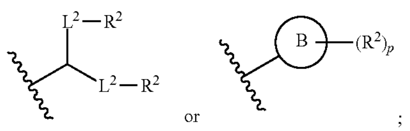

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, $OC(O)N(R^N)$, $NR^NC(O)O$ or $—NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$ C(O)O, OC(O), OC(O)O, $—OC(O)N(R^N)$, $NR^NC(O)O$, C(O)S, SC(O), $C(=NR^N)$, $C(=NR^N)N(R^N)$, $NR^NC(=NR^N)$ $NR^NC(=NR^N)N(R^N)$, C(S), $C(S)N(R^N)$, $NR^NC(S)$, $NR^NC(S)N(R^N)$ S(O), OS(O), S(O)O, —OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$ $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $—N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

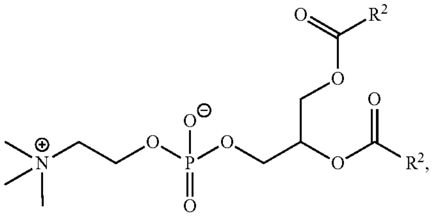

wherein each instance of $R^2$ is independently unsubstituted alkyl, unsubstituted alkenyl, or unsubstituted alkynyl.

In some embodiments, the phospholipids may be one or more of the phospholipids described in PCT/US2018/037922 (published as WO 2018232357).

A) Phospholipid Head Modifications

In certain embodiments, a phospholipid useful or potentially useful in the present disclosure comprises a modified phospholipid head (e.g., a modified choline group). In certain embodiments, a phospholipid with a modified head is DSPC, or analog thereof, with a modified quaternary amine. For example, in embodiments of Formula (IV), at least one of $R^1$ is not methyl. In certain embodiments, at least one of $R^1$ is not hydrogen or methyl. In certain embodiments, the compound of Formula (IV) is of one of the following formulae:

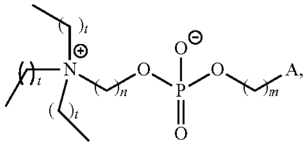

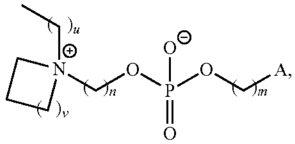

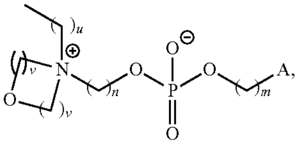

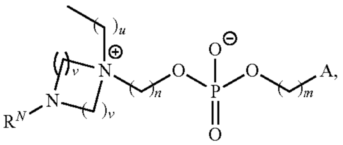

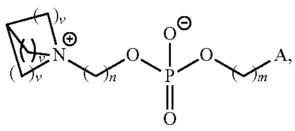

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, a compound of Formula (IV) is of Formula (IV-a):

(IV-a)

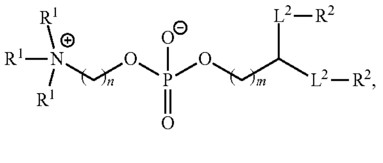

or a salt thereof.

In certain embodiments, a phospholipid useful or potentially useful in the present disclosure comprises a cyclic moiety in place of the glyceride moiety. In certain embodiments, a phospholipid useful in the present disclosure is DSPC, or analog thereof, with a cyclic moiety in place of the glyceride moiety. In certain embodiments, the compound of Formula (IV) is of Formula (IV-b):

(IV-b)

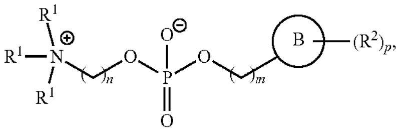

or a salt thereof.

B) Phospholipid Tail Modifications

In certain embodiments, a phospholipid useful or potentially useful in the present disclosure comprises a modified tail. In certain embodiments, a phospholipid useful or potentially useful in the present disclosure is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IV) is of Formula (IV-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$ C(O)O, OC(O), —OC(O)O, $OC(O)N(R^N)$, $NR^NC(O)O$, C(O)S, SC(O), $C(=NR^N)$, $C(=NR^N)N(R^N)$, $NR^NC(=NR^N)$, $—NR^NC(=NR^N)N(R^N)$, C(S), $C(S)N(R^N)$, $NR^NC(S)$, $NR^NC(S)N(R^N)$ S(O), OS(O), S(O)O, OS(O)O, $OS(O)_2$, $S(O)_2O$, $OS(O)_2O$, $N(R^N)S(O)$, $S(O)N(R^N)$, $N(R^N)S(O)N(R^N)$, $—OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$.

In certain embodiments, the compound of Formula (IV) is of Formula (IV-c):

(IV-c)

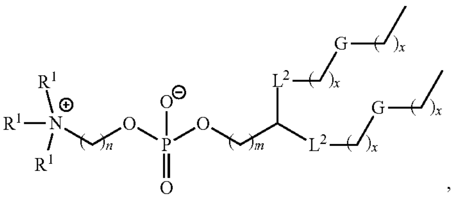

, or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$ C(O)O, OC(O), OC(O)O, $OC(O)N(R^N)$, $NR^NC(O)O$, C(O)S, SC(O), $C(=NR^N)$, $C(=NR^N)N(R^N)$, $—NR^NC(=NR^N)$ $NR^NC(=NR^N)N(R^N)$, C(S), $C(S)N(R^N)$, $NR^NC(S)$, $NR^NC(S)N(R^N)$ S(O), OS(O), S(O)O, OS(O)O, $OS(O)_2$, $S(O)_2O$, $OS(O)_2O$, $N(R^N)S(O)$, $S(O)N(R^N)$, $N(R^N)S(O)N(R^N)$, $—OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$. Each possibility represents separate embodiments.

In certain embodiments, a phospholipid useful or potentially useful in the present disclosure comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present disclosure is a compound of Formula (IV), wherein n is 1, 3, 4, 5, 6, 7, 8, 9, or 10. For example, in certain embodiments, a compound of Formula (IV) is of one of the following formulae:

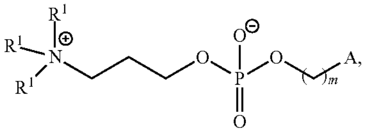

,

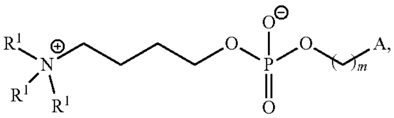

, or a salt thereof.

b) Alternative Lipids

In certain embodiments, a phospholipid useful or potentially useful in the present disclosure comprises a modified phosphocholine moiety, wherein the alkyl chain linking the quaternary amine to the phosphoryl group is not ethylene (e.g., n is not 2). Therefore, in certain embodiments, a phospholipid useful.

In certain embodiments, an alternative lipid is used in place of a phospholipid.

In certain embodiments, an alternative lipid is oleic acid.

In certain embodiments, the alternative lipid is one of the following:

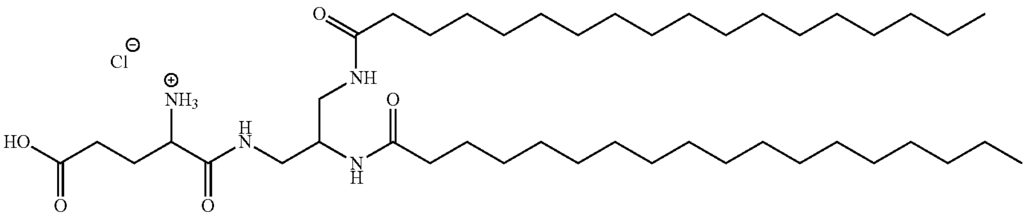

,

-continued

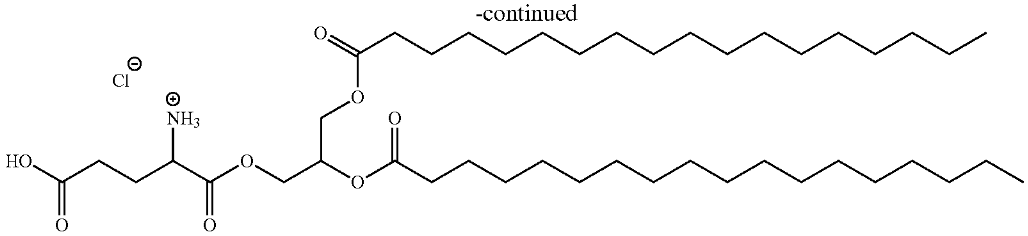

,

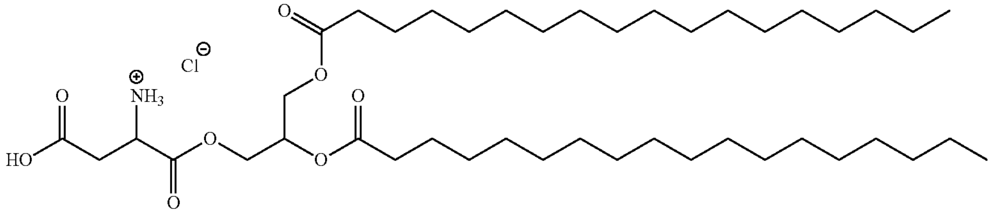

,

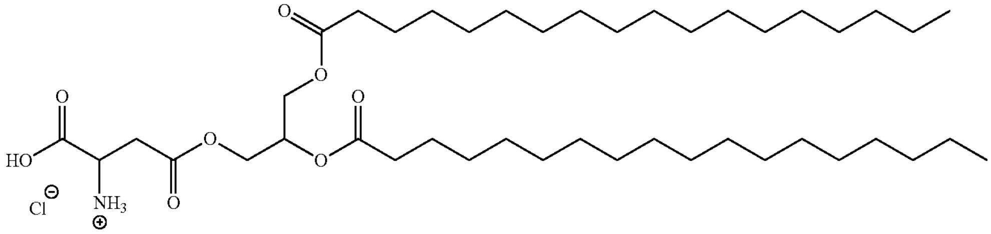

,

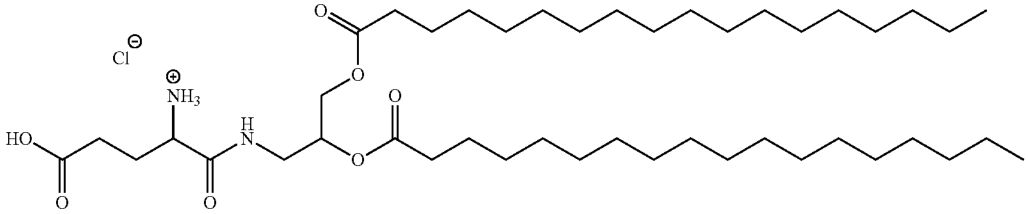

,

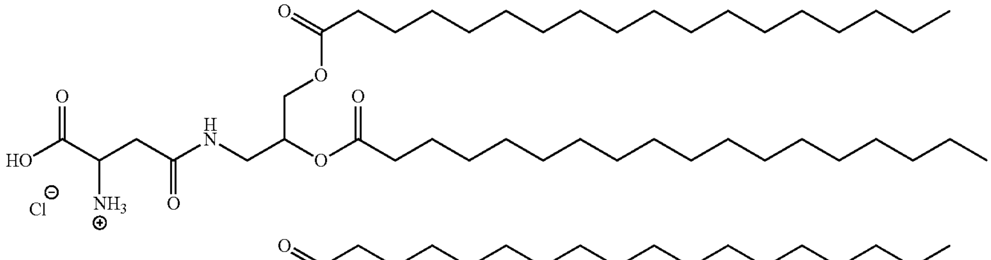

, and

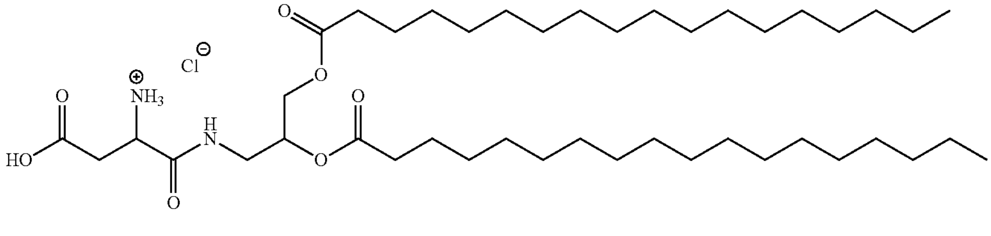

.

c) Structural Lipids

The lipid composition of a lipid nanoparticle disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in PCT/US2018/037922 (published as WO2018232357).

In some embodiments, the structural lipid is cholesterol. In some embodiments, the amount of the structural lipids (e.g., cholesterol) in the lipid composition ranges from about 20 mol % to about 60 mol %.

d) Polyethylene Glycol (PEG)-Lipids

The lipid composition of a lipid nanoparticle disclosed herein can comprise one or more polyethylene glycol (PEG) lipids.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but is not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In some embodiments, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons. In some embodiments, the PEG-lipid is $PEG_{2k}$-DMG.

In some embodiments, the lipid nanoparticles described herein can comprise a PEG lipid which is a non-diffusible PEG. Non-limiting examples of non-diffusible PEGs include PEG-DSG and PEG-DSPE. PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

Thus, the lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

As noted above, in some embodiments the PEG-modified lipids are a modified form of PEG DMG. PEG-DMG has the following structure:

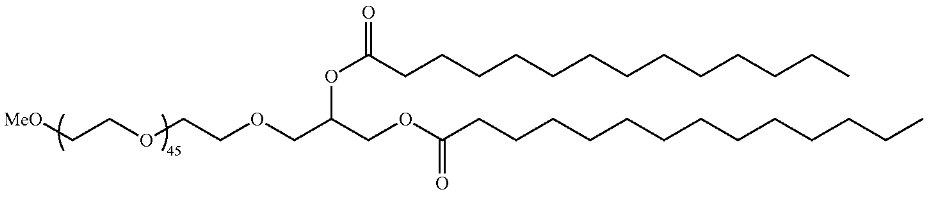

In some embodiments, PEG lipids useful in the present disclosure can be PEGylated lipids described in International Publication No. WO2012099755, which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain.

In certain embodiments, a PEG-OH or hydroxy-PEGylated lipid comprises an —OH group at the terminus of the PEG chain. Each possibility represents separate embodiments.

In certain embodiments, a PEG lipid useful in the present disclosure is a compound of Formula (V). Provided herein are compounds of Formula (V):

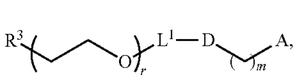

(V)

or salts thereof, wherein:

$R^3$ is $-OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^N)$, S, C(O), C(O)N$(R^N)$, $NR^N$C(O) C(O)O, OC(O), OC(O)O, —OC(O)N$(R^N)$, $NR^N$C(O)O, or $NR^N$C(O)N$(R^N)$;

D is a moiety obtained by click chemistry or a moiety cleavable under physiological conditions;

m is 0, 1, 2, 3, 4, 5, 6, 7, 8, 9, or 10;

A is of the formula:

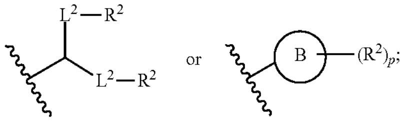

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, $OC(O)N(R^N)$, $NR^NC(O)O$, or $—NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$ C(O)O, OC(O), OC(O)O, $—OC(O)N(R^N)$, $NR^NC(O)O$, C(O)S, SC(O), $C(═NR^N)$, $C(═NR^N)N(R^N)$, $NRC(═NR^N)$, $—NR^NC(═NR^N)N(R^N)$, C(S), $C(S)N(R^N)$, $NR^NC(S)$, $NR^NC(S)N(R^N)$ S(O), OS(O), S(O)O, —OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $—N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (V) is a PEG-OH lipid (i.e., $R^3$ is $—OR^O$, and $R^O$ is hydrogen). In certain embodiments, the compound of Formula (V) is of Formula (V—OH).

(V-OH)

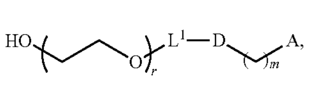

or a salt thereof.

In certain embodiments, a PEG lipid useful in the present disclosure is a PEGylated fatty acid. In certain embodiments, a PEG lipid useful in the present disclosure is a compound of Formula (VI).

Provided herein are compounds of Formula (VI):

(VI)

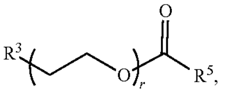

or a salts thereof, wherein:

$R^3$ is $—OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), $C(O)N(R^N)$, $—NR^NC(O)$, $NR^NC(O)N(R^N)$, C(O)O, OC(O), OC(O)O, $OC(O)N(R^N)$, NC(O)O C(O)S, —SC(O), $C(═NR^N)$, $C(═NR^N)N(R^N)$, $NR^NC(═NR^N)$, $NR^NC(═NR^N)N(R^N)$, C(S), $C(S)N(R^N)$, $—NR^NC(S)$, $NR^NC(S)N(R^N)$, S(O), OS(O), S(O)O, OS(O)O, $OS(O)_2$, $S(O)_2O$, $OS(O)_2O$, $—N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $—S(O)_2N(R^N)$, $N(R^N)S(O)_2N(R^N)$, $OS(O)_2N(R^N)$, or $N(R^N)S(O)_2O$; and each instance of $R^N$ is independently hydrogen, optionally substituted alkyl, or a nitrogen protecting group.

In certain embodiments, the compound of Formula (VI) is of Formula (VI—OH):

(VI-OH)

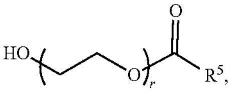

or a salt thereof. In some embodiments, r is 45.

In yet other embodiments the compound of Formula (VI) is:

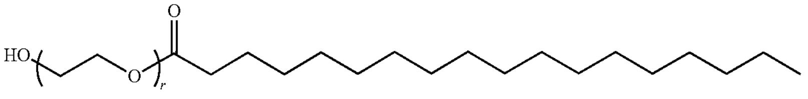

, or a salt thereof.

In some embodiments, the compound of Formula (VI) is (Compound I)

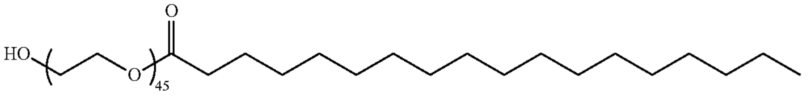

.

In some aspects, the lipid composition of the pharmaceutical compositions disclosed herein does not comprise a PEG-lipid.

In some embodiments, the PEG-lipids may be one or more of the PEG lipids described in PCT/US2018/037922 (published as WO 2018232357).

In some embodiments, a PEG lipid comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and/or mixtures thereof. In some embodiments, the PEG-modified lipid is PEG-DMG, PEG-c-DOMG (also referred to as PEG-DOMG), PEG-DSG and/or PEG-DPG.

In some embodiments, a LNP comprises an ionizable cationic lipid of any of Formula I, II or III, a phospholipid comprising DSPC, a structural lipid, and a PEG lipid comprising PEG-DMG.

In some embodiments, a LNP comprises an ionizable cationic lipid of any of Formula I, II or III, a phospholipid comprising DSPC, a structural lipid, and a PEG lipid comprising a compound having Formula VI.

In some embodiments, a LNP comprises an ionizable cationic lipid of any of Formula I, II or III, a phospholipid comprising a compound having Formula IV, a structural lipid, and the PEG lipid comprising a compound having Formula V.

In some embodiments, a LNP comprises an ionizable cationic lipid of any of Formula I, II or III, a phospholipid comprising a compound having Formula IV, a structural lipid, and the PEG lipid comprising a compound having Formula VI.

In some embodiments, a LNP comprises an ionizable cationic lipid of any of Formula I, II or III, a phospholipid comprising a compound having Formula IV, a structural lipid, and a PEG lipid comprising a compound having Formula V or VI.

In some embodiments, a LNP comprises an ionizable cationic lipid of

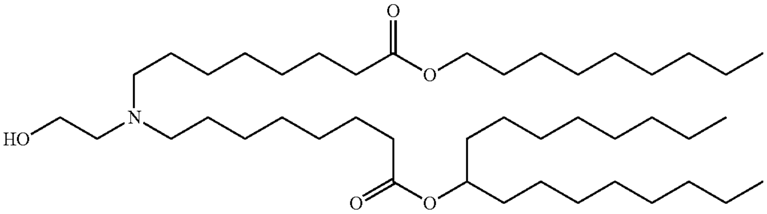

, and a PEG lipid comprising Formula VI.

In some embodiments, a LNP comprises an ionizable cationic lipid of

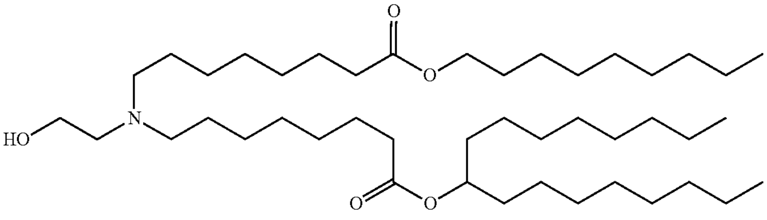

, and an alternative lipid comprising oleic acid.

In some embodiments, a LNP comprises an ionizable cationic lipid of

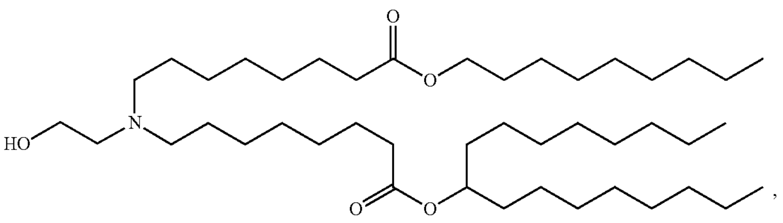 [SMILES: CCCCCCCCCOC(=O)CCCCCCCN(CCO)CCCCCCCC(=O)OC(CCCCCCCC)CCCCCCCC]

an alternative lipid comprising oleic acid, a structural lipid comprising cholesterol, and a PEG lipid comprising a compound having Formula VI.

In some embodiments, a LNP comprises an ionizable cationic lipid of

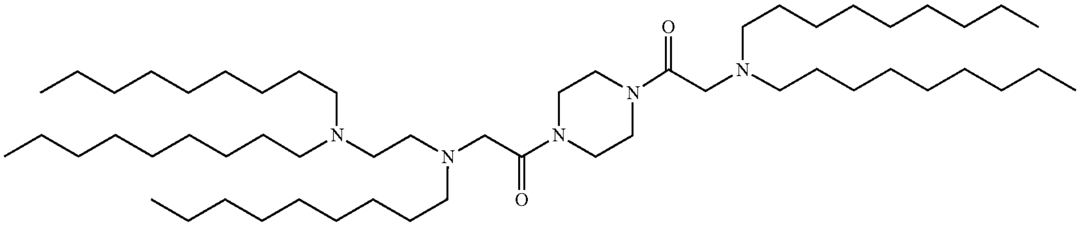 [SMILES: CCCCCCCCCN(CCCCCCCCC)CCN(CCCCCCCCC)CC(=O)N1CCN(C(=O)CN(CCCCCCCCC)CCCCCCCCC)CC1]

a phospholipid comprising DOPE, a structural lipid comprising cholesterol, and a PEG lipid comprising a compound having Formula VI.

In some embodiments, a LNP comprises an ionizable cationic lipid of

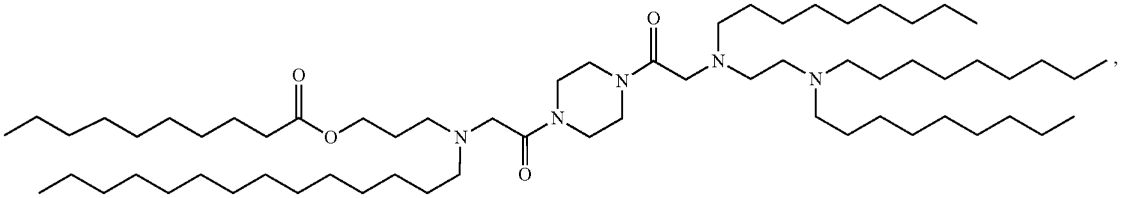 [SMILES: CCCCCCCCCCCCCCN(CCCOC(=O)CCCCCCCCC)CC(=O)N1CCN(C(=O)CN(CCCCCCCCC)CCN(CCCCCCCCC)CCCCCCCCC)CC1]

a phospholipid comprising DOPE, a structural lipid comprising cholesterol, and a PEG lipid comprising a compound having Formula VII.

In some embodiments, a LNP comprises an N:P ratio of from about 2:1 to about 30:1.

In some embodiments, a LNP comprises an N:P ratio of about 6:1.

In some embodiments, a LNP comprises an N:P ratio of about 3:1.

In some embodiments, a LNP comprises a wt/wt ratio of the ionizable cationic lipid component to the RNA of from about 10:1 to about 100:1.

In some embodiments, a LNP comprises a wt/wt ratio of the ionizable cationic lipid component to the RNA of about 20:1.

In some embodiments, a LNP comprises a wt/wt ratio of the ionizable cationic lipid component to the RNA of about 10:1. the disclosure has a mean diameter from about 50 nm to about 150 nm.

In some embodiments, a LNP has a mean diameter from about 70 nm to about 120 nm.

2. Pharmaceutical Compositions

The LNP compositions may also be formulated as pharmaceutical compositions. Pharmaceutical compositions can optionally comprise one or more additional active substances, e.g., therapeutically and/or prophylactically active substances. Pharmaceutical compositions can be sterile and/or pyrogen-free. General considerations in the formulation and/or manufacture of pharmaceutical agents can be found, for example, in Remington: The Science and Practice of Pharmacy 21st ed., Lippincott Williams & Wilkins, 2005 (incorporated herein by reference in its entirety). In some embodiments, compositions are administered to humans, human patients or subjects. The phrase "active ingredient" generally refers to polynucleotides to be delivered as described herein.

Formulations and pharmaceutical compositions described herein can be prepared by any method known or hereafter developed in the art of pharmacology, based on the disclosure and guidance provided herein. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one LNP. As a non-limiting example, the composition can contain 1, 2, 3, 4 or 5 LNPs. In some embodiments, the compositions described herein can comprise more than one type of LNP. In this context, each LNP may comprise the same or different lipid components and/or the same or different polynucleotide cargo.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present disclosure provides compositions, pharmaceutical compositions, and pharmaceutical formulations that comprise an LNP described herein. The LNPs described herein can be formulated using one or more excipients to: (1) increase stability; (2) increase cell transfection; (3) permit the sustained or delayed release (e.g., from a depot formulation of the polynucleotide); (4) alter the biodistribution (e.g., target the LNP to specific tissues or cell types); (5) increase the translation of encoded protein in vivo; and/or (6) alter the release profile of encoded protein in vivo.

A pharmaceutically acceptable excipient, as used herein, includes, but is not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cryoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, M D, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinylpyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc., and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Exemplary antioxidants include, but are not limited to, alpha tocopherol, ascorbic acid, ascorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions is maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The composition or pharmaceutical composition described herein can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition described herein can contain a bulking agent in lyophilized polynucleotide formulations to yield a "pharmaceutically elegant" cake, stabilize the lyophilized polynucleotides during long term (e.g., 36 month) storage. Exemplary bulking agents can include, but are not limited to sucrose, trehalose, mannitol, glycine, lactose, raffinose, and combinations thereof.

3. Forms of Administration

The compositions described above can be administered by any route that results in a therapeutically effective outcome. These include, but are not limited to oral, pulmonary, rectal, parenteral, transdermal, subcutaneous, intravenous, intramuscular, intraperitoneal, inhalational, buccal, sublingual, intrapleural, intrathecal, intranasal, and the like. Examples of routes of administration include parenteral, e.g., intravenous, intradermal, subcutaneous, oral (e.g., inhalation), transdermal (topical), and transmucosal administration. In some embodiments, compositions can be administered in a way that allows them cross the blood-brain barrier, vascular barrier, or other epithelial barrier. In some embodiments, a formulation for a route of administration can include at least one inactive ingredient.

The compositions can be formulated using the methods described herein. The compositions can contain polynucleotides that can be modified and/or unmodified. The compositions can further include, but are not limited to, cell penetration agents, a pharmaceutically acceptable carrier, a delivery agent, a bioerodible or biocompatible polymer, a solvent, and a sustained-release delivery depot. The compositions can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride, and sodium hydroxide.

Injectable preparations, for example, sterile injectable aqueous or oleaginous suspensions, can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables. The sterile formulation can also comprise adjuvants such as local anesthetics, preservatives, and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013, which is herein incorporated by reference in its entirety).

4. Methods and Reduced-Adduct Compositions

Also provided are reduced-adduct LNP compositions and methods for preparing such compositions. The methods for preparing the lipid nanoparticle compositions disclosed herein advantageously minimize the amount of adduct impurity present in the lipid nanoparticle composition, e.g., by preventing or reducing the reaction between decomposed ionizable lipid and polynucleotide.

Without being bound by theory, it is believed that degradation pathways can result in loss in mRNA potency. For instance, electrophilic impurities such as aldehydes, ketones, anhydrides, dienes, or any combination thereof can result in mRNA degradation, e.g., via the formation of adduct impurities. Thus, some embodiments comprise monitoring and controlling the level of the raw material, formulation process, and final drug product to prevent or reduce such adduct formation and ensure the quality and potency of LNP-formulated nucleic acid products. As disclosed above, in some embodiments, an LNP composition as described herein comprises low amounts of one or more or all of N-oxide compounds, lipid aldehyde compounds, alkyl halide compounds, anhydride compounds, ketone compounds, and conjugated diene compounds, or is free or substantially free or one or more or all of such compounds, as discussed above.

In some embodiments, the process comprises performing one or more of the following steps before combining the ionizable lipid and the polynucleotide: (a) producing the ionizable lipid in the presence of a scavenging agent; (b) producing the ionizable lipid in the presence of a reductive treatment agent; (c) treating the ionizable lipid with a reducing agent; (d) treating the ionizable lipid with a chelating agent; (e) treating the polynucleotide with a reducing agent; and (f) treating the polynucleotide with a chelating agent. Some embodiments comprise then combining the ionizable lipid with the polynucleotide. The steps performed before combining the ionizable lipid and polynucleotide can include any one of the steps or a combination of any of the steps described above, e.g., the combination can include two, three, four, or five of the steps described above.

Additionally or alternatively, some embodiments comprise a process for preparing a lipid nanoparticle composition comprising an ionizable lipid and a polynucleotide, wherein the process comprises combining the ionizable lipid and the polynucleotide to provide a lipid nanoparticle composition, and then treating the composition to reduce adduct formation. In some embodiments, the treating comprises one or more of: (a) treating the composition with a reducing agent; (b) treating the composition with a chelating agent; (c) adjusting the pH of the composition; (d) adjusting the temperature of the composition; and (e) adjusting the buffer in the composition. The treating can include any one of the steps or a combination of any one of the steps described above, e.g., the combination can include two, three, four, or five of the steps described above.

Some embodiments provide a process for preparing a lipid nanoparticle composition comprising a polynucleotide and an ionizable lipid, wherein the composition comprises a reduced amount of an ionizable lipid-polynucleotide adduct impurity as compared to a control composition, the process comprising combining a first preparation comprising the ionizable lipid and a second preparation comprising the polynucleotide, wherein one or both of the preparations has been treated with a reducing agent, a chelating agent, or a combination thereof, wherein in the control composition neither the first nor second preparation has been treated with a reducing agent or a chelating agent.

As illustrated in the examples below, ionizable lipid-polynucleotide adduct can be detected by subjecting a sample of a composition comprising a polynucleotide and an ionizable lipid to reverse-phase ion pair HPLC (RP IP HPLC), and, optionally, detecting a main peak characteristic of the polynucleotide and a late-eluting peak characteristic of the adduct.

a. Reductive Treatment of Lipids

Some embodiments comprise removing impurities (e.g., electrophilic impurities) from an ionizable lipid. In some embodiments, electrophilic impurities are removed from an ionizable lipid prior to formation of an LNP, e.g., during production of the ionizable lipid. Exemplary electrophilic impurities include aldehydes, ketones, anhydrides, dienes, halides, or any combination thereof.

Some embodiments comprise exposing an ionizable lipid, or intermediate or precursor thereof (e.g., during formation of the lipid), to a scavenging agent and/or a reductive treatment agent—e.g., during formation of the lipid—to remove electrophilic impurities.

The scavenging agent can be any agent that lowers the amount of electrophilic impurities in a sample, for instance by reacting with aldehydes, ketones, anhydrides, dienes, or any combination thereof in the sample. Exemplary scavenging agents include aminooxy compounds. In some embodiments, the scavenging agent is selected from (O-(2,3,4,5,6-Pentafluorobenzyl)hydroxyl amine hydrochloride) (PFBHA), methoxyamine (e.g., methoxyamine hydrochloride), benzyloxyamine (e.g., benzyloxyamine hydrochloride), ethoxy amine (e.g., ethoxyamine hydrochloride), 4-[2-(aminooxy)ethyl]morpholine dihydrochloride, butoxyamine (e.g., tert-butoxyamine hydrochloride), 4-Dimethylaminopyridine (DMAP), 1,4-diazabicyclo[2.2.2]octane (DABCO), Triethylamine (TEA), Piperidine 4-carboxylate (BPPC), and combinations thereof.

Some embodiments comprise contacting an ionizable lipid solution, or intermediate or precursor thereof (e.g., during formation of the lipid) with a reductive treatment agent. In some embodiments, the reductive treatment agent comprises a boron compound, such as a boron compound selected from sodium borohydride, bis(pinacolato)diboron, lithium borohydride; sodium cyano borohydride, polymer-supported borohydride, sodium triacetoxyborohydride, and combinations thereof. In some embodiments, the reductive treatment agent comprises Si-DPP (immobilized diphenylphosphine on silica, from Silicycle (product name SiliaBond Diphenylphosphine)), Ag-Thiol (immobilized thiol on agarose, from Pierce (product name Reduce-Imm Immobilized Reductant Columns)), Si-Cysteine (immobilized cysteine on silica, from Silicycle (product name SiliaMetS Cysteine)), Si-Thiol (immobilized thiol on silica, from Silicycle (product name SiliaMetS Thiol), potassium metabisulfite, sodium thioglycolate, TCEP, sodium thiosulfate, sodium hypodisulfite, N-acetyl cysteine, glutathione, DTT, cystamine, DTE, DDT, homocysteine, lipoic acid, or a combination thereof.

Some embodiments comprise treating the lipid, or an intermediate or precursor thereof, with both (i) one or more aminooxy compounds and (ii) one or more boron compounds (e.g., simultaneously or sequentially). Some embodiments comprise treating the lipid, or an intermediate or precursor thereof, with both (i) one or more aminooxy compounds and (ii) one or more DMAP, DABCO, BPPC and TEA compounds (e.g., simultaneously or sequentially).

In some embodiments, the reductive treatment agent is in a polar solvent, such as acetonitrile, propionitrile, water, acetic acid, methanol, ethanol, propanol, isopropyl alcohol, butanol. cyclopentyl methyl ether, diethyl ether, tetrahydrofuran, methyl tetrahydrofuran, or combinations thereof.

In some embodiments, the reductive treatment involves reducing the amount of transition metals in the preparation to less than about 500 ppm or to less than about 250 ppm or to less than about 100 ppm, or to less than about 50 ppm. In some embodiments, the method further involves reducing the amount of transition metals in the preparation to less than 500 ppm, less than 250 ppm, less than 100 ppm, or less than 50 ppm. In some embodiments, the method further involves reducing the amount of transition metals in the preparation to between 5 ppm and 500 ppm, between 25 ppm and 250 ppm, or between 50 and 100 ppm. In some embodiments, the method further involves reducing the amount of transition metals in the preparation between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, each ionizable lipid comprises at least one tertiary amino group that is capable of being oxidized. Exemplary transition metals include, but are not limited to, Pd, Cu, Fe, Ni, Pb, and Mn.

In some embodiments, an ionizable lipid solution comprises less than 5 mol % aldehydes, such as less than 4 mol %, less than 3 mol %, less than 2 mol %, less than 1 mol %, less than 0.75 mol %, less than 0.5 mol %, less than 0.7 mol %, less than 0.6 mol %, less than 0.5 mol %, less than 0.4 mol %, less than 0.3 mol %, less than 0.2 mol %, less than 0.1 mol %, less than 0.05 mol %, less than 0.04 mol %, less than 0.03 mol %, less than 0.02 mol %, less than 0.01 mol %, or less than 0.005 mol % aldehydes (e.g., as measured by LC-UV). In some embodiments, the ionizable lipid solution is substantially free (e.g., below the detection limit) of aldehydes. In some embodiments, the ionizable lipid solution comprises about 500 ppm or less of aldehydes, such as about 400 ppm or less, about 300 ppm or less, about 200 ppm or less, about 150 ppm or less, about 100 ppm or less, about 75 ppm or less, about 50 ppm or less, about 25 ppm or less, or about 10 ppm or less of aldehydes.

In some embodiments, an ionizable lipid solution comprises less than 5 mol % ketones, such as less than 4 mol %, less than 3 mol %, less than 2 mol %, less than 1 mol %, less than 0.75 mol %, less than 0.5 mol %, less than 0.7 mol %, less than 0.6 mol %, less than 0.5 mol %, less than 0.4 mol %, less than 0.3 mol %, less than 0.2 mol %, less than 0.1 mol %, less than 0.05 mol %, less than 0.04 mol %, less than 0.03 mol %, less than 0.02 mol %, less than 0.01 mol %, or less than 0.005 mol % ketones (e.g., as measured by LC-UV). In some embodiments, the ionizable lipid solution is substantially free (e.g., below the detection limit) of ketones. In some embodiments, the ionizable lipid solution comprises about 500 ppm or less of ketones, such as about 400 ppm or less, about 300 ppm or less, about 200 ppm or less, about 150 ppm or less, about 100 ppm or less, about 75 ppm or less, about 50 ppm or less, about 25 ppm or less, or about 10 ppm or less of ketones.

In some embodiments, an ionizable lipid solution comprises less than 5 mol % anhydrides, such as less than 4 mol %, less than 3 mol %, less than 2 mol %, less than 1 mol %, less than 0.75 mol %, less than 0.5 mol %, less than 0.7 mol %, less than 0.6 mol %, less than 0.5 mol %, less than 0.4 mol %, less than 0.3 mol %, less than 0.2 mol %, less than 0.1 mol %, less than 0.05 mol %, less than 0.04 mol %, less than 0.03 mol %, less than 0.02 mol %, less than 0.01 mol %, or less than 0.005 mol % anhydrides (e.g., as measured by LC-UV). In some embodiments, the ionizable lipid solution is substantially free (e.g., below the detection limit) of anhydrides. In some embodiments, the ionizable lipid solution comprises about 500 ppm or less of anhydrides, such as about 400 ppm or less, about 300 ppm or less, about 200 ppm or less, about 150 ppm or less, about 100 ppm or less, about 75 ppm or less, about 50 ppm or less, about 25 ppm or less, or about 10 ppm or less of anhydrides.

In some embodiments, an ionizable lipid solution comprises less than 5 mol % dienes, such as less than 4 mol %, less than 3 mol %, less than 2 mol %, less than 1 mol %, less than 0.75 mol %, less than 0.5 mol %, less than 0.7 mol %, less than 0.6 mol %, less than 0.5 mol %, less than 0.4 mol %, less than 0.3 mol %, less than 0.2 mol %, less than 0.1 mol %, less than 0.05 mol %, less than 0.04 mol %, less than 0.03 mol %, less than 0.02 mol %, less than 0.01 mol %, or less than 0.005 mol % dienes (e.g., as measured by LC-UV). In some embodiments, the ionizable lipid solution is substantially free (e.g., below the detection limit) of dienes. In some embodiments, the ionizable lipid solution comprises about 500 ppm or less of dienes, such as about 400 ppm or less, about 300 ppm or less, about 200 ppm or less, about 150 ppm or less, about 100 ppm or less, about 75 ppm or less, about 50 ppm or less, about 25 ppm or less, or about 10 ppm or less of dienes.

In some embodiments, an ionizable lipid solution comprises less than 5 mol % alkyl halides, such as less than 4 mol %, less than 3 mol %, less than 2 mol %, less than 1 mol %, less than 0.75 mol %, less than 0.5 mol %, less than 0.7 mol %, less than 0.6 mol %, less than 0.5 mol %, less than 0.4 mol %, less than 0.3 mol %, less than 0.2 mol %, less than 0.1 mol %, less than 0.05 mol %, less than 0.04 mol %, less than 0.03 mol %, less than 0.02 mol %, less than 0.01 mol %, or less than 0.005 mol % alkyl halides (e.g., as measured by LC-UV). In some embodiments, the ionizable lipid solution is substantially free (e.g., below the detection limit) of alkyl halides. In some embodiments, the ionizable lipid solution comprises about 500 ppm or less of halides, such as about 400 ppm or less, about 300 ppm or less, about 200 ppm or less, about 150 ppm or less, about 100 ppm or less, about 75 ppm or less, about 50 ppm or less, about 25 ppm or less, or about 10 ppm or less of alkyl halides. In some embodiments, the alkyl halide compound comprises one or more selected from alkyl iodide compounds and alkyl bromide compounds.

In some embodiments, a lipid solution is treated with at least 0.005 mol % of a scavenging agent and/or reductive treatment agent, such as 0.01 mol %, 0.05 mol %, 0.1 mol %, 0.15 mol %, 0.2 mol %, 0.3 mol %, 0.5 mol %, 0.75 mol %, 1 mol %, 1.25 mol %, 1.3 mol %, 1.5 mol %, 1.75 mol % 2 mol %, 2.5 mol %, 3 mol %, 3.5 mol %, 3.9 mol %, 4 mol %, 4.5 mol %, or 5 mol % or more of a scavenging agent and/or reductive treatment agent. In embodiments where more than one scavenging agent and/or reductive treatment agent is used, such amounts can be independently applied to each scavenging agent and/or reductive treatment agent or can represent a total amount of scavenging and and/or reductive agent used.

In some embodiments, the lipid solution is exposed to the reductive treatment agent for a period of time effective to allow removal of one or more electrophiles, such as for a period of 5 minutes or more, such as 10 min, 15 min, 20 min, 30 min, 60 min, 90 min, 120 min, 240 min, 480 min, 960 min, 1,020 min, 1,080 min, 1,140 min, 1,200 min, 1,260 min, 1,320 min, 1,400 min, 1,440 min, 2,000 min, 2,500 min, 3,000 min, or more.

Some embodiments comprise removing the scavenging agent and/or reductive treatment agents from the lipid solution, e.g., via chromatography (such as wet chromatography, e.g., normal phase silica gel chromatography). In some embodiments, substantially all of the reductive treatment agent is removed from the lipid solution. In some embodiments, the lipid solution contains trace amounts of reductive treatment agent. In some embodiments, the lipid solution contains 1 ppm of reductive treatment agent (e.g., boron) or more, such as 2 ppm, 3 ppm, 4 ppm, 5 ppm, 6 ppm, 7 ppm. 8 ppm, 9 ppm or 10 ppm of reductive treatment agent.

Some embodiments comprise removing impurities formed during the reductive treatment process (e.g., ethyl ester impurities). Thus, in some embodiments the lipid solution and or lipid nanoparticle contains substantially no ethyl ester impurities formed during the reductive treatment process. In some embodiments, the lipid solution or lipid nanoparticle composition comprises 5% or less, such as 4%, 3%, 2%, or 1% or less ethyl ester impurities formed during the reductive treatment process.

In exemplary embodiments, ionizable lipid Compound III is produced with a reductive treatment process. For instance, some embodiments comprise methods of making Compound III, comprising: reacting Compounds 10D and 10G (see Example 10) in an alkylation reaction to produce a crude Compound III; treating the crude Compound III with a first reductive treatment agent in an alcohol and isolating Compound III in hydrocarbon solvent; treating isolated Compound III in hydrocarbon solvent with a second reductive treatment agent; washing Compound III in heptane with bicarbonate solution; and purifying Compound III with chromatography. In some embodiments, the first reductive treatment agent is $NaBH_4$, $LiAlH_4$ or DIBAH, and the alcohol is ethanol. In some embodiments, the hydrocarbon solvent is n-pentane, n-hexane or n-heptane. In some embodiments, the second reductive treatment agent is bis(pinacolato)diborane.

b. Nanoparticle Formation/Adduct Inhibition

Also provided are methods for inhibiting the formation of ionizable lipid-polynucleotide adduct impurity in a composition of lipid nanoparticles, said composition comprising ionizable lipids and polynucleotides.

Some embodiments comprise combining a first preparation and a second preparation to form a lipid nanoparticle composition, wherein the first preparation comprises ionizable lipids and the second preparation comprises polynucleotides, wherein one or both of the ionizable lipid and polynucleotide preparations has been treated with a reducing agent, a chelating agent, or a combination thereof prior to the combining step. Thus, some embodiments comprise a preparation comprising ionizable lipids (optionally without the presence of a polynucleotide) and a reducing agent, a chelating agent, or a combination thereof. Some embodiments comprise a preparation comprising a polynucleotide (optionally without the presence of an ionizable lipid) and a reducing agent, a chelating agent, or a combination thereof. Some embodiments comprise a composition comprising an ionizable lipid, a polynucleotide, and a reducing agent, a chelating agent, or a combination thereof.

Some embodiments comprise treating a lipid nanoparticle composition with a reducing agent, a chelating agent, or a combination thereof.

Some embodiments comprise both (i) treating one or both of a lipid preparation and a polynucleotide composition with a reducing agent, a chelating agent, or a combination thereof prior to lipid nanoparticle formation, and then (ii) treating the lipid nanoparticle composition with a reducing agent, a chelating agent, and a combination thereof.

Exemplary chelating agents include, but are not limited to, immobilized iminodiacetic acid.

Reducing agents can be immobilized or free reducing agents. Exemplary immobilized reducing agents include, but are not limited to Si-DPP (immobilized diphenylphosphine on silica, from Silicycle (product name SiliaBond Diphenylphosphine)), Ag-Thiol (immobilized thiol on agarose, from Pierce (product name Reduce-Imm Immobilized Reductant Columns)), Si-Cysteine (immobilized cysteine on silica, from Silicycle (product name SiliaMetS Cysteine)), and Si-Thiol (immobilized thiol on silica, from Silicycle (product name SiliaMetS Thiol).

Exemplary free reducing agents (which includes free antioxidants) include, but are not limited to, potassium metabisulfite, sodium thioglycolate, TCEP, sodium thiosulfate, N-acetyl cysteine, glutathione, DTT, cystamine, DTE, DDT, homocysteine, and lipoic acid.

Some embodiments comprise limiting the amount of time the polynucleotide, lipid, and/or lipid nanoparticle is exposed to an acidic environment (e.g., a pH of 7 or less, such as a pH of 6 or less, 5 or less, or 4 or less). In some embodiments, the polynucleotide, lipid, and/or lipid nanoparticle is exposed to an acidic environment for a period of 5 minutes or less, such as 4 minutes or less, 3 minutes or less, 2 minutes or less, 1 minute or less, 45 seconds or less, 30 seconds or less, 25 seconds or less, 20 seconds or less, 15 seconds or less, 10 seconds or less, or 5 seconds or less.

In some embodiments, mRNA is loaded into a lipid nanoparticle using a post-hoc loading process, e.g., as disclosed in WO/2020/160397, which is incorporated herein by reference in its entirety. In some embodiments, the mRNA is exposed to an acidic environment (e.g., pH<pKa of ionizable lipid) for about 5 minutes or less, such as 4 minutes or less, 3 minutes or less, 2 minutes or less, 1 minute or less, 45 seconds or less, 30 seconds or less, 25 seconds or less, 20 seconds or less, 15 seconds or less, 10 seconds or less, or 5 seconds or less before neutralization. 10 seconds is the minimum. In some embodiments, the mRNA is exposed to an acidic environment for at least 10 seconds, such as from 10 seconds to 5 minutes, 10 seconds to 2 minutes, 10 seconds to 1 minute, or 10 seconds to 30 seconds.

Some embodiments comprise adjusting the pH of a lipid nanoparticle composition to about 7.0 to about 9.0, such as about 7.4 or 7.5 Some embodiments include treating mixtures of ionizable lipids and polynucleotides with TRIS (tris(hydroxymethyl)aminomethane) buffer at a pH of between about 7.0 and 9.0 or at about 7.4 or at about 7.5. Thus, some embodiments comprise a LNP composition at a pH of about 7.0 to about 9.0, e.g., in a TRIS buffer at a pH of 7.4 or 7.5.

In some embodiments, the method further involves reducing the amount of transition metals in the preparation to less than about 500 ppm or to less than about 250 ppm or to less than about 100 ppm, or to less than about 50 ppm. In some embodiments, the method further involves reducing the amount of transition metals in the preparation to less than 500 ppm, less than 250 ppm, less than 100 ppm, or less than 50 ppm. In some embodiments, the method further involves reducing the amount of transition metals in the preparation to between 5 ppm and 500 ppm, between 25 ppm and 250 ppm, or between 50 and 100 ppm. In some embodiments, the method further involves reducing the amount of transition metals in the preparation between 0 ppm and 50 ppm, between 50 ppm and 100 ppm, between 100 ppm and 200 ppm, between 200 ppm and 300 ppm, between 300 ppm and 400 ppm, or between 400 ppm and 500 ppm. In some embodiments, each ionizable lipid comprises at least one tertiary amino group that is capable of being oxidized. Exemplary transition metals include, but are not limited to, Pd, Cu, Fe, Ni, Pb, and Mn.

In some embodiments, the method further involves storing the lipid nanoparticle composition at a temperature at about 25° C. or below, or at about 5° C. or below, or at about −20° C. or below. In some embodiments, the lipid nanoparticle composition is stored at a temperature at about 25° C. or below, or at about 5° C. or below, or at about −20° C. or below. In some embodiments, the composition is stored for at least 1 day, 2 days, 3 days, 4 days, 5 days, 6 days, 1 week, 2 weeks, 3 weeks, 1 month, 2 months, 3 months, or indefinitely.

Figure 20:
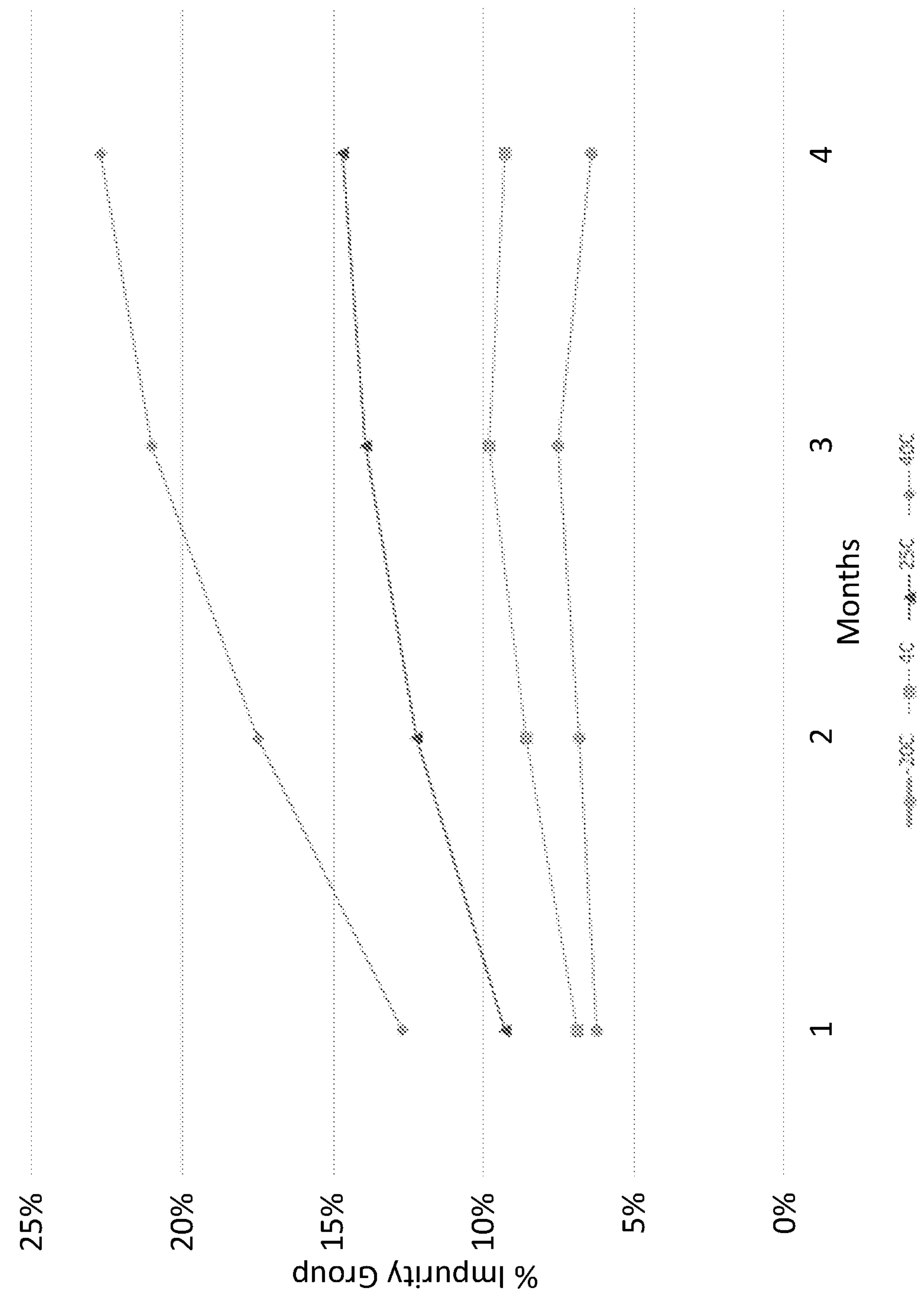
FIG. 20 is a graph showing percentage of IG detected over time in LNP compositions comprising mRNA and Compound III stored at select temperatures (40° C.: (♦); 25° C.: (▲); 4° C.: (■); –20° C.: (●)).

Some embodiments comprise a composition that has a 5% or less increase in ionizable lipid-polynucleotide adduct impurity (e.g., 4%, 3%, 2%, 1%, or 0.5% or less) at storage for a period of 1 month or more (e.g., 2 months, 3 months, 4 months, 5 months, 6 months, 9 months, or 12 months or more). In some embodiments, the storage is at a temperature of about 0° C. or more, such as 2° C., 5° C., 8° C., 10° C., 15° C., 20° C., or 25° C. (see, e.g., FIG. 20, showing experimental results demonstrating stability). In some embodiments the composition has 1% or less increase in ionizable lipid-polynucleotide adduct impurity after storage for 3 months or more at 5° C.

To the extent the foregoing discussion has been made in the context of lipid nanoparticle compositions comprising ionizable lipids and polynucleotides, it will be understood that the disclosed methods also pertain to other compositions comprising ionizable lipids and polynucleotides, including liposome compositions and lipoplex compositions, and that the present disclosure includes liposome-containing polynucleotide compositions and lipoplex-containing polynucleotide compositions having a reduced amount of ionizable lipid-polynucleotide adduct, and methods of making such compositions.

In some embodiments, the methods and/or compositions are useful for inhibiting the formation of N-oxides in a preparation of ionizable lipids and/or lipid nanoparticles. In some embodiments, the N-oxide is an N-oxide of the ionizable lipid.

In some embodiments, the methods and/or compositions are useful for inhibiting the formation of lipid aldehydes in a preparation of ionizable lipids and/or lipid nanoparticles. In some embodiments, the lipid aldehydes comprise one or more compounds having an aldehyde group and a straight or branched $C_{6-30}$ saturated or unsaturated carbon chain optionally interrupted by one or more —C(O)O— ester groups.

In some embodiments, the methods and/or compositions are useful for inhibiting reaction of lipid aldehydes with polynucleotides in a mixture of ionizable lipids and polynucleotides. In some embodiments, the methods and/or compositions are useful for inhibiting adduct impurity or reduces the amount of adduct impurity as compared to a control composition (e.g., where in the control composition neither the first nor second preparation has been treated with a reducing agent or a chelating agent).

4. Methods of Use

The polynucleotides, pharmaceutical compositions and formulations described herein are used in the preparation, manufacture and therapeutic use to treat and/or prevent a disease or condition. Thus, some embodiments include methods of treating and/or preventing a disease or condition, comprising administering to a subject in need thereof an LNP composition disclosed herein.

The LNP compositions are particularly well suited for the treatment of a disease or condition in a subject in which the disease or condition is associated with a mutant or aberrantly expressed mRNA. In this regard, the LNP composition used in the method of treatment or prevention comprises a functional version of the mRNA and administration of the LNP composition to the subject allows for the intracellular deliver of the mRNA followed by de novo synthesis of functional polypeptide encoded by the mRNA within target cells. Thus, provided herein is a method of treating and/or preventing a disease or condition, comprising administering to a subject in need thereof a therapeutically effective amount of an LNP composition described herein, wherein the disease or condition is associated with a mutant or aberrantly expressed mRNA, and wherein the LNP composition comprises a functional version of the mRNA. The skilled artisan will understand that a “functional mRNA” is an mRNA that is expressed in a cell and is translated to produce a functional polypeptide.

5. Definitions

In order that the present disclosure can be more readily understood, certain terms are defined. As used in this application, except as otherwise expressly provided herein, each of the following terms shall have the meaning set forth below. Additional definitions are set forth throughout the application.

The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

In this specification and the appended claims, the singular forms “a”, “an” and “the” include plural referents unless the context clearly dictates otherwise. The terms “a” (or “an”), as well as the terms “one or more,” and “at least one” can be used interchangeably herein. In certain aspects, the term “a” or “an” means “single.” In other aspects, the term “a” or “an” includes “two or more” or “multiple.”

Furthermore, “and/or” where used herein is to be taken as specific disclosure of each of the two specified features or components with or without the other. Thus, the term “and/or” as used in a phrase such as “A and/or B” herein is intended to include “A and B,” “A or B,” “A” (alone), and “B” (alone). Likewise, the term “and/or” as used in a phrase such as “A, B, and/or C” is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language “comprising,” otherwise analogous aspects described in terms of “consisting of” and/or “consisting essentially of” are also provided.

Units, prefixes, and symbols are denoted in their Système International de Unites (SI) accepted form. Numeric ranges are inclusive of the numbers defining the range. Where a range of values is disclosed, it is to be understood that each intervening integer value, and each fraction thereof, between the disclosed upper and lower limits of that range is also specifically disclosed, along with each subrange between such values. The upper and lower limits of any range can independently be included in or excluded from the range, and each range where either, neither or both limits are included is also encompassed within the disclosure. Where a value is explicitly disclosed, it is to be understood that values, which are about the same quantity or amount as the disclosed value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

About: The term “about” as used in connection with a numerical value throughout the specification and the claims denotes an interval of accuracy, familiar and acceptable to a person skilled in the art. Unless otherwise understood in the art, such interval of accuracy is ±10%.

As used herein, the term “alkyl”, “alkyl group”, or “alkylene” means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl", "alkenyl group", or "alkenylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. For example, C18 alkenyl may include one or more double bonds. A C18 alkenyl group including two double bonds may be a linoleyl group. Unless otherwise specified, an alkenyl group described herein refers to both unsubstituted and substituted alkenyl groups.

As used herein, the term "alkynyl", "alkynyl group", or "alkynylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, C18 alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2 dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, the term "heteroalkyl", "heteroalkenyl", or "heteroalkynyl", refers respectively to an alkyl, alkenyl, alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. Unless otherwise specified, heteroalkyls, heteroalkenyls, or heteroalkynyls described herein refers to both unsubstituted and substituted heteroalkyls, heteroalkenyls, or heteroalkynyls, i.e., optionally substituted heteroalkyls, heteroalkenyls, or heteroalkynyls.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., C(O)OH), an alcohol (e.g., a hydroxyl, OH), an ester (e.g., C(O)OR, OC(O)R), an aldehyde (e.g., C(O)H), a carbonyl (e.g., C(O)R, alternatively represented by C═O), an acyl halide (e.g., C(O)X, in which X is a halide selected from bromide, fluoride, chloride, and iodide), a carbonate (e.g., OC(O)OR), an alkoxy (e.g., OR), an acetal (e.g., $C(OR)_2R''$, in which each OR are alkoxy groups that can be the same or different and R" is an alkyl or alkenyl group), a phosphate (e.g., $P(O)_4^{3-}$), a thiol (e.g., SH), a sulfoxide (e.g., S(O)R), a sulfinic acid (e.g., S(O)OH), a sulfonic acid (e.g., $S(O)_2OH$), a thial (e.g., C(S)H), a sulfate (e.g., $S(O)_4^{2-}$), a sulfonyl (e.g., $S(O)_2$), an amide (e.g., $C(O)NR_2$, or N(R)C(O)R), an azido (e.g., $N_3$), a nitro (e.g., $NO_2$), a cyano (e.g., CN), an isocyano (e.g., NC), an acyloxy (e.g., OC(O)R), an amino (e.g., $NR_2$, NRH, or $NH_2$), a carbamoyl (e.g., $OC(O)NR_2$, $OC(O)NRH$, or $OC(O)NH_2$), a sulfonamide (e.g., $S(O)_2NR_2$, $S(O)_2NRH$, $S(O)_2NH_2$, N(R) $S(O)_2R$, N(H) $S(O)_2R$, N(R) $S(O)_2H$, or $N(H)S(O)_2H$), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

When used with respect to two or more moieties, the terms "linked" and "attached," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide can be considered biologically active if even a portion of the polynucleotide is biologically active or mimics an activity considered biologically relevant.

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA can be single units or multimers or comprise one or more components of a complex or higher order structure.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides or polypeptide fragments.

Domain: As used herein, when referring to polypeptides, the term "domain" refers to a motif of a polypeptide having one or more identifiable structural or functional characteristics or properties (e.g., binding capacity, serving as a site for protein-protein interactions).

Enantiomer: As used herein, the term "enantiomer" means each individual optically active form of a compound, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Engineered: As used herein, embodiments are "engineered" when they are designed to have a feature or property, whether structural or chemical, that varies from a starting point, wild type or native molecule.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein wherein N-terminal, and/or C-terminal, and/or internal subsequences have been deleted. In some preferred aspects, the fragments of a protein are functional fragments.

Functional: As used herein, a "functional" biological molecule is a biological molecule in a form in which it exhibits a property and/or activity by which it is characterized. Thus, a functional fragment of a polynucleotide is a polynucleotide capable of expressing a functional protein fragment.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,165Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the disclosure. It is recognized that the compounds can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the disclosure, the chemical structures depicted herein, and therefore the compounds of the disclosure, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the disclosure can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Lipid: As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, polyketides, and prenol lipids. In some instances, the amphiphilic properties of some lipids leads them to form liposomes, vesicles, or membranes in aqueous media.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule. Molecules can be modified in many ways including chemically, structurally, and functionally. In some embodiments, the mRNA molecules are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Naturally occurring: As used herein, "naturally occurring" means existing in nature without artificial aid.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides.

Exemplary nucleic acids or polynucleotides include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term "polypeptide", as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Pseudouridine: As used herein, pseudouridine (w) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine (m1ψ) (also known as N1-methyl-pseudouridine), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, 1-methyl-3-(3-amino-3-carboxypropyl)pseudouridine (acp3 ψ), and 2'-O-methyl-pseudouridine (ψm).

Purified: As used herein, "purify," "purified," "purification" means to make substantially pure or clear from unwanted components, material defilement, admixture or imperfection. When "purified" is used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Salts: In some aspects, the pharmaceutical composition disclosed herein comprises salts of some of the lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which can contain cellular components, such as proteins or nucleic acid molecule.

Single unit dose: As used herein, a "single unit dose" is a dose of any therapeutic administered in one dose/at one time/single route/single point of contact, i.e., single administration event.

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Synthetic: The term "synthetic" means produced, prepared, and/or manufactured by the hand of man. Synthesis of polynucleotides or other molecules can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a liver, a kidney, a lung, a spleen, or a vascular endothelium in vessels (e.g., intra-coronary or intra-femoral). An "off-target tissue" refers to any one or more tissue types in which the expression of the encoded protein does not result in a desired biological and/or pharmacological effect.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules can be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Transcription: As used herein, the term "transcription" refers to methods to produce mRNA (e.g., an mRNA sequence or template) from DNA (e.g., a DNA template or sequence)

Transfection: As used herein, "transfection" refers to the introduction of a polynucleotide (e.g., exogenous nucleic acids) into a cell wherein a polypeptide encoded by the polynucleotide is expressed (e.g., mRNA) or the polypeptide modulates a cellular function (e.g., siRNA, miRNA).

As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Variant: The term variant as used in present disclosure refers to both natural variants (e.g., polymorphisms, isoforms, etc.), and artificial variants in which at least one amino acid residue in a native or starting sequence (e.g., a wild type sequence) has been removed and a different amino acid inserted in its place at the same position. These variants can be described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

6. Equivalents and Scope

Those skilled in the art will recognize, or be able to ascertain using no more than routine experimentation, many equivalents to the specific embodiments in accordance with the disclosure described herein. The scope of the present disclosure is not intended to be limited to the above description.

In addition, it is to be understood that any particular embodiment of the present disclosure that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference in their entireties, even if not expressly stated in the citation. In case of conflicting statements of a cited source and the instant application, the statement in the instant application shall control.

Section and table headings are not intended to be limiting.

EXAMPLES

Example 1. Detection of mRNA-Aldehyde (Branched or Unbranched) Adduct Impurity Species by HPLC To detect and quantify the amount of IG present in LNP formulations comprising polynucleotides and lipid, a protocol was developed (FIG. 2) that included (1) extraction of the polynucleotide molecules (e.g. precipitation, liquid:liquid extraction); (2) assessment of integrity (e.g. purity, length) of the isolated polynucleotides by known methods (e.g. fragment analyzer, gel electrophoresis); and (3) analysis of the isolated polynucleotides by HPLC. Representative data generated by this protocol is displayed in FIG. 2.

RNA was extracted from the LNP formulation by precipitation in ammonium acetate in isopropanol; resuspended in water to target a final RNA concentration of 0.1 mg/mL; and assessed by fragment analyzer capillary electrophoresis and ion pair reversed phase HPLC (performed on a Thermo DNApac RP 100×2.1 mm column at 65° C., with mobile phases containing 50 mM dibutylammonium acetate and 100 mM triethylammonium acetate in water and acetonitrile). Elution with an acetonitrile gradient provided an RNA separation primarily driven by mRNA length and sensitive to any added hydrophobic elements. Two prominent peaks were apparent on the HPLC chromatogram (FIG. 2), including a "main peak" comprising non-adduct mRNA and an "IG" peak comprising mRNA with one or more covalent modifications. The mass fraction of RNA containing at least one lipid adduct was determined by integrating the area under the curve (AUC) of all RNA peaks (including products shorter than the full-length product, the full-length product, and the hydrophobic modified RNA) and taking the late-eluting region as an area percent of the total peak area.

Figure 3:
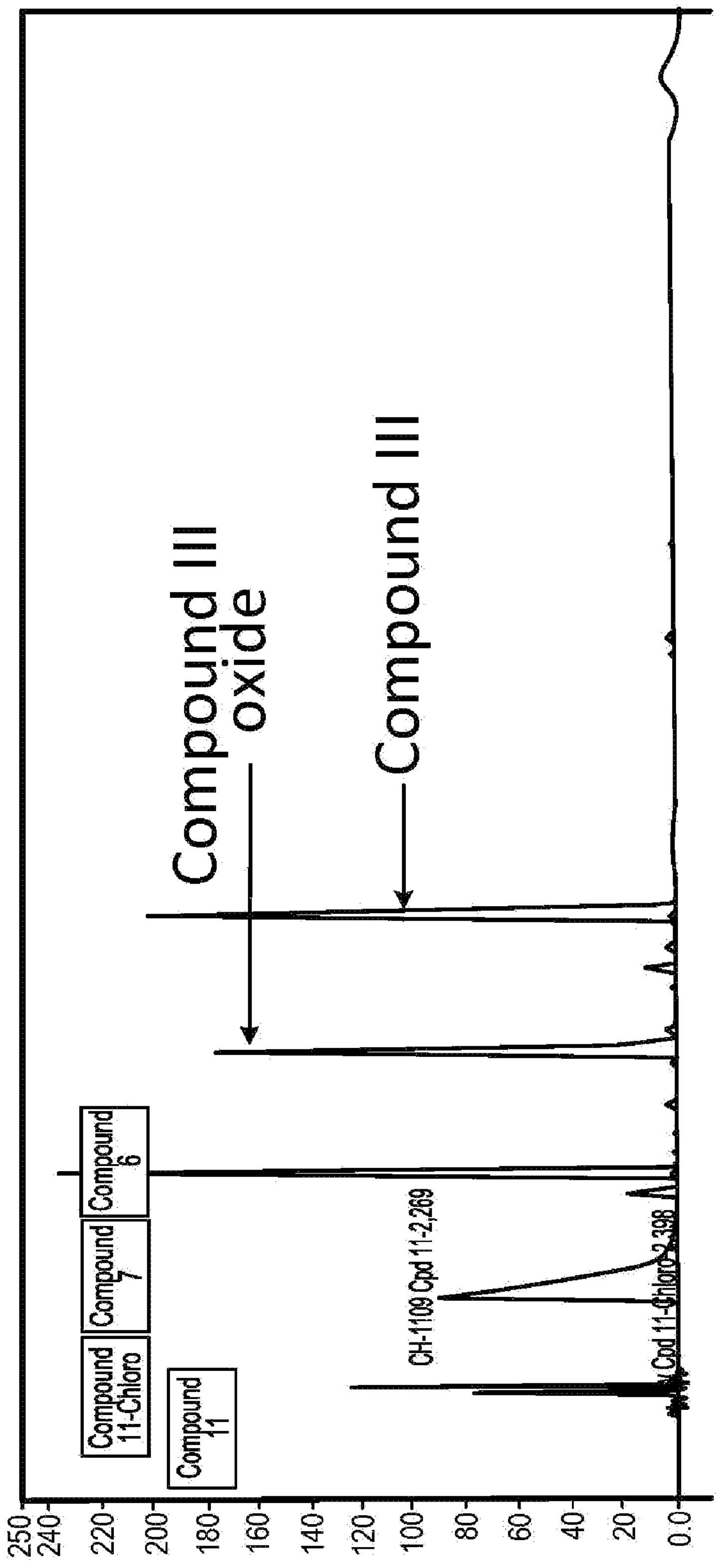
FIG. 3 shows overlaid chromatograms of compositions comprising Compound III or Compound III-N-oxide analyzed by reversed phase HPLC with charged aerosol detection (CAD).
Figure 4:
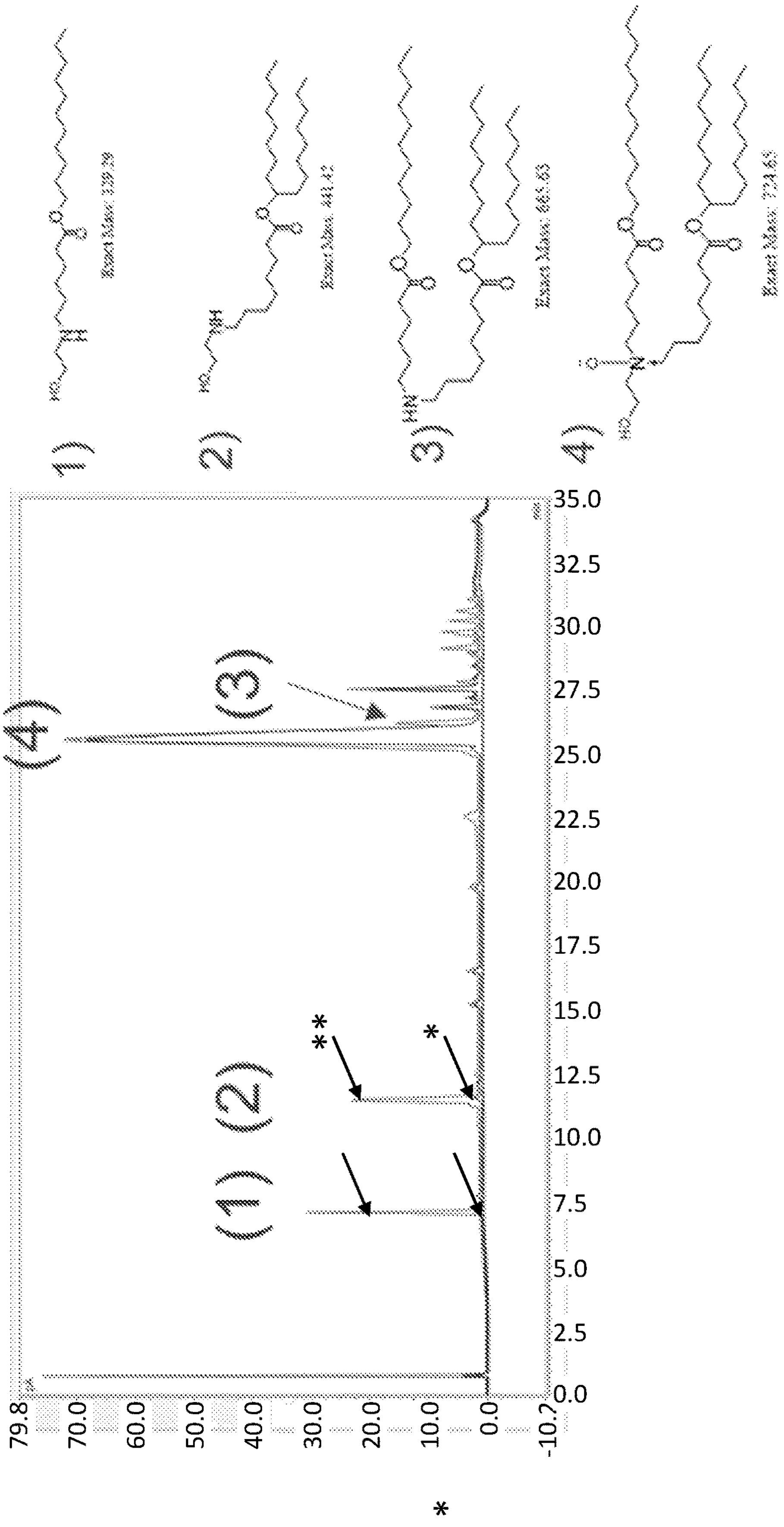
FIG. 4 shows overlaid chromatograms of compositions containing synthesized Compound III-N-oxide either in neutral buffer (*) or in acidic buffer (**) analyzed by reversed phase HPLC with charged aerosol detection (CAD).

Example 2. Decomposition of Compound III-N-Oxide Species into Secondary Amines and Reactive Aldehydes Compound III raw material was assessed by reversed phase HPLC with charged aerosol detection (CAD). The separation was performed on a Thermo Acclaim C30 150×3 mm column at 40° C. FIG. 3 shows baseline resolution of Compound III and its N-oxide standard, along with other in-process impurities. In FIG. 4, the decomposition of Compound III-N-oxide into three secondary amines was observed by HPLC-CAD when prepared in aqueous, acidic conditions. The identity of the corresponding aldehydes was confirmed upon labeling with aminooxy-PEG.

Example 3. Formation of IG in Mixtures Comprising Compound III and mRNA

Compound III was dissolved in ethanol at a concentration of 4 mg/mL, and the RNA diluted in sodium acetate buffer pH 5.5; the RNA and lipids were then mixed in 25% ethanol. Samples were held at 25° C., and the RNA was periodically extracted by precipitation in isopropanol and analyzed by ion pair reversed phase (FIGS. 5 and 6A, data marked by *).

Figure 5:
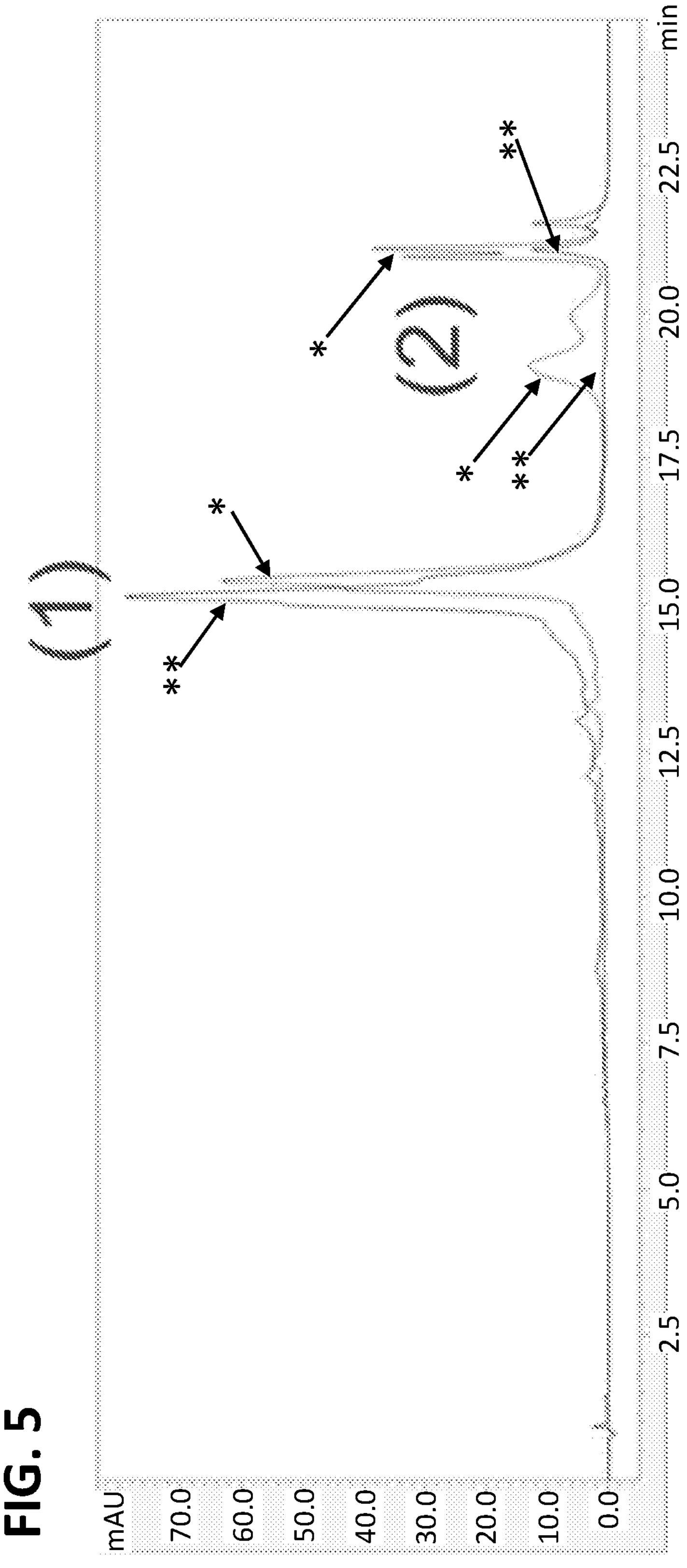
FIG. 5 shows overlaid HPLC chromatograms of compositions comprising mRNA and Compound III (*) and of compositions comprising mRNA, Compound III, and aminooxy-PEG (**); (1) main peak; (2) IG.
Figure 6A:
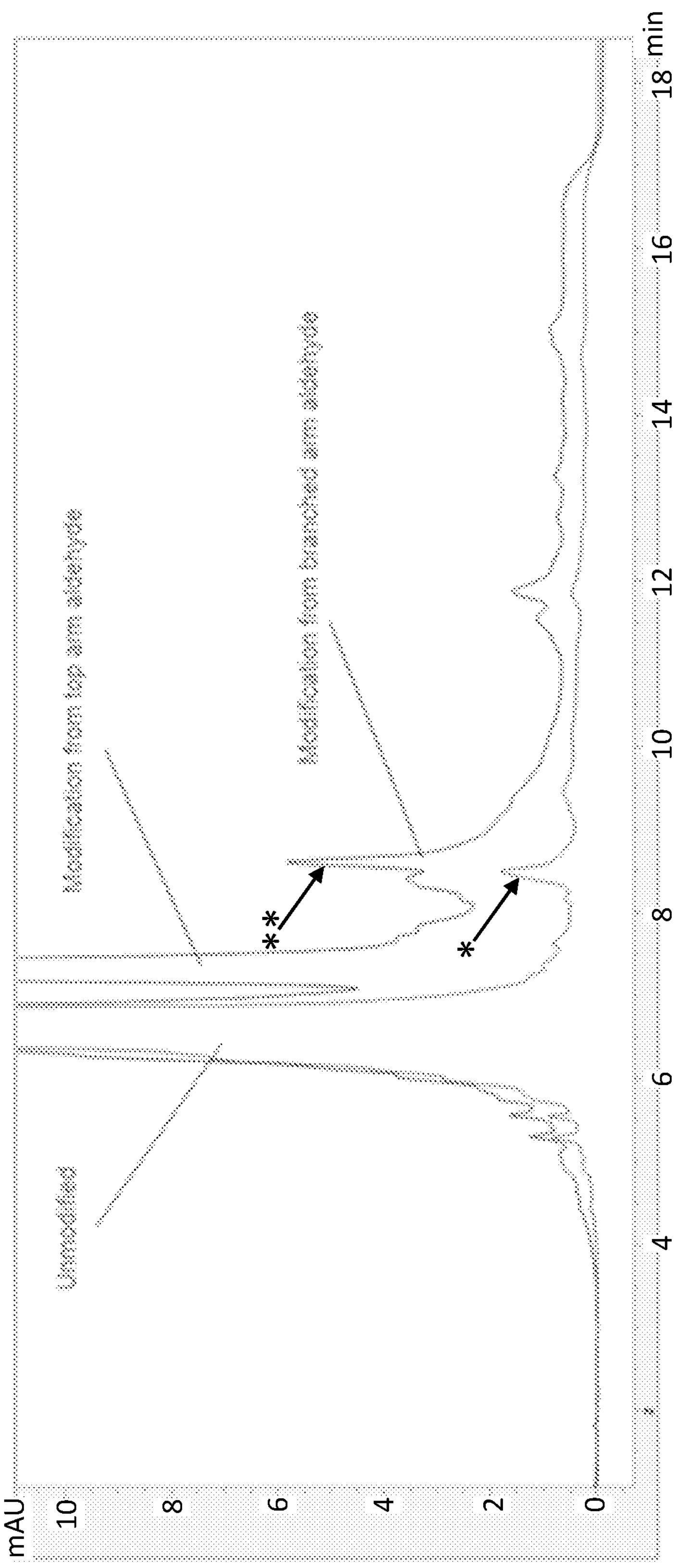
FIG. 6A shows overlaid HPLC chromatograms of compositions comprising mRNA alone (*) and of compositions comprising mRNA and synthesized Compound III-N-oxide (**).

In subsequent experiments the lipid was prepared with amino-oxy PEG as an aldehyde and ketone scavenger prior to mixing with the RNA, which resulted in dramatically less IG formation and the complete elimination of some IG species (FIG. 5, data marked by **).

Figure 6B:
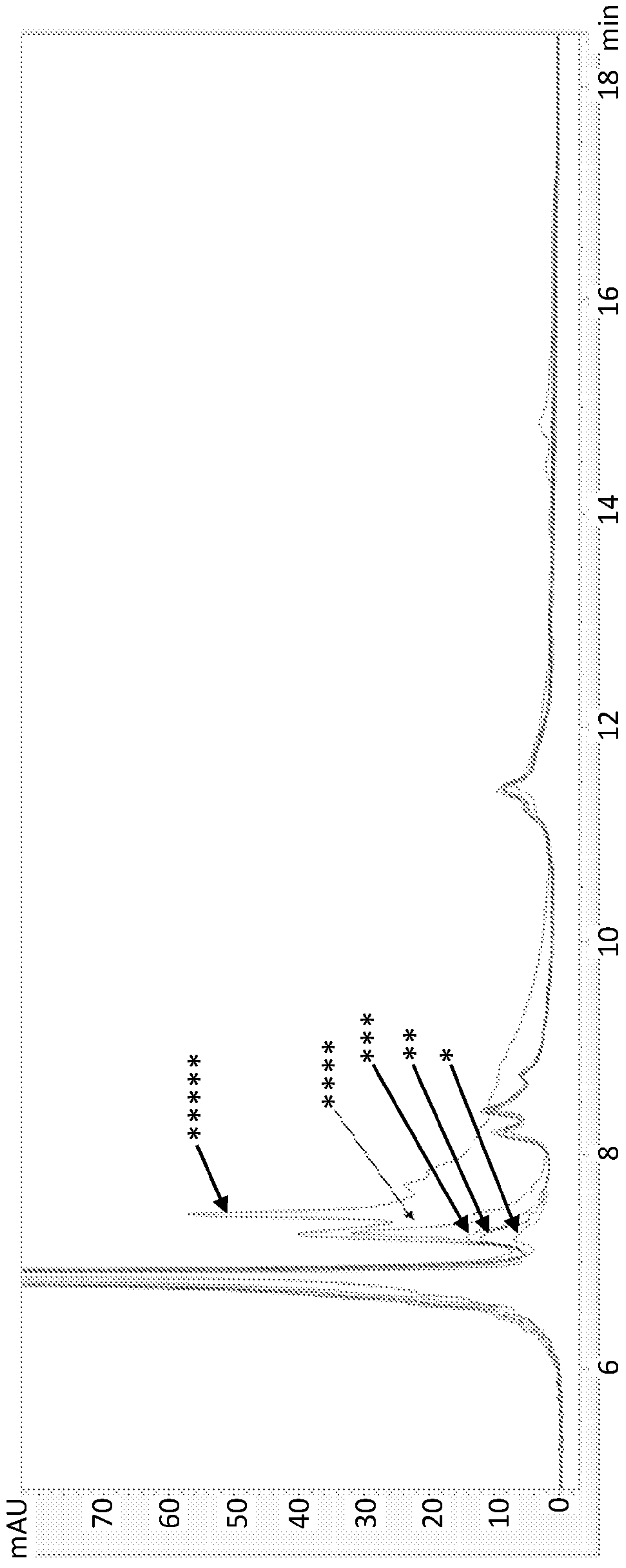
FIG. 6B shows overlaid HPLC chromatograms of compositions comprising mRNA, Compound III, and straight chain aldehyde; compositions with lowest to highest amounts of straight chain aldehyde are marked by arrows as follows: 0 percent (*), 0.03 percent (), 0.10 percent (*), 0.50 percent (**), and 2 percent (***).
Figure 6C:
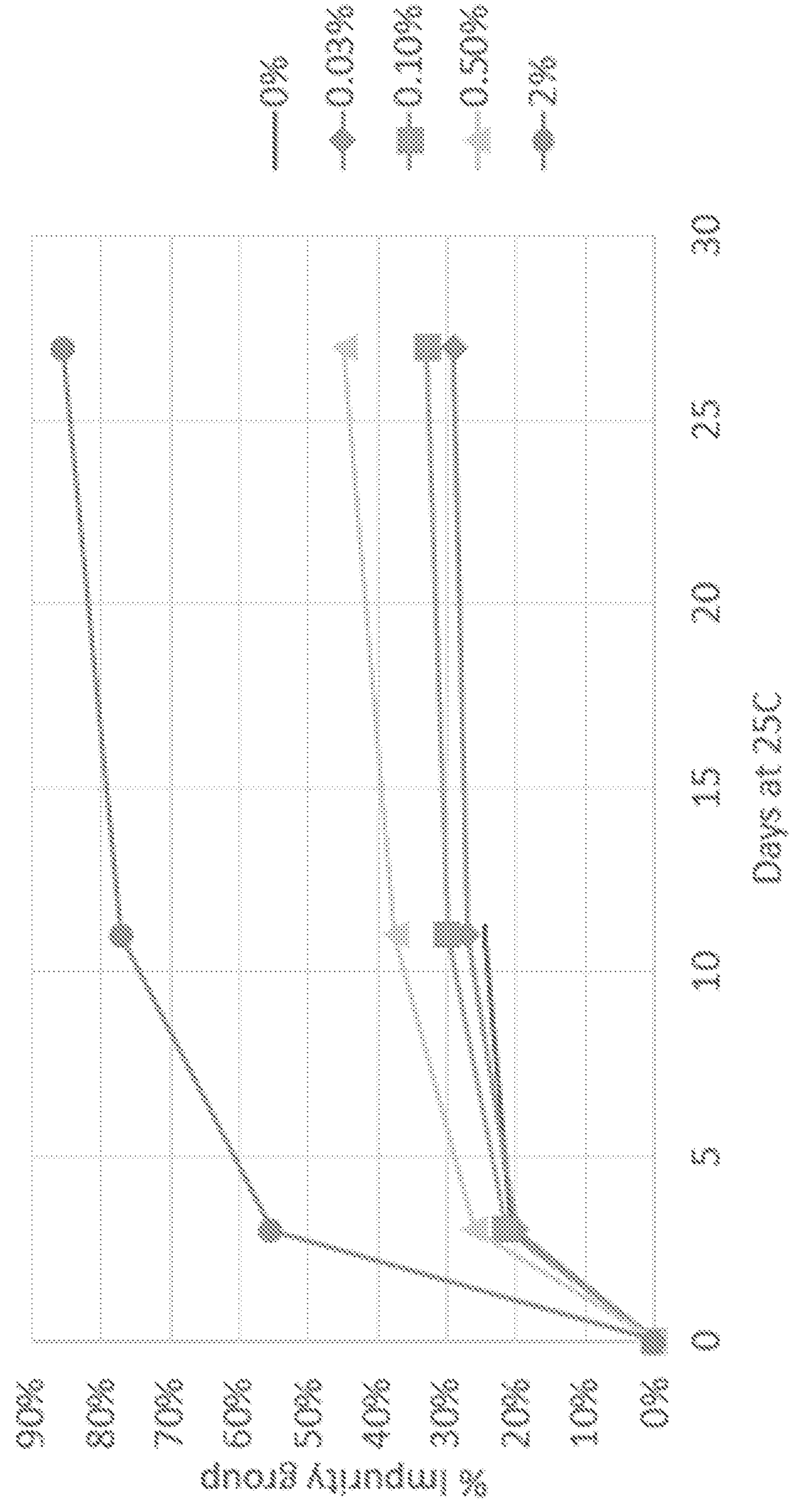
FIG. 6C is a graph showing results of percentage IG detected in compositions comprising mRNA, Compound III, and various concentrations (0% (–), 0.03% (♦), 0.10% (■), 0.50% (▲), or 2% (●)) of straight chain aldehyde.
Figure 7:
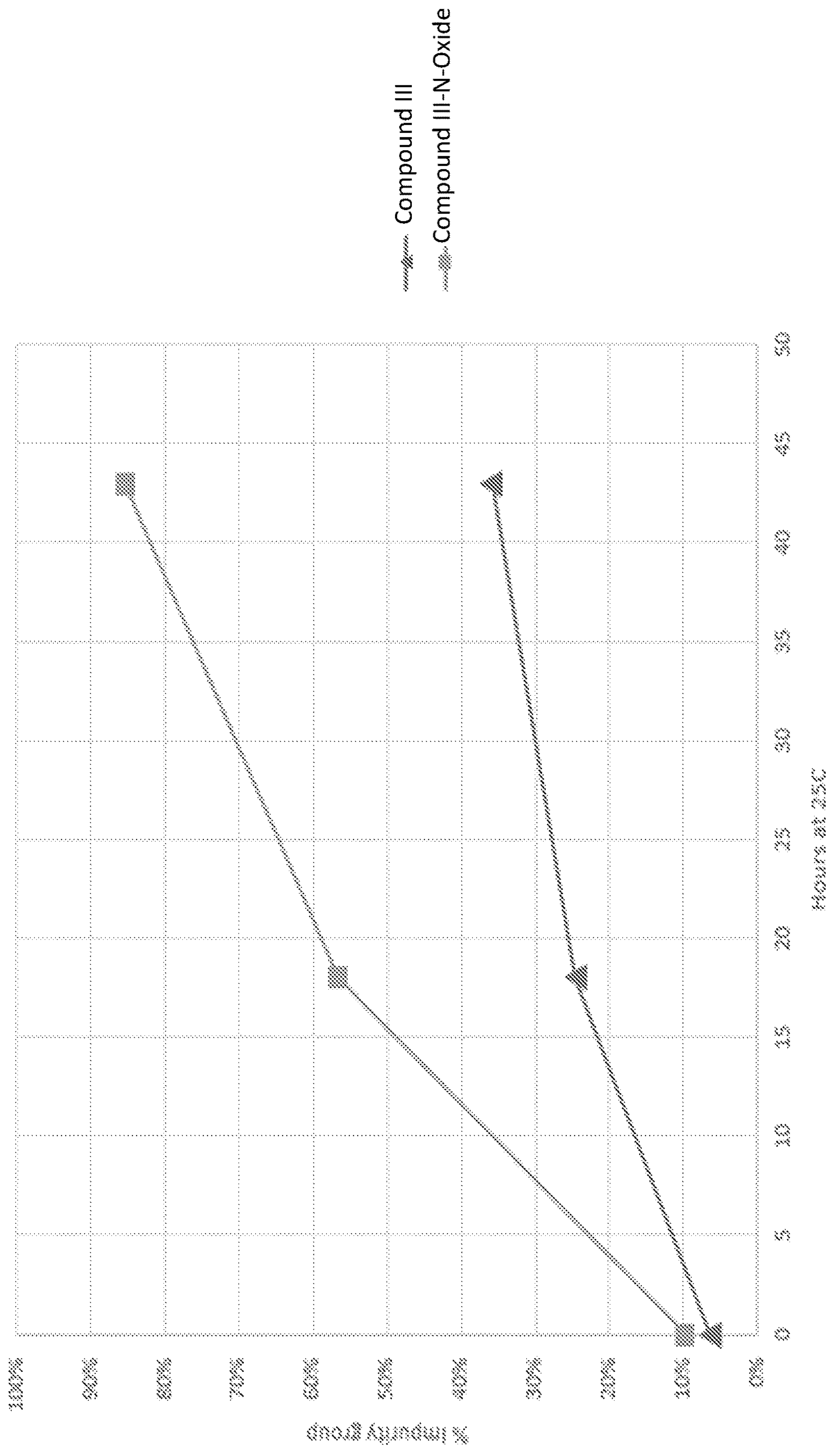
FIG. 7 is a graph showing percentage of IG detected in compositions comprising mRNA and synthesized Compound III-N-oxide (■) or comprising mRNA with Compound III (▲).
Figure 8:
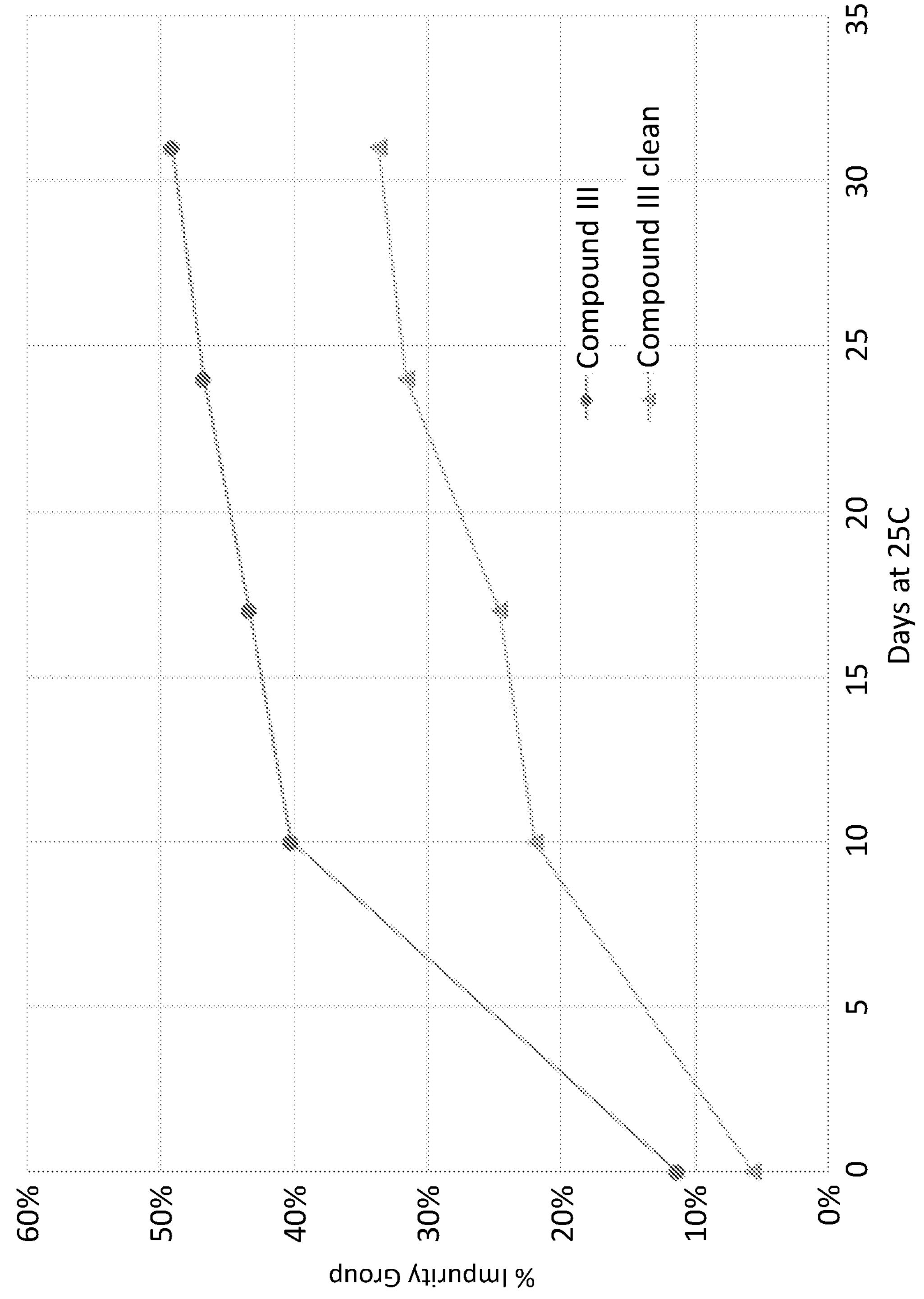
FIG. 8 is a graph showing percentage of IG detected in lipid nanoparticle (LNP) compositions comprising mRNA and Compound III (●) or comprising mRNA and Compound III that was purified chromatographically to greater than 99 percent with no detectable Compound III-N-oxide component (▲).

Without wishing to be bound to a particular theory, applicants propose that IG formation can be driven by Compound III-N-oxide reacting with RNA. Towards testing this theory, binary mixtures of synthesized Compound III-N-oxide and RNA were prepared and analyzed by the protocol described in Example 1 to quantify IG. IG was detected in the aforementioned binary mixtures and, further, the amount of IG detected in those mixtures containing synthesized Compound III-N-oxide was higher than the amount of IG detected in binary mixtures of Compound III and RNA (FIG. 6 and FIG. 7). In FIG. 6A, an IG involving a branched aldehyde produced by the decomposition of Compound III-N-oxide with mRNA resulted in one peak, consistent with one of the retention times observed in the Compound III IG profile. In FIG. 6B-C, a spike series of the straight chain aldehyde results in the increase in the earliest-eluting IG peak, confirming its identity. Peak tailing at the highest spiked level is likely due to the accumulation of multiple modifications per mRNA molecule. In FIG. 7, a binary mixture of pure Compound III-N-oxide with mRNA results in dramatically higher IG than Compound III itself, suggesting N-oxide as a key reactive impurity. Additionally, the percentage of IG increased over time in binary mixtures containing Compound III and RNA and in binary mixtures containing Compound III-N-oxide and RNA. Together, this data is consistent with IG formation driven and caused by reaction of Compound III-N-oxide with RNA. Notably, binary mixtures prepared with chromatographically purified Compound III (up to 99% purity with no detectable Compound III-N-oxide) and RNA still formed IG over time (FIG.

8). The latter result suggests that Compound III can decompose into Compound III-N-oxide over time and Compound III-N-oxide can react with RNA to form IG.

Figure 9:
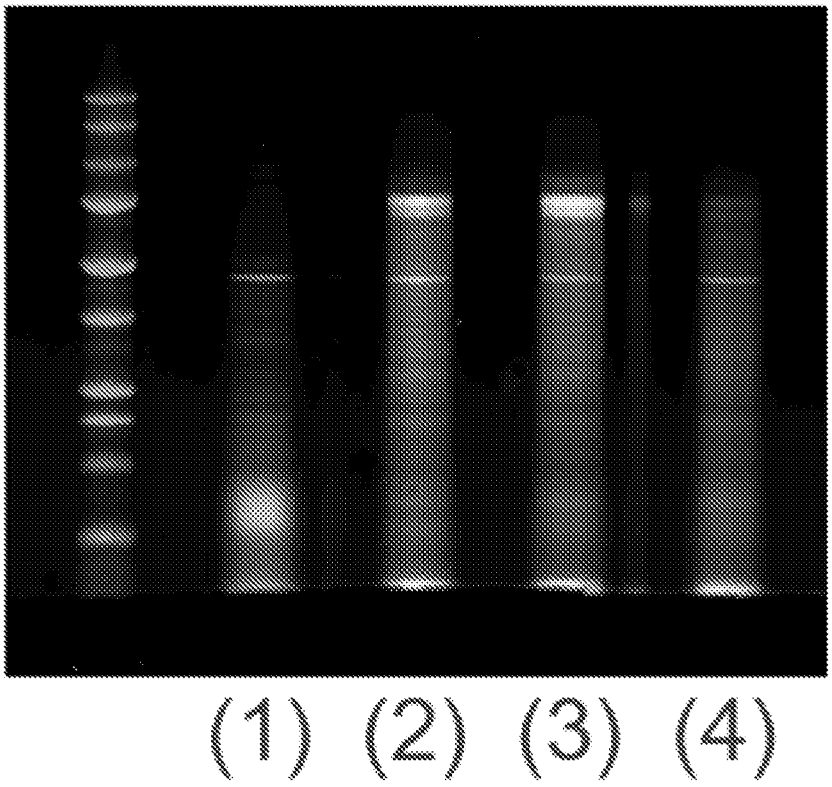
FIG. 9 is a gel showing protein content separated by electrophoresis from cell-free translation reactions comprising non-translating control (1), deformulated LNPs that had comprised mRNA and Compound III (2), main peak isolated by HPLC from formulated LNPs comprising mRNA and Compound III (3), or IG isolated by HPLC from formulated LNPs comprising mRNA and Compound III (4).
Figure 10A:
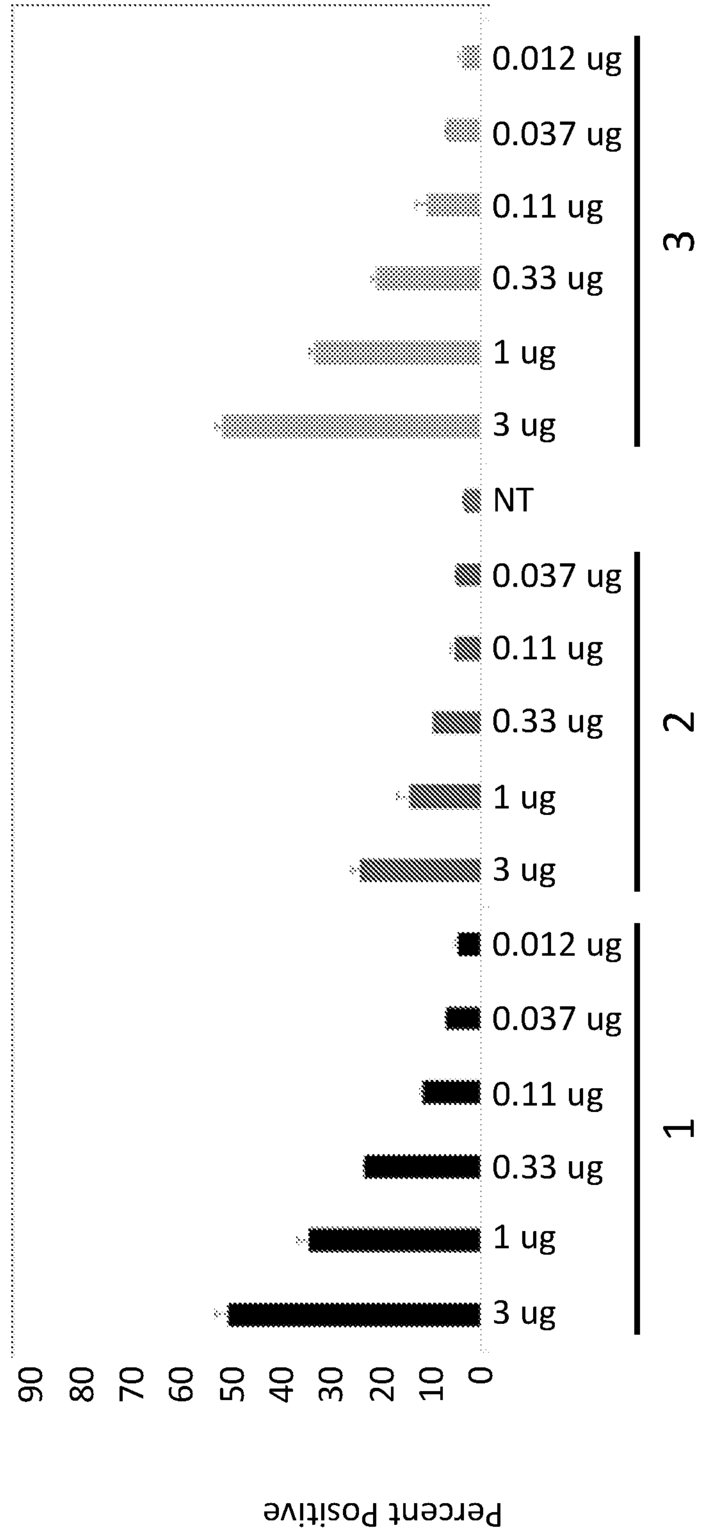
FIGS. 10A-10B are bar graphs showing results of fluorescent activated cell sorting (FACs) with cells transfected either with unmodified RNA (1), main peak isolated by HPLC from LNPs comprising mRNA and MC3 (3), or IG isolated by HPLC from LNPs comprising mRNA and MC3 (2).

Example 4. Isolated Impurity Group has Low Competency as a Translation Template To assess whether or not (and to what extent) IG is an adequate translation template, cell-free translation assays and in vitro expression assays were performed with different templates and the amount of protein translated from the templates was quantified by gel electrophoresis and fluorescent activated cell sorting. The templates tested included non-translating control, deformulated LNPs that had comprised mRNA and Compound III, main peak isolated by HPLC from formulated LNPs comprising mRNA and Compound III, and IG isolated by HPLC from formulated LNPs comprising mRNA and Compound III. In brief, RNA was extracted from lipid nanoparticles by precipitation in isopropanol as described in Example 1. The unmodified RNA population and impurity group population were isolated by ion pair reversed phase HPLC and exchanged into water by ultrafiltration with 30 kDa cutoff filters. The initial extracted RNA and two separated fractions were then normalized to 0.1 mg/mL in water and analyzed by cell-free translation (FIG. 9) and in vitro expression in cells (FIG. 10)

Cell-free translation assays were performed in wheat germ extract with incorporation of the methionine analogue azidohomoalanine (AHA), which was then fluorescently labeled by a click reaction with dibenzocyclooctyne IRDye 800CW (DBCO). Briefly, the extracted, diluted RNA was denatured and then combined with a master mix containing the wheat germ extract in potassium acetate and an amino acid mix with AHA in place of methionine. The plate was incubated at room temperature protected from light, and then the click reaction was performed by adding DBCO and incubating for an additional hour at room temperature. The resulting reaction was analyzed by SDS Page gel with fluorescent detection. A clear full-length protein band was present in lane 2 (the extracted mRNA) and lane 3 (the isolated main peak), but almost entirely absent in lane 4 (the isolated IG). See FIG. 9.

Figure 10B:
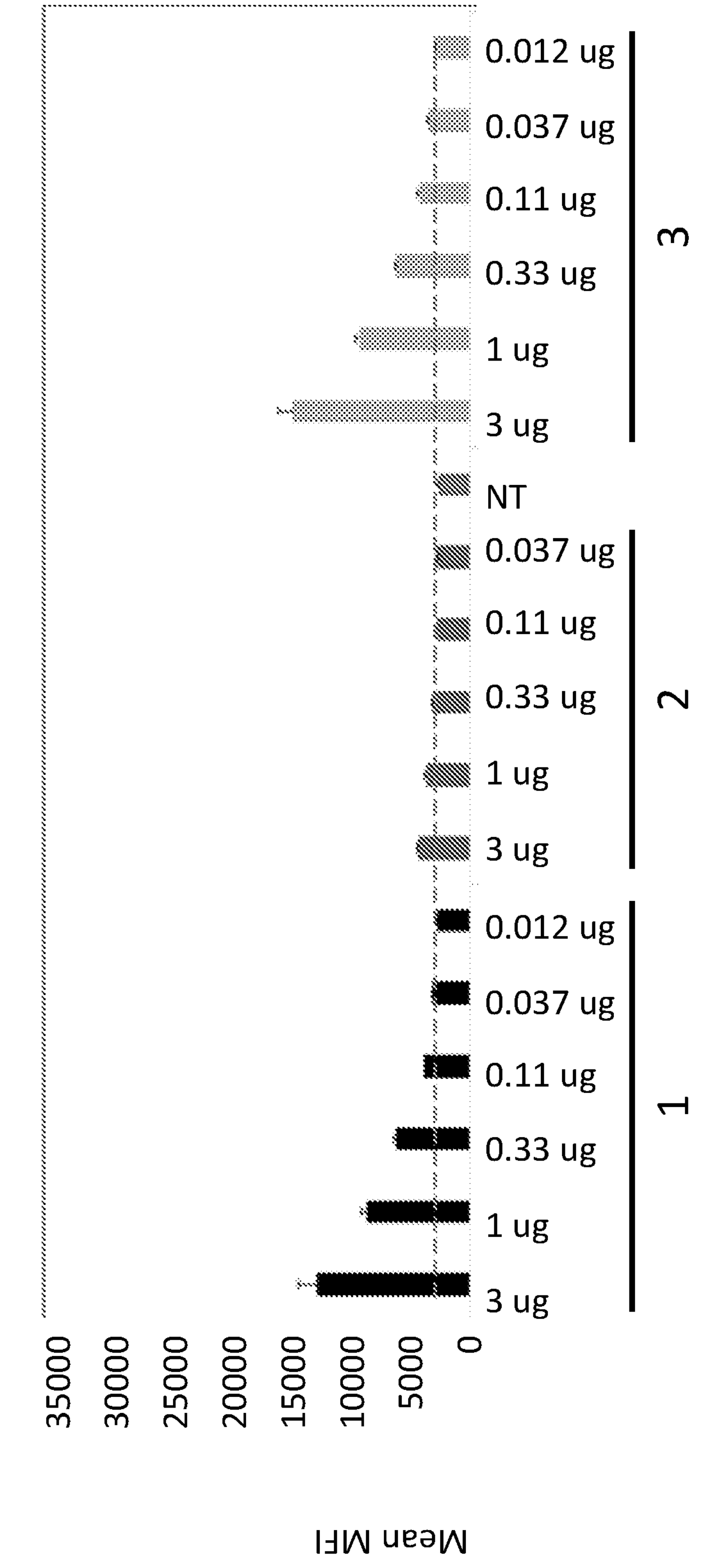

In vitro expression of the extracted sample and two isolated peaks were performed in human cervical cancer HeLa cells with lipofectamine as a transfection agent. Expression of the 6-point dose curve was evaluated at 18 hours by FACS (FIG. 10). Fluorescence levels were comparable in cells transfected with unmodified RNA (data marked as "1") and in cells transfected with main peak isolated by HPLC from LNPs comprising mRNA and MC3 (data marked as "3"). In contrast, fluorescence levels were reduced in cells transfected with IG isolated by HPLC from LNPs comprising mRNA and MC3 (FIG. 9). Additionally, the isolated impurity group transfection (data marked as "2") showed very low signal for total expression (FIG. 10B) compared to the extracted mRNA (data marked as "1") and main peak (data marked as "3"). The residual expression is again likely due to the residual intact RNA. Together the data in FIG. 9 and FIG. 10 indicate that IG is a poor template for translation compared to unmodified RNA and RNA formulated for short times with un-treated lipid.

Example 5. Pre-Treatment of Compound III with Immobilized Reducing Agents

Figure 11:
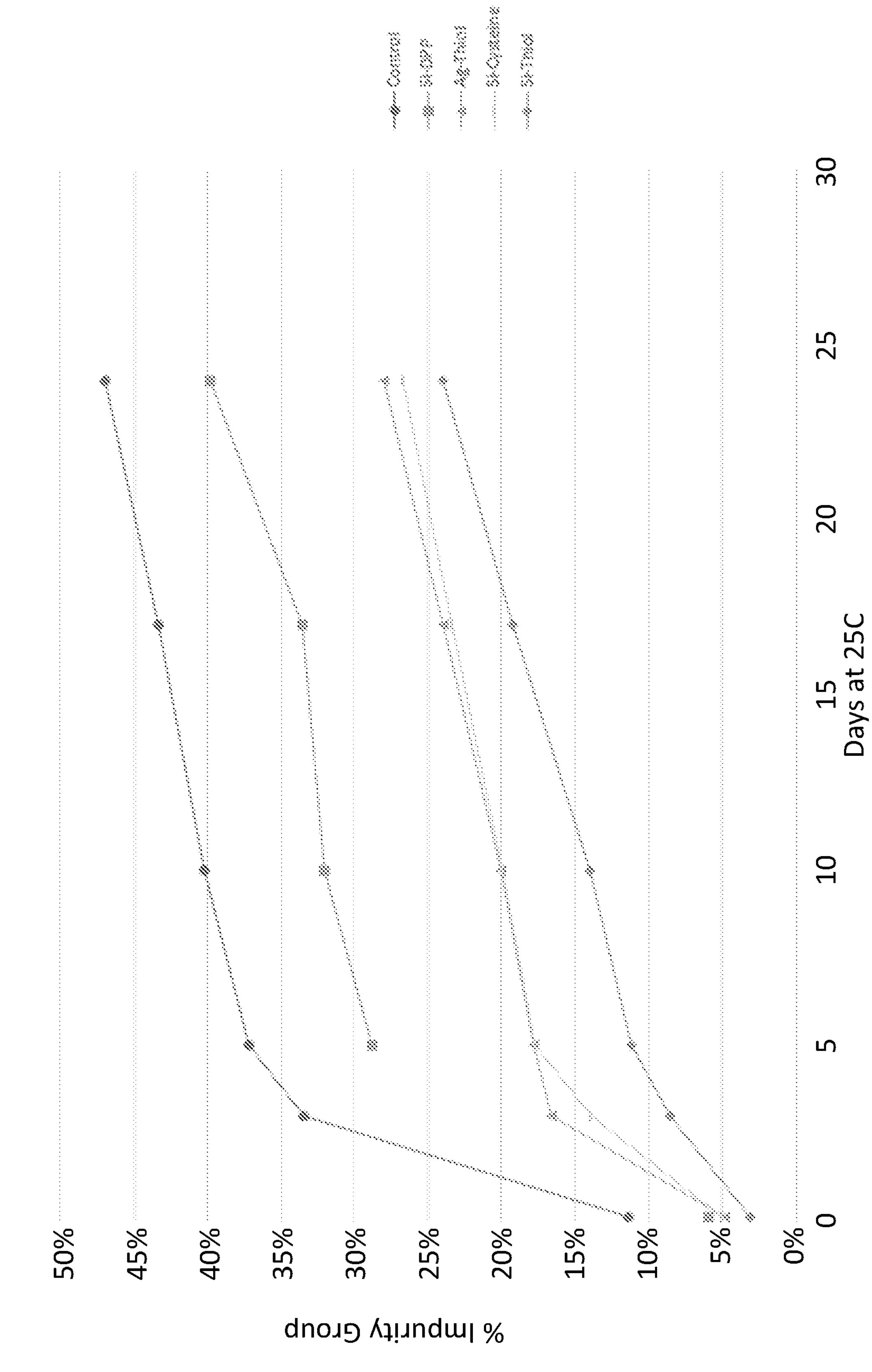
FIG. 11 is a graph showing percentage of IG detected in LNP compositions comprising mRNA and Compound III (●) or comprising mRNA and Compound III that was pre-treated prior to formulation with select immobilized reducing agents—e.g. Si-DPP (■), Ag-Thiol (▲), Si-Cysteine (–), or Si-Thiol (♦).

To determine if treatment of Compound III with reducing agents can confer reduced percentage of IG formed in binary mixtures of RNA and Compound III, binary mixtures of RNA and Compound III that was pre-treated with select reducing agents were prepared and the percentage of IG was quantified according to the protocol detailed in Example 1. In brief, packed beds of silica- and agarose-based immobilized reducing agents were prepared in spin columns; reducing agents were selected from the group including Si-DPP, Ag-Thiol, Si-Cysteine, or Si-Thiol. The resins were first treated with a reducing solution of 10 mM DTT and 10 mM EDTA in 10 mM TrisHCl pH7.5, followed by ethanol to remove residual water. A solution of Compound III was then applied to the resin, agitated by inversion to create a slurry, and allowed to incubate. The lipids were recovered from the resin by centrifugation. Control binary mixtures of RNA and Compound III contained IG at ~10 percent after 0 days, ~40 percent after 5 days, and ~45 percent after 25 days (FIG. 11). In contrast, the binary mixtures of RNA and Compound III that were pre-treated with either Ag-Thiol, Si-Cysteine, or Si-Thiol exhibited reduced levels of IG compared to control binary mixtures (FIG. 11). A significant decrease in the initial rate of IG formation was observed, pointing to the elimination of reactive species by the immobilized reducing agents.

Figure 12A:
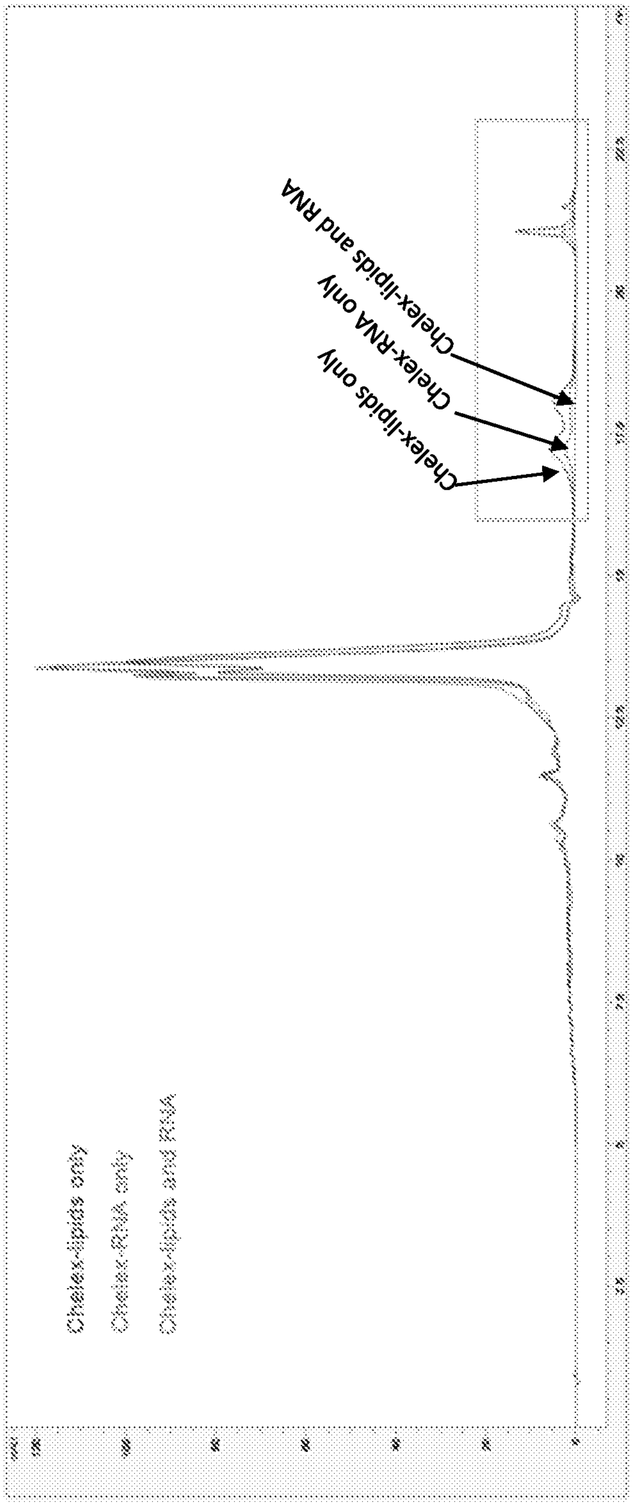
FIGS. 12A-12B are overlaid HPLC chromatograms of LNP compositions comprising mRNA and Compound III for which no components (bottom curve) or at least one component (Compound III ("lipids"): top curve; mRNA: middle curve) was pre-treated prior to formulation with Chelex-100 resin containing immobilized iminodiacetic acid.
Figure 12B:
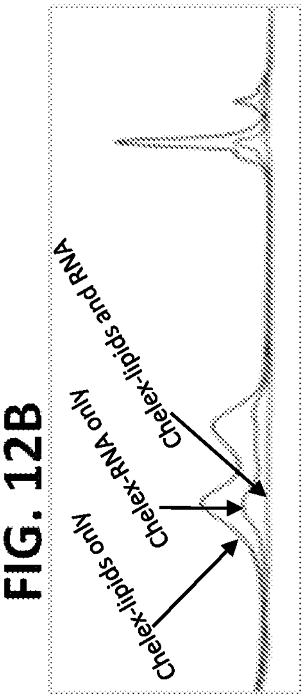
Figure 13:
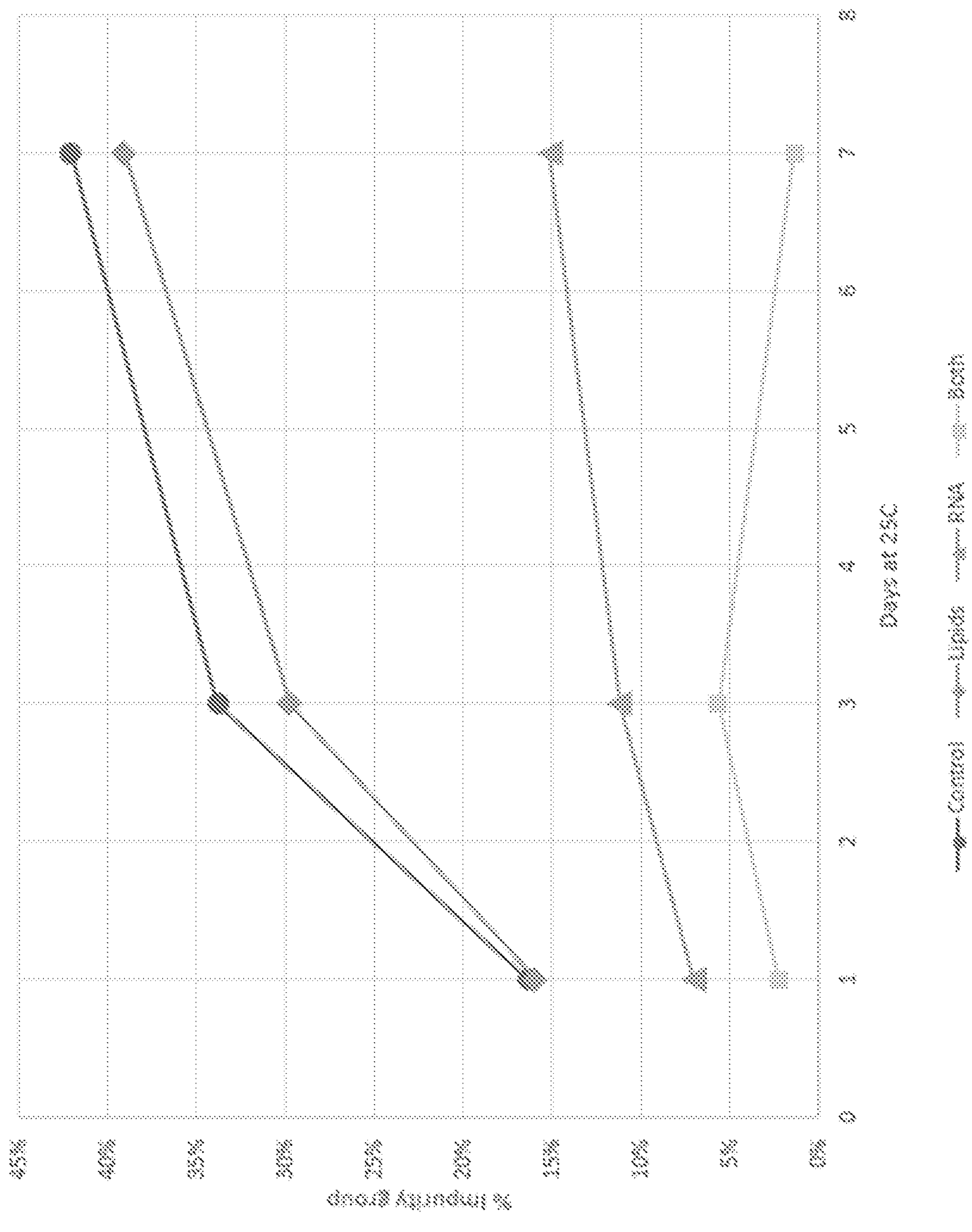
FIG. 13 is a graph showing percentage of IG detected in LNP compositions comprising mRNA and Compound III for which no components or at least one component was pre-treated prior to formulation with Chelex-100 resin containing immobilized iminodiacetic acid; only mRNA pre-treated (▲); only Compound III ("lipids") pre-treated (♦); both mRNA and Compound III pre-treated (■); neither mRNA nor Compound III pre-treated ("control") (●).

Example 6. Removal of Trace Metals from Compound III, mRNA, or Both by Pre-Treatment with Chelex-100 Resin To determine if removal of trace metals from Compound III and/or RNA confers reductions in the percentage of IG formed in binary mixtures of RNA and Compound III, binary mixtures were prepared with RNA and Compound III in which one or both components were pre-treated with Chelex-100 resin and the percentage of IG was quantified according to the protocol detailed in Example 1. In brief, packed beds of molecular biology grade Chelex-100 resin containing immobilized iminodiacetic acid that chelates trace metals (Bio-Rad Inc.) were prepared in 2 mL spin columns. The Chelex-100 resin was washed with sodium acetate pH 5.5 until the pH of the eluent was stable at below-neutral. For the aqueous RNA purification, RNA was diluted in sodium acetate pH 5.5 and applied to the bed, which was suspended into a slurry and allowed to incubate. For the lipid purification, the buffered resin was then washed with at least 4 column volumes of neat ethanol to prevent the introduction of water to the lipid sample, and the lipid solution was then applied and similarly allowed to incubate. Both resins were then eluted by centrifugation, and the resulting solution used to prepare binary mixtures as described in Example 3. Samples were stored at 25° C. and the percentage of IG was quantified by HPLC over time (FIG. 12A-12B and FIG. 13). Control binary mixtures of RNA and Compound III contained IG at ~15 percent after 1 day, ~35 percent after 3 days, and ~40 percent after 7 days. In contrast, binary mixtures of RNA and Compound III in which the RNA or both the RNA and Compound III were pre-treated with Chelex-100 resin exhibited reduced levels of IG compared to control binary mixtures (FIG. 13). Treatment of the aqueous RNA solution resulted in a significant reduction in IG, and an additional benefit was seen by also treating the lipids.

Figure 14:
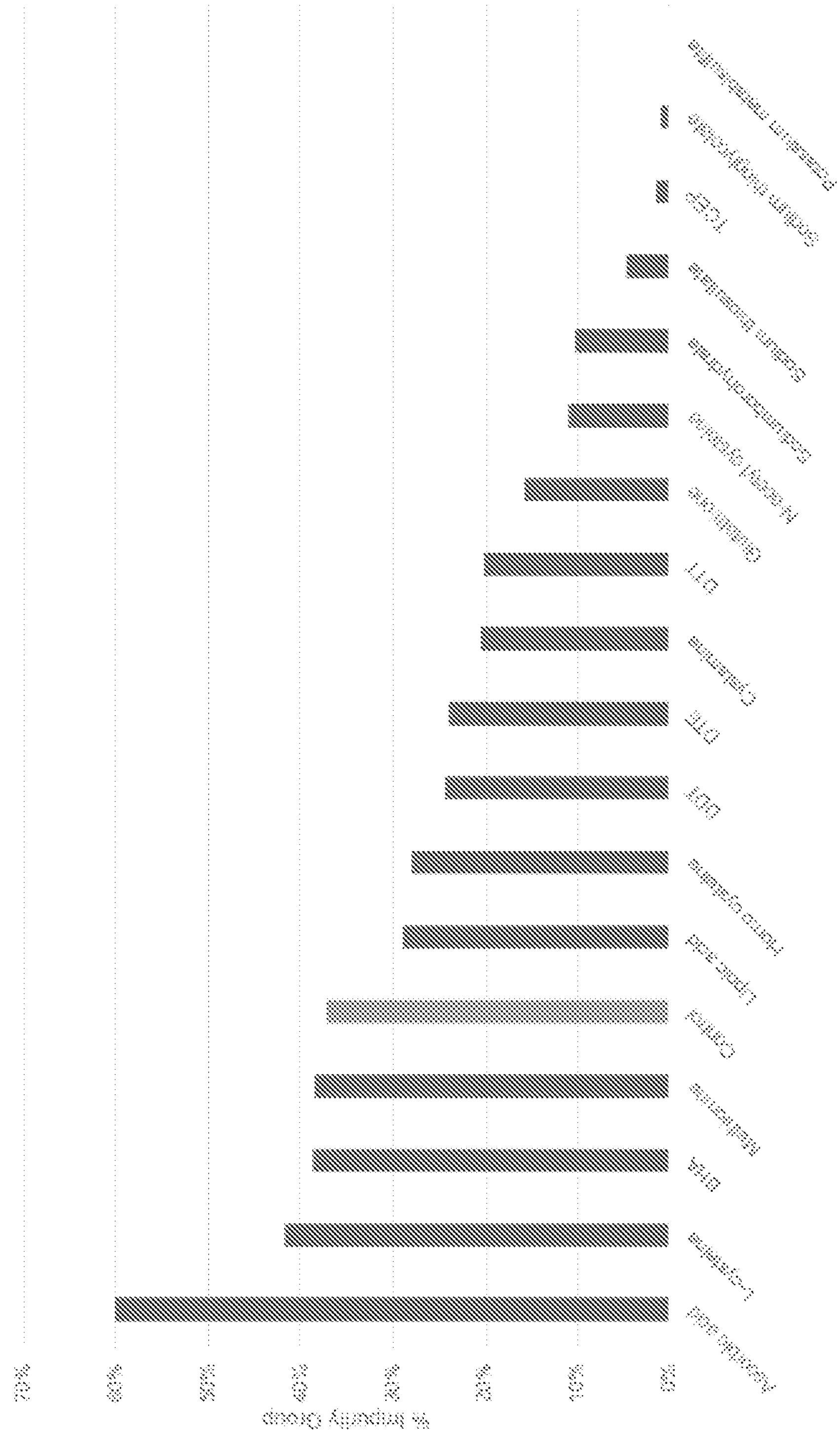
FIG. 14 is a graph showing percentage of IG detected in LNP compositions comprising mRNA and Compound III or comprising mRNA, Compound III, and 1 mM of select anti-oxidants—e.g. ascorbic acid, L-cysteine, BHA, methionine, lipoic acid, homo cysteine, DDT, DTE, cystamine, DTT, glutathione, N-acetyl cysteine, sodium borohydrate, sodium thiosulfate, TCEP, or sodium thioglycolate, or potassium metabisulfite.
Figure 15:
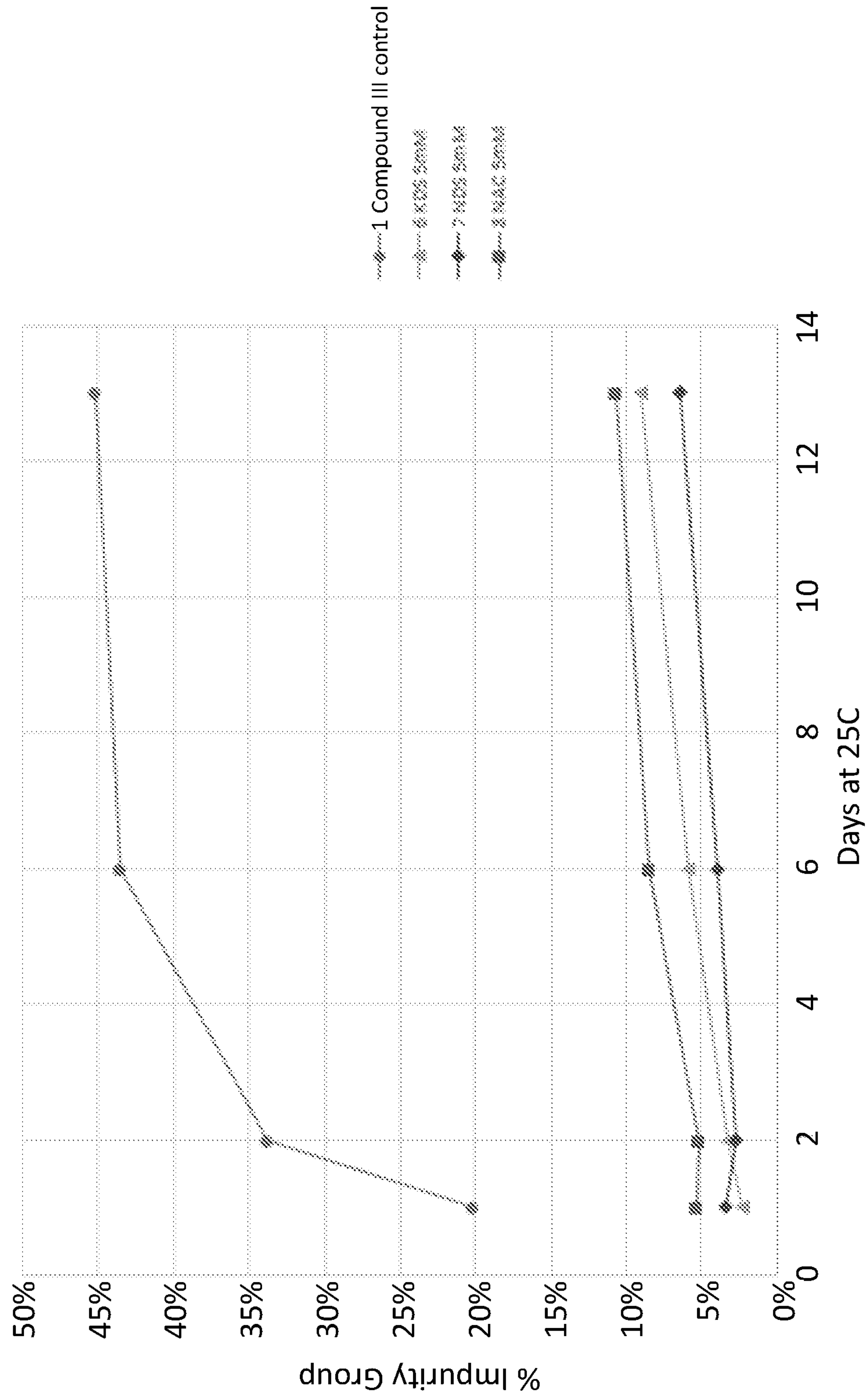
FIG. 15 is a graph showing percentage of IG detected in LNP compositions comprising mRNA and Compound III (●) or comprising mRNA, Compound III, and 5 mM of select reducing agents—e.g. potassium metabisulfite (▲), sodium metabisulfite (♦), or N-acetylcysteine (■).

Example 7. Treatment of RNA and/or Lipids with Select Anti-Oxidants and Reducing Agents Conferred Alterations to the Percentage of Impurity Group Formed To determine if treatment with reducing agents or anti-oxidants confers reductions in the percentage of IG formed in binary mixtures of RNA and Compound III, binary mixtures were prepared with RNA and Compound III in which the RNA component was prepared with select reducing agents or anti-oxidants and the percentage of IG in the resulting binary mixtures was quantified according to the protocol detailed in Example 1. The reducing agents and anti-oxidants tested included ascorbic acid, L-cysteine, BHA, methionine, lipoic acid, homo cysteine, DDT, DTE, cystamine, DTT, glutathione, N-acetyl cysteine, sodium borohydrate, sodium thiosulfate, TCEP, and sodium thioglycolate, potassium metabisulfite, and sodium metabisulfite. In brief, reducing agent and antioxidant stock solutions were freshly prepared in water at concentrations of 0.25 M to 1 M, with the exception of lipoic acid and L-cysteine which were prepared in ethanol. For the data shown in FIG. 14, RNA was prepared in sodium acetate pH 5.5 and aliquoted into individual vials, then spiked with each of the prepared antioxidant or reducing agent stocks to a concentration of 1.33 mM. Addition of 4 mg/mL Compound III in ethanol to 25% of the total volume then resulted in a 1 mM final reducing agent or antioxidant concentration in each. Samples were held at 25° C. and the percentage of IG was quantified by HPLC after 18 hours (FIG. 14). For the data in FIG. 15, a similar protocol was followed with one exception being the reducing agents were at 5 mM concentration. Notably, treatment with lipoic acid, homo cysteine, DDT, DTE, cystamine, DTT, glutathione, N-acetyl cysteine, sodium borohydrate, sodium thiosulfate, TCEP, sodium thioglycolate, and potassium metabisulfite conferred reduced levels of IG in the binary mixtures of RNA and Compound III after 18 hours (FIG. 14) with the latter six compounds conferring less than 10 percent IG detected after 18 hours compared to ~35 percent IG detected in control binary mixtures (FIG. 14). For the majority of the reducing agents and antioxidants tested, some reduction in IG formation was seen, most effectively for the strong and thiol-based reducing agents such as TCEP, thioglycolate, and metabisulfite. Notably, treatment with 5 mM potassium metabisulfite or 5 mM sodium metabisulfite or 5 mM acetyl cysteine conferred reduced levels of IG in binary mixtures of RNA and Compound III with less than 10 percent IG detected after 13 days of incubation at 25° C. compared to ~45 percent IG detected in control binary mixtures (FIG. 15). In FIG. 15, potassium metabisulfite, sodium metabisulfite, and N-acetyl cysteine were all effective at eliminating the fast initial rate of IG formation in Compound III binaries.

Figure 16:
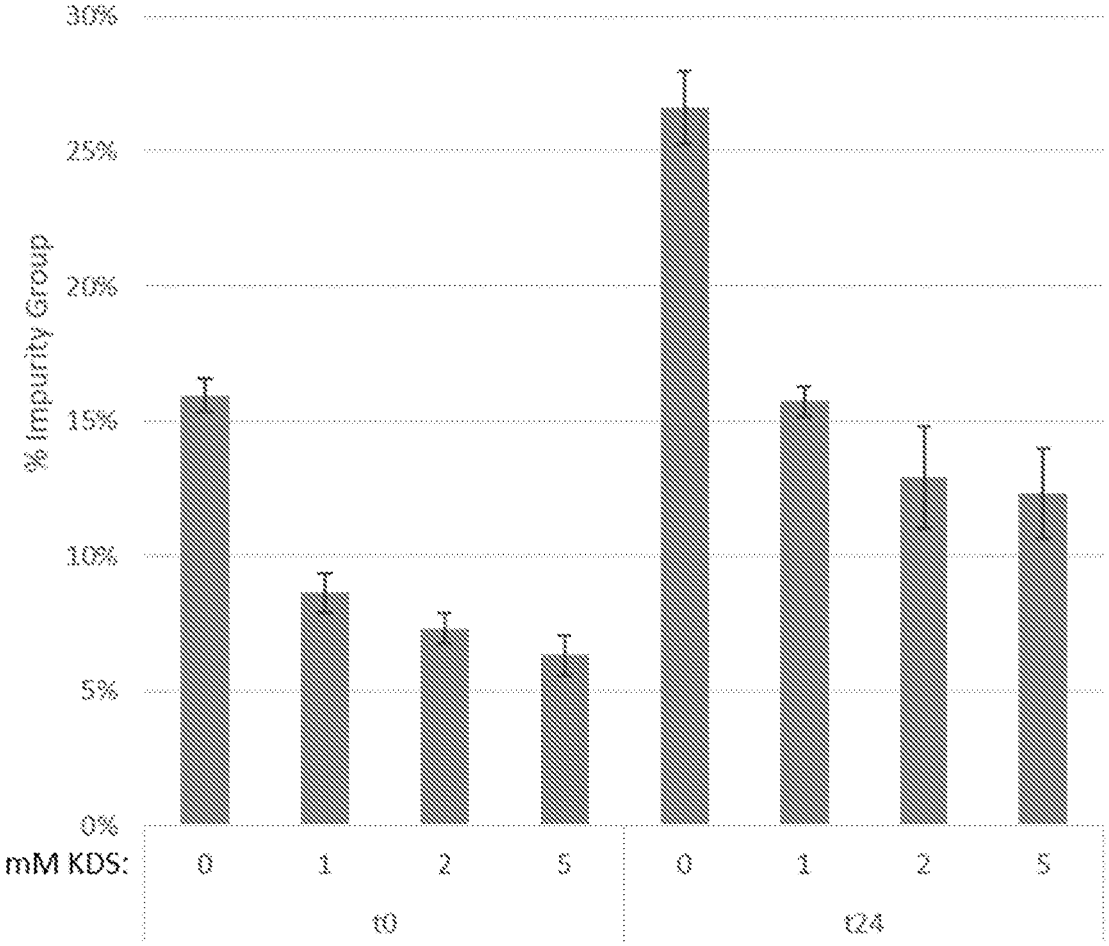
FIG. 16 is a graph showing percentage of IG detected in LNP compositions comprising mRNA and Compound III prepared with select concentrations of sodium metabisulfite (KDS) prior to formulation and for which KDS was removed following formulation by dialysis with 20 mM Tris.

FIG. 16 is a graph showing percentage of IG detected in LNP compositions comprising mRNA and Compound III prepared with select concentrations of sodium metabisulfite (KDS) prior to formulation and for which KDS was removed following formulation by dialysis with 20 mM Tris.

The percentage IG detected in binary mixtures of mRNA and Compound III was reduced when treated with higher concentrations after formulation (t=0 h) and following 24 hours (FIG. 16).

Figure 17:
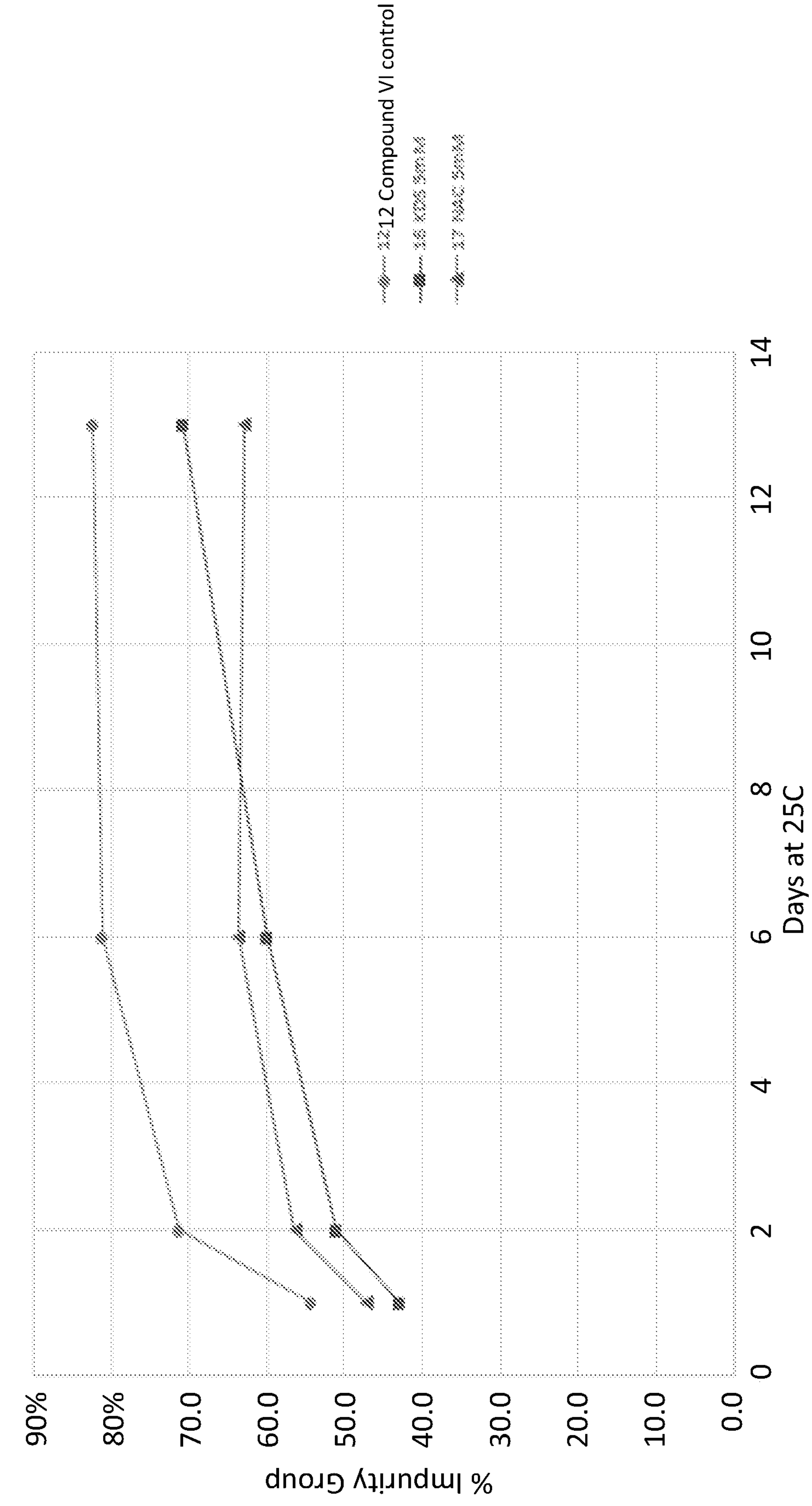
FIG. 17 is a graph showing percentage of IG detected in LNP compositions comprising mRNA and Compound VI (●) or comprising mRNA, Compound VI, and 5 mM of select reducing agents—e.g. potassium metabisulfite (■), or N-acetylcysteine (▲).

To determine if treatment with reducing agents or antioxidants confers reductions in the percentage of IG formed in binary mixtures of RNA and Compound VI, binary mixtures were prepared with RNA and Compound VI in which the RNA component was prepared with select reducing agents at 5 mM concentration and the percentage of IG in the resulting binary mixtures was quantified according to the protocol detailed in Example 1. The control binary mixtures of RNA and Compound VI contained IG at ~55 percent after 1 day, ~70 percent after 2 days, and ~80 percent after 13 days. In contrast, treatment of binary mixtures of RNA and Compound VI with select reducing agents conferred IG at ~45 percent after 1 day, ~55% after 2 days, and ~60-70% after 13 days (FIG. 17).

Figure 18:
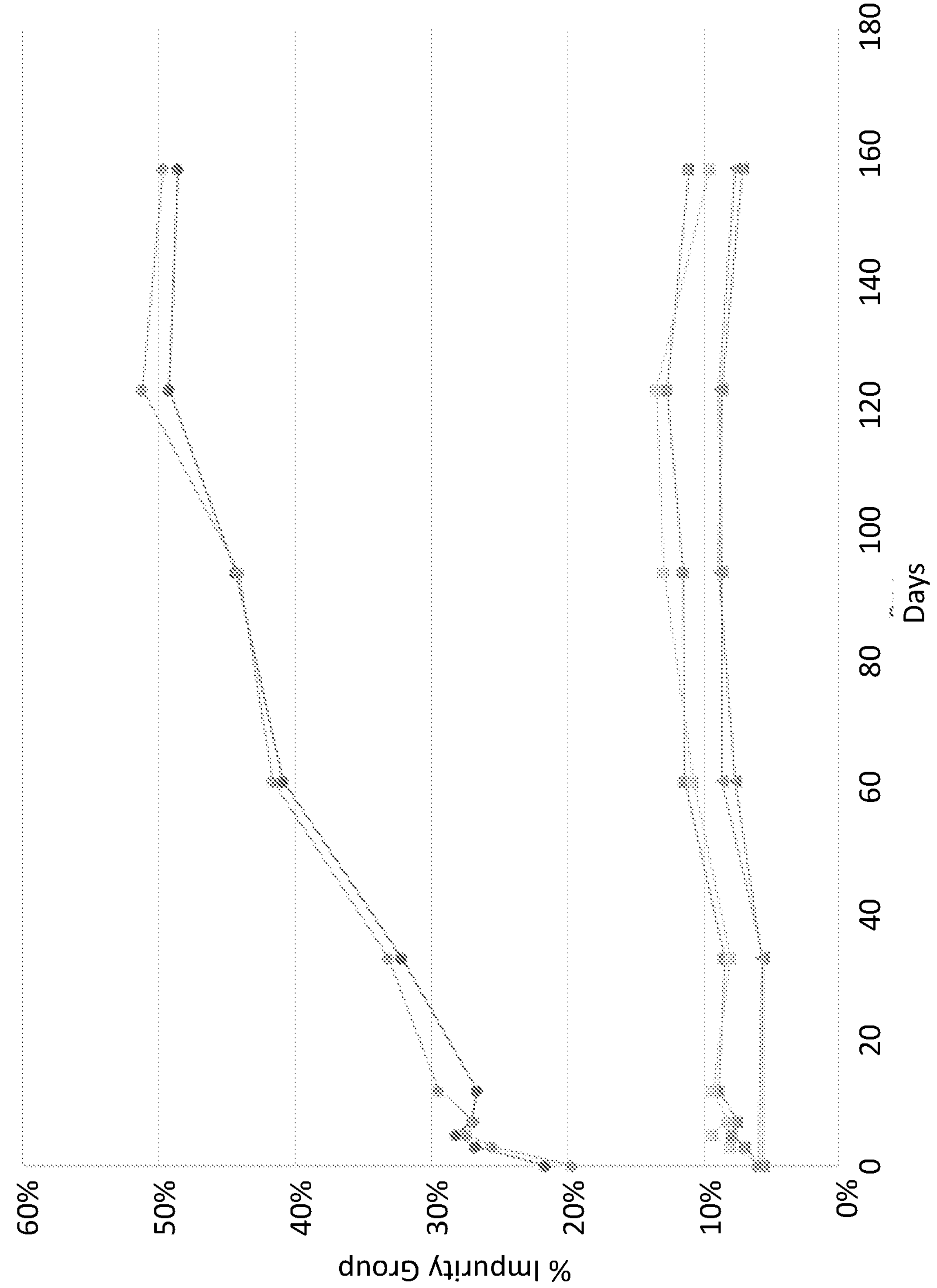
FIG. 18 is a graph showing percentage of IG detected in LNP compositions comprising mRNA (formulated at two different concentrations), Compound III, and either PBS and stored at 5° C. (●) or Tris and stored at 5° C. (■), or at –20° C. (▲).

Example 8. Determination of how Different Buffering Agents and pH of RNA and/or Lipids Prior to LNP Formulation Conferred Alterations to the Percentage of Impurity Group Formed in LNP To determine if different buffering conditions confer reductions in the percentage of IG formed in binary mixtures of RNA and Compound III, binary mixtures were prepared with RNA and Compound III and buffered with PBS or Tris at and the percentage of IG in the resulting binary mixtures was quantified according to the protocol detailed in Example 1. In brief, a single batch of LNPs was split mid-process into four aliquots, two of which were prepared in a final buffer of 1×PBS and the other two of which were prepared in a final buffer of 100 mM Tris-HCl pH 7.4. One of each buffer condition was prepared at a final RNA concentration of 1.27 mg/mL, and the other diluted to 0.98 mg/mL. The PBS lots were stored at 5° C., and the two Tris-buffered lots were further split for two storage conditions each, 5° C. and −20° C. The percentage of IG is lower in binary mixtures buffered with Tris compared to binary mixtures buffered with PBS (FIG. 18). Notably, the percentage of IG is relatively similar over time, around 10 percent, in binary mixtures buffered with Tris and stored either at 5° C. or 20° C.

Figure 19:
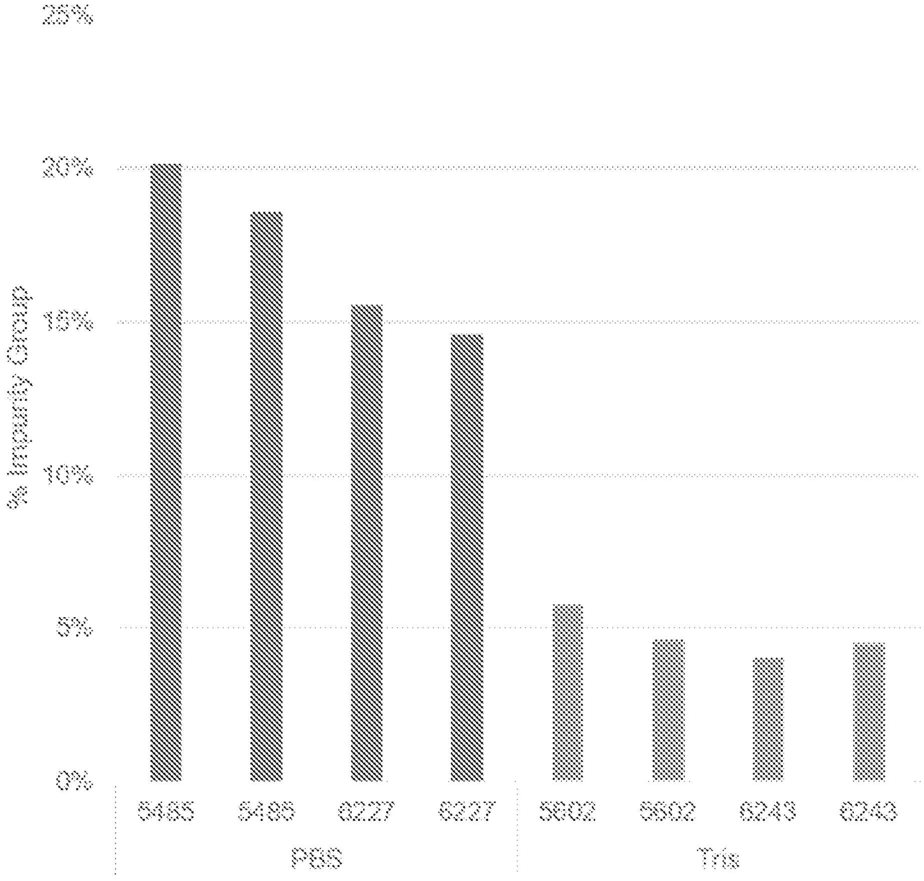
FIG. 19 is a graph showing percentage of IG detected in LNP compositions comprising mRNA and Compound VI either in 1×PBS or in 100 mM Tris.

To determine if different buffering conditions confer reductions in the percentage of IG formed in binary mixtures of RNA and Compound VI, binary mixtures were prepared with RNA and Compound VI and buffered PBS or Tris at and the percentage of IG in the resulting binary mixtures was quantified according to the protocol detailed in Example 1. FIG. 19 shows a series of sequential batches of the same RNA formulated in Compound VI LNPs, and stored at 5° C. in either PBS (1×PBS, pH 7.2) or Tris final buffers (20 mM Tris, 8% sucrose, pH 8). The percentage of IG is lower in binary mixtures buffered with Tris compared to binary mixtures buffered with PBS (FIG. 19).

In both lipid systems, storage in Tris buffers results in significantly less IG formation.

Figure 21:
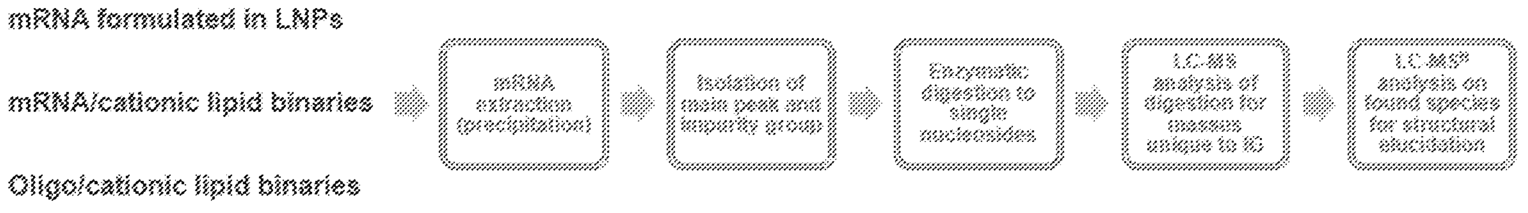
FIG. 21 is a schematic diagram of how mRNA-aldehyde adduct impurity species can be detected by enzymatic digestion to nucleosides and LC-MS/MS analysis.
Figure 21:
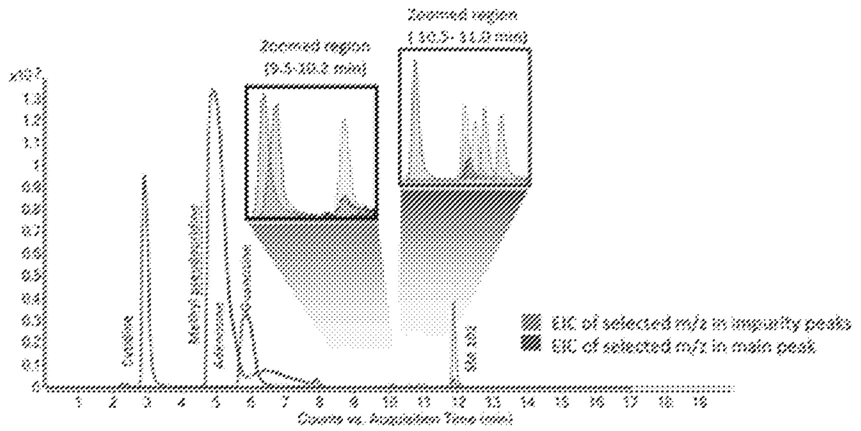
Figure 21:
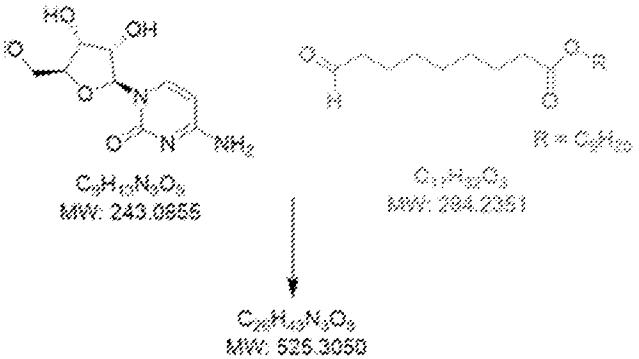

Example 9. Detection of mRNA-Aldehyde Adduct (IG Group) Species by Enzymatic Digestion to Nucleosides and LC-MS/MS Analysis To detect the lipid adduct species on the single nucleoside level an enzymatic digestion and LC-MS/MS analysis method was developed (see schematic in FIG. 21). In brief, the RNA extracted from LNP formulations or lipid:RNA binaries was subjected to an enzymatic digestion to single nucleosides, using S1 nuclease and benzonase. This digest was then analyzed by reversed phase HPLC-MS to identify the later-eluting hydrophobic modified nucleosides. By first isolating the unmodified main peak and adduct peak, or extracting multiple timepoints to obtain a low-IG and high-IG samples, differential analysis was performed to identify all species unique to the impurity group. One observed reaction specific to the straight chain aldehyde is shown here (FIG. 21). For mRNAs of approximately 2000 nt in length, these late-eluting peaks have been observed on the level of three orders of magnitude below the four unmodified nucleosides, consistent with very few or even single modifications per mRNA molecule.

Example 10: Production of Compound III
Compound III was produced in accordance with the following scheme:
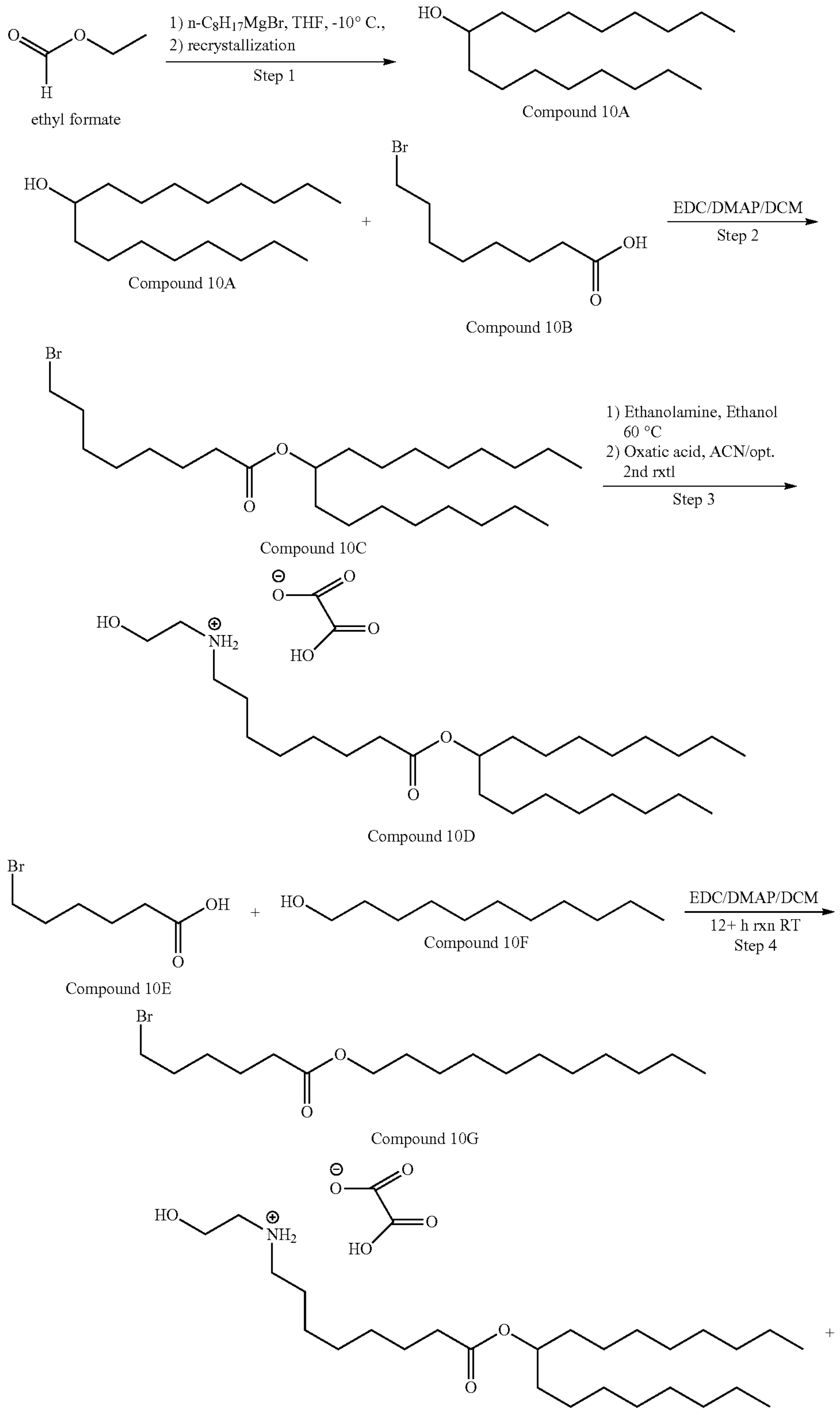
Compound 10D -continued

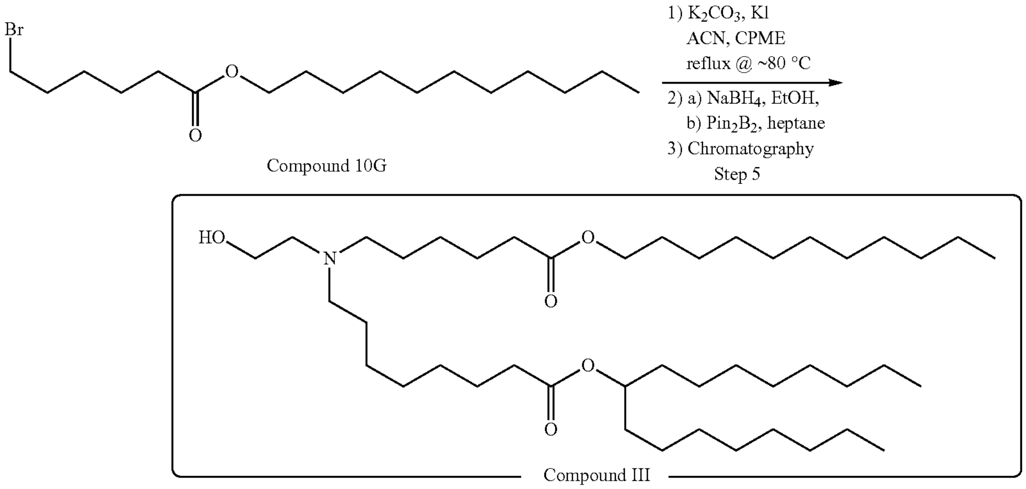

Compound 10G

Compound III

Step 1: Synthesis of Compound 10A

A Grignard addition of n-octylmagnesium chloride to ethyl formate in tetrahydrofuran was performed with temperature control (−20° C. to −10° C.) during reagent addition and exothermic reaction progress. The crude material was isolated and purified by recrystallization from a mixture of acetone and water to produce an intermediate Compound 10A.

Step 2: Synthesis of Compound 10C

The Compound 10A alcohol was coupled with a Compound 10B acid by Steglich esterification using 4-(dimethylamino) pyridine (DMAP), N-ethyl-N'-(3-dimethylamino-propyl)carbodiimide hydrochloride (EDC) in dichloromethane (DCM) to produce intermediate ester Compound 10C.

Step 3: Synthesis of Compound 10D

An alkylation reaction of Compound 10C was performed with excess ethanolamine in ethanol by stirring at 60° C.-70° C. for several hours followed by oxalate salt formation, and purification by recrystallization to produce Compound 10D.

Step 4: Synthesis of Compound JOG Compound 10E was esterified with Compound 10F using DMAP, EDC in DCM under Steglich conditions at 10° C.-25° C. Following isolation of the crude, silica gel plug purification and solvent removal were executed to produce intermediate Compound 10G.

Step 5-1: Synthesis of Crude Compound III

Coupling was performed by an alkylation reaction of Compound 10D and Compound 10G using potassium carbonate and potassium iodide in cyclopentyl-methyl ether (CPME) and acetonitrile (ACN) at elevated temperature to produce Compound III.

Potassium carbonate was added to the reactor, followed by the addition of potassium iodide. The reactor was charged with ACN. The first starting material, Compound 10G solid was added to the reactor as a slurry. Next, a CPME solution of the second starting material, Compound 10D, was added to the reactor. The mixture was stirred and heated to ~80° C. for more than 20 hours. The reaction was then cooled to 20-25° C. then the heterogeneous solution was filtered and washed in n-heptane. The crude product was concentrated at ≤40° C. in vacuo resulting in an oil.

Step 5-2: Reductive Treatment of Crude Compound III

Crude Compound III was transferred as an ethanol solution to a reactor (if necessary) and concentrated in vacuo at ≤40° C. to perform azeotropic distillation with ethanol. The crude product was dissolved in ethanol and treated with less than a molar equivalent of $NaBH_4$ at ambient temperature. The reaction was quenched with acetone and workup with n-heptane and 5% $NaHCO_3$ aqueous solution twice. The organic layer was concentrated at ≤40° C. in vacuo resulting in an oil. Crude Compound III was dissolved in n-heptane and treated with $B_2Pin_2$ at ambient temperature. This mixture was extracted with a 5% $NaHCO_3$ aqueous solution and brine solution to remove leftover reagent. Crude Compound III was concentrated at <40° C. in vacuo resulting in an oil. The resulting oil was resuspended into a 40-60% w/w n-heptane solution.

Step 5-3: Purification of Crude Compound III

Reduced Crude Compound III was loaded onto a stainless-steel column, which was packed with silica gel as a slurry in toluene. It was first eluted with by a gradient of n-heptane and increasing level of isopropyl acetate. The eluate was transferred to a rotary evaporator flask through a filter. The solvent obtained was completely evaporated under vacuum (referred to as the degassing step) to yield Purified Compound III.

Figure 22:
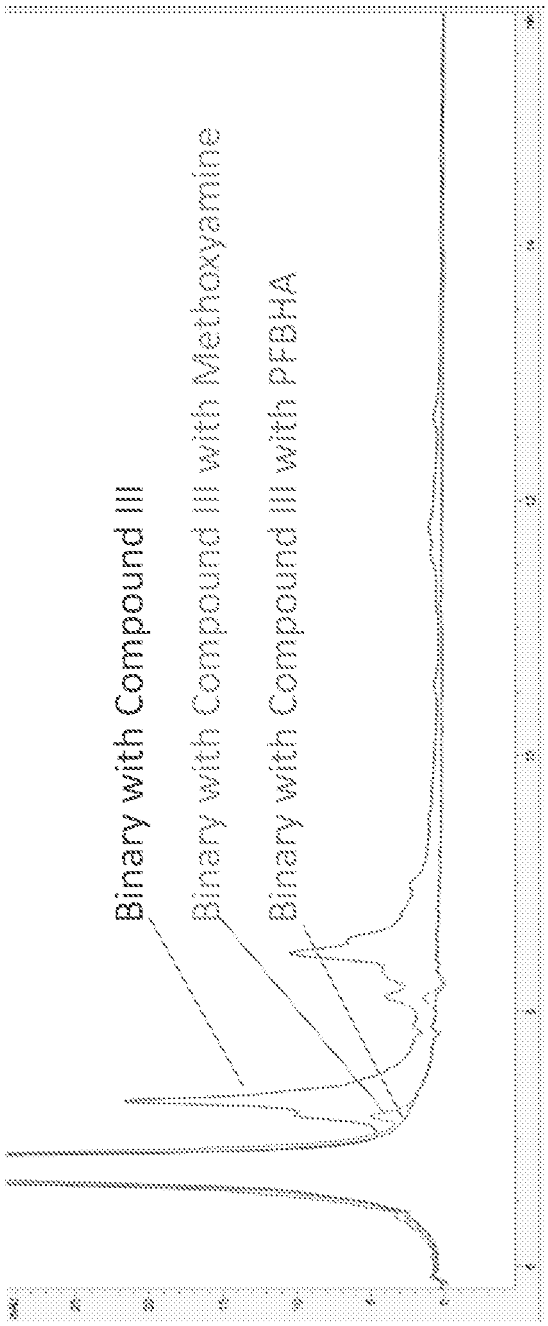
FIG. 22 shows overlaid HPLC chromatograms of compositions comprising mRNA and Compound III (Blue) alone, Compound III with Methoxyamine hydrochloride (green), and Compound III with PFBHA hydrochloride.
Figure 23:
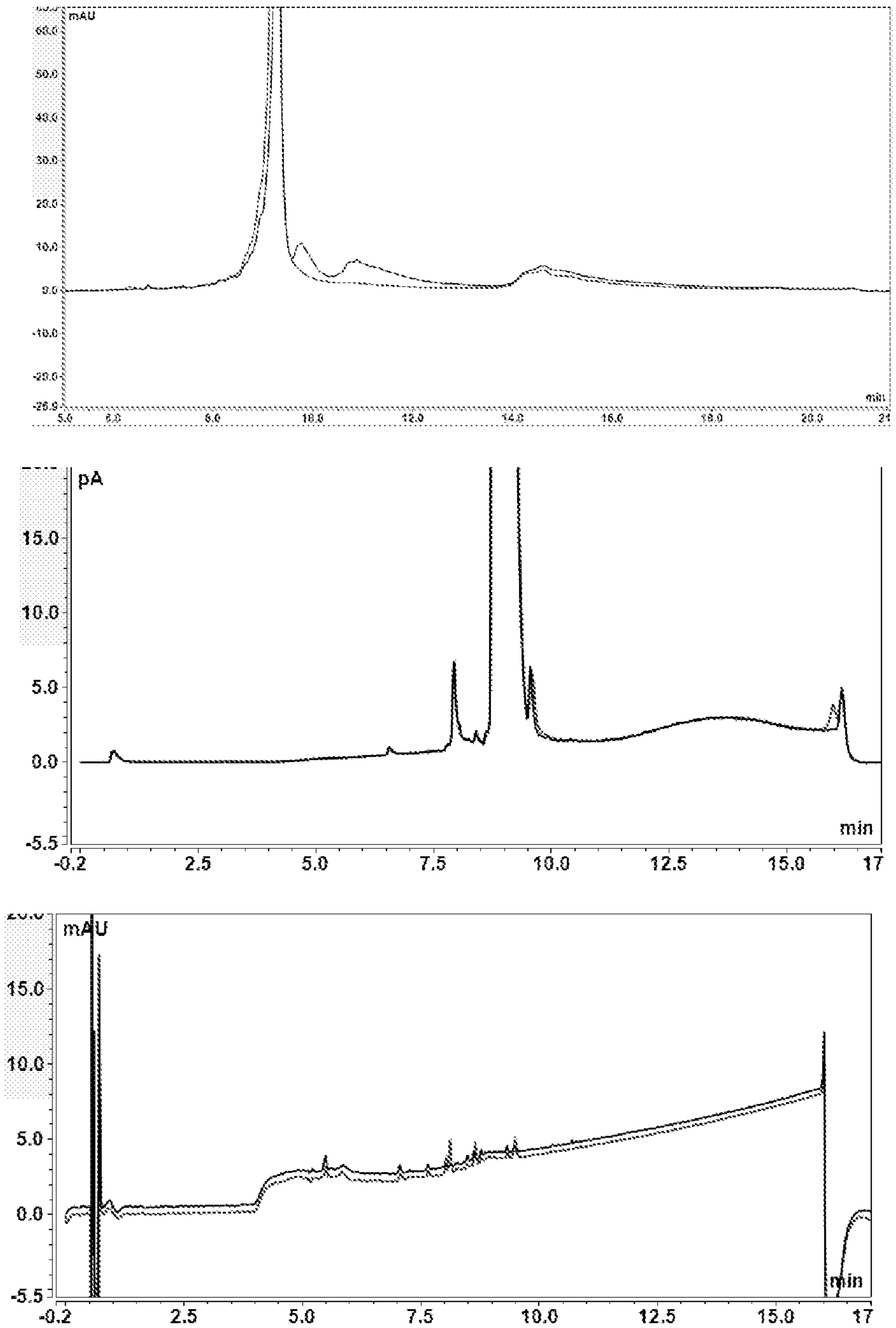
FIG. 23 shows overlaid mRNA purity profile (RPIP, top panel), Lipid purity profile (CAD, mid panel), and PFBHA profile (UV@280 nm, bottom panel) of compositions comprising mRNA and Compound III extracted with n-heptane (black) and Compound III treated with PFBHA hydrochloride and extracted with n-Heptane (blue (bottom line in top and bottom figure).

Example 11: Pre-Treatment of Compound III with Aminooxy Functionality Containing Agents Binary mixtures of RNA and Compound III that was pre-treated with selected Aminoxy functionality containing agents were prepared and the percentage of IG was quantified according to the protocol detailed in Example 1. O-(2,3,4,5,6-Pentafluorobenzyl)hydroxylamine hydrochloride (PFBHA) and Methoxyamine hydrochloride were used as representative Aminoxy functionality containing agents. In brief, Aminoxy functionality containing agents stock solutions were freshly prepared in ethanol at concentrations of 100 mM. For the data shown in FIG. 22, 4 mg/mL Compound III in ethanol was spiked with 10 ul of Aminoxy functionality containing agents stock solutions (100 mM). 1:3 ratios of this solution to RNA in sodium acetate (pH 5.5) was mixed in individual vials. Sample vials were held at 25° C. and the percentage of IG was quantified by HPLC after 18 hours (FIG. 22). Notably, treatment with PFBHA and Methoxyamine conferred reduced levels of IG in the binary mixtures of RNA and Compound III after 18 hours, conferring less than 1 percent IG detected after 18 hours compared to ~20 percent IG detected in control binary mixtures. FIG. 23 is an overlay chromatograph showing overall mRNA profile detected in binary compositions comprising mRNA and Compound III prepared with select concentrations of PFBHA prior to binary mix with mRNA solution and for which PFBHA was removed following extraction of Compound III with n-heptane solvent. When compared with compositions before n-heptane extraction, n-heptane extracted Compound III treated with PFBHA similar showed similar IG reduction (data not shown).

Example 12: Production of LNP Delivery Systems with Reduced Adduct Impurities

Lipid nanoparticles are prepared using a variety of ionizable lipids and mRNA molecules. The lipid nanoparticles are prepared using any 1, 2, 3, 4, 5, 6, 7, or all of the following processes for inhibiting or reducing ionizable lipid-polynucleotide adduct impurities:

1. Treatment of crude ionizable lipid with a scavenging agent
2. Treatment of crude ionizable lipid with a reductive treatment agent
3. Treatment of ionizable lipid with a reducing agent
4. Treatment of ionizable lipid with a chelating agent
5. Treatment of mRNA with a reducing agent
6. Treatment of mRNA with a chelating agent
7. Treatment of LNP with a reducing agent
8. Treatment of LNP with a chelating agent The experiments are performed with each of the following ionizable lipids:

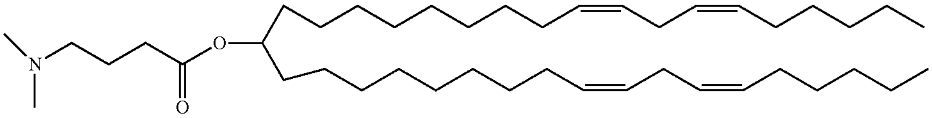
,
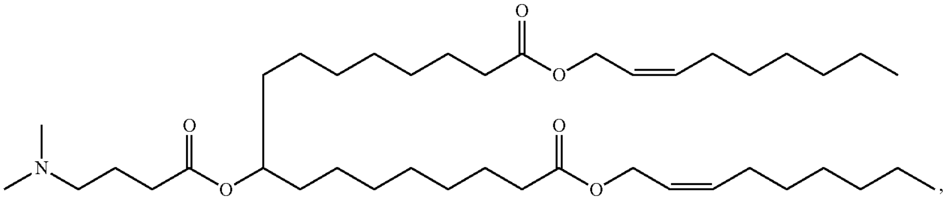
,
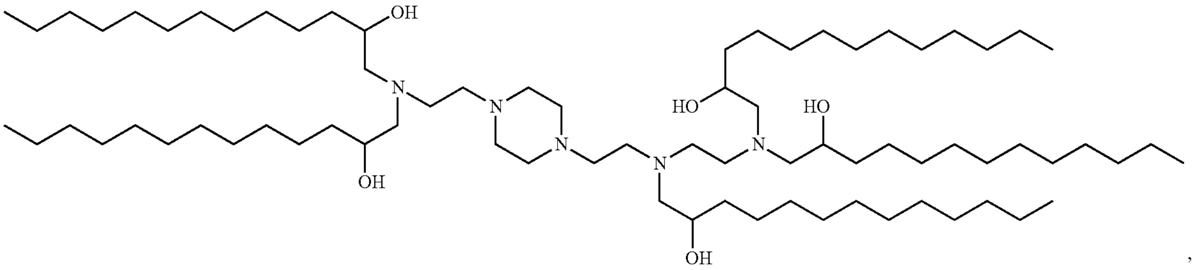
,
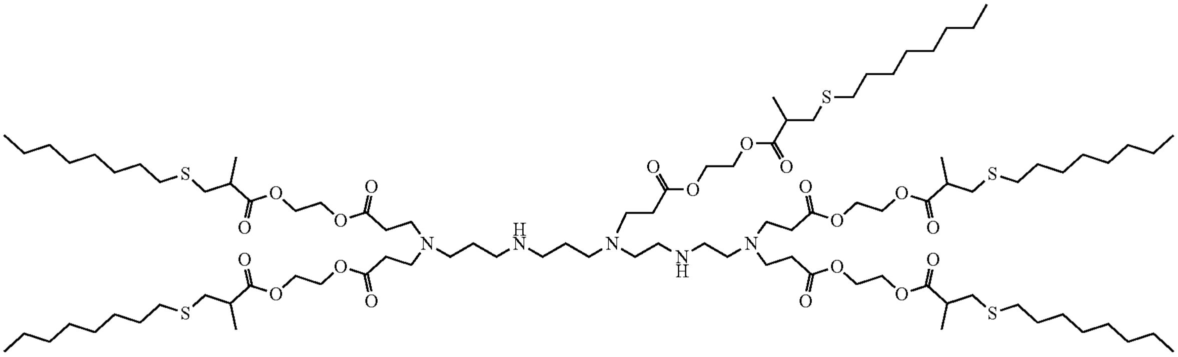
,
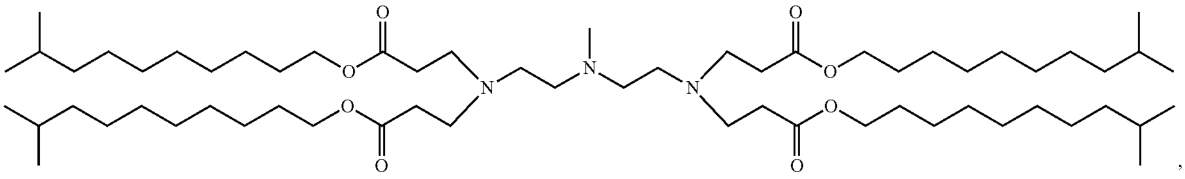
,

-continued

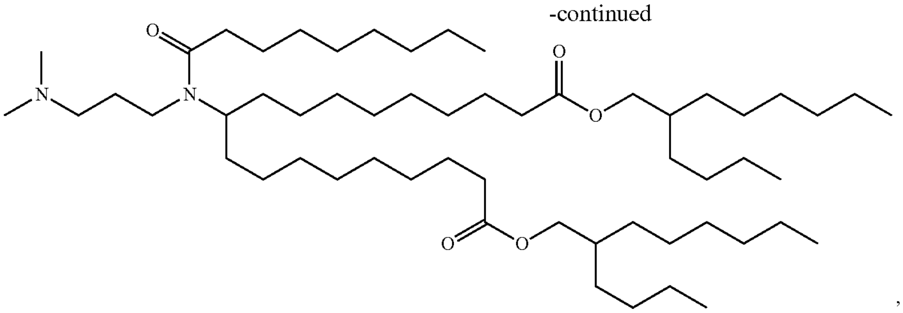

,

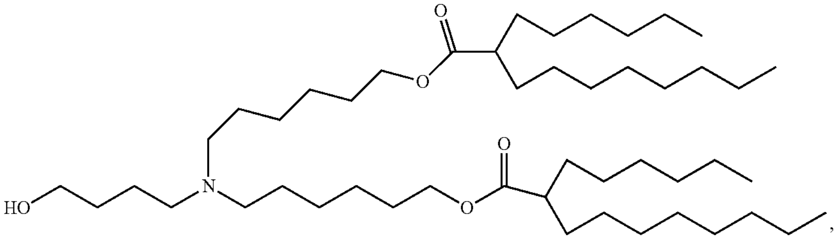

,

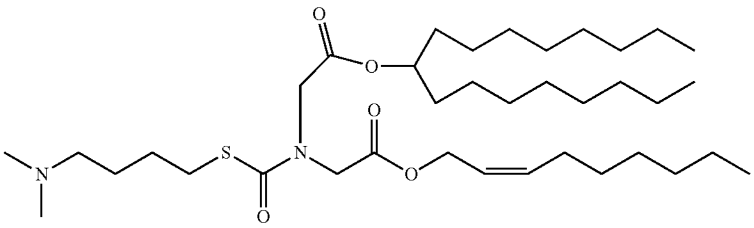

,

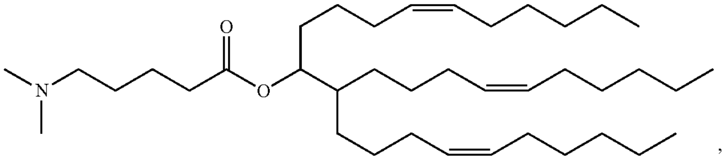

,

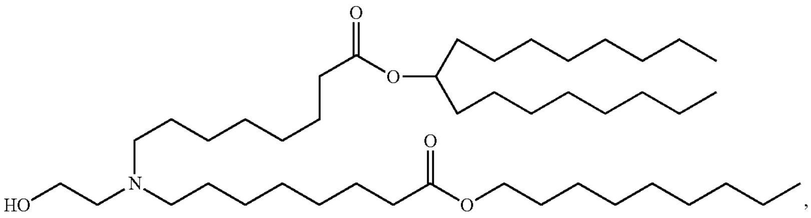

, and

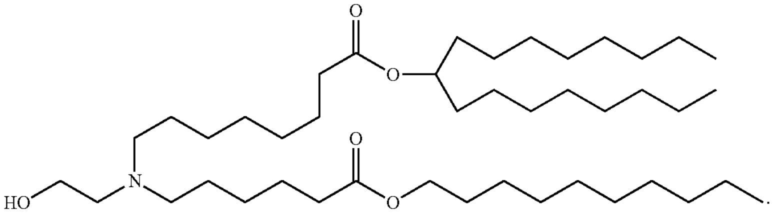

.

The experiments result in formation of LNPs with reduced adduct impurities.

Example 13: A Novel Mechanism for the Loss in mRNA Activity in LNP Delivery Systems Methods—Experiments were Performed Using the Following Methods:

RNA Extraction from mRNA-LNPs mRNA was extracted from mRNA-LNP formulations or lipid binary mixtures by isopropanol precipitation. Precipitation was performed with a 10× dilution of mRNA-LNP in 60 mM ammonium acetate in isopropanol, vortexing, then centrifugation at 4° C. Supernatant was discarded. The pellet was washed with neat isopropanol, vortexed and centrifuged again at 4° C., then dried in vacuo and resuspended in RNase-free water.

Reverse Phase Ion Pair Chromatography (RP-IP)

Separation was performed on a DNAPac RP column with 4-μm particles and dimensions of 2.1×100 mm (Thermo Fisher Scientific) at a flow rate of 0.35 mL/minute and column temperature of 65° C. Mobile phase A had 50 mM dibutylammonium acetate (TCI America), 100 mM triethylammonium acetate (Sigma-Aldrich) and mobile phase B had 50% acetonitrile (Sigma-Aldrich), 50 mM dibutylammonium acetate, and 100 mM triethylammonium. Separation was accomplished by step-gradient with an initial 1.5-minute hold at 25% B, a 3.0-minute gradient from 25-50% B, a 14.5-minute gradient from 50-56% B, and a 0.5-minute gradient and hold at 100% B. Modified gradient conditions for LP resolution were performed with an initial 1.5-minute hold at 25% B, a 1-minute gradient from 25-45% B, a 12.5-minute gradient from 45-100% B, and a 0.5-minute gradient and hold at 100% B. Approximately 2 μg of mRNA were injected. mRNA was detected by UV at 260 nm. LP was quantified as the relative percent of the total chromatographic peak area.

Capillary Electrophoresis

Separation was performed on a Fragment Analyzer (Agilent Technologies), an automated multiplexed CE system equipped with an LED light source and CCD detector. RNA Analysis Kit (Agilent Technologies DNF-489-0500) was used. The RNA separation gel was mixed with an intercalating dye (AATI) at a v/v ratio of 10,000:1 for use as the separation matrix. RNA was denatured at 70° C. for 2 minutes and cooled on ice prior to analysis. Denatured RNA samples were electrokinetically injected at 5 kV for 6 seconds, and electrophoresis was performed for 40 minutes at 8 kV. An RNA ladder (AATI) was similarly analyzed as a calibrator for nucleotide sizing. Results were analyzed using PRO Size 2.0 software.

Size Exclusion Chromatography

Separation was performed on a Zenix SEC-300 150×4.6 mm protein SEC column (Sepax) on a Waters H-Class UPLC (Waters). The mobile phase condition was 100 mM Tris acetate/2.5 mM EDTA pH 8 with an isocratic flow of 0.25 mL/minute and UV detection at 260 nm.

Binary Model Preparation mRNA-lipid binaries were formed by mixture of mRNA and ionizable lipid. Unless otherwise noted, a standard 2,000-nucleotide mRNA was prepared at 0.135 mg/mL in 37.5 mM sodium acetate pH 5.3 (Sigma Aldrich) and mixed at a 3:1 ratio with an ionizable lipid solution at 4 mg/mL in ethanol, followed by incubation at room temperature for 24 hours. Isopropanol precipitation as described above was performed to isolate the RNA prior to further analysis.

Enzymatic Digestion of mRNA to Ribonucleosides

Total nuclease digestion was performed. mRNA was incubated with 15 units of benzonase (Millipore), 2 units of phosphodiesterase I (Sigma-Aldrich), and 1.3 units of quick calf intestinal alkaline phosphatase (New England Biolabs) in buffer containing Tris-HCl (Invitrogen), NaCl, and MgCl2 (Invitrogen) at 37° C. for 2 hours.

Positive Mode LC-MS/MS

Nucleosides were separated in an increasing water/acetonitrile gradient containing 0.1% formic acid at 0.4 mL/minute on an Accucore C30 column with 2.6 μm particles and dimensions of 2.1×250 mm (Thermo Scientific) at 50° C. Ultraviolet detection of mRNA was monitored at 260 nm. Mass spectral data were acquired on an Agilent 6530 QTOF (Agilent Technologies) in positive electrospray ionization (ESI) mode. The mass range was 100-2000 m/z, drying gas temperature was 290° C. at a flow rate of 11 L/min, and the nebulizer gas pressure was 35 psi. The capillary, fragmentor, and octupole voltage were set at 3500, 100 and 750 V, respectively. External calibration was used for accurate mass measurement. For tandem mass spectrometry (MS/MS), precursor ions were subjected to collision induced dissociation and MS/MS fragmentation analysis.

Tandem Mass Spectrometry (MS/MS)

MS/MS experiments using CID were performed following RP-HPLC separation. Acquisition of a full mass scan was followed by targeted MS/MS scans of precursor ions of interest. Data were acquired on an Agilent 6530 QTOF (Agilent Technologies) for MS/MS analysis. Normalized collision energy for ion activation was 30 arbitrary units. Narrow ion isolation width (~1.3 m/z) was used for isolation.

N-Oxide Precipitation and Labeling

An N-oxide standard of ionizable lipid was generated. The N-oxide compound was dissolved in ethanol at 4 mg/mL. One milliliter of the N-oxide solution was added dropwise to 3 mL of 37.5 mM sodium acetate pH 5.3 (Sigma Aldrich), followed by incubation at room temperature for 24 hours. Prior to LC-CAD-MS analysis, 1 mM of aminooxy-PEG (Thermo Fisher) was used as a labeling agent to detect and identify aldehydes present in the system.

Aldehyde Spike Study

Synthetic aldehyde standards corresponding to the 17-carbon linear chain and 25-carbon branched chain of a cationic lipid were generated. Aldehyde solutions were individually prepared at 4 mg/mL in ethanol and mixed with a 4 mg/mL ionizable lipid solution in ethanol to various target compositions, listed in % w/w of the aldehyde to ionizable lipid. Binary preparations, intact mRNA HPLC analyses, and digested nucleoside LC/MS analyses were then performed as described above.

Reverse Phase Ultra Performance Liquid Chromatography with Charged Aerosol Detection (RP-UPLC-CAD)

LNP formulations were diluted in ethanol and the supernatant was analyzed. Lipid standards were separately diluted and analyzed to identify and quantify lipid components. RP-UPLC separation was performed on an ACE Excel 2 Super C18 column (Advanced Chromatography Technologies) with 2.1×150 mm dimensions heated to 60° C. Mobile phase A consisted of 0.1% trifluoroacetic acid (TFA) (Thermo Fisher Scientific) in water and mobile phase B consisted of 60/40/0.1% isopropyl alcohol/tetrahydrofuran/TFA (Thermo Fisher Scientific). Lipids were eluted by step-gradient with an initial 1.5-minute hold at 5% B, a 4.5-minute gradient from 5-48% B and 4-minute hold, a 1-minute gradient from 48-56% B and 12-minute hold, and an 8-minute gradient from 56-96% B and 2-minute hold. Lipids were detected by CAD using an evaporator temperature of 35° C. and analytical gas regulation mode. in vitro expression.

Expression in BJ Fibroblasts

In vitro expression in BJ fibroblasts was performed as previously described in Nelson J, Sorensen E, et al, Impact of mRNA chemistry and manufacturing process on innate immune activation, Science Advances, 24 Jun. 2020, Vol 6 no 26. Extracted mRNA was transfected with lipofectamine. An hEPO mRNA standard was included as an assay control.

Expression by Flow Cytometry

In vitro expression was performed in HeLa cells (ATCC, catalog #CCL-2). Cells were seeded in MEM with 10% FBS, 1× Glutamax, and 1× sodium pyruvate at 37° C. at 15,000 cells in a total volume of 100 μL per well and grown for 24 hours. Extracted mRNA was transfected with lipofectamine L2000 (Life Technologies, catalog #11668019) at 1,333 ng of mRNA per well and incubated for 18-20 hours at 37° C. Cells were treated with Cytoxfix/Cytoperm buffer (BD Biosciences catalog #554714) and primary antibody prior to FACS analysis on a Becton Dickinson Fortessa and data analysis using FlowJow software.

Figure 24:
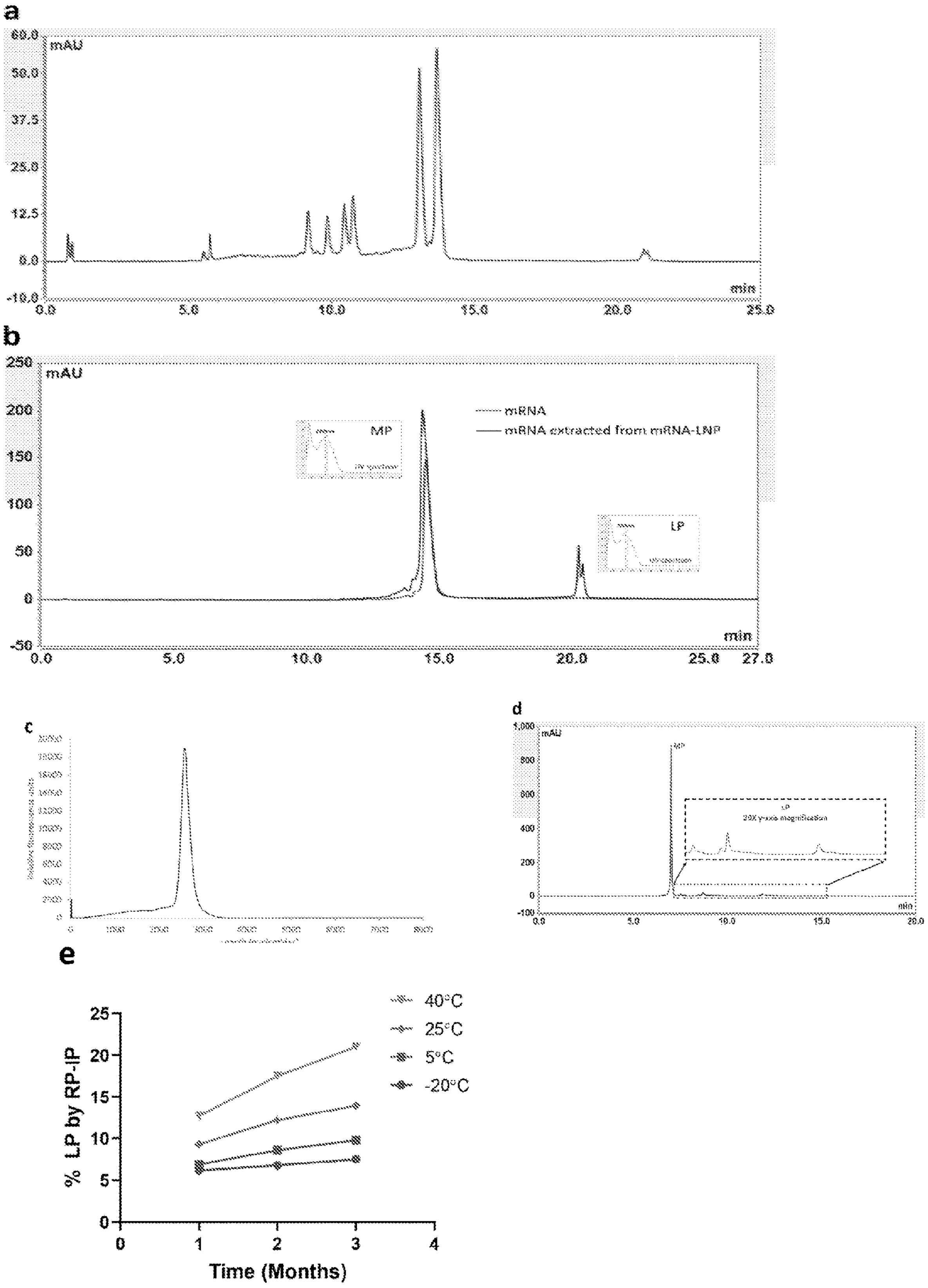
FIG. 24A-24E show identification of a late-eluting peak (LP) in formulated mRNA-LNPs by RP-IP.

Discovery of Novel Lipid-Modified mRNA Species in Formulated mRNA-LNP System Using Above Methods The assessment of mRNA stability is a key activity in the development of mRNA-based vaccines and therapeutic products due to the relatively labile nature of RNA molecules, and mRNA degradation is typically a shelf-life limiting parameter. Reverse phase ion pair high performance liquid chromatography (RP-IP HPLC) and agarose or polyacrylamide gel or capillary electrophoresis (CE) are powerful tools to assess mRNA integrity. In RP-IP HPLC, the separation can be driven by hydrophobic interactions between the analyte and stationary phase; however since the phosphodiester mRNA backbone is highly polar, high salt concentrations can be used to neutralize the negative charge and allow retention based on the hydrophobicity of the aromatic nucleobases. Alkylammonium salts can increase the hydrophobic interactions, driving selectivity based on the number of charges conferred by the length of the sequence and enabling high resolution size-based separations (FIG. 24A). This can provide a similar separation to CE, which is driven by size and charge; however, based on the ion pair system used, RP-IP can retain some selectivity to variations in mRNA hydrophobicity due to sequence, since nucleobase hydrophobicity increases from cytosine as the least hydrophobic to adenine as the most, or chemical modifications.

When RP-IP HPLC mRNA integrity analysis was applied to mRNA extracted from an mRNA-LNP, a late-eluting peak (LP) was detected by HPLC (FIG. 24B) that was not observed by CE (FIG. 24C). In FIG. 24B, the LP elutes at a retention time (RT) of 21 minutes, substantially resolved from the mRNA elution region of 10-16 minutes. The UV spectrum of the LP had the same maximum absorbance at 260 nm as the mRNA main peak (MP), confirming it as an RNA-related population (FIG. 24B, inset). Equivalent levels of the LP were observed under various analytical conditions, including modified RNA extraction, RP-IP mobile phase conditions, and stationary phase selection and temperature, suggesting it was not a separation artifact.

Since the LP eluted substantially later than mRNAs of all lengths, modified gradient conditions were applied, under which it was apparent that the LP is not a single homogenous species but rather a heterogenous mixture of resolved, well-defined peaks (FIG. 24D). These conditions generate a characteristic fingerprint, with the relative retention driven by the hydrophobicity of the species. Significantly, when mRNA-LNP formulations were monitored over time at elevated temperatures, levels of the LP increased with increasing storage temperature (FIG. 24E).

Figure 25:
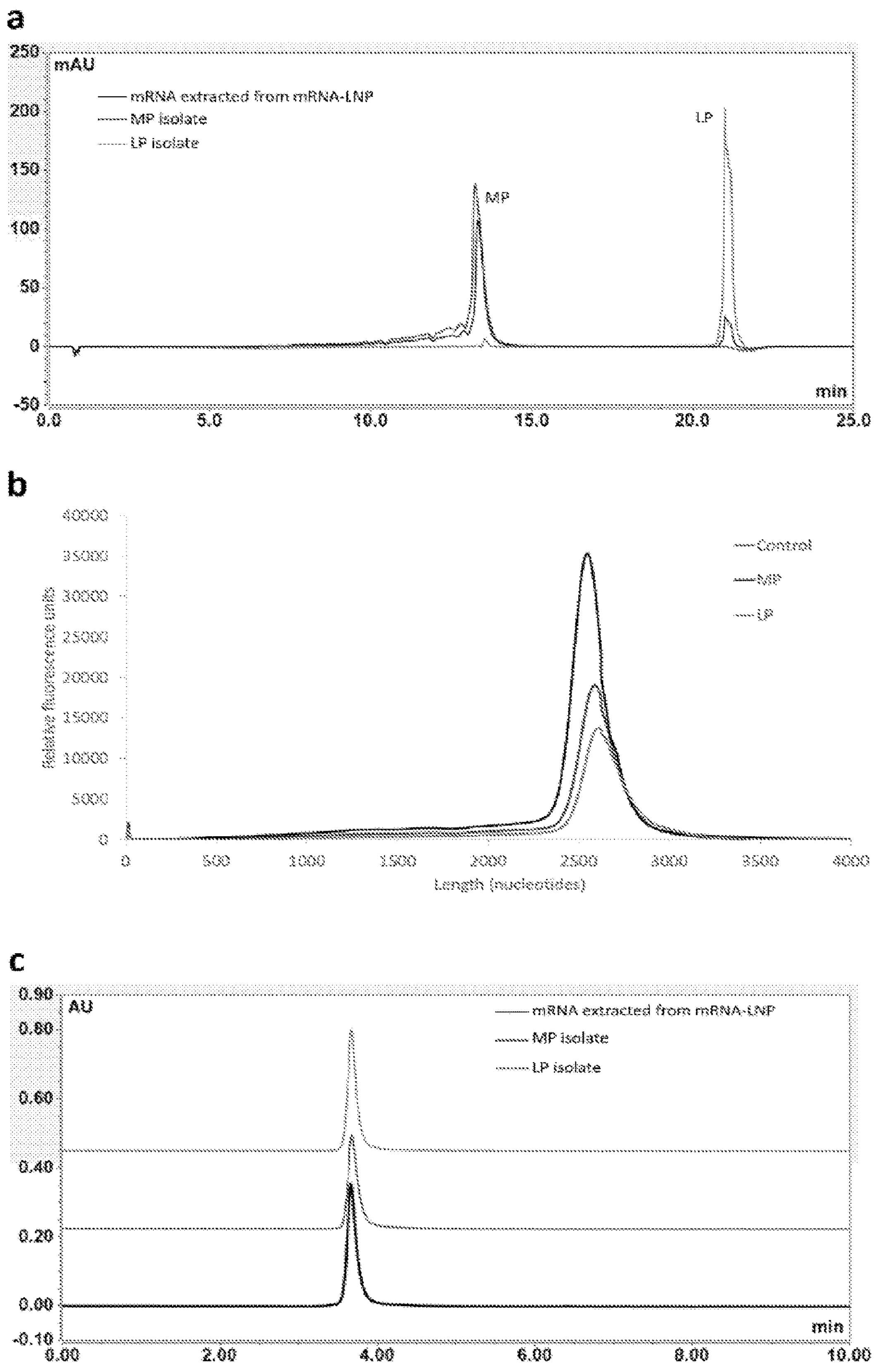
FIG. 25A-25C show second dimension intact analysis of isolated main peak (MP) and LP.

Characterization of the Modified mRNA Fraction mRNA was extracted from LNPs and fractionated by RP-IP to generate purified MP and LP fractions. Upon reanalysis by RP-IP, separation of the MP and LP was preserved (FIG. 25A); however, by CE, no difference in migration time between MP and LP was observed (FIG. 25B). Size exclusion chromatography (SEC) at ambient conditions was applied to the MP and LP to investigate the role of tertiary structure. Typical mRNA molecules are extensively structured, with intra- and inter-molecular structures generated through hydrogen bonding, Coulombic interactions, and hydrophobic effects. These interactions lead to a sequence-, salt-, and temperature-dependent ensemble of structures typically denatured under RP or CE conditions but which can be resolved by native SEC. The SEC profiles of the MP and LP fractions were identical to mRNA extracted from the LNP, with a dominantly monomeric profile (FIG. 25C). Together, these results strongly implicated additional hydrophobicity as the origin of the LP.

Compositional analysis was pursued to differentiate the LP and MP. Bulk chemical measurements such as UV in FIG. 24B did not distinguish the LP from the MP. Fourier-transform infrared spectroscopy (FT-IR) revealed minor differences that may be consistent with chemical modification (data not shown). Next generation sequencing (NGS) and digest-based mass spectrometry (MS) approaches, including a) RNA oligonucleotide mapping, b) nucleotide profiling, and c) nucleoside profiling, were pursued to elucidate molecular differences. These bottom-up MS approaches cleave or digest the mRNA to oligonucleotides or nucleotide/nucleosides that can be analyzed by liquid chromatography (LC)-MS and further studied by tandem mass spectrometry (MS/MS) approaches. Both NGS and RNA oligonucleotide mapping showed an identical profile between the MP and LP, suggesting low abundance of non-site-specific modifications. Nucleotide profiling by LC-UV showed an identical composition of nucleobases, and MS analysis failed to identify modifications in the LP, possibly due to poor ionization of the lipid modified nucleotide species in negative electrospray ionization mode.

Identification of Lipid-Modified Nucleosides

Figure 26:
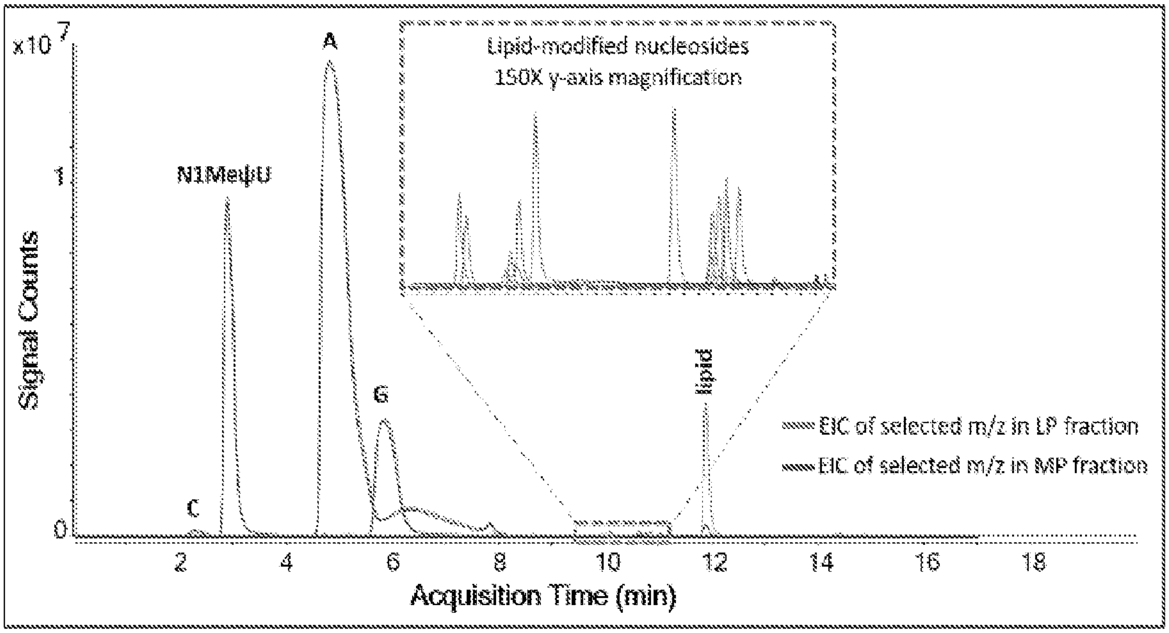
FIG. 26A-26B show identification of single modified nucleosides by LC/MS/MS.
Figure 26:
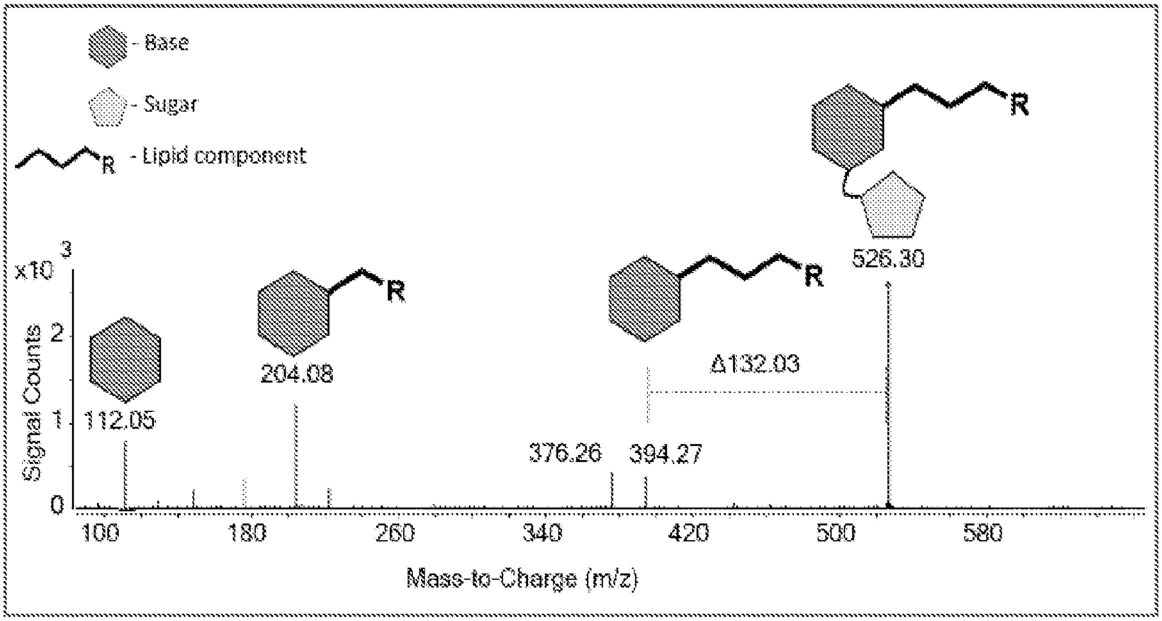

Nucleoside profiling was performed by enzymatic digestion of the LP and MP fractions and analysis using positive mode LC-MS/MS. While the UV and total ion-current chromatograms showed identical composition of the four unmodified nucleobases for the MP and LP fractions, differential analysis revealed several abundant mass-to-charge (m/z) values that were exclusively found in the isolated LP, with abundances of less than 1% relative to total unmodified nucleosides (FIG. 26A). Under the LC conditions used, these unique masses eluted significantly later (9.5-11 minutes) than the unmodified nucleosides (2-8 minutes) but not as late as the ionizable lipid eluting at 12 minutes, indicating that they had an intermediate hydrophobicity between nucleoside and ionizable lipid.

For structural elucidation of each detected reacted nucleoside, elemental composition was assigned based on high-resolution MS data. Further MS/MS analyses across the reacted nucleosides showed covalent addition of additional mass via the nucleobase, as exemplified by the fragmentation pattern of ion of m/z 526.30 in FIG. 26B. The presence of a fragment ion at m/z 112.05 corresponds to the protonated monoisotopic mass of cytosine. The neutral mass loss of 132.05 Da corresponds to the monoisotopic residue mass of ribose, indicating that ribose is in a terminal position. Across several lipid systems studied, a variety of lipid adducts were observed, with reactions across all four mRNA nucleobases demonstrated in model systems.

Reaction Modeling to Identify Contributors to Adduct Formation

Figure 27:
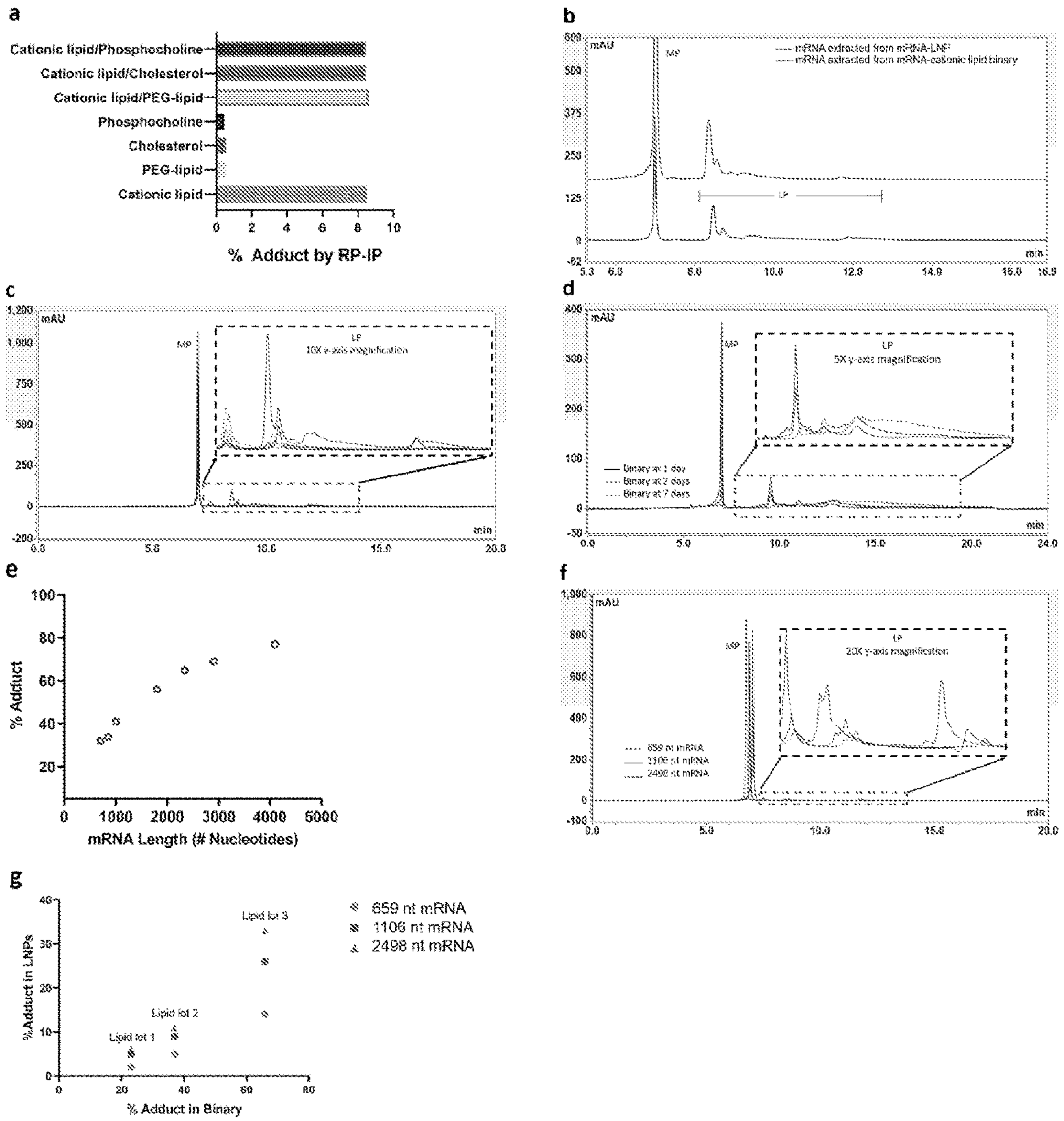
FIG. 27A-27G shows contribution of mRNA and lipid to adduct formation.

To investigate the source of reactions, combinations of mRNA with the individual LNP components (ionizable cationic lipid, PEG lipid, sterol, and phosphocholine) were studied. LP was observed in preparations with the ionizable lipid component (FIG. 27A). When the RP-IP chromatogram of a binary combination of mRNA and ionizable lipid was compared to that of mRNA-LNP formulated with the same ionizable lipid, an identical LP peak profile was observed by RP-IP (FIG. 27B), suggesting the same reactions are occurring in this simplified system. Over 100 different ionizable lipid chemistries were evaluated, all of which generated quantifiable levels of mRNA lipid adduct, demonstrating a broad class effect. The RP-IP profile of these adduct species varied in LP abundance and retention times across different chemistries (data not shown), as the hydrophobicity of the resulting modification varied with the lipid structure. Across different lots of a given ionizable lipid tested in the binary system, the relevant abundance of a consistent set of LP species varied significantly (FIG. 27C), suggesting that these reactions are driven by impurities of the ionizable lipid rather than chemical reactivity of the lipid per se. To provide insight into the chromatographic behavior of the intact adducted mRNA, a highly reactive ionizable lipid from the chemistry screen was studied in this system (FIG. 27D). At 1 day, a discrete shift in retention produced LP peaks at 10-12 minutes, then as the reaction progressed, increased tailing from 12.5-22.5 minutes was observed as the MP was depleted. This behavior is indicative that a single adduct event results in the shift to 10 minutes, and accumulation of multiple adducts per mRNA molecule drives the further increase in retention time.

The binary system was used to study contributions from the mRNA molecule as well. A series of mRNA sequences varying from 700 to over 4000 nucleotides in length was prepared at equivalent masses in individual binary reactions, resulting in increasing LP with mRNA length (FIG. 27E). Since the relative UV intensity of the LP peak in the RP-IP assay is correlated with relative mass, this observation is consistent with a constant rate of reaction on the single base level, each of which has an increased impact and shifts more mass to LP as sequence length increases. This correlation highlights the relevance of these reactions for mRNA as a high molecular weight nucleic acid polymer. Looking at the chromatographic profile, the same adduct peaks can be observed across mRNAs of different lengths in FIG. 27F, with a decrease in retention time of each LP region with increasing mRNA length. Considering the average hydrophobicity of the adducted mRNA sequence: as sequence length increases, the same modification makes of less of the total molecule and has less impact on retention. FIG. 27G shows a positive correlation between adduct formation and mRNA length, with more adduct at longer mRNA lengths.

Oxidative Impurities of Ionizable Lipid as Driver of Adducts Formation

Figure 28:
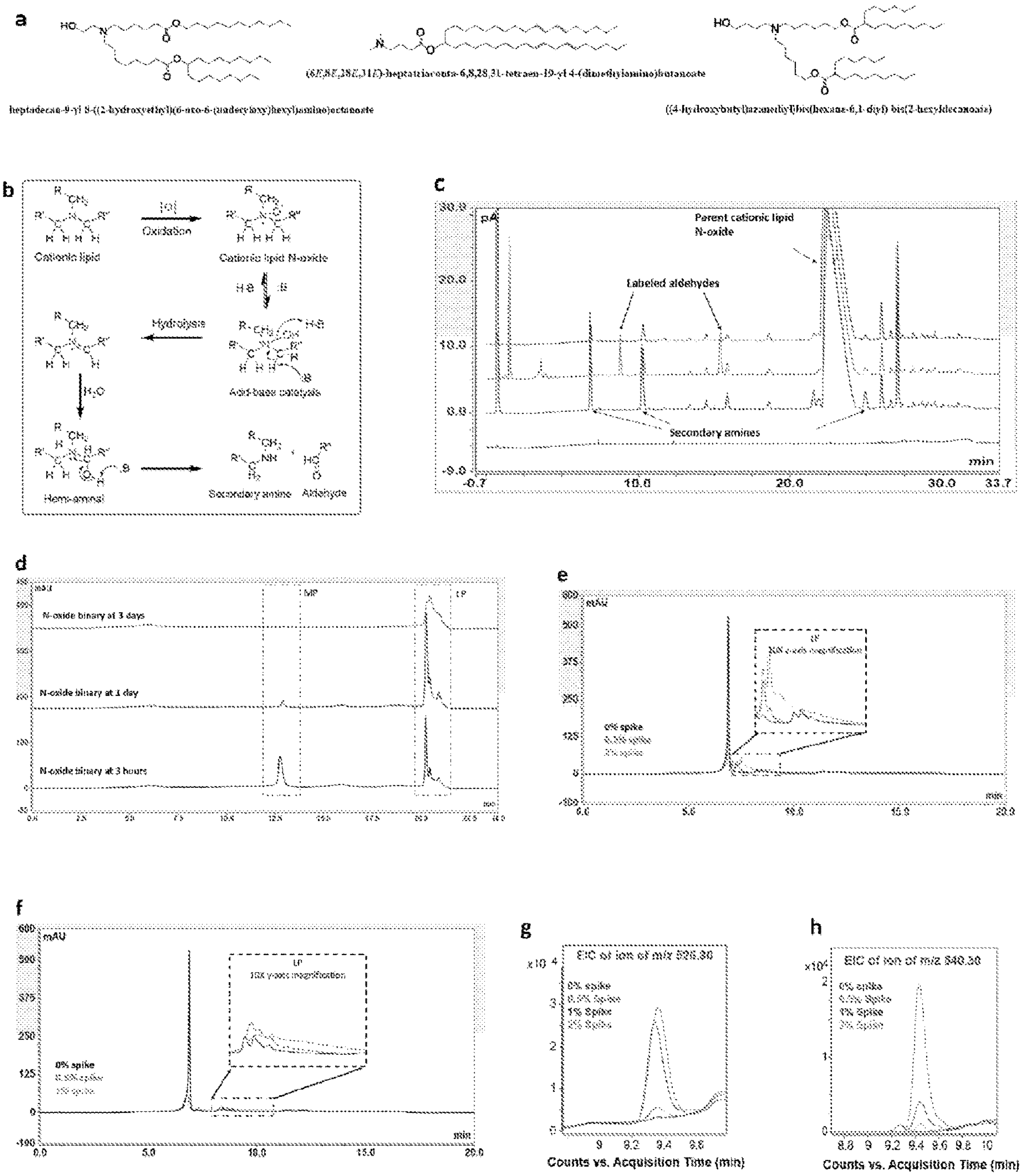
FIG. 28A-28H show N-oxide as a driver of adduct formation, via driving aldehyde generation that contributes to adduct formation.

Having implicated impurities of the ionizable lipid as the driver of adduct formation (FIGS. 28A-28C), impurities and degradants that are common among but unique to the ionizable amino-lipid family were considered. N-oxide was identified as leading to high levels of LP, with almost complete conversion of the mRNA to LP within 3 days in the binary system (FIG. 28D). N-oxide formation is a degradation pathway for tertiary-amine-containing molecules under oxidative stress. Although relatively stable, N-oxide can further hydrolyze to secondary amines and aldehyde counterparts, as shown in FIG. 28A, possibly typically through metal catalysis. The relevance of N-oxide hydrolysis in the absence of metal catalysts was evaluated. N-oxide standard was generated from a representative ionizable lipid, precipitated in acidic buffer, and analyzed by reverse phase ultra-high-performance liquid chromatography with charged aerosol detection (RP-UPLC-CAD) and MS/MS detection (FIG. 28C). Three peaks generated under these conditions at retention time 8.7, 10.3, and 25 minutes were identified by MS/MS as the three secondary amines resulting from hydrolysis of the N-oxide. To detect the residual mass, the degraded N-oxide solution was derivatized with an aminooxy-PEG to label all aldehyde functionalities. Unique peaks at 9.5 minutes and 16 minutes were detected by CAD corresponding to the aldehyde products of N-oxide hydrolysis; the third, small aldehyde, likely elutes in the column void. These studies demonstrate that even in relatively mild acidic conditions, N-oxide hydrolysis can generate secondary amines and aldehydes without the use of metallic catalysts.

Investigation of mRNA Adduction by Aldehydes

Two representative aldehydes from the N-oxide degradation pathway of an ionizable lipid were studied: a linear, 17-carbon chain, and a branched, 25-carbon chain. The aldehydes were individually spiked into the ionizable lipid as impurities prior to precipitation in binary reactions. Significant increases in lipid-mRNA adduct levels were observed with increasing spike concentration for both aldehydes. By RP-IP, peaks corresponding to mRNA adducts with the smaller linear aldehyde elute at 7.5 minutes (FIG. 28D), while peaks corresponding to reactions with the larger branched aldehyde elute later at 8-10 minutes (FIG. 28E). The resolution between these species, differing by 8 carbons, highlights the remarkable selectivity of the RP-IP method to minute differences on the intact mRNA molecule. The increase in tailing at the highest spike concentration may be due to the accumulation of multiple lipid adducts per mRNA strand, in contrast to the initial discrete shift that occurs for each aldehyde with a single addition. These reactions were further confirmed on the single nucleoside level through enzymatic digestion and positive mode LC-MS/MS analysis. Using cytidine as an example, when the aldehyde in FIG. 28E was prepared at various concentrations in the binary, there was a corresponding increase in two resulting nucleoside masses (m/z 526.3 and 540.3), which were further elucidated by MS/MS as the products of aldehyde addition (FIG. 28F). When mRNA from the linear aldehyde binary was subjected to enzymatic digestion and positive mode LC-MS/MS analysis, there was a corresponding increase in 2 resulting nucleoside masses of m/z 526.3 (FIG. 28G) and 540.3 (FIG. 28H) which were further elucidated by MS/MS as being products of aldehyde addition to cytidine (see FIG. 26B). While hydrolysis of N-oxide is one pathway for the generation of aldehydes in the LNP system, similar species may be present as lipid raw material impurities or oxidative degradants, generating the diversity of adduct species observed on the intact mRNA and single nucleoside level.

Impact of Lipid-mRNA Adduct on Protein Expression and Product Shelf Life

MP and LP fractions were isolated by RP-IP from two mRNA formulations in which the mRNA encoded the human erythropoietin (hEPO) protein and analyzed in vitro in BJ fibroblasts for protein expression. The isolated MP showed comparable expression to the unfractionated extracted mRNA and hEPO assay control, whereas the isolated LP showed almost no protein production (FIG.

Figure 29:
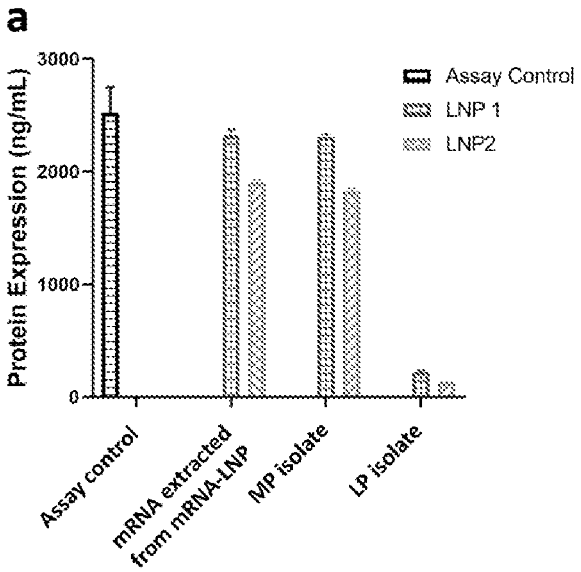
FIG. 29A-29B show that mRNA adduction reduces protein expression.
Figure 29:
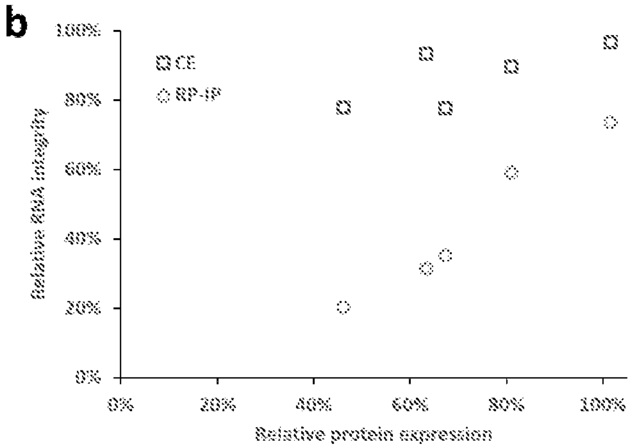

29A). In a separate study, five LNP formulations were incubated to various levels of degradation, after which the mRNA was extracted from the LNP and analyzed by RP-IP, CE, and in vitro protein expression (FIG. 29B). The relative mRNA purity by RP-IP (including adduct as an impurity) had a strong correlation with protein expression, whereas a comparatively poor correlation between mRNA integrity measured by CE and protein expression results, with all samples within 20% relative purity by CE. Extrapolating the correlation, a total loss in protein production would occur while the CE electropherogram suggests that mRNA purity remains greater than 60%. These data demonstrate the potential of these adduct reactions to reduce activity of mRNA-LNP products, and the inadequacy of CE to determine mRNA quality in LNP formulations.

Given the impact of RNA-lipid adduct on protein expression, the thorough characterization and control of adduct levels must be a critical activity throughout the research, development, and manufacture of mRNA-LNP products to ensure mRNA activity. The potential impact to refrigerated vaccine stability was assessed. Two vaccine formulations utilizing the same mRNA sequence and lipid system are shown, with proper adduct controls in place for Vaccine B and poor control in Vaccine A. An initial delta in 15% indicates rapid adduct formation in processing or prior to product testing, followed by loss in almost 50% of mRNA integrity to adduct formation over 3 months at 5 C. By contrast, Vaccine B demonstrates comparatively low levels of adduct with a negligible increase over time.

CONCLUSIONS

A novel lipid-modified class of mRNA impurities generated by electrophilic degradants and impurities originating in the ionizable lipid which disrupt mRNA translation was identified, which impacts the activity of LNP-formulated mRNA products. RP-IP HPLC provides remarkable specificity and sensitivity to detect adducted mRNA molecules, which are otherwise difficult to identify due to the low rate of modification. Indeed, the data suggests that even single adduct events are detected on the intact mRNA by RP-IP HPLC, whereas even purified LP is not distinguished by CE methodology typically employed. Because of the impact to protein translation, these species represent a variable affecting product activity that is hidden to certain analytical techniques traditionally utilized to assess mRNA integrity in mRNA-LNP such as CE.

Furthermore, the formation of these mRNA-lipid adducts can be evaluated starting from formulation design into clinical evaluation and through to commercialization by using appropriate RP-IP HPLC methodologies.

As one mechanism, the hydrolysis of N-oxide to aldehydes is broadly relevant to tertiary amines used in the LNP formulation of siRNA and mRNA. It is highly probable therefore that formation of this class of adducts has hitherto been missed by historically applied analytical technologies such as CE, and subsequently an important critical quality attribute of mRNA-LNP has not been addressed. This represents a gap in control of mRNA-LNP's particularly as it pertains to consistency and control of manufacture and activity of the resultant drug product. The pathway reported herein generates an important class of previously un-reported impurities that may be present in lipid-based mRNA formulations. These reactions can be mitigated through raw material control, manufacturing process parameters, formulation design, and LNP storage conditions. In the research, development, and manufacture of LNP-formulated nucleic acid products it is critical to monitor and control lipid adduct formation to ensure the quality, consistency, and activity of the pharmaceutical product.

What is claimed is:

1. A method of inhibiting formation of one or both of N-oxides and aldehydes in a composition comprising an ionizable lipid and a polynucleotide, wherein the ionizable lipid comprises a tertiary amine group and can decompose into a secondary amine and/or reactive aldehyde species capable of interacting with the polynucleotide to form an ionizable lipid-polynucleotide adduct impurity, wherein the method comprises treating one or both of the ionizable lipid and the polynucleotide before combining the ionizable lipid and the polynucleotide to prepare the composition, to reduce the formation of ionizable lipid-polynucleotide adduct impurity, wherein less than about 10% of the polynucleotide in the composition is in the form of ionizable lipid-polynucleotide adduct impurity, as measured by reverse phase ion pair high performance liquid chromatography (RP-IP HPLC).

2. The method according to claim 1, wherein the treating comprises one or more of:

treating the ionizable lipid with a scavenging agent before combining the ionizable lipid and the polynucleotide;

treating the ionizable lipid with a reductive treatment agent before combining the ionizable lipid and the polynucleotide;

treating the ionizable lipid with a reducing agent before combining the ionizable lipid and the polynucleotide;

treating the ionizable lipid with a chelating agent before combining the ionizable lipid and the polynucleotide;

treating the polynucleotide with a reducing agent before combining the ionizable lipid and the polynucleotide; and treating the polynucleotide with a chelating agent before combining the ionizable lipid and the polynucleotide.

3. The method according to claim 2, wherein:

the scavenging agent comprises one or more of (O-(2,3,4,5,6-Pentafluorobenzyl) hydroxylamine hydrochloride) (PFBHA), methoxyamine hydrochloride, benzyloxyamine hydrochloride, ethoxyamine hydrochloride, 4-[2-(aminooxy) ethyl]morpholine dihydrochloride, tert-butoxyamine hydrochloride, 4-dimethylaminopyridine (DMAP), 1,4-diazabicyclo [2.2.2]octane (DABCO), triethylamine (TEA), piperidine 4-carboxylate (BPPC), and combinations thereof;

the reductive treatment agent comprises one or more of sodium borohydride and bis (pinacolato) diboron;

the reducing agent comprises one or both of an immobilized reducing agent and a free reducing agent, wherein (i) the immobilized reducing agent is one or more of immobilized diphenylphosphine on silica (Si-DPP), immobilized thiol on agarose (Ag-Thiol), immobilized cysteine on silica (Si-Cysteine), immobilized thiol on silica (Si-Thiol), and combinations thereof, and (ii) the free reducing agent is one or more of potassium metabisulfite, sodium thioglycolate, tris (2-carboxyethyl) phosphine (TCEP), sodium thiosulfate, N-acetyl cysteine, glutathione, dithiothreitol (DTT), cystamine, dithioerythritol (DTE), dichlorodiphenyltrichloroethane (DDT), homocysteine, lipoic acid, and combinations thereof; and the chelating agent comprises immobilized iminodiacetic acid.

4. The method of claim 1, further comprising one or more of (i) adjusting the pH of the composition to a pH of from about 7 to about 9; (ii) adjusting a buffer in the composition to be from about 20 mM to about 150 mM tris (hydroxymethyl) aminomethane (TRIS); and (iii) adjusting the temperature of the composition to be 25° C. or less.

5. The method of claim 1, wherein the polynucleotide is messenger RNA (mRNA).

6. The method of claim 5, wherein the composition comprises lipid nanoparticles (LNPs) containing the mRNA.

7. The method of claim 5, wherein the composition comprises liposomes containing the mRNA.

8. The method of claim 5, wherein the composition comprises lipoplexes containing the mRNA.

9. The method of claim 5, wherein the mRNA comprises an N1-methyl-pseudouridine (mlψ) nucleobase.

10. The method of claim 1, wherein less than about 5% of the polynucleotide in the composition is in the form of the ionizable lipid-polynucleotide adduct impurity.

11. The method of claim 1, wherein less than about 1% of the polynucleotide in the composition is in the form of the ionizable lipid-polynucleotide adduct impurity.

12. The method of claim 1, wherein the ionizable lipid-polynucleotide adduct impurity comprises an alkyl halide-polynucleotide adduct impurity.

13. The method of claim 1, wherein an amount of alkyl halide compounds in the composition is less than about 50 ppm.

14. The method of claim 1, wherein the ionizable lipid-polynucleotide adduct impurity comprises an aldehyde-polynucleotide adduct impurity.

15. The method of claim 1, wherein an amount of lipid aldehydes in the composition is less than about 50 ppm.

16. The method of claim 2, wherein the treating comprises one or more of:

treating the ionizable lipid with a reducing agent before combining the ionizable lipid and the polynucleotide; and treating the polynucleotide with a reducing agent before combining the ionizable lipid and the polynucleotide, wherein the reducing agent is a free reducing agent.

17. The method of claim 16, wherein the free reducing agent is one or more of potassium metabisulfite, sodium thioglycolate, tris (2-carboxyethyl) phosphine (TCEP), sodium thiosulfate, N-acetyl cysteine, glutathione, dithiothreitol (DTT), cystamine, dithioerythritol (DTE), dichlorodiphenyltrichloroethane (DDT), homocysteine, and lipoic acid.

18. The method of claim 2, wherein the treating comprises one or more of:

treating the ionizable lipid with a chelating agent before combining the ionizable lipid and the polynucleotide; and treating the polynucleotide with a chelating agent before combining the ionizable lipid and the polynucleotide.

19. The method of claim 18, wherein the chelating agent comprises one or more of ethylenediaminetetraacetic acid (EDTA), citric acid monohydrate, disodium edetate, fumaric acid, malic acid, phosphoric acid, sodium edetate, tartaric acid, and trisodium edetate.

20. The method of claim 2, wherein the treating comprises treating the ionizable lipid with a scavenging agent before combining the ionizable lipid and the polynucleotide, wherein the scavenging agent comprises one or more of (O-(2,3,4,5,6-Pentafluorobenzyl) hydroxylamine hydrochloride) (PFBHA), methoxyamine, methoxyamine hydrochloride, benzyloxyamine, benzyloxyamine hydrochloride, ethoxyamine, ethoxyamine hydrochloride, 4-[2-(aminooxy) ethyl]morpholine dihydrochloride, butoxyamine, butoxyamine hydrochloride, 4-dimethylaminopyridine (DMAP), 1,4-diazabicyclo [2.2.2]octane (DABCO), triethylamine (TEA), and piperidine 4-carboxylate (BPPC).

21. The method of claim 20, wherein the scavenging agent comprises one or more of PFBHA and methoxyamine hydrochloride.

22. The method of claim 1, wherein the ionizable lipid is

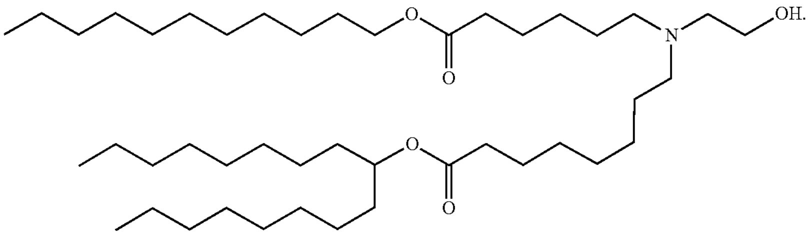 [SMILES: CCCCCCCCCCCOC(=O)CCCCCN(CCO)CCCCCCCC(=O)OC(CCCCCCCC)CCCCCCCC]

23. The method of claim 1, wherein the ionizable lipid is
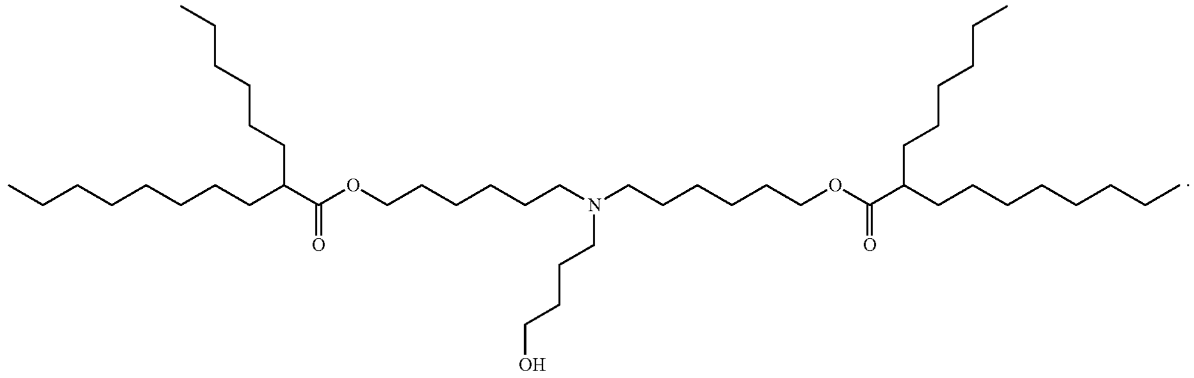 [SMILES: CCCCCCCCC(CCCCCC)C(=O)OCCCCCCN(CCCCO)CCCCCCOC(=O)C(CCCCCC)CCCCCCCC]
* * * * *